(12) United States Patent
Capurso et al.

(10) Patent No.: US 11,155,814 B2
(45) Date of Patent: Oct. 26, 2021

(54) METHODS FOR USING DNA REPAIR FOR CELL ENGINEERING

(71) Applicant: Caribou Biosciences, Inc., Berkeley, CA (US)

(72) Inventors: Daniel Capurso, Weatogue, CT (US); Andrew P. May, San Francisco, CA (US); Megan Van Overbeek, Oakland, CA (US)

(73) Assignee: Caribou Biosciences, Inc., Berkeley, CA (US)

( * ) Notice: Subject to any disclaimer, the term of this patent is extended or adjusted under 35 U.S.C. 154(b) by 466 days.

(21) Appl. No.: 16/078,014

(22) PCT Filed: Feb. 21, 2017

(86) PCT No.: PCT/US2017/018679
§ 371 (c)(1),
(2) Date: Aug. 21, 2018

(87) PCT Pub. No.: WO2017/147056
PCT Pub. Date: Aug. 31, 2017

(65) Prior Publication Data
US 2019/0055549 A1    Feb. 21, 2019

Related U.S. Application Data

(60) Provisional application No. 62/344,876, filed on Jun. 2, 2016, provisional application No. 62/298,129, filed on Feb. 22, 2016.

(51) Int. Cl.
*C12N 15/00* (2006.01)
*C12N 15/11* (2006.01)
*C12N 15/90* (2006.01)
*C12N 15/10* (2006.01)

(52) U.S. Cl.
CPC ............ *C12N 15/11* (2013.01); *C12N 15/102* (2013.01); *C12N 15/90* (2013.01); *C12N 15/902* (2013.01); *C12N 15/907* (2013.01); *C12N 2310/20* (2017.05); *C12N 2800/80* (2013.01)

(58) Field of Classification Search
CPC .. C12N 2310/20; C12N 15/11; C12N 15/102; C12N 15/90; C12N 15/902; C12N 15/907; C12N 2800/80
See application file for complete search history.

(56) References Cited

U.S. PATENT DOCUMENTS

| | | |
|---|---|---|
| 6,569,681 B1 | 5/2003 | Ivanov |
| 2007/0155014 A1 | 7/2007 | Bertolini et al. |
| 2007/0179160 A1 | 8/2007 | Helleday |
| 2012/0231449 A1 | 9/2012 | Mermod et al. |
| 2014/0304847 A1 | 10/2014 | Kuhn et al. |
| 2015/0005327 A1 | 1/2015 | Helleday |
| 2016/0040155 A1 | 2/2016 | Maizels et al. |
| 2016/0215275 A1* | 7/2016 | Zhong ................ C12N 15/111 |
| 2018/0000822 A1 | 1/2018 | Helleday |
| 2019/0218257 A1* | 7/2019 | Romesberg ............ C12N 15/90 |

FOREIGN PATENT DOCUMENTS

| | | |
|---|---|---|
| WO | WO2001/090404 | 11/2001 |
| WO | WO/2011/078662 | 6/2011 |
| WO | WO2016/073990 | 5/2016 |

OTHER PUBLICATIONS

Hu et al (PNAS Aug. 5, 2014, vol. 111 No. 31, pp. 11461-11466) (Year: 2014).*
Allen, C., Halbrook, J., Nickoloff, J.A. Interactive Competition Between Homologous Recombination and Non-Homologous End Joining[1]1NIH grant CA77693 to J.A.N. Mol Cancer Res. Oct. 1, 2003; 1(12)913-920. (2003).
Boboila C, Jankovic M, Yan CT, et al. Alternative end-joining catalyzes robust IgH locus deletions and translocations in the combined absence of ligase 4 and Ku70. Proceedings of the National Academy of Sciences of the United States of America. 107(7):3034-3039. doi:10.1073/pnas.0915067107. (2010).
Boboila C, Yan C, Wesemann DR, et al. Alternative end-joining catalyzes class switch recombination in the absence of both Ku70 and DNA ligase 4. The Journal of Experimental Medicine. 207(2):417-427. (2010) doi:10.1084/jem.20092449.
Chu, V.T., Weber, T., Wefers, B., Wurst, W., Sander, S., Rajewsky, K., Kühn, R. Increasing the efficiency of homology-directed repair for CRISPR-Cas9-induced precise gene editing in mammalian cells. Nat Biotechnol. May 2015; 33(5):543-548. (2015) doi: 10.1038/nbt.3198. Epub Mar. 24, 2015.
Dueva, R., Iliakis, G. Alternative pathways of non-homologous end joining (NHEJ) in genomic instability and cancer. Translational Cancer Research, 2(3):163-177. (2013) doi:10.21037/1152.
Frank-Vaillant, M., Marcand S. NHEJ regulation by mating type is exercised through a novel protein, Lif2p, essential to the Ligase IV pathway. Genes & Development. 15(22):3005-3012. (2001) doi:10.1101/gad.206801.
Hanakahi, L.A., Bartlet-Jones, M., Chappell, C., Pappin, D., West, S.C. Binding of Inositol Phosphate to DNA-PK and Stimulation of Double-Strand Break Repair. Cell, Sep. 15, 2000; 102(6):721-729. (2000).
Maassen, N., Freese, S., Schruff, B., Passoth, V., Klinner, U. Nonhomologous end joining and homologous recombination DNA repair pathways in integration mutagenesis in the xylose. fermenting yeast *Pichia stipitis*. FEMS Yeast Research, 8:735-743. (2008) doi:10.1111/j.1567-1364.2008.00383.x.

(Continued)

Primary Examiner — Catherine S Hibbert
(74) Attorney, Agent, or Firm — Barbara G. McClung

(57) ABSTRACT

Methods for gene editing and predicting non-random editing events are described. The methods use Clustered Regularly Interspaced Short Palindromic Repeats (CRISPR) systems to characterize and manipulate DNA repair outcomes at Cas-initiated double-strand breaks (DSBs) to anticipate functional outcomes.

9 Claims, 53 Drawing Sheets

Specification includes a Sequence Listing.

(56) References Cited

OTHER PUBLICATIONS

Maruyama T, Dougan SK, Truttmann M, Bilate AM, Ingram JR, Ploegh HL. Inhibition of non-homologous end joining increases the efficiency of CRISPR/Cas9-mediated precise genome editing. Nature biotechnology. 33(5):538-542. (2015) doi:10.1038/nbt.3190.
PCT International Search Report for related International Application No. PCT/US2017/018679.
Perrault, R., Wang, H. ,Wang, M., Rosidi, B., Iliakis, G. Backup pathways of NHEJ are suppressed by DNA-PK. First published: May 20, 2004 https://doi.org/10.1002/jcb.20104.
Robert F, Barbeau M, Éthier S, Dostie J, Pelletier J. Pharmacological inhibition of DNA-PK stimulates Cas9-mediated genome editing. Genome Medicine. 7(1):93. (2015) doi:10.1186/s13073-015-0215-6.
Sfeir A, Symington LS. Microhomology-mediated end joining: a back-up survival mechanism or dedicated pathway? Trends in biochemical sciences. 40(11):701-714. (2015) doi:10.1016/j.tibs.2015.08.006.
Shibata A, Moiani D, Arvai AS, et al. DNA Double Strand Break Repair Pathway Choice Is Directed by Distinct MRE11 Nuclease Activities. Molecular cell. 53(1):7-18. (2014) doi:10.1016/j.molcel.2013.11.003.
Simsek D, Jasin M. Alternative end-joining is suppressed by the canonical NHEJ component Xrcc4/ligase IV during chromosomal translocation formation. Nature structural & molecular biology. 17(4):410-416. (2010) doi:10.1038/nsmb.1773.
Terasawa M., Shinohara A., Shinohara M. Canonical Non-Homologous End Joining in Mitosis Induces Genome Instability and Is Suppressed by M-phase-Specific Phosphorylation of XRCC4. PLOS Genetics 10(8): e1004563. (2014) https://doi.org/10.1371/journal.pgen.1004563.
Vasileva A, Linden RM, Jessberger R. Homologous recombination is required for AAV-mediated gene targeting. Nucleic Acids Research. 34(11):3345-3360. (2006) doi:10.1093/nar/gkl455.
Overbeek, M. et al., "DNA Repair Profiling Reveals Nonrandom Outcomes at Cas9-Mediated Breaks," Poster at Cold Spring Harbour Meeting: Genome Engineering: The CRISPR-Cas Revolution, Aug. 17-20, 2016.
Overbeek, M. et al., "DNA Repair Profiling Reveals Nonrandom Outcomes at Cas9-Mediated Breaks", Mol. Cell, (2016), 63:633-646.

* cited by examiner

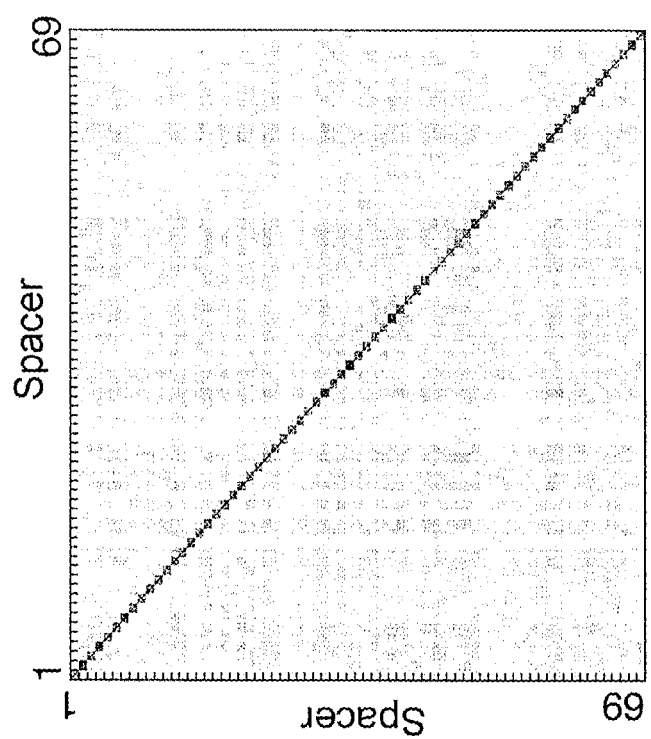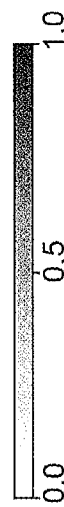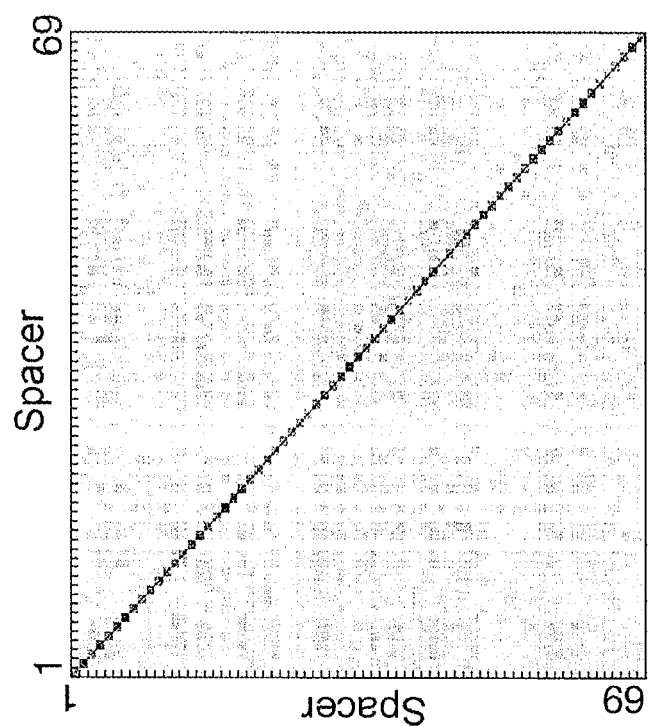
FIG. 2A
FIG. 2B
FIG. 2C

Spacer Group 15 Sequence:
GGCAGTGCAGATGAAAATACTGGG ← SEQ ID NO: 649

| Target | hg38 coordinates | Region | Gene |
|---|---|---|---|
| 15a | chr12:308620020-308620043 | noncoding | -- |
| 15b | chr2:129496621-129496644 | noncoding | -- |
| 15c | chr2:68125583-68125606 | intron | WDR92 |
| 15d | chr20:53421490-53421512 | intron | TSHZ2 |
| 15e | chr7:76361952-76361974 | noncoding | -- |
| 15f | chr7:44799840-44799863 | exon | PPIA |
| 15g | chr11:43466710-43466733 | intron | TTC17 |

FIG. 3A

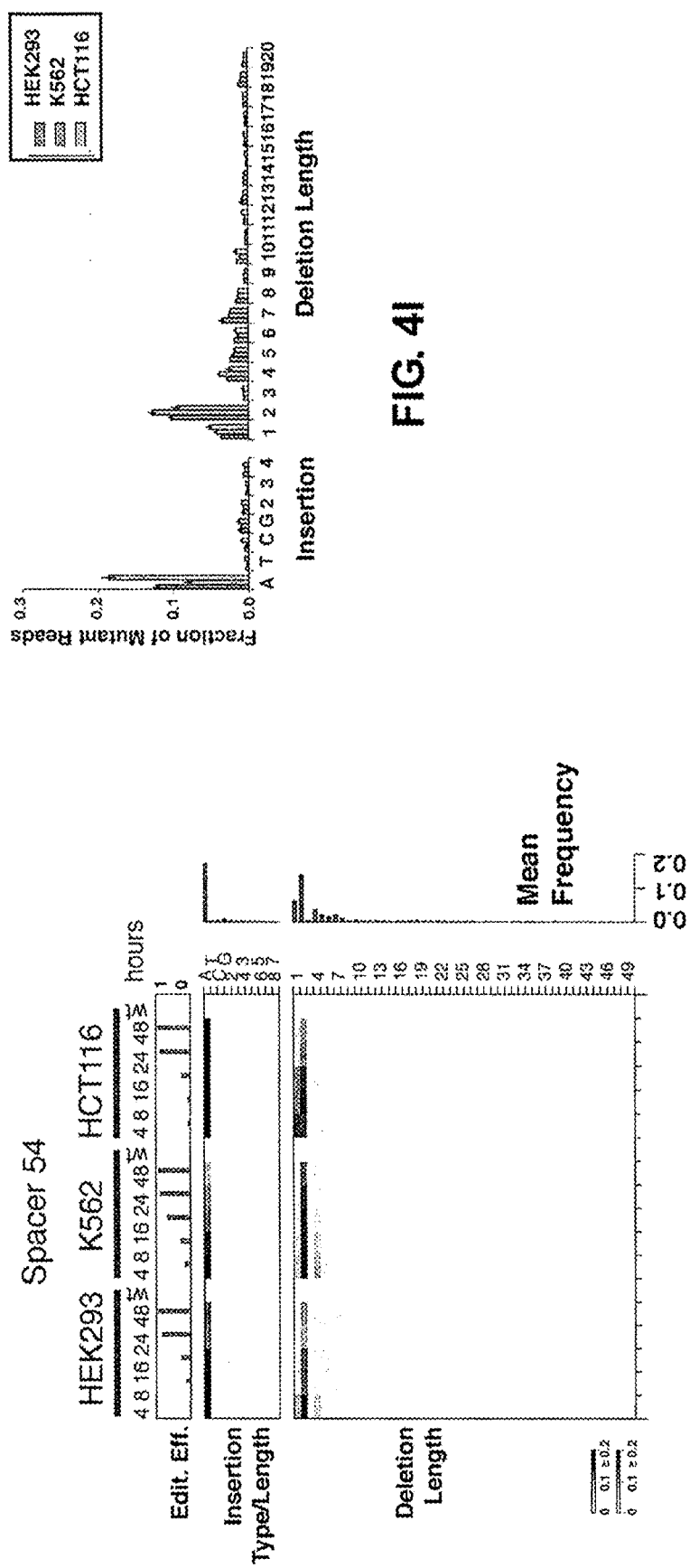

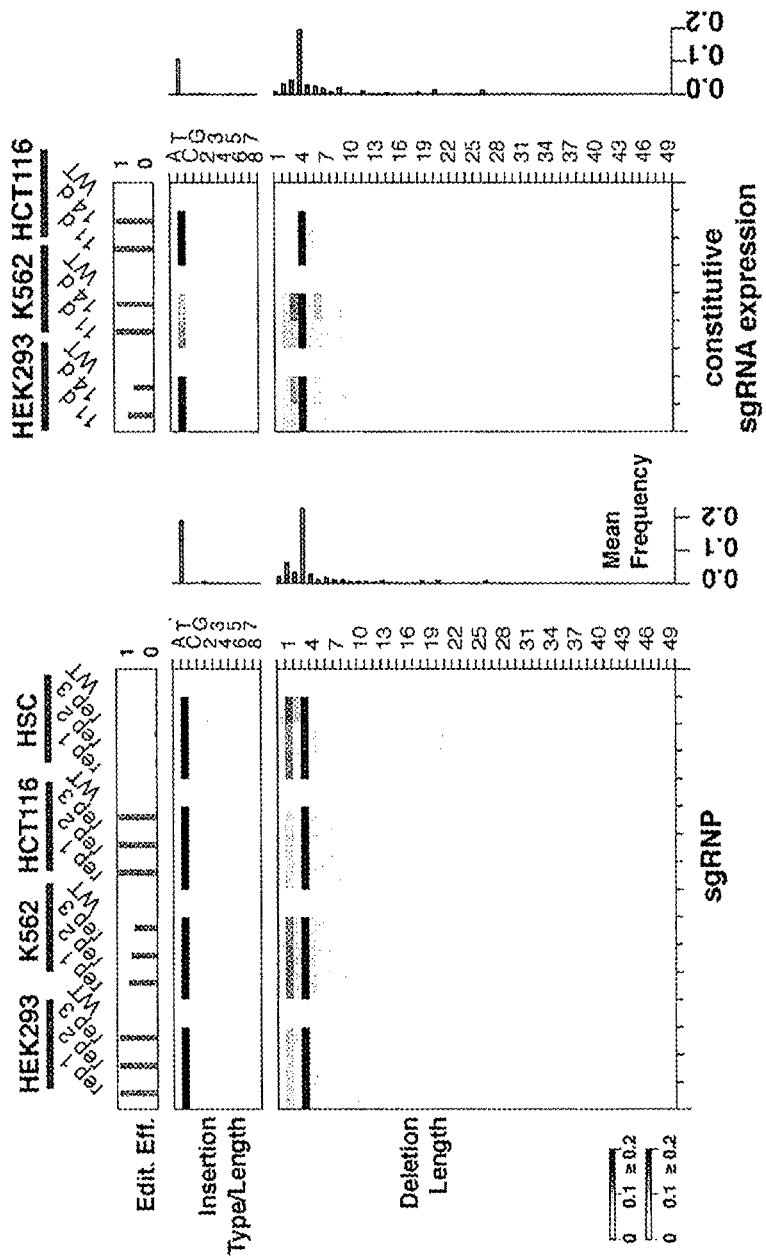

| Spacer group: | Ground Truth | HEK293 AP clustering | K562 AP clustering |
|---|---|---|---|
| 1 | 1, 1, 1 | 1, 1, 1 | 1, 1, 1 |
| 2 | 2, 2 | 2, 2 | 3, 3, 3, 3, 3, 3, 3, 2 |
| 3 | 3, 3, 3, 3, 3, 3, 3 | 3, 3, 3, 3, 3, 3, 3, 8, 12 | 4, 4, 4, 4 |
| 4 | 4, 4, 4, 4 | 4, 4, 4, 4, 12 | 6, 6, 6, 6, 6, 6, 6, 6, 6, 14 |
| 5 | 5, 5 | 5, 5 | 7, 7, 7 |
| 6 | 6, 6, 6, 6, 6, 6, 6, 6, 6 | 6, 6, 6, 6, 6, 6, 6, 6, 6, 14 | 8, 8, 8, 8, 8 |
| 7 | 7, 7, 7 | 7, 7, 7 | 9, 9, 9, 9, 9 |
| 8 | 8, 8, 8, 8, 8 | 8, 8, 8, 8 | 10, 10, 13 |
| 9 | 9, 9, 9, 9, 9 | 9, 9, 9, 9, 9, 14 | 11, 11, 11, 11, 11, 11, 11 |
| 10 | 10, 10, 10 | 10, 10, 10 | 12, 12 |
| 11 | 11, 11, 11, 11, 11, 11, 11 | 11, 11, 11, 11, 11, 11, 11 | 13, 13, 13 |
| 12 | 12, 12 | 13, 13, 13 | 14, 14 |
| 13 | 13, 13, 13, 13 | 15, 15, 15, 15, 15, 15 | 15, 15, 15, 15, 15, 15 |
| 14 | 14, 14, 14 | 16, 16, 16, 16, 16, 16 | 16, 16, 16, 16, 16, 16 |
| 15 | 15, 15, 15, 15, 15, 15 | 17, 17, 17, 17 | 17, 17, 17, 17 |
| 16 | 16, 16, 16, 16, 16, 16 | 18, 18, 18 | 18, 18, 18 |
| 17 | 17, 17, 17, 17 | 19, 19, 19 | 19, 19, 19 |
| 18 | 18, 18, 18 | 20, 20, 20, 20, 20, 20, 20 | 20, 20, 20, 20 |
| 19 | 19, 19, 19 | 21, 21, 21, 21, 21, 14 | 20, 20, 20, 20 |
| 20 | 20, 20, 20, 20, 20, 20, 20 | 22, 22, 22, 22, 22, 22, 22, 13 | 21, 21, 21, 21, 21 |
| 21 | 21, 21, 21, 21, 21 | | 22, 22, 22, 22, 22, 22, 22, 22, 22, 2, 5, 5 |
| 22 | 22, 22, 22, 22, 22, 22, 22, 22 | | |

FIG. 11C

| | ARI clustering of top 10 indels | ARI clustering of indels ranked by frequency |
|---|---|---|
| HEK293 (3 replicates) | 0.870 ± 0.024 | 0.897 ± 0.054 |
| K562 (3 replicates) | 0.865 ± 0.057 | 0.893 ± 0.044 |

FIG. 11D

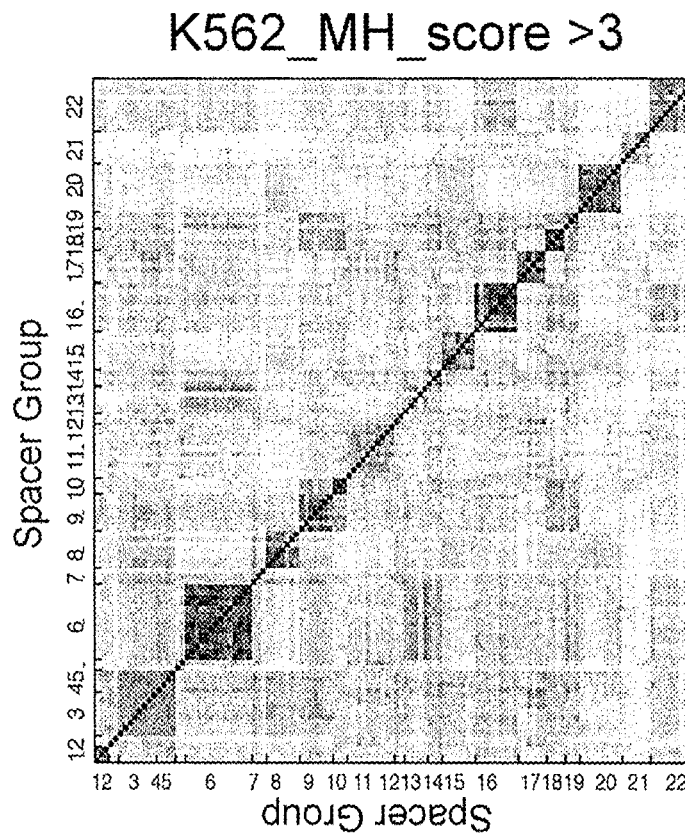
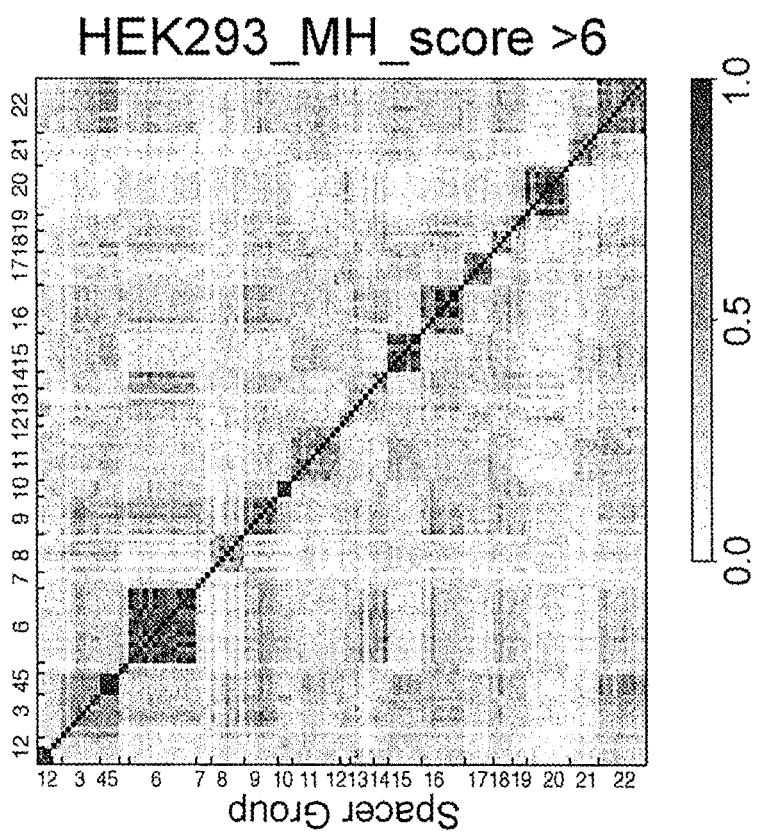
FIG. 12B
FIG. 12A cont.

| | All MH_score deletions | Removed MH_score > 6 deletions | Removed MH_score > 4 deletions | Removed MH_score > 3 deletions |
|---|---|---|---|---|
| HEK293 (3 replicates) | 0.870 ± 0.024 | 0.704 ± 0.039 | 0.674 ± 0.012 | 0.661 ± 0.041 |
| K562 (3 replicates) | 0.865 ± 0.057 | 0.705 ± 0.057 | 0.723 ± 0.018 | 0.743 ± 0.021 |

FIG. 12C

| MH_score cutoff | Microhomology allowed (IUPAC symbols*) |
|---|---|
| 6 | N, NN, WWW |
| 4 | N, WW |
| 3 | N |

*IUPAC symbols

N: aNy (A, T, C, G)
W: Weak (A, T)
S: Strong (C, G)

FIG. 12D

METHODS FOR USING DNA REPAIR FOR CELL ENGINEERING

CROSS-REFERENCE TO RELATED APPLICATIONS

This application is a national stage entry of International Application No. PCT/US2017/018679, filed 21 Feb. 2017, which claims the benefit of U.S. Provisional Patent Application Ser. No. 62/344,876, filed 2 Jun. 2016, and U.S. Provisional Patent Application Ser. No. 62/298,129, filed 22 Feb. 2016, the contents of which are herein incorporated by reference in their entirety.

TECHNICAL FIELD

The present invention relates to DNA repair methods for modulating DNA repair outcomes, such as in gene editing applications.

BACKGROUND OF THE INVENTION

The CRISPR system has been widely adopted as a versatile tool for genome engineering in human cells (see, e.g., Jinek et al., "A programmable dual-RNA-guided DNA endonuclease in adaptive bacterial immunity," Science (2012) 337:816-821; and Jinek et al., "RNA-programmed genome editing in human cells" Elife (2013) 2:e00471). CRISPR-associated proteins, such as Cas9, are programmable and can be targeted to create chromosomal double-strand breaks (DSBs) at sites in genomic DNA by a single-guide RNA (sgRNA) molecule designed to complement the sequence of interest (Jinek et al., "A programmable dual-RNA-guided DNA endonuclease in adaptive bacterial immunity," Science (2012) 337:816-821). Following DSB generation, DNA repair machinery is recruited to promote DNA transactions at the break site and the outcome of this process dictates the functionality of the repair. In the absence of a donor template, this process has been thought to result in random DNA repair outcomes. Despite the critical role that DNA repair outcomes play in defining the nature of a genome edit, the specific insertion/deletion (indel) mutations that result from Cas-initiated DSB repair have not been well characterized to date. There remains an outstanding need, therefore, for detailed characterization of DNA repair outcomes at Cas-initiated DSBs to anticipate functional outcomes.

Gene inactivation can be achieved through repair of Cas/sgRNA-dependent DSBs at target sites by mutation-prone end-joining pathways (e.g., classical non-homologous end-joining (c-NHEJ), alternative end-joining (alt-EJ)/microhomology mediated end-joining (MMEJ)) that produce mainly indels at the break site (Mandal et al., "Efficient ablation of genes in human hematopoietic stem and effector cells using CRISPR/Cas9" Cell Stem Cell (2014) 15:643-652; Hou et al., "Genome editing of CXCR4 by CRISPR/cas9 confers cells resistant to HIV-1 infection" Sci Rep (2015) 5:15577; Canver et al., "BCL11A enhancer dissection by Cas9-mediated in situ saturating mutagenesis" Nature (2015) 527:192-197). Repair through the alt-EJ/MMEJ pathway frequently results in large deletions between microhomology sites (Deriano and Roth, "Modernizing the nonhomologous end joining repertoire: alternative and classical NHEJ share the stage" Annual Review of Genetics (2013) 47:433-455).

Biochemical and cell-based studies monitoring re-ligation of linearized plasmids suggest that c-NHEJ is an accurate process for blunt and cohesive ends (see, e.g., Boulton and Jackson, "*Saccharomyces cerevisiae* Ku70 potentiates illegitimate DNA double-strand break repair and serves as a barrier to error-prone DNA repair pathways" (1996) EMBO J. 15:5093-5103; Feldmann et al., "DNA double-strand break repair in cell-free extracts from Ku80-deficient cells: implications for Ku serving as an alignment factor in non-homologous DNA end joining" Nucleic Acids Res (2000) 28:2585-2596; Smith et al., "Impact of DNA ligase IV on the fidelity of end joining in human cells" Nucleic Acids Res (2003) 31:2157-2167).

However, the repair of lymphocyte-specific programmed DSBs and DSBs generated from extrinsic agents such as radiomimetic drugs and ionizing radiation by c-NHEJ has been thought to result in random outcomes (Li et al., "Multiple end joining mechanisms repair a chromosomal DNA break in fission yeast" DNA Repair (Amst.) (2012) 11:120-130; Dolan et al., "Integrated Stochastic Model of DNA Damage Repair by Non-homologous End Joining and p53/p21-Mediated Early Senescence Signalling" PLoS Comput. Biol. (2015) 11:e1004246; Boboila et al., "Classical and alternative end-joining pathways for repair of lymphocyte-specific and general DNA double-strand breaks" Adv. Immunol. (2012) 116:1-49). A study performed in yeast comparing the repair of DSBs with "ragged" ends induced by IR and "clean" ends induced by endonuclease cleavage revealed different processing requirements for break repair (Barlow et al., "Differential regulation of the cellular response to DNA double-strand breaks in G1" (2008) Mol. Cell 30:73-85).

Repair outcomes resulting from end joining pathways have been analyzed in detail for certain specialized nucleases, including RAG-induced V(D)J recombination (Purugganan et al., "Ku80 is required for addition of N nucleotides to V(D)J recombination junctions by terminal deoxynucleotidyl transferase" Nucleic Acids Res (2001) 29:1638-1646; Corneo et al., "Rag mutations reveal robust alternative end joining" Nature (2007) 449: 483-486), repair at I-SceI meganuclease sites (Rouet et al., "Introduction of double-strand breaks into the genome of mouse cells by expression of a rare-cutting endonuclease" Mol. Cell. Biol. (1994) 14:8096-8106; Lloyd et al., "Single molecule PCR reveals similar patterns of non-homologous DSB repair in tobacco and *Arabidopsis*" PLoS One (2012) 7:e32255.2012; Bindra et al., "Development of an assay to measure mutagenic non-homologous end joining repair activity in mammalian cells" (2013) Nucleic Acids Res 41: e115-e115; Soong et al., "Development of a novel method to create double-strand break repair fingerprints using next-generation sequencing" DNA Repair (2015) 26:44-53), and repair of DSBs induced by HO endonuclease (Moore and Haber, "Cell cycle and genetic requirements of two pathways of nonhomologous end joining repair of double-strand breaks in *Saccharomyces cerevisiae*" Mol. Cell. Biol. (1996) 16:2164-2173; Li et al., "Multiple end joining mechanisms repair a chromosomal DNA break in fission yeast" DNA Repair (Amst.) (2012) 11:120-130). The Moore and Haber study describes a characteristic "CA" insertion after repair of an HO endonuclease-induced DSB in *S. cerevisiae*, whereas Li et al. describe a characteristic insertion of an "A" nucleotide after repair of an HO endonuclease-induced DSB in *S. pombe*. Both studies identify genetic dependencies of these signature repair events. The range of sequences for which these DSB repair outcomes has been measured is, however, limited.

In contrast, Cas9, which can be easily targeted to any site in a genome that lies adjacent to a protospacer-adjacent motif (PAM) (e.g. NGG for *Streptococcus pyogenes* Cas9), enables large-scale analysis of DNA repair outcomes throughout the genome. Previous studies analyzing DNA repair outcomes following Cas9 activity (Tan et al., "Off-target assessment of CRISPR-Cas9 guiding RNAs in human iPS and mouse ES cells" Genesis (2015) 53:225-236) identified a small number of signature deletions in clonally isolated lines that were attributed to MMEJ activity (Koike-Yusa et al., "Genome-wide recessive genetic screening in mammalian cells with a lentiviral CRISPR-guide RNA library" Nat. Biotechnol. (2014) 32:267-273).

There are several different CRISPR-Cas systems and the nomenclature and classification of these have changed as the systems have been characterized. In particular, CRISPR-Cas systems have recently been reclassified into two classes, containing five types and sixteen subtypes. Makarova et al. (Nature Reviews Microbiology (2015) 13:1-15). This classification is based upon identifying all cas genes in a CRISPR-Cas locus and then determining the signature genes in each CRISPR-Cas locus, thereby determining whether the CRISPR-Cas systems should be placed in either Class 1 or Class 2 based upon the genes encoding the effector module, i.e., the proteins involved in the interference stage. These CRISPR-Cas systems are described in greater detail below.

The use of such CRISPR-Cas systems for predicting the outcome of genome editing would be highly advantageous.

SUMMARY

The DNA repair patterns at over 200 sites in the human genome are characterized and described in detail herein. The DNA repair profiles of these sites demonstrate that the distribution of indels resulting from DNA repair at Cas9-mediated DSBs is nonrandom and consistent across experimental replicates, cell lines and reagent delivery methods. Furthermore, these patterns are dependent on the sequence of the target, i.e., they are determined by the protospacer sequence rather than the genomic context, and can be modulated by inhibiting specific components of the DNA repair machinery. Additionally, it has been found that the PAM-distal nucleotide in the protospacer sequence, nucleotide 17 at Cas9 targets (Cas9 cleaves between positions 17 and 18), is highly predictive of which nucleotide is most frequently inserted.

Thus, DNA repair profiling in cell lines can be used to anticipate the repair outcomes at a given target site in cells. The invention described herein provides methods for using and modulating end-joining DNA-repair machinery to generate precise edits, as well as methods for predictably inserting a single base pair at particular positions in protospacer regions.

In one embodiment, a method is provided for restoring genetic function. The method comprises: (1) identifying a genetic mutation that reduces the function of a gene product; (2) engineering one or more site-directed nucleases to cut within the vicinity of the identified genetic mutation; (3) introducing the one or more nucleases into a cell; (4) cleaving DNA within the cell with the one or more nucleases; (5) profiling DNA repair outcomes of nuclease-dependent breaks; (6) selecting one or more nucleases that produce the desired outcomes; and (7) engineering a cell with the selected one or more nucleases, to restore genetic function.

In an additional embodiment, a method for altering genetic function is provided. The method comprises: (1) identifying a genetic region of interest where alteration changes the function of a gene product; (2) engineering one or more site-directed nucleases to cut within the vicinity of the identified genetic region; (3) introducing the one or more nucleases into a cell; (4) cleaving DNA within the cell with the one or more nucleases; (5) profiling DNA repair outcomes of nuclease-dependent breaks; (6) selecting one or more nucleases that produce the desired outcomes; (7) engineering a cell with the selected one or more nucleases, to alter genetic function.

In both of the embodiments above, the site-directed nuclease can be a catalytically active Cas protein that is complexed to a guide polynucleotide. In certain embodiments, the Cas protein is a Cas9 protein, such as a Cas9 protein from *Streptococcus pyogenes* or an orthologous Cas9 protein.

In another embodiment, a method of modulating DNA repair outcomes is provided. The method comprises: (1) contacting a selected target nucleic acid comprising a region to be modified with (a) an agent that suppresses non-homologous end-joining (NHEJ), thereby favoring alternative end-joining (alt-EJ)/microhomology mediated end-joining (MMEJ); and (b) a DNA binding molecule that targets the selected target nucleic acid; and (2) producing one or more double-strand breaks in the targeted region using a programmable endonuclease, thereby triggering DNA repair pathways to repair the breaks, whereby repair of the cleaved target nucleic acid proceeds substantially by MMEJ and is done in the absence of a donor polynucleotide, thereby modulating the DNA repair outcome.

In additional embodiments, the invention is directed to a method of modulating DNA repair outcomes. The method comprises contacting a selected target nucleic acid comprising a region to be modified with (a) an agent that suppresses non-homologous end-joining (NHEJ), thereby favoring alternative end-joining (alt-EJ)/microhomology mediated end-joining (MMEJ); and (b) one or more complexes comprising: (i) a catalytically active Cas protein and (ii) a first guide polynucleotide that comprises a spacer adapted to bind to and cleave the selected target nucleic acid at a site adjacent the region to be modified, whereby repair of the cleaved target nucleic acid proceeds by MMEJ without a donor polynucleotide, thereby modulating the DNA repair outcome.

In another embodiment, the invention is directed to a method of modulating DNA repair outcomes comprising: (1) contacting a selected target nucleic acid comprising a region to be modified with (a) an agent that suppresses alternative end joining (alt-EJ)/microhomology mediated end-joining (MMEJ), thereby favoring non-homologous end joining (NHEJ); and (b) a DNA binding molecule that targets the selected target nucleic acid; and (2) producing one or more double-strand breaks in the targeted region using a programmable endonuclease, thereby triggering DNA repair pathways to repair the breaks, whereby repair of the cleaved target nucleic acid proceeds substantially by NHEJ and is done in the absence of a donor polynucleotide, thereby modulating the DNA repair outcome.

In additional embodiments, the invention is directed to a method of modulating DNA repair outcomes. The method comprises contacting a selected target nucleic acid comprising a region to be modified with (a) an agent that suppresses alternative end-joining (alt-EJ)/microhomology mediated end-joining (MMEJ), thereby favoring non-homologous end-joining (NHEJ); and (b) one or more complexes comprising: (i) a catalytically active Cas protein and (ii) a first guide polynucleotide that comprises a spacer adapted to bind to and cleave the selected target nucleic acid at a site adjacent the region to be modified, whereby repair of the cleaved target nucleic acid proceeds by c-NHEJ without a donor polynucleotide, thereby modulating the DNA repair outcome.

In another embodiment, the invention is directed to a method of modulating DNA repair outcomes. The method comprises: (1) contacting a selected target nucleic acid comprising a region to be modified with (a) a first agent that suppresses alternative end-joining (alt-EJ)/microhomology mediated end-joining (MMEJ), and a second agent that suppresses non-homologous end-joining (NHEJ), thereby favoring homology directed repair (HDR), and (b) a DNA binding molecule that targets the selected target nucleic acid; (2) producing one or more double-strand breaks in the targeted region using a programmable endonuclease; and (3) inserting at least a portion of a donor polynucleotide into said target nucleic acid at the double-strand break by an HDR DNA repair pathway, thereby modulating the DNA repair outcome.

In certain embodiments of the methods above, the agent(s) in (1), such as an inhibitor of c-NHEJ and/or MMEJ, including without limitation, peptide inhibitors, small molecules, compounds, etc., prevent activity of certain components of the NHEJ and/or MMEJ pathways, and do not interact directly with the region to be modified. Alternatively, the agent can be delivered directly to the region to be modified.

In additional embodiments, the invention is directed to a method to discover homology directed repair (HDR) "hotspots," i.e., regions that demonstrate a propensity to incorporate nucleotide information from a donor template. The method comprises: (1) identifying a region of interest to either reduce or restore the function of a gene product or a region that is a "safe harbor" to insert novel genetic information without disrupting neighboring gene function; (2) engineering one or more site-directed nucleases to cut within the vicinity of the identified genetic mutation; (3) introducing the one or more nucleases into a cell; (4) cleaving DNA within the cell with the one or more nucleases; (5) profiling DNA repair outcomes of nuclease-dependent breaks; (6) determining the relative contribution of c-NHEJ and MMEJ to the repair pattern; and (7) predicting HDR hotspots based on the contributions in step (6).

In yet a further embodiment, the invention is directed to a method to enhance HDR efficiency through modulating end-joining pathways. The method comprises: (1) identifying a region of interest to either reduce or restore the function of a gene product or a region that is a "safe harbor" to insert novel genetic information without disrupting neighboring gene function. This region has a particular ratio of c-NHEJ versus MMEJ events previously discovered through DNA repair profiling; (2) engineering one or more site-directed nucleases to cut within the vicinity of the identified genetic region; (3) introducing the one or more nucleases into a cell with donor templates; (4) cleaving DNA within the cell with the one or more nucleases to initiate the incorporation of nucleotide information from a donor template (HDR); (5) promoting HDR activity with an agent that suppresses either or both MMEJ and NHEJ, thereby favoring HDR; (6) profiling DNA repair outcomes of nuclease-dependent breaks to confirm HDR events; (7) selecting one or more nucleases that produce the desired outcomes; and (8) engineering a cell with the selected one or more nucleases, to alter existing genetic function or to introduce new genetic function.

In certain embodiments, the methods are performed in a cell, such as a eukaryotic cell.

In additional embodiments, the methods can be performed using cells with certain genetic mutations as a screen for sensitivity to certain compounds that modulate choice between DNA repair pathways.

In additional embodiments, the methods can be performed using cells to reveal certain genetic liabilities in a screen for sensitivity to certain compounds that modulate choice between DNA repair pathways.

In additional embodiments, the invention is directed to a method for predictably inserting a particular single nucleotide at a target site following Cas-mediated cleavage. The method comprises: (1) selecting a gene comprising a target region to be modified; (2) designing a guide polynucleotide, such as sgRNA, to target a selected protospacer in the target region; (3) producing a double-strand break in the target region using a programmable endonuclease, wherein the protospacer in the target region is cleaved at nucleotide position 17; and (4) inserting a particular nucleotide at the cleavage site.

In additional embodiments of all of the above-described methods, the Cas protein is a Cas9 protein, such as a Cas9 protein from *Streptococcus pyogenes* or an orthologous Cas9 protein.

In any of the embodiments described above, the guide polynucleotide can be a sgRNA, or a guide designed for use with Cas proteins other than Cas9. In other embodiments, a dual-guide system can be used. Such guides are discussed in detail below.

These aspects and other embodiments of the methods described herein will readily occur to those of ordinary skill in the art in view of the disclosure herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SEQUENCE LISTING

The sequences referred to herein are listed in the Sequence Listing submitted as an ASCII text file entitled CBI021-10 ST25.txt, which was created on 24 Jul. 2018 and 119,850 bytes in size. The Sequence Listing entitled CBI021-10 ST25.txt is incorporated herein by reference in its entirety.

BRIEF DESCRIPTION OF THE DRAWINGS

FIGS. 2A-2C show that DNA repair profiles are unique to each spacer sequence.

FIGS. 3A-3F show the results of an experiment using multiple target single spacer (MTSS) sequences and demonstrate that DNA repair outcomes at Cas9-mediated DSBs are sequence-dependent.

FIGS. 4A-4I show that the distribution of DNA repair outcomes after Cas9 cleavage changes over time.

FIGS. 7A-7F show that DNA repair outcome profiling in cell lines is predictive for human primary cells.

FIGS. 11A-11D show that DNA repair outcomes are more similar within spacer groups than between spacer groups.

FIGS. 12A-12D show that similarity of DNA repair outcomes within spacer groups is not fully explained by microhomology.

DETAILED DESCRIPTION OF THE INVENTION

Figure 1A:
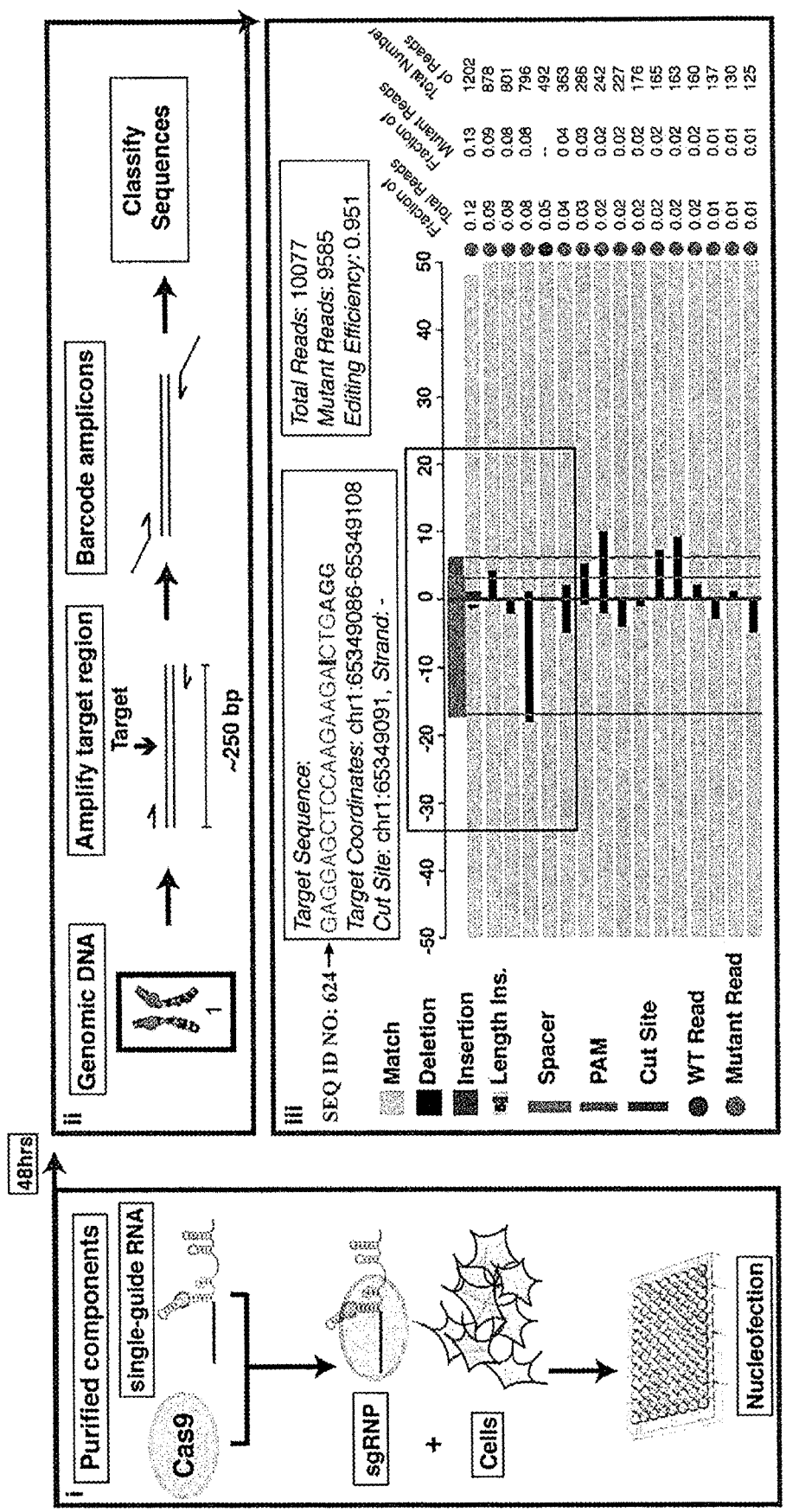
FIGS. 1A-1C depict the profiling of DNA repair outcomes after Cas9 cleavage.

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a sgRNA/Cas9 complex" includes one or more such complexes, reference to "a mutation" includes one or more mutations, and the like. It is also to be understood that when reference is made to an embodiment using a sgRNA to target Cas9 or dCas9 to a target site, one skilled in the art can use an alternative embodiment of the invention based on the use of a dual-guide RNA (e.g. crRNA/tracrRNA) in place of the sgRNA.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, preferred materials and methods are described herein.

In view of the teachings of the present specification, one of ordinary skill in the art can apply conventional techniques of immunology, biochemistry, chemistry, molecular biology, microbiology, cell biology, genomics, and recombinant polynucleotides, as taught, for example, by the following standard texts: Antibodies: A Laboratory Manual, Second edition, E. A. Greenfield, 2014, Cold Spring Harbor Laboratory Press, ISBN 978-1-936113-81-1; Culture of Animal Cells: A Manual of Basic Technique and Specialized Applications, 6th Edition, R. I. Freshney, 2010, Wiley-Blackwell, ISBN 978-0-470-52812-9; Transgenic Animal Technology, Third Edition: A Laboratory Handbook, 2014, C. A. Pinkert, Elsevier, ISBN 978-0124104907; The Laboratory Mouse, Second Edition, 2012, H. Hedrich, Academic Press, ISBN 978-0123820082; Manipulating the Mouse Embryo: A Laboratory Manual, 2013, R. Behringer, et al., Cold Spring Harbor Laboratory Press, ISBN 978-1936113019; PCR 2: A Practical Approach, 1995, M. J. McPherson, et al., IRL Press, ISBN 978-0199634248; Methods in Molecular Biology (Series), J. M. Walker, ISSN 1064-3745, Humana Press; RNA: A Laboratory Manual, 2010, D. C. Rio, et al., Cold Spring Harbor Laboratory Press, ISBN 978-0879698911; Methods in Enzymology (Series), Academic Press; Molecular Cloning: A Laboratory Manual (Fourth Edition), 2012, M. R. Green, et al., Cold Spring Harbor Laboratory Press, ISBN 978-1605500560; Bioconjugate Techniques, Third Edition, 2013, G. T. Hermanson, Academic Press, ISBN 978-0123822390; Methods in Plant Biochemistry and Molecular Biology, 1997, W. V. Dashek, CRC Press, ISBN 978-0849394805; Plant Cell Culture Protocols (Methods in Molecular Biology), 2012, V. M. Loyola-Vargas, et al., Humana Press, ISBN 978-1617798177; Plant Transformation Technologies, 2011, C. N. Stewart, et al., Wiley-Blackwell, ISBN 978-0813821955; Recombinant Proteins from Plants (Methods in Biotechnology), 2010, C. Cunningham, et al., Humana Press, ISBN 978-1617370212; Plant Genomics: Methods and Protocols (Methods in Molecular Biology), 2009, D. J. Somers, et al., Humana Press, ISBN 978-1588299970; Plant Biotechnology: Methods in Tissue Culture and Gene Transfer, 2008, R. Keshavachandran, et al., Orient Blackswan, ISBN 978-8173716164.

Clustered Regularly Interspaced Short Palindromic Repeats (CRISPR) and CRISPR-associated proteins (Cas) are found in prokaryotic immune systems. These systems provide resistance against exogenous genetic elements, such as viruses and plasmids, by targeting their nucleic acids for degradation, in a sequence-specific manner. There are three main stages in CRISPR-Cas immune system: (1) acquisition, (2) expression, and (3) interference. Acquisition involves cleaving the genome of invading viruses and plasmids and integrating segments (termed protospacers) of this genomic DNA into the CRISPR locus of the host organism. The segments that are integrated into the host genome are known as spacers, which mediate protection from subsequent attack by the same (or sufficiently related) virus or plasmid. Expression involves transcription of the CRISPR locus and subsequent enzymatic processing to produce short mature CRISPR RNAs, each containing a single spacer sequence. Interference is induced after the CRISPR RNAs associate with Cas proteins to form effector complexes, which are then targeted to complementary protospacers in foreign genetic elements to induce nucleic acid degradation.

A CRISPR locus includes a number of short repeating sequences referred to as "repeats." Repeats can form hairpin structures and/or repeats can be unstructured single-stranded sequences. The repeats occur in clusters. Repeats frequently diverge between species. Repeats are regularly interspaced with unique intervening sequences, referred to as "spacers," resulting in a repeat-spacer-repeat locus architecture. Spacers are identical to or are homologous with known foreign invader sequences. A spacer-repeat unit encodes a crisprRNA (crRNA). A crRNA refers to the mature form of the spacer-repeat unit. A crRNA contains a spacer sequence that is involved in targeting a target nucleic acid (e.g., possibly as a surveillance mechanism against foreign nucleic acid). A spacer sequence is typically located towards the 5' end of a crRNA (e.g. in a Type I (e.g. CASCADE) system; for a description of the CASCADE complex see, e.g., Jore, M. M. et al., "Structural basis for CRISPR RNA-guided DNA recognition by CASCADE," Nature Structural & Molecular Biology (2011) 18:529-536) or at the 3' end of the spacer of a crRNA in a Type II system (e.g., in a Type II CRISPR system, described more fully below), directly adjacent to the first stem.

Thus, crRNA has a region of complementarity to a potential DNA target sequence and a second region that forms base-pair hydrogen bonds with the tracrRNA to form a secondary structure, typically to form at least a stem structure. The tracrRNA and a crRNA interact through a number of base-pair hydrogen bonds to form secondary RNA structures. Complex formation between tracrRNA/crRNA and a Cas9 protein (described more fully below) results in conformational change of the Cas protein that facilitates binding to DNA, endonuclease activities of the Cas9 protein, and crRNA-guided site-specific DNA cleavage by the endonuclease. For a Cas9 protein/tracrRNA/crRNA complex to cleave a DNA target sequence, the DNA target sequence is adjacent to a cognate protospacer adjacent motif (PAM).

A CRISPR locus comprises polynucleotide sequences encoding for CRISPR associated genes (cas) genes. Cas genes are involved in the biogenesis and/or the interference stages of crRNA function. Cas genes display extreme sequence (e.g., primary sequence) divergence between species and homologues. For example, cas1 homologues can comprise less than 10% primary sequence identity between homologues. Some cas genes comprise homologous secondary and/or tertiary structures. For example, despite extreme sequence divergence, many members of the Cas6 family of CRISPR proteins comprise an N-terminal ferredoxin-like fold. Cas genes are named according to the organism from which they are derived. For example, cas genes in *Staphylococcus epidermidis* can be referred to as Csm-type, cas genes in *Streptococcus thermophilus* can be referred to as Csn-type, and cas genes in *Pyrococcus furiosus* can be referred to as Cmr-type.

The integration stage of a CRISPR system refers to the ability of the CRISPR locus to integrate new spacers into the crRNA array upon being infected by a foreign invader. Acquisition of the foreign invader spacers can help confer immunity to subsequent attacks by the same foreign invader. Integration typically occurs at the leader end of the CRISPR locus. Cas proteins (e.g., Cas1 and Cas2) are involved in integration of new spacer sequences. Integration proceeds similarly for some types of CRISPR systems (e.g., Type I-III).

Mature crRNAs are processed from a longer polycistronic CRISPR locus transcript (i.e., pre-crRNA array). A pre-crRNA array comprises a plurality of crRNAs. The repeats in the pre-crRNA array are recognized by cas genes. Cas genes bind to the repeats and cleave the repeats. This action can liberate the plurality of crRNAs. crRNAs can be subjected to further events to produce the mature crRNA form such as trimming (e.g., with an exonuclease). A crRNA may comprise all, some, or none of the CRISPR repeat sequence.

Interference refers to the stage in the CRISPR system that is functionally responsible for combating infection by a foreign invader. CRISPR interference follows a similar mechanism to RNA interference (RNAi: e.g., wherein a target RNA is targeted (e.g., hybridized) by a short interfering RNA (siRNA)), which results in target RNA degradation and/or destabilization. CRISPR systems perform interference of a target nucleic acid by coupling crRNAs and Cas genes, thereby forming CRISPR ribonucleoproteins (crRNPs). crRNA of the crRNP guides the crRNP to foreign invader nucleic acid, (e.g., by recognizing the foreign invader nucleic acid through hybridization). Hybridized target foreign invader nucleic acid-crRNA units are subjected to cleavage by Cas proteins. Target nucleic acid interference typically requires a protospacer adjacent motif (PAM) in a target nucleic acid.

By a "CRISPR-Cas system" as used herein, is meant any of the various CRISPR-Cas classes, types and subtypes. CRISPR systems are currently classified into two classes, Class 1 or Class 2, based upon the genes encoding the effector module, i.e., the proteins involved in the interference stage, and include five types (Types I-V) and sixteen subtypes (Makarova et al., Nature Reviews Microbiology (2015) 13:1-15).

Class 0.1 systems have a multi-subunit crRNA-effector complex, whereas Class 2 systems have a single protein, such as Cas9, Cpf1, C2c1, C2c2, C2c3, or a crRNA-effector complex. Class 1 systems comprise Type I, Type III and Type IV systems. Class 2 systems comprise Type II and Type V systems.

Type I systems have a Cas3 protein that has helicase activity and cleavage activity. Type I systems are further divided into seven subtypes (I-A to I-F and I-U). Each type I subtype has a defined combination of signature genes and distinct features of operon organization. For example, subtypes I-A and I-B have the cas genes organized in two or more operons, whereas subtypes I-C through I-F appear to have the cas genes encoded by a single operon. Type I systems have a multiprotein crRNA-effector complex that is involved in the processing and interference stages of the CRISPR-Cas immune system. In *Escherichia coli*, this multiprotein complex is known as CRISPR-associated complex for antiviral defense (CASCADE). Subtype I-A comprises csa5 which encodes a small subunit protein and a cas8 gene that is split into two, encoding degraded large and small subunits and also has a split cas3 gene. An example of an organism with a subtype I-A CRISPR-Cas system is *Archaeoglobus fulgidus*.

Subtype I-B has a cas1-cas2-cas3-cas4-cas5-cas6-cas7-cas8 gene arrangement and lacks a csa5 gene. An example of an organism with subtype I-B is *Clostridium kluyveri*. Subtype I-C does not have a cas6 gene. An example of an organism with subtype I-C is *Bacillus halodurans*. Subtype I-D has a Cas10d instead of a Cas8. An example of an organism with subtype I-D is *Cyanothece* sp. Subtype I-E does not have a cas4. An example of an organism with subtype I-E is *Escherichia coli*. Subtype I-F does not have a cas4 but has a cas2 fused to a cas3 gene. An example of an organism with subtype I-F is *Yersinia pseudotuberculosis*. An example of an organism with subtype I-U is Geobacter sulfurreducens.

All type III systems possess a cas10 gene, which encodes a multidomain protein containing a Palm domain (a variant of the RNA recognition motif (RRM)) that is homologous to the core domain of numerous nucleic acid polymerases and cyclases and that is the largest subunit of type III crRNA-effector complexes. All type III loci also encode the small subunit protein, one Cas5 protein and typically several Cas7 proteins. Type III can be further divided into four subtypes, III-A through III-D. Sub-type III-A has a csm2 gene encoding a small subunit and also has cas1, cas2 and cas6 genes. An example of an organism with subtype III-A is *Staphylococcus epidermidis*. Subtype III-B has a cmr5 gene encoding a small subunit and also typically lacks cas1, cas2 and cas6 genes. An example of an organism with subtype III-B is *Pyrococcus furiosus*. Subtype III-C has a Cas10 protein with an inactive cyclase-like domain and lacks a cas1 and cas2 gene. An example of an organism with subtype III-C is *Methanothermobacter thermautotrophicus*. Subtype III-D has a Cas10 protein that lacks the HD domain and a cas1 and cas2 gene, and has a cas5-like gene known as csx10. An example of an organism with subtype III-D is *Roseiflexus* sp.

Type IV systems encode a minimal multisubunit crRNA-effector complex comprising a partially degraded large subunit, Csf1, Cas5, Cas7, and in some cases, a putative small subunit. Type IV systems lack cas1 and cas2 genes. Type IV systems do not have subtypes, but there are two distinct variants. One Type IV variant has a DinG family helicase, whereas a second type IV variant lacks a DinG family helicase, but has a gene encoding a small α-helical protein. An example of an organism with a Type IV system is Acidithiobacillus *ferrooxidans*.

Type II systems include cas1, cas2 and cas9 genes. There are two strands of RNA in Type II systems, a CRISPR RNA (crRNA) and a transactivating CRISPR RNA (tracrRNA). The tracrRNA hybridizes to a complementary region of pre-crRNA causing maturation of the pre-crRNA to crRNA. The duplex formed by the tracrRNA and crRNA is recognized by, and associates with a multidomain protein, Cas9, encoded by the cas9 gene, which combines the functions of the crRNA-effector complex with target DNA cleavage. Cas9 is directed to a target nucleic acid by a sequence of the crRNA that is complementary to, and hybridizes with, a sequence in the target nucleic acid.

It has been demonstrated that these minimal components of the RNA-based immune system can be reprogrammed to target DNA in a site-specific manner by using a single protein and two RNA guide sequences or a single RNA molecule. Type II systems are further divided into three subtypes, subtypes II-A, II-B and II-C. Subtype II-A contains an additional gene, csn2. An example of an organism with a subtype II-A system is *Streptococcus thermophilus*. Subtype II-B lacks csn2, but has cas4. An example of an organism with a subtype II-B system is *Legionella pneumophila*. Subtype II-C is the most common Type II system found in bacteria and has only three proteins, Cas1, Cas2 and Cas9. An example of an organism with a subtype II-C system is *Neisseria lactamica*.

As explained above, crRNA biogenesis in a Type II CRISPR system comprises a tracrRNA. The tracrRNA is typically modified by endogenous RNaseIII. The tracrRNA hybridizes to a crRNA repeat in the pre-crRNA array. Endogenous RNaseIII is recruited to cleave the pre-crRNA. Cleaved crRNAs are subjected to exoribonuclease trimming to produce the mature crRNA form (e.g., 5' trimming). The tracrRNA typically remains hybridized to the crRNA. The tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid activates a wild-type, cognate Cas9 for target nucleic acid cleavage. Target nucleic acid in a Type II CRISPR system comprises a PAM. In some embodiments, a PAM is essential to facilitate binding of a site-directed polypeptide (e.g., Cas9) to a target nucleic acid.

Cas9 is an exemplary Type II CRISPR Cas protein and serves as an endonuclease. The mature crRNA that is base-paired to trans-activating crRNA (tracrRNA) forms a two-part RNA structure, also called a "dual-guide," which directs the Cas9 to introduce double-strand breaks (DSBs) in target DNA. Cas9 can be programmed by the tracrRNA/crRNA to cleave, site-specifically, target DNA using two distinct endonuclease domains (HNH and RuvC/RNase H-like domains) (see U.S. Published Patent Application No. 2014/0068797 to Doudna et al., published 6 Mar. 2014 and incorporated herein by reference in its entirety; see also Jinek et al., "A programmable dual-RNA-guided DNA endonuclease in adaptive bacterial immunity," Science (2012) 337:816-821), one for each strand of the DNA's double helix. RuvC and HNH together produce double-strand breaks, and separately can produce single-stranded breaks.

At sites complementary to the crRNA-guide (spacer) sequence, the Cas9 HNH nuclease domain cleaves the complementary strand and the Cas9 RuvC-like domain cleaves the non-complementary strand. Dual-crRNA/tracrRNA molecules have been engineered into single-chain crRNAItracrRNA molecules. These single-chain crRNA/tracrRNA direct target sequence-specific Cas9 double-strand DNA cleavage.

Typically, each CRISPR-Cas9 system comprises a tracrRNA and a crRNA. However, this requirement can be bypassed by using an engineered sgRNA, described more fully below, containing a designed hairpin that mimics the tracrRNA-crRNA complex (Jinek et al., "A programmable dual-RNA-guided DNA endonuclease in adaptive bacterial immunity," Science (2012) 337:816-821). The part of the sgRNA sequence that is complementary to the target sequence is known as a protospacer.

Base-pairing between the sgRNA and target DNA causes double-strand breaks (DSBs) due to the endonuclease activity of Cas9. Binding specificity is determined by both sgRNA-DNA base pairing and a short DNA motif (protospacer adjacent motif (PAM) sequence: NGG) juxtaposed to the DNA complementary region (Jinek et al., "A programmable dual-RNA-guided DNA endonuclease in adaptive bacterial immunity," Science (2012) 337:816-821). Thus, a Type II CRISPR system only requires a minimal set of two molecules—the Cas9 protein and the sgRNA.

A large number of Cas9 orthologs are known in the art as well as their associated tracrRNA and crRNA components (see, e.g., "Supplementary Table S2. List of bacterial strains with identified Cas9 orthologs," Fonfara, Ines, et al., "Phylogeny of Cas9 Determines Functional Exchangeability of Dual-RNA and Cas9 among Orthologous Type II CRISPR/Cas Systems," Nucleic Acids Research (2014) 42:2577-2590, including all Supplemental Data; Chylinski K., et al., "Classification and evolution of type II CRISPR-Cas systems," Nucleic Acids Research (2014) 42:6091-6105, including all Supplemental Data.); Esvelt, K. M., et al., "Orthogonal Cas9 proteins for RNA-guided gene regulation and editing," Nature Methods (2013) 10:1116-1121). A number of orthogonal Cas9 proteins have been identified including Cas9 proteins from *Neisseria meningitidis, Streptococcus thermophilus* and *Staphylococcus aureus*.

As used herein, "a Cas protein" such as "a Cas9 protein," "a Cas3 protein," "a Cpf1 protein," etc. refers to a Cas protein derived from any species, subspecies or strain of bacteria that encodes the Cas protein of interest, as well as variants and orthologs of the particular Cas protein in question. The Cas proteins can either be directly isolated and purified from bacteria, or synthetically or recombinantly produced, or can be delivered using a construct encoding the protein, including without limitation, naked DNA, plasmid DNA, a viral vector and mRNA for Cas expression. Non-limiting examples of Cas proteins include Cas1, Cas1B, Cas2, Cas3, Cas4, Cas5, Cas6, Cas7, Cas8, Cas9 (also known as Csn1 and Csx12), Cas10, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, C2C1, C2C2, C2C3, homologues thereof, or modified versions thereof. These enzymes are known; for example, the amino acid sequence of *Streptococcus pyogenes* Cas9 protein may be found in the SwissProt database (available at the website uniprot.org) under accession number Q99ZW2. In some embodiments, the CRISPR protein is codon-optimized for expression in a cell of interest. In some embodiments, the CRISPR protein directs cleavage of one or two strands at the location of the target sequence. In some embodiments, the CRISPR protein lacks DNA strand cleavage activity, or acts as a nickcase. The choice of Cas protein will depend upon the particular conditions of the methods used as described herein.

Variants and modifications of Cas9 proteins are known in the art. U.S. Patent Publication 2014/0273226 to Wu, published Sep. 18, 2014, incorporated herein by reference in its entirety, discusses the *Streptococcus pyogenes* Cas9 gene, Cas9 protein, and variants of the Cas9 protein including host-specific codon-optimized Cas9 coding sequences (e.g., ¶¶0129-0137 therein) and Cas9 fusion proteins (e.g., ¶¶233-240 therein). U.S. Patent Publication 2014/0315985 to May et al., published Oct. 23, 2014, incorporated herein by reference in its entirety, teaches a large number of exemplary wild-type Cas9 polypeptides (e.g., SEQ ID NO: 1-256, SEQ ID NOS: 795-1346, therein) including the sequence of Cas9 from *Streptococcus pyogenes* (SEQ ID NO: 8, therein). Modifications and variants of Cas9 proteins are also discussed (e.g., ¶¶504-608, therein). Non-limiting examples of Cas9 proteins include Cas9 proteins from *Streptococcus pyogenes* (GI:15675041); *Listeria innocua* Clip 11262 (GI:16801805); *Streptococcus mutans* UA159 (GI:24379809); *Streptococcus thermophilus* LMD-9 (*S. thermophilus* A, GI:11662823; *S. thermophilus* B, GI:116627542); *Lactobacillus buchneri* NRRL B-30929 (GI:331702228); *Treponema denticola* ATCC 35405 (GI:42525843); *Francisella novicida* U112 (GI:118497352); *Campylobacter jejuni* subsp. *Jejuni* NCTC 11168 (GI:218563121); *Pasteurella multocida* subsp. *multocida* str. Pm70 (GI:218767588); *Neisseria meningitidis* Zs491 (GI:15602992) and *Actinomyces naeslundii* (GI:489880078).

The term "Cas9 protein" as used herein refers to Type II CRISPR-Cas9 proteins (as described, e.g., in Chylinski, K., (2013) "The tracrRNA and Cas9 families of type II CRISPR-Cas immunity systems," RNA Biol. 2013 10(5): 726-737), including, but not limited to Cas9, Cas9-like, proteins encoded by Cas9 orthologs, Cas9-like synthetic proteins, and variants and modifications thereof. The term, as used herein, refers to Cas9 wild-type proteins derived from Type II CRISPR-Cas9 systems, modifications of Cas9 proteins, variants of Cas9 proteins, Cas9 orthologs, and combinations thereof. Cas9 proteins can be derived from any of various bacterial species which genomes encode such proteins. Cas proteins for use in the present methods are described further below.

Cpf1, another CRISPR-Cas protein found in Type V systems, prefers a "TTN" PAM motif that is located 5' to its protospacer target, not 3', like Cas9, which recognizes a "NGG" PAM motif. Thus, Cpf1 recognizes a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 only requires a crRNA that is about 43 bases long. 24 nt represents the protospacer and 19 nt the constitutive direct repeat sequence. Cpf1 appears to be directly responsible for cleaving the 43 base crRNAs apart from the primary transcript (Fonfara et al., (2016) "The CRISPR-associated DNA-cleaving enzyme Cpf1 also processes precursor CRISPR RNA," Nature 532:517-521).

Aspects of the present invention can be practiced by one of ordinary skill in the art following the guidance of the specification to use CRISPR-Cas proteins, such as CRISPR-Cas9, Cas3, Cpf1 proteins and Cas-protein encoding polynucleotides, including, but not limited to proteins encoded by the native sequences and proteins encoded by Cas orthologs, Cas-like synthetic proteins, and variants and modifications thereof. The cognate RNA components of these Cas proteins can be manipulated and modified for use in the practice of the present invention by one of ordinary skill in the art following the guidance of the present specification.

The term "sgRNA" typically refers to a single-guide RNA (i.e., a single, contiguous polynucleotide sequence) that essentially comprises a crRNA connected at its 3' end to the 5' end of a tracrRNA through a "loop" sequence (see, e.g., U.S. Published Patent Application No. 20140068797 to Doudna et al., published 6 Mar. 2014, incorporated herein by reference in its entirety). sgRNA interacts with a cognate Cas protein essentially as described for tracrRNA/crRNA polynucleotides, as discussed above. Similar to crRNA, sgRNA has a spacer, a region of complementarity to a potential DNA target sequence, adjacent a second region that forms base-pair hydrogen bonds that form a secondary structure, typically a stem structure. The term includes truncated single-guide RNAs (tru-sgRNAs) of approximately 17-18 nt (see, e.g., Fu, Y. et. al., "Improving CRISPR-Cas nuclease specificity using truncated guide RNAs," Nat Biotechnol. (2014) 32:279-284). The term also encompasses functional miniature sgRNAs with expendable features removed, but that retain an essential and conserved module termed the "nexus" located in the portion of sgRNA that corresponds to tracrRNA (not crRNA). See, e.g., U.S. Published Patent Application No. 2014/0315985 to May et al., published 23 Oct. 2014, incorporated herein by reference in its entirety; Briner et al., "Guide RNA Functional Modules Direct Cas9 Activity and Orthogonality," Molecular Cell (2014) 56:333-339. The nexus is located immediately downstream of (i.e., located in the 3' direction from) the lower stem in Type II CRISPR-Cas9 systems. The nexus confers the binding of a sgRNA or a tracrRNA to its cognate Cas9 protein and confers an apoenzyme to haloenzyme conformational transition.

With reference to a crRNA or sgRNA, a "spacer" or "spacer element," as used herein refers to the polynucleotide sequence that can specifically hybridize to a target nucleic acid sequence. The spacer element interacts with the target nucleic acid sequence through hydrogen bonding between complementary base pairs (i.e., paired bases). A spacer element binds to a selected DNA target sequence. Accordingly, the spacer element is a DNA target-binding sequence. The spacer element determines the location of Cas protein's site-specific binding and endonucleolytic cleavage. Spacer elements range from ~17- to ~84 nucleotides in length, depending on the Cas protein with which they are associated, and have an average length of 36 nucleotides (Marraffini, et al., "CRISPR interference: RNA-directed adaptive immunity in bacteria and archaea," Nature reviews Genetics (2010) 11:181-190). For example, for SpyCas9, the functional length for a spacer to direct specific cleavage is typically about 12-25 nucleotides. Variability of the functional length for a spacer element is known in the art (e.g., U.S. Published Patent Application No. 2014/0315985 to May et al., published 23 Oct. 2014, incorporated herein by reference in its entirety).

U.S. Patent Publication No. 2014/0315985 to May et al., published 23 Oct. 2014, incorporated herein by reference in its entirety; and Briner et al., "Guide RNA Functional Modules Direct Cas9 Activity and Orthogonality," Molecular Cell (2014) 56:333-339, disclose consensus sequences and secondary structures of predicted sgRNAs for several sgRNA/Cas9 families.

Ran et al., "In vivo genome editing using *Staphylococcus aureus* Cas9," Nature (2015) 520:186-191, including all extended data) present the crRNA/tracrRNA sequences and secondary structures of eight Type II CRISPR-Cas9 systems (see Extended Data FIG. 1 of Ran, et al.). Furthermore, Fonfara, et al., ("Phylogeny of Cas9 Determines Functional Exchangeability of Dual-RNA and Cas9 among Orthologous Type II CRISPR/Cas Systems," Nucleic Acids Research (2014) 42:2577-2590, including all Supplemental Data, in particular Supplemental Figure S11) present the crRNA/tracrRNA sequences and secondary structures of eight Type II CRISPR-Cas9 systems.

By "guide polynucleotide" such as a guide RNA, is meant any polynucleotide that site-specifically guides a Cas endonuclease (e.g., Cas9, Cas3, etc.), or a deactivated Cas endonuclease (e.g., dCas9) to a target nucleic acid. Many such guide polynucleotides are known, including, but not limited to, sgRNA (including miniature and truncated sgRNAs), crRNA, dual-guide RNA, including but not limited to, crRNA/tracrRNA molecules, as described above, and the like.

The terms "wild-type," "naturally-occurring" and "unmodified" are used herein to mean the typical (or most common) form, appearance, phenotype, or strain existing in nature; for example, the typical form of cells, organisms, characteristics, polynucleotides, proteins, macromolecular complexes, genes, RNAs, DNAs, or genomes as they occur in and can be isolated from a source in nature. The wild-type form, appearance, phenotype, or strain serve as the original parent before an intentional modification. Thus, mutant, variant, engineered, recombinant, and modified forms are not wild-type forms.

As used herein, the terms "engineered," "genetically engineered," "recombinant," "modified," and "non-naturally occurring" are interchangeable and indicate intentional human manipulation.

As used herein, the terms "nucleic acid," "nucleotide sequence," "oligonucleotide," and "polynucleotide" are interchangeable. All refer to a polymeric form of nucleotides. The nucleotides may be deoxyribonucleotides (DNA) or ribonucleotides (RNA), or analogs thereof, and they may be of any length. Polynucleotides may perform any function and may have any secondary structure and three-dimensional structure. The terms encompass known analogs of natural nucleotides and nucleotides that are modified in the base, sugar and/or phosphate moieties. Analogs of a particular nucleotide have the same base-pairing specificity (e.g., an analog of A base pairs with T). A polynucleotide may comprise one modified nucleotide or multiple modified nucleotides. Examples of modified nucleotides include methylated nucleotides and nucleotide analogs. Nucleotide structure may be modified before or after a polymer is assembled. Following polymerization, polynucleotides may be additionally modified via, for example, conjugation with a labeling component or target-binding component. A nucleotide sequence may incorporate non-nucleotide components. The terms also encompass nucleic acids comprising modified backbone residues or linkages that (i) are synthetic, naturally occurring, and non-naturally occurring, and (ii) have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), and morpholino structures.

Polynucleotide sequences are displayed herein in the conventional 5' to 3' orientation unless explicitly otherwise noted.

As used herein, the term "complementarity" refers to the ability of a nucleic acid sequence to form hydrogen bond(s) with another nucleic acid sequence (e.g., through traditional Watson-Crick base pairing). A percent complementarity indicates the percentage of residues in a nucleic acid molecule that can form hydrogen bonds with a second nucleic acid sequence. When two polynucleotide sequences have 100% complementarity, the two sequences are perfectly complementary, i.e., all of a first polynucleotide's contiguous residues hydrogen bond with the same number of contiguous residues in a second polynucleotide.

As used herein, the term "sequence identity" generally refers to the percent identity of bases or amino acids determined by comparing a first polynucleotide or polypeptide to a second polynucleotide or polypeptide using algorithms having various weighting parameters. Sequence identity between two polypeptides or two polynucleotides can be determined using sequence alignment by various methods and computer programs (e.g., BLAST, CS-BLAST, FASTA, HMMER, L-ALIGN, etc.), available through the worldwide web at sites including GENBANK (ncbi.nlm.nih.gov/genbank/) and EMBL-EBI (ebi.ac.uk.). Sequence identity between two polynucleotides or two polypeptide sequences is generally calculated using the standard default parameters of the various methods or computer programs. Generally, the Cas proteins for use herein will have at least about 75% or more sequence identity to the wild-type or naturally occurring sequence of the Cas protein of interest, such as about 80%, such as about 85%, 90%, 91%, 92%, 93%, 94%, 95%, 96%, 97%, 98%, 99%, or complete identity.

As used herein a "stem-loop structure" or "stem-loop element" refers to a polynucleotide having a secondary structure that includes a region of nucleotides that are known or predicted to form a double-stranded region (the "stem element") that is linked on one side by a region of predominantly single-stranded nucleotides (the "loop element"). The term "hairpin" element is also used herein to refer to stem-loop structures. Such structures are well known in the art. The base pairing may be exact. However, as is known in the art, a stem element does not require exact base pairing. Thus, the stem element may include one or more base mismatches or non-paired bases.

As used herein, the term "recombination" refers to a process of exchange of genetic information between two polynucleotides.

As used herein, the term "homology-directed repair" or "HDR" refers to DNA repair that takes place in cells, for example, during repair of double-strand and single-strand breaks in DNA. HDR requires nucleotide sequence homology and uses a "donor template" (donor template DNA, polynucleotide donor, or oligonucleotide (used interchangably herein) to repair the sequence where the double-strand break occurred (e.g., DNA target sequence). This results in the transfer of genetic information from, for example, the donor template DNA to the DNA target sequence. HDR may result in alteration of the DNA target sequence (e.g., insertion, deletion, mutation) if the donor template DNA sequence or oligonucleotide sequence differs from the DNA target sequence and part or all of the donor template DNA polynucleotide or oligonucleotide is incorporated into the DNA target sequence. In some embodiments, an entire donor template DNA polynucleotide, a portion of the donor template DNA polynucleotide, or a copy of the donor polynucleotide is copied or integrated at the site of the DNA target sequence.

As used herein the terms "classical non-homologous end joining" or "c-NHEJ" refer to the repair of double-strand breaks in DNA by direct ligation of one end of the break to the other end of the break without a requirement for a donor template DNA. NHEJ in the absence of a donor template DNA often results in small insertions or deletions of nucleotides at the site of the double-strand break, also referred to as "indels." This DNA repair pathway is genetically defined and requires the activity of Ligase IV, DNA-PKcs, Polμ, Polλ, and the Ku70/80 heterodimer, among other proteins (see, e.g., Sfeir and Symington, "Microhomology-Mediated End Joining: A Back-up Survival Mechanism or Dedicated Pathway?" Trends Biochem Sci (2015) 40:701-714).

"Microhomology-mediated end joining (MMEJ)," a form of alternative nonhomologous end-joining (alt-NHEJ), is another pathway for repairing double-strand breaks in DNA. MMEJ is associated with deletions flanking a DSB and involves alignment of microhomologous sequences internal to the broken ends before joining. The proposed mechanism entails 5'-3' resection of the DNA ends at a DSB, annealing of the microhomologies (1-16 nucleotides of homology), removal of heterologous flaps, gap filling DNA synthesis, and ligation. MMEJ is genetically defined and requires the activity of CtIP, PARP1, Polθ, Lig1 and Lig3, among other proteins (see, e.g., Sfeir and Symington, "Microhomology-Mediated End Joining: A Back-up Survival Mechanism or Dedicated Pathway?" Trends Biochem Sci (2015) 40:701-714).

Alternative mechanisms of DNA insertion that do not require sequence homology between the donor and the target sequence can also be used for nucleic acid insertion. These mechanisms involve various components of the cellular DNA repair machinery and it is to be understood that the scope of the invention is not bound by the use of any particular mechanism for insertion of nucleic acid after target nucleic acid is cut or nicked by a site-specific polynucleotide.

By "donor polynucleotide" is meant a polynucleotide that can be directed to, and inserted into a target site of interest to modify the target nucleic acid. All or a portion of the donor polynucleotide can be inserted into the target nucleic acid. The donor polynucleotide is used for repair of the break in the target DNA sequence resulting in the transfer of genetic information (i.e., polynucleotide sequences) from the donor at the site or in close proximity to the break in the DNA. Accordingly, new genetic information (i.e., polynucleotide sequences) may be inserted or copied at a target DNA site. The donor polynucleotide can be double- or single-strand DNA, RNA, a vector, plasmid, or the like. Non-symmetrical polynucleotide donors can also be used that are composed of two DNA oligonucleotides. They are partially complementary, and each can include a flanking region of homology. The donor polynucleotide can be used to insert or replace polynucleotide sequences in a target sequence, for example, to introduce a polynucleotide that encodes a protein or functional RNA (e.g., siRNA), to introduce a protein tag, to modify a regulatory sequence of a gene, or to introduce a regulatory sequence to a gene (e.g. a promoter, an enhancer, an internal ribosome entry sequence, a start codon, a stop codon, a localization signal, or polyadenylation signal), to modify a nucleic acid sequence (e.g., introduce a mutation), and the like.

Targeted DNA modifications using donor polynucleotides for large changes (e.g., more than 100 bp insertions or deletions) traditionally use plasmid-based donor templates that contain homology arms flanking the site of alteration. Each arm can vary in length, but is typically longer than about 100 bp, such as 100-1500 bp, e.g., 100 . . . 200 . . . 300 . . . 400 . . . 500 . . . 600 . . . 700 . . . 800 . . . 900 . . . 1000 . . . 1500 bp or any integer between these values. However, these numbers can vary, depending on the size of the donor polynucleotide and the target polynucleotide. This method can be used to generate large modifications, including insertion of reporter genes such as fluorescent proteins or antibiotic resistance markers. For transfection in cells, such as HEK cells, approximately 100-1000 ng, e.g., 100 . . . 200 . . . 300 . . . 400 . . . 500 . . . 600 . . . 700 . . . 800 . . . 900 . . . 1000 ng or any integer between these values, of a typical size donor plasmid (e.g., approximately 5 kb) containing a sgRNA/Cas9 vector, can be used for one well in 24-well plate (see, e.g., Yang et al., "One Step Generation of Mice Carrying Reporter and Conditional Alleles by CRISPR/Cas-Mediated Genome Engineering" Cell (2013) 154:1370-1379).

Single-stranded and partially double-stranded oligonucleotides, such as DNA oligonucleotides, have been used in place of targeting plasmids for short modifications (e.g., less than 50 bp) within a defined locus without cloning. To achieve high HDR efficiencies, single-stranded oligonucleotides containing flanking sequences on each side that are homologous to the target region can be used, and can be oriented in either the sense or antisense direction relative to the target locus. The length of each arm can vary in length, but the length of at least one arm is typically longer than about 10 bases, such as from 10-150 bases, e.g., 10 . . . 20 . . . 30 . . . 40 . . . 50 . . . 60 . . . 70 . . . 80 . . . 90 . . . 100 . . . 110 . . . 120 . . . 130 . . . 140 . . . 150, or any integer within these ranges. However, these numbers can vary, depending on the size of the donor polynucleotide and the target polynucleotide. In a preferred embodiment, the length of at least one arm is 10 bases or more. In other embodiments, the length of at least one arm is 20 bases or more. In yet other embodiments, the length of at least one arm is 30 bases or more. In some embodiments, the length of at least one arm is less than 100 bases. In further embodiments, the length of at least one arm is greater than 100 bases. In some embodiments, the length of at least one arm is zero bases. For single-stranded DNA oligonucleotide design, typically an oligonucleotide with around 100-150 bp total homology is used. The mutation is introduced in the middle, giving 50-75 bp homology arms for a donor designed to be symmetrical about the target site. In other cases, no homology arms are required, and the donor polynucleotide is inserted using non-homologous DNA repair mechanisms.

As used herein, the term "modulate" refers to a change in the quantity, degree or amount of a function. For example, the methods disclosed herein may modulate, e.g., enhance, decrease or inhibit, DNA repair function, such as HDR, NHEJ, MMEJ, and the like. Moreover, the methods can be used to modulate the function of a gene product, such as a protein, to reduce or restore activity of the protein.

Modulation can be assayed by determining any characteristic directly or indirectly affected by the expression of the target gene. Such characteristics include, e.g., changes in targeting efficiency, RNA or protein levels, protein activity, product levels, associated gene expression, or activity level of reporter genes. Thus, "modulation" of gene expression includes both gene activation and gene repression.

The terms "vector" and "plasmid" are used interchangeably and, as used herein, refer to a polynucleotide vehicle to introduce genetic material into a cell. Vectors can be linear or circular. Vectors can integrate into a target genome of a host cell or replicate independently in a host cell. Vectors can comprise, for example, an origin of replication, a multicloning site, and/or a selectable marker. An expression vector typically comprises an expression cassette. Vectors and plasmids include, but are not limited to, integrating vectors, prokaryotic plasmids, eukaryotic plasmids, plant synthetic chromosomes, episomes, viral vectors, cosmids, and artificial chromosomes. As used herein, the term "expression cassette" is a polynucleotide construct, generated recombinantly or synthetically, comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in an expression vector.

As used herein, the term "expression cassette" is a polynucleotide construct, generated recombinantly or synthetically, comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in an expression vector.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like.

As used herein, the term "operably linked" refers to polynucleotide sequences or amino acid sequences placed into a functional relationship with one another. For instance, a promoter or enhancer is operably linked to a coding sequence if it regulates, or contributes to the modulation of, the transcription of the coding sequence. Operably linked DNA sequences encoding regulatory sequences are typically contiguous to the coding sequence. However, enhancers can function when separated from a promoter by up to several kilobases or more. Accordingly, some polynucleotide elements may be operably linked but not contiguous.

As used herein, the term "expression" refers to transcription of a polynucleotide from a DNA template, resulting in, for example, an mRNA or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene product." Expression may include splicing the mRNA in a eukaryotic cell, if the polynucleotide is derived from genomic DNA.

As used herein, the term "amino acid" refers to natural and synthetic (unnatural) amino acids, including amino acid analogs, modified amino acids, peptidomimetics, glycine, and D or L optical isomers.

As used herein, the terms "peptide," "polypeptide," and "protein" are interchangeable and refer to polymers of amino acids. A polypeptide may be of any length. It may be branched or linear, it may be interrupted by non-amino acids, and it may comprise modified amino acids. The terms may be used to refer to an amino acid polymer that has been modified through, for example, acetylation, disulfide bond formation, glycosylation, lipidation, phosphorylation, cross-linking, and/or conjugation (e.g., with a labeling component or ligand). Polypeptide sequences are displayed herein in the conventional N-terminal to C-terminal orientation.

Polypeptides and polynucleotides can be made using routine techniques in the field of molecular biology (see, e.g., standard texts discussed above). Furthermore, essentially any polypeptide or polynucleotide can be custom ordered from commercial sources.

The term "binding," as used herein, includes a non-covalent interaction between macromolecules (e.g., between a protein and a polynucleotide, between a polynucleotide and a polynucleotide, and between a protein and a protein). Such non-covalent interaction is also referred to as "associating" or "interacting" (e.g., when a first macromolecule interacts with a second macromolecule, the first macromolecule binds to second macromolecule in a non-covalent manner). Some portions of a binding interaction may be sequence-specific; however, all components of a binding interaction do not need to be sequence-specific, such as a protein's contacts with phosphate residues in a DNA backbone. Binding interactions can be characterized by a dissociation constant (Kd). "Affinity" refers to the strength of binding. An increased binding affinity is correlated with a lower Kd. An example of non-covalent binding is hydrogen bond formation between base pairs.

As used herein, the term "isolated" can refer to a nucleic acid or polypeptide that, by the hand of a human, exists apart from its native environment and is therefore not a product of nature. Isolated means substantially pure. An isolated nucleic acid or polypeptide can exist in a purified form and/or can exist in a non-native environment such as, for example, in a recombinant cell.

As used herein, a "host cell" generally refers to a biological cell. A cell can be the basic structural, functional and/or biological unit of a living organism. A cell can originate from any organism having one or more cells. Examples of host cells include, but are not limited to: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, sunflower, sorghum, millet, alfalfa, oil-producing *Brassica* (for example, but not limited to, oilseed rape/canola), pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. Agardh*, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.). Furthermore, a cell can be a stem cell or progenitor cell.

As used herein, the term "biological sample" refers to a sample of tissue or fluid, cultured cells isolated from a subject, or an environmental sample. Typical samples include but are not limited to, samples derived from blood, plasma, serum, fecal matter, urine, bone marrow, bile, spinal fluid, lymph fluid, samples of the skin, secretions of the skin, respiratory, intestinal, and genitourinary tracts, tears, saliva, milk, organs, tumors, biopsies, cells desired for gene editing, cell lines, and also samples of in vitro cell culture constituents including but not limited to conditioned media resulting from the growth of cells and tissues in culture medium, e.g., recombinant cells, and cell components. Environmental samples can be from water, dirt, rocks, and the like.

The present methods can be used in a number of genome-editing applications. In the absence of a donor template, DNA repair was previously thought to result in random outcomes. Through sequencing and detailed classification of indel classes, it is demonstrated herein that the distributions of DNA repair outcomes at Cas9-mediated DSBs are, in fact, nonrandom and dependent on the target site sequence. This observation has been unrecognized to date for the small indels formed by c-NHEJ-dependent repair. As shown in the examples, the frequency with which different microhomology opportunities are used by MMEJ were quantified. At the target sites profiled, a large range of repair outcomes was observed. At some sites, one or two dominant outcomes comprised a large fraction of total edits (e.g., FIGS. 6A-6E) whereas, at other sites, a collection of many reproducible, yet lower-frequency repair outcomes occurred (e.g., FIGS. 1A-1C). As described herein, each target has a unique and highly reproducible DNA repair pattern that is not explained by microhomology alone (FIGS. 2A-2C) (Bae et al. "Microhomology-based choice of Cas9 nuclease target sites" (2014) Nat. Methods 11:705-706).

There are numerous settings where using non-random DNA repair patterns as a predictive tool for genome editing experiments is advantageous. DNA repair profiling can be used to improve the ability to generate a gene knockout by facilitating the avoidance of in-frame mutations (FIGS. 6A-6E). Alternatively, an in-frame mutation can be used to dissect out a single amino acid in a functional domain of a protein. Furthermore, more tractable cell lines can be used rationally to model c-NHEJ/MMEJ indels intended for ultimate application in primary cells. As shown in the examples, this was conducted in peripheral blood-derived hematopoietic stem cells (HSCs) and DNA repair profiling revealed DNA repair outcomes with strong similarity to those observed in research cell lines (FIGS. 7A-7F).

Although editing of genomic locations to correct or introduce specific variants can be approached using DNA donor templates and HDR repair pathways, the efficiency of DNA insertion remains low, particularly in primary cells. In the methods described herein, specific, high frequency DNA editing outcomes can be induced at certain targets without the use of donor DNA, thus using pathways other than those utilized in gene-editing using HDR pathways.

For example, c-NHEJ and MMEJ pathways may be employed to restore the reading frame of mutant BRCA2 alleles with a single nucleotide insertion or specific four base deletions (FIGS. 7A-7F).

Additionally, these outcomes can be further exploited with the use of agents that suppress NHEJ, thereby favoring MMEJ pathways, so that DNA repair proceeds substantially by MMEJ pathways. By "substantially" is meant that more than 50% of the repairs are conducted using MMEJ pathways, such as more than 55% . . . 60% . . . 65% . . . 70% . . . 75% . . . 80% . . . 85% . . . 90% . . . 95% . . . 99% or more. For example, the repair outcome can be substantially MMEJ with other repair pathways occurring that represent a minor percentage of overall repair. Additionally, all NHEJ repair activity can be suppressed if desired in order to produce a cleaner profile. Such agents include chemical inhibitors (FIGS. 5A-5D). NHEJ is initiated when free DNA ends are bound by Ku70 and Ku80, which recruit the catalytic subunit of DNA-dependent protein kinase (DNA-PKcs). The resulting complex, known as the DNA-dependent protein kinase (DNA-PK) complex, phosphorylates downstream targets leading to activation of the DNA damage response and initiation of NHEJ. Thus, suppression of the NHEJ key enzymes Ku70, Ku80, or DNA Ligase IV inhibit DNA-PK and can be used in the present methods to modulate DNA repair outcomes by inhibiting NHEJ. Such inhibitors include without limitation, NU7441 (Leahy et al., "Identification of a highly potent and selective DNA-dependent protein kinase (DNA-PK) inhibitor (NU7441) by screening of chromenone libraries" Bioorg. Med. Chem. Lett. (2004) 14:6083-6087); KU-0060648 (Robert et al., "Pharmacological inhibition of DNA-PK stimulates Cas9-mediated genome editing" Genome Med (2015) 7:93); DNA Ligase IV inhibitor, Scr7 (Maruyama et al., "Increasing the efficiency of precise genome editing with CRISPR-Cas9 by inhibition of nonhomologous end joining" Nat. Biotechnol. (2015) 33:538-542); NU7026 (Wilimore et al. "A novel DNA-dependent protein kinase inhibitor, NU7026, potentiates the cytotoxicity of topoisomerase II poisons used in the treatment of leukemia" Blood (2004) 103); anti-EGFR-antibody C225 (Cetuximab) (Dittmann et al., "Inhibition of radiation-induced EGFR nuclear import by C225 (Cetuximab) suppresses DNA-PK activity" Radiother and Oncol (2005) 76:157), and the like.

Similarly, agents that suppress MMEJ pathways can be used to favor NHEJ, such that DNA repair proceeds substantially using NHEJ pathways. By "substantially" is meant that more than 50% of the repairs are conducted using NHEJ pathways, such as more than 55% . . . 60% . . . 65% . . . 70% . . . 75% . . . 80% . . . 85% . . . 90% . . . 95% . . . 99% or more. For example, the repair outcome can be substantially NHEJ with other repair pathways occurring that represent a minor percentage of overall repair. Additionally, all MMEJ repair activity can be suppressed if desired in order to produce a cleaner profile. Such agents include chemical inhibitors and the like. In this regard, several factors are required for MMEJ including FEN1, Ligase III, MRE11, NBS1, PARP1 and XRCC1 (Sharma et al., Cell Death Dis. (2015) 6:e1697). Thus, inhibitors of these factors or genes encoding therefore, will find use in suppressing MMEJ-directed repair. For example, Mirin and derivatives thereof have been shown to inhibit MRE11 (Shibata et al., Molec. Cell (2014) 53:7-18) and have little effect on NHEJ and can therefore be used to suppress MMEJ and favor NHEJ-directed repair. Additionally, DNA Polymerase theta (Polθ; encoded by PolQ) is a critical MMEJ factor in mammalian cells. PolQ loss results in increased rates of HDR. Thus, inhibiters of PolQ can be used to suppress MMEJ. CtIP has also been shown to play a critical role in MMEJ. Thus, inhibitors of CtIP will also find use herein. See, Sfeir and Symington, "Microhomology-Mediated End Joining: A Back-up Survival Mechanism or Dedicated Pathway?" Trends Biochem Sci (2015) 40:701-714), for a review of MMEJ and in particular, Table 1 therein for a list of genetic determinants of MMEJ, suppression of which could be used to favor NHEJ pathways.

In other contexts, agents that suppress both NHEJ and MMEJ pathways, such as one or more agents as described above, can be used in the presence of donor polynucleotides in order to substantially favor HDR. A first agent can be used to suppress NHEJ pathways and a second agent can be used to suppress MMEJ pathways. In some embodiments, the same agent can be used to suppress both pathways. If two agents are used, they can be provided concurrently, or one before the other.

Methods of determining which pathways are substantially favored are well known in the art and described in detail herein in the examples. See, also, Truong et al., "Microhomology-mediated end joining and homologous recombination share the initial end resection step to repair DNA double-strand breaks in mammalian cells" Proc. Natl. Acad. Sci. U.S.A. (2013) 110:7720-7725; Bennardo et al., "Alternative-NHEJ is a mechanistically distinct pathway of mammalian chromosome break repair" PLoS Genet. (2008) 4:e1000110; Simsek and Jasin, "Alternative end-joining is suppressed by the canonical NHEJ component Xrcc4-ligase IV during chromosomal translocation formation" Nat. Struct. Mol. Biol. (2010) 17:410-416; Ira et al., "DNA end resection, homologous recombination and DNA damage check point activation require CDK1" Nature (2004) 431: 1011-1017; Haber et al., "In vivo biochemistry: physical monitoring of recombination induced by site-specific endonucleases" Bioessays (1995) 17:609-620; Rouet et al., "Introduction of double-strand breaks into the genome of mouse cells by expression of a rare-cutting endonuclease" Mol. Cell. Biol. (1994) 14:8096-8106; and Frank et al., "Late embryonic lethality and impaired V(D)J recombination in mice lacking DNA ligase IV" Nature (1998) 396: 173-177.

Moreover, the methods described herein can be used for repair profiling to screen patient cells for sensitivity to certain chemotherapeutics. For example, BRCA1-deficient cells can be screened for certain PARP inhibitors (inhibitors of the enzyme poly ADP ribose polymerase) where Cas9 is simply a double-strand break initiator. Alternatively, the methods can be used to discover new genetic liabilities in a screen setting.

It is readily apparent that the ability to predictably modulate DNA repair outcomes by favoring NHEJ, MMEJ in the absence of a donor, as well as HDR using a donor polynucleotide, can be used in a large number of contexts.

In another embodiment, a method for designing a guide polynucleotide for predictably inserting a single nucleotide at a target site following Cas-mediated cleavage is provided. Following CRISPR-Cas cleavage of a target site, one of the more common DNA repair outcomes is a single base pair insertion. Thus, the ability to predict which nucleotide is most frequently inserted at Cas cleavage sites, such as Cas9 cleavage sites, from the underlying DNA sequence, is highly valuable for the design of therapeutics and other precision applications. The ability to predict which nucleotide is most frequently inserted at Cas9 targets can be used to repair with specificity single base pair deletions, such as deletions that play a role in producing genetic defects. Additionally, the discovery that protospacers with A or T at position 17 have more frequent single base pair insertions can be used to select guides that are likely to have a higher fraction of frameshift mutations for inactivating a gene.

As explained above, a guide polynucleotide, such as sgRNA, is a short synthetic RNA sequence composed of a "scaffold" sequence necessary for Cas-binding, such as Cas9 binding, and a user-defined approximately 17-86 nucleotide "spacer" or "targeting" sequence which defines the genomic target to be modified. Thus, one can change the genomic target of Cas9 by changing the targeting sequence present in the sgRNA.

As shown in the examples, a data set of the repair outcomes of over 200 Cas9 targets in a human cell line (K562) was used as input for predictive analyses. A classifier accurately predicted which nucleotide was most frequently inserted at Cas9 targets based on the PAM-distal, cut-site nucleotide (protospacer position 17) and further analyses revealed that the position-17 nucleotide explained substantial portions of the variance in the frequencies of insertions of A or T. Thus, guide polynucleotides, such as sgRNAs, can be designed to target selected protospacers where it is desirable to insert a particular nucleotide, such as an A or a T, at base 17 of the protospacer targeted.

Methods of designing particular guide polynucleotides, such as sgRNAs, are known and described herein. See the examples herein, as well as Briner et al., "Guide RNA Functional Modules Direct Cas9 Activity and Orthogonality," Molecular Cell (2014) 56:333-339. To do so, the genomic sequence for the gene to be targeted is first identified. The exact region of the selected gene to target will depend on the specific application. For example, in order to activate or repress a target gene using, for example, Cas activators or repressors, guide polynucleotides can be targeted to the promoter driving expression of the gene of interest. For genetic knock-outs, guide polynucleotides are commonly designed to target 5' constitutively expressed exons which reduces the chances or removal of the targeted region from mRNA due to alternative splicing. Exons near the N-terminus can be targeted because frameshift mutations here will increase the likelihood of the production of a nonfunctional protein product. Alternatively, guide polynucleotides can be designed to target exons that code for known essential protein domains. In this regard, non-frameshift mutations such as insertions or deletions are more likely to alter protein function when they occur in protein domains that are essential for protein function. For gene editing using HDR, the target sequence should be close to the location of the desired edit. In this case, the location where the edit is desired is identified and a target sequence is selected nearby.

Using the methods described herein, any desired nucleic acid sequence for modification can be targeted, including without limitation, protein coding sequences in order to reduce or restore the function of the gene product; regions that have a propensity to incorporate nucleotide sequences from a donor template, termed "HDR hotspots" herein; safe harbor regions, i.e., regions where nucleotide sequences can be inserted without disrupting neighboring gene function; non-coding regulatory regions in nucleic acid sequences; and the like.

For example, protein coding sequences for targeting by the methods described herein include, but are not limited to, mammalian antibodies (ABs) (IgG, IgA, IgM, IgE), antibody fragments such as Fc regions, antibody Fab regions, antibody heavy chains, antibody light chains, antibody CDRs, nanobodies, chimeric antibodies and other IgG domains; T cell receptors (TCR); endonucleases and exonucleases, such as TALENS, CRISPR nucleases such as Cas9, Cas3, Cpf1, ZnFN, meganucleases, nuclease domains such as HNH domain, RuvC domain; recombinases such as Cre, Tre, Brec1, Flp, γ-integrase, Int14 integrase, XerD recombinase, HP1 integrase; DNA topoisomerases; transposons such as the Te1/mariner family, To12, piggyBac, Sleeping beauty; RAG proteins; retrotransposons such as LTR-retrotransposons and non-LTR retrotransposons (Alu, SINE, LINE); enzymes including but not limited to arginases, glycosydases, proteases, kinases, and glycosylation enzymes such as glycosyltransferase; anticoagulants such as protein C, Protein S and antithrombin; coagulants such as thrombin; nucleases such as DNAses, RNAses, helicases, GTPases; DNA or RNA binding proteins; reporter molecules, such as Green Fluorescent Protein (GFP); cell penetrating peptides and their fusions with cargo proteins; membrane proteins such as GPCRs, pain receptors such as TRP channels and ion channels; cell surface receptors including but not limited to EGFR, FGFR, VEGFR, IGFR and ephrin receptor; cell adhesion molecules like integrins and cadherins; ion channels; rhodopsins; immunoreceptors such as CD28, CD80, PD-1, PD-L1, CTLA-4, CXCR4, CXCR5, B2M, TRACA, TRBC; proteins known to be involved with genetic defects; secreted proteins including but not limited to hormones, cytokines, growth factors; vaccine antigens such as viral proteins from human immunodeficiency virus (HIV), Dengue, cytomegalovirus (CMV), Ebola, Zika and oncolytic viruses; snake toxin proteins and peptides including but not limited to phospholipases and metalloproteases; ribosomal cyclic peptides.

Guide polynucleotides, such as sgRNAs, can be designed to target any DNA sequence containing the appropriate PAM necessary for each programmable nuclease, such as a Cas endonuclease, e.g., Cas9, Cpf1 and the like. Additional PAMs can also be created in the target DNA using a type of codon optimization, where silent mutations are introduced into amino acid codons in order to create new PAM sequences. For example, for strategies using Cas9, which recognizes an NGG PAM, a CGA serine codon can be changed to CGG, preserving the amino acid coding but adding a site where double-strand breaks can be introduced. The entire coding region or parts of the coding region can thus be optimized with suitable PAM sites on the coding and non-coding strand for DNA repair after nuclease cleavage. PAM optimized DNA sequences can be manufactured, e.g., commercially, and cloned into suitable vectors.

The sgRNAs can be delivered to a cell. If the cell constitutively expresses a Cas endonuclease, such as Cas9, Cpf1, or the like, the Cas endonuclease will then be recruited to the target site to cleave the DNA. If the cell does not express a Cas endonuclease, complexes of Cas proteins, such as Cas9 proteins, and guide RNAs, such as sgRNAs (sgRNA/Cas9 complexes) are delivered to the cells to make double-strand breaks, thereby triggering the DNA repair pathways in the cells. The cells are then screened using methods well known in the art, such as using high-throughput screening techniques including, but not limited to, fluorescence-activated cell sorting (FACS)-based screening platforms, microfluidics-based screening platforms, and the like. These techniques are well known in the art and reviewed in e.g., Wojcik et al., Int. J. Molec. Sci. (2015) 16:24918-24945. The cells can then be expanded and re-transfected with additional guide complexes to introduce further diversity and this process can be repeated iteratively until a population with the desired properties is obtained. Single cell clones are sorted from the population, expanded and sequenced to recover the mutations that resulted in the desired function.

As discussed above, the methods described herein make use of programmable endonucleases derived from the CRISPR-Cas system. For each of the above-described embodiments, when Cas9 proteins are used, any of various Cas9-derived proteins can be used, as well as other CRISPR-Cas proteins as detailed above.

A number of catalytically active Cas9 proteins are known in the art and, as explained above, a Cas9 protein for use herein can be derived from any bacterial species, subspecies or strain that encodes the same. Although in certain embodiments herein, the methods are exemplified using *Streptococcus pyogenes* Cas9, orthologs from other bacterial species will find use herein. The specificity of these Cas9 orthologs is well known. Also useful are proteins encoded by Cas9-like synthetic proteins, and variants and modifications thereof. As explained above, the sequences for hundreds of Cas9 proteins are known and any of these proteins will find use with the present methods.

Additionally, it is to be understood that other Cas nucleases, in place of or in addition to Cas9, may be used, including any of the Cas proteins described in detail above, such as derived from any of the various CRISPR-Cas classes, types and subtypes.

Moreover, in the embodiments described herein, sgRNA is used as an exemplary guide polynucleotide, however, it will be recognized by one of skill in the art that other guide polynucleotides that site-specifically guide endonucleases, such as CRISPR-Cas proteins to a target nucleic acid can be used.

If CRISPR complexes are used, they can be produced using methods well known in the art. For example, guide RNA components of the complexes can be produced in vitro and Cas9 components can be recombinantly produced and then the two complexed together using methods known in the art. Additionally, cell lines such as but not limited to HEK293 cells, are commercially available that constitutively express *Streptococcus pyogenes* Cas9 as well as *Streptococcus pyogenes* Cas9-GFP fusions. In this instance, cells expressing Cas9 can be transfected with the guide RNA components and complexes are purified from the cells using standard purification techniques, such as but not limited to affinity, ion exchange and size exclusion chromatography. See, e.g., Jinek M., et al., "A programmable dual-RNA-guided DNA endonuclease in adaptive bacterial immunity," Science (2012) 337:816-821.

More than one set of complexes can be used, such as 2-30 or more, for example 5-20, 8-15, etc., or any number within these ranges.

The complexes, such as sgRNA/Cas9 complexes may be introduced to cells at differing concentrations. For example, sgRNA/Cas9 and sgRNA/dCas9 complexes can be introduced at a ratio of 1:2, 1:3, 1:4, 1:5, 1:6, 1:7, 1:8, 1:9, 1:10, 10:1, 9:1, 8:1, 7:1, 6:1, 5:1, 4:1, 3:1, or 2:1. Additionally, all of these components, i.e., sgRNA and Cas9, may be provided separately, e.g., as separately assembled complexes, using separate DNA or RNA constructs, or together, in a single construct, or in any combination.

sgRNA/Cas9 complexes may be introduced at differing time points. For example, sgRNA/Cas9 complexes can be introduced at least 1 minute apart, 5 minutes apart, 10 minutes apart, 30 minutes apart, 1 hour apart, 5 hours apart, or 15 hours apart or more. sgRNA/Cas9 complexes can be introduced at most 1 minute apart, 5 minutes apart, 10 minutes apart, 30 minutes apart, 1 hour apart, 5 hours apart, or 15 hours apart or more. One set of complexes can be purified out before introducing another set of complexes. sgRNA/Cas9 complexes may be differentially regulated (i.e. differentially expressed or stabilized) via exogenously supplied agents (e.g. inducible DNA promoters or inducible Cas9 proteins).

Thus, in exemplary embodiments as described above, a sgRNA, complexed with Cas9 (sgRNA/Cas9 complex) is directed to a genomic locus of interest to induce double-strand breaks. The binding specificity is determined by both sgRNA-DNA base pairing and the PAM sequence juxtaposed to the DNA complementary region.

In all of the embodiments of the above-described methods, the various components can be produced by synthesis, or for example, using expression cassettes encoding a programmable endonuclease, such as a Cas protein, guide polynucleotide, etc. The various components can be provided to a cell or used in vitro. These components can be present on a single cassette or multiple cassettes, in the same or different constructs. Expression cassettes typically comprise regulatory sequences that are involved in one or more of the following: regulation of transcription, post-transcriptional regulation, and regulation of translation. Expression cassettes can be introduced into a wide variety of organisms including bacterial cells, yeast cells, plant cells, and mammalian cells. Expression cassettes typically comprise functional regulatory sequences corresponding to the organism(s) into which they are being introduced.

In one aspect, all or a portion of the various components for use in the methods are produced in vectors, including expression vectors, comprising polynucleotides encoding therefor. Vectors useful for producing components for use in the present methods include plasmids, viruses (including phage), and Integra table DNA fragments (i.e., fragments integratable into the host genome by homologous recombination). A vector replicates and functions independently of the host genome, or may, in some instances, integrate into the genome itself. Suitable replicating vectors will contain a replicon and control sequences derived from species compatible with the intended expression host cell. Transformed host cells are cells that have been transformed or transfected with the vectors constructed using recombinant DNA techniques General methods for construction of expression vectors are known in the art. Expression vectors for most host cells are commercially available. There are several commercial software products designed to facilitate selection of appropriate vectors and construction thereof, such as insect cell vectors for insect cell transformation and gene expression in insect cells, bacterial plasmids for bacterial transformation and gene expression in bacterial cells, yeast plasmids for cell transformation and gene expression in yeast and other fungi, mammalian vectors for mammalian cell transformation and gene expression in mammalian cells or mammals, viral vectors (including retroviral, lentiviral, and adenoviral vectors) for cell transformation and gene expression and methods to easily enable cloning of such polynucleotides. Snap-Gene™ (GSL Biotech LLC, Chicago, Ill.; snapgene.com/resources/plasmid_files/your_time_is_valuable/), for example, provides an extensive list of vectors, individual vector sequences, and vector maps, as well as commercial sources for many of the vectors.

Expression cassettes typically comprise regulatory sequences that are involved in one or more of the following: regulation of transcription, post-transcriptional regulation, and regulation of translation. Expression cassettes can be introduced into a wide variety of organisms including bacterial cells, yeast cells, mammalian cells, and plant cells. Expression cassettes typically comprise functional regulatory sequences corresponding to the host cells or organism(s) into which they are being introduced. Expression vectors can also include polynucleotides encoding protein tags (e.g., poly-His tags, hemagglutinin tags, fluorescent protein tags, bioluminescent tags, nuclear localization tags). The coding sequences for such protein tags can be fused to the coding sequences or can be included in an expression cassette, for example, in a targeting vector.

In some embodiments, polynucleotides encoding one or more of the various components are operably linked to an inducible promoter, a repressible promoter, or a constitutive promoter.

Several expression vectors have been designed for expressing guide polynucleotides. See, e.g., Shen, B. et al. "Efficient genome modification by CRISPR-Cas9 nickase with minimal off-target effects" (2014) March 2. doi: 10.1038/nmeth.2857. 10.1038/nmeth.2857. Additionally, vectors and expression systems are commercially available, such as from New England Biolabs (Ipswich, Mass.) and Clontech Laboratories (Mountain View, Calif.). Vectors can be designed to simultaneously express a target-specific sgRNA using a U2 or U6 promoter, a Cas9 and/or dCas9, and if desired, a marker protein, for monitoring transfection efficiency and/or for further enriching/isolating transfected cells by flow cytometry.

Vectors can be designed for expression of various components of the described methods in prokaryotic or eukaryotic cells. Alternatively, transcription can be in vitro, for example using T7 promoter regulatory sequences and T7 polymerase. Other RNA polymerase and promoter sequences can be used.

Vectors can be introduced into and propagated in a prokaryote. Prokaryotic vectors are well known in the art. Typically a prokaryotic vector comprises an origin of replication suitable for the target host cell (e.g., oriC derived from *E. coli*, pUC derived from pBR322, pSC101 derived from *Salmonella*), 15A origin (derived from p15A) and bacterial artificial chromosomes). Vectors can include a selectable marker (e.g., genes encoding resistance for ampicillin, chloramphenicol, gentamicin, and kanamycin). Zeocin™ (Life Technologies, Grand Island, N.Y.) can be used as a selection in bacteria, fungi (including yeast), plants and mammalian cell lines. Accordingly, vectors can be designed that carry only one drug resistance gene for Zeocin for selection work in a number of organisms. Useful promoters are known for expression of proteins in prokaryotes, for example, T5, T7, Rhamnose (inducible), Arabinose (inducible), and PhoA (inducible). Furthermore, T7 promoters are widely used in vectors that also encode the T7 RNA polymerase. Prokaryotic vectors can also include ribosome binding sites of varying strength, and secretion signals (e.g., mal, sec, tat, ompC, and pelB). In addition, vectors can comprise RNA polymerase promoters for the expression of sgRNAs. Prokaryotic RNA polymerase transcription termination sequences are also well known (e.g., transcription termination sequences from *Streptococcus pyogenes*).

Integrating vectors for stable transformation of prokaryotes are also known in the art (see, e.g., Heap, J. T., et al., "Integration of DNA into bacterial chromosomes from plasmids without a counter-selection marker," Nucleic Acids Res. (2012) 40:e59).

Expression of proteins in prokaryotes is typically carried out in *Escherichia coli* with vectors containing constitutive or inducible promoters directing the expression of either fusion or non-fusion proteins.

A wide variety of RNA polymerase promoters suitable for expression of the various components are available in prokaryotes (see, e.g., Jiang, Y., et al., "Multigene editing in the *Escherichia coli* genome via the CRISPR-Cas9 system," Environ Microbiol. (2015) 81:2506-2514); Estrem, S. T., et al., (1999) "Bacterial promoter architecture: subsite structure of UP elements and interactions with the carboxy-terminal domain of the RNA polymerase alpha subunit," Genes Dev. 15; 13(16):2134-47).

In some embodiments, a vector is a yeast expression vector comprising one or more components of the above-described methods. Examples of vectors for expression in *Saccharomyces cerivisae* include, but are not limited to, the following: pYepSec1, pMFa, pJRY88, pYES2, and picZ. Methods for gene expression in yeast cells are known in the art (see, e.g., Methods in Enzymology, Volume 194, "Guide to Yeast Genetics and Molecular and Cell Biology, Part A," (2004) Christine Guthrie and Gerald R. Fink (eds.), Elsevier Academic Press, San Diego, Calif.). Typically, expression of protein-encoding genes in yeast requires a promoter operably linked to a coding region of interest plus a transcriptional terminator. Various yeast promoters can be used to construct expression cassettes for expression of genes in yeast. Examples of promoters include, but are not limited to, promoters of genes encoding the following yeast proteins: alcohol dehydrogenase 1 (ADH1) or alcohol dehydrogenase 2 (ADH2), phosphoglycerate kinase (PGK), triose phosphate isomerase (TPI), glyceraldehyde-3-phosphate dehydrogenase (GAPDH; also known as TDH3, or triose phosphate dehydrogenase), galactose-1-phosphate uridyl-transferase (GALT), UDP-galactose epimerase (GAL10), cytochrome ci (CYC1), acid phosphatase (PHOS) and glycerol-3-phosphate dehydrogenase gene (GPD1). Hybrid promoters, such as the ADH2/GAPDH, CYC1/GAL10 and the ADH2/GAPDH promoter (which is induced at low cellular-glucose concentrations, e.g., about 0.1 percent to about 0.2 percent) also may be used. In *S. pombe*, suitable promoters include the thiamine-repressed nmtl promoter and the constitutive cytomegalovirus promoter in pTL2M.

Yeast RNA polymerase III promoters (e.g., promoters from 5S, U6 or RPR1 genes) as well as polymerase III termination sequences are known in the art (see, e.g., www.yeastgenome.org; Harismendy, O., et al., (2003) "Genome-wide location of yeast RNA polymerase III transcription machinery," The EMBO Journal. 22(18):4738-4747.)

In addition to a promoter, several upstream activation sequences (UASs), also called enhancers, may be used to enhance polypeptide expression. Exemplary upstream activation sequences for expression in yeast include the UASs of genes encoding these proteins: CYC1, ADH2, GAL1, GALT, GAL10, and ADH2. Exemplary transcription termination sequences for expression in yeast include the termination sequences of the α-factor, CYC1, GAPDH, and PGK genes. One or multiple termination sequences can be used.

Suitable promoters, terminators, and coding regions may be cloned into *E. coli*-yeast shuttle vectors and transformed into yeast cells. These vectors allow strain propagation in both yeast and *E. coli* strains. Typically, the vector contains a selectable marker and sequences enabling autonomous replication or chromosomal integration in each host. Examples of plasmids typically used in yeast are the shuttle vectors pRS423, pRS424, pRS425, and pRS426 (American Type Culture Collection, Manassas, Va.). These plasmids contain a yeast 2 micron origin of replication, an *E. coli* replication origin (e.g., pMB1), and a selectable marker.

The various components can also be expressed in insects or insect cells. Suitable expression control sequences for use in such cells are well known in the art. In some embodiments, it is desirable that the expression control sequence comprises a constitutive promoter. Examples of suitable strong promoters include, but are not limited to, the following: the baculovirus promoters for the piO, polyhedrin (polh), p 6.9, capsid, UAS (contains a Gal4 binding site), Ac5, cathepsin-like genes, the *B. mori* actin gene promoter; *Drosophila melanogaster* hsp70, actin, α-1-tubulin or ubiquitin gene promoters, RSV or MMTV promoters, copia promoter, gypsy promoter, and the cytomegalovirus IE gene promoter. Examples of weak promoters that can be used include, but are not limited to, the following: the baculovirus promoters for the ie1, ie2, ieO, etl, 39K (aka pp31), and gp64 genes. If it is desired to increase the amount of gene expression from a weak promoter, enhancer elements, such as the baculovirus enhancer element, hr5, may be used in conjunction with the promoter.

For the expression of some of the components of the present invention in insects, RNA polymerase III promoters are known in the art, for example, the U6 promoter. Conserved features of RNA polymerase III promoters in insects are also known (see, e.g., Hernandez, G., (2007) "Insect small nuclear RNA gene promoters evolve rapidly yet retain conserved features involved in determining promoter activity and RNA polymerase specificity," Nucleic Acids Res. 2007 January; 35(1):21-34).

In another aspect, the various components are incorporated into mammalian vectors for use in mammalian cells. A large number of mammalian vectors suitable for use with the systems of the present invention are commercially available (e.g., from Life Technologies, Grand Island, N.Y.; NeoBiolab, Cambridge, Mass.; Promega, Madison, Wis.; DNA2.0, Menlo Park, Calif.; Addgene, Cambridge, Mass.).

Vectors derived from mammalian viruses can also be used for expressing the various components of the present methods in mammalian cells. These include vectors derived from viruses such as adenovirus, papovirus, herpesvirus, polyomavirus, cytomegalovirus, lentivirus, retrovirus, vaccinia and Simian Virus 40 (SV40) (see, e.g., Kaufman, R. J., (2000) "Overview of vector design for mammalian gene expression," Molecular Biotechnology, Volume 16, Issue 2, pp 151-160; Cooray S., et al., (2012) "Retrovirus and lentivirus vector design and methods of cell conditioning," Methods Enzymol.507:29-57). Regulatory sequences operably linked to the components can include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like. Commonly used promoters are constitutive mammalian promoters CMV, EF1a, SV40, PGK1 (mouse or human), Ubc, CAG, CaMKIIa, and beta-Act, and others known in the art (Khan, K. H. (2013) "Gene Expression in Mammalian Cells and its Applications," Advanced Pharmaceutical Bulletin 3(2), 257-263). Furthermore, mammalian RNA polymerase III promoters, including H1 and U6, can be used.

In some embodiments, a recombinant mammalian expression vector is capable of preferentially directing expression of the nucleic acid in a particular cell type (e.g., using tissue-specific regulatory elements to express a polynucleotide). Tissue-specific regulatory elements are known in the art and include, but are not limited to, the albumin promoter, lymphoid-specific promoters, neuron-specific promoters (e.g., the neurofilament promoter), pancreas-specific promoters, mammary gland-specific promoters (e.g., milk whey promoter), and in particular promoters of T cell receptors and immunoglobulins. Developmentally-regulated promoters are also encompassed, e.g., the murine hox promoters and the alpha-fetoprotein promoter.

Numerous mammalian cell lines have been utilized for expression of gene products including HEK 293 (Human embryonic kidney) and CHO (Chinese hamster ovary). These cell lines can be transfected by standard methods (e.g., using calcium phosphate or polyethyleneimine (PEI), or electroporation). Other typical mammalian cell lines include, but are not limited to: HeLa, U2OS, 549, HT1080, CAD, P19, NIH 3T3, L929, N2a, Human embryonic kidney 293 cells, MCF-7, Y79, SO-Rb50, Hep G2, DUKX-X11, J558L, and Baby hamster kidney (BHK) cells.

Methods of introducing polynucleotides (e.g., an expression vector) into host cells are known in the art and are typically selected based on the kind of host cell. Such methods include, for example, viral or bacteriophage infection, transfection, conjugation, electroporation, calcium phosphate precipitation, polyethyleneimine-mediated transfection, DEAE-dextran mediated transfection, protoplast fusion, lipofection, liposome-mediated transfection, particle gun technology, direct microinjection, and nanoparticle-mediated delivery.

The present invention also includes methods of modulating in vitro or in vivo transcription using the various components and complexes described herein. In one embodiment, a guide polynucleotide/Cas protein complex can repress gene expression by interfering with transcription when the guide polynucleotide directs DNA target binding of the complex to the promoter region of the gene. Use of the complexes to reduce transcription also includes complexes wherein the Cas protein is fused to a known down regulator of a target gene (e.g., a repressor polypeptide). For example, expression of a gene is under the control of regulatory sequences to which a repressor polypeptide can bind. A guide polynucleotide can direct DNA target binding of a repressor protein complex to the DNA sequences encoding the regulatory sequences or adjacent the regulatory sequences such that binding of the repressor protein complex brings the repressor protein into operable contact with the regulatory sequences. Similarly, Cas9 can be fused to an activator polypeptide to activate or increase expression of a gene under the control of regulatory sequences to which an activator polypeptide can bind.

The present invention also encompasses gene-therapy methods for preventing or treating diseases, disorders, and conditions using the various methods described herein. In one embodiment, a gene-therapy method uses the introduction of nucleic acid sequences into an organism or cells of an organism (e.g., patient) to achieve expression of components of the present invention to provide modification of a target function. For example, cells from an organism may be engineered, ex vivo, by (i) introduction of vectors comprising expression cassettes expressing the various components, (ii) direct introduction of sgRNA and/or donor polynucleotides and Cas9 proteins, or (iii) introduction of combinations of these components. The engineered cells are provided to an organism (e.g., patient) to be treated.

Examples of gene-therapy and delivery techniques for therapy are known in the art (see, e.g., Kay, M. A., (2011) "State-of-the-art gene-based therapies: the road ahead," Nature Reviews Genetics 12, 316-328; Wang et al., "State-of-the-art human gene therapy: part I. Gene delivery technologies," Discov Med. (2014) 18:67-77; Wang et al., "State-of-the-art human gene therapy: part II. Gene therapy strategies and clinical applications," Discov Med. (2014) 18:151-61; "The Clinibook: Clinical Gene Transfer State of the Art," Odile Cohen-Haguenauer (Editor), EDP Sciences (Oct. 31, 2012), ISBN-10: 2842541715).

In some aspects, components of the present invention are delivered using nanoscale delivery systems, such as nanoparticles. Additionally, liposomes and other particulate delivery systems can be used. For example, vectors including the components of the present methods can be packaged in liposomes prior to delivery to the subject or to cells derived therefrom, such as described in U.S. Pat. Nos. 5,580,859; 5,264,618; 5,703,055, all incorporated herein by reference in their entireties. Lipid encapsulation is generally accomplished using liposomes that are able to stably bind or entrap and retain nucleic acid.

The methods described herein can also be used to generate non-human genetically modified organisms. Generally, in these methods expression cassettes comprising polynucleotide sequences of the various components, as well as a targeting vector are introduced into zygote cells to site-specifically introduce a selected polynucleotide sequence at a DNA target sequence in the genome to generate a modification of the genomic DNA. The selected polynucleotide sequence is present in the targeting vector. Modifications of the genomic DNA typically include, insertion of a polynucleotide sequence, deletion of a polynucleotide sequence, or mutation of a polynucleotide sequence, for example, gene correction, gene replacement, gene tagging, transgene insertion, gene disruption, gene mutation, mutation of gene regulatory sequences, and so on. In one embodiment of methods to generate non-human genetically modified organisms, the organism is a mouse. Generating transgenic mice involves five basic steps (Cho A., et al., "Generation of Transgenic Mice," Current protocols in cell biology, (2009); CHAPTER.Unit-19.11): (1) purifying a transgenic construct (e.g., expression cassettes comprising the various components of the various methods described herein, as well as a targeting vector); (2) harvesting donor zygotes; (3) microinjecting the transgenic construct into the mouse zygote; (4) implanting the microinjected zygotes into pseudo-pregnant recipient mice; and (5) performing genotyping and analysis of the modification of the genomic DNA established in founder mice.

In another embodiment of methods to generate non-human genetically modified organisms, the organism is a plant. Thus, the components described herein are used to effect efficient, cost-effective gene editing and manipulation in plant cells. It is generally preferable to insert a functional recombinant DNA in a plant genome at a non-specific location. However, in certain instances, it may be useful to use site-specific integration to introduce a recombinant DNA construct into the genome. Recombinant vectors for use in plant are known in the art. The vectors can include, for example, scaffold attachment regions (SARs), origins of replication, and/or selectable markers.

Methods and compositions for transforming plants by introducing a recombinant DNA construct into a plant genome includes any of a number of methods known in the art. One method for constructing transformed plants is microprojectile bombardment. *Agrobacterium*-mediated transformation is another method for constructing transformed plants. Alternatively, other non-*Agrobacterium* species (e.g., *Rhizobium*) and other prokaryotic cells that are able to infect plant cells and introduce heterologous nucleotide sequences into the infected plant cell's genome can be used. Other transformation methods include electroporation, liposomes, transformation using pollen or viruses, chemicals that increase free DNA uptake, or free DNA delivery by means of microprojectile bombardment. DNA constructs of the present invention may be introduced into the genome of a plant host using conventional transformation techniques that are well known to those skilled in the art (see, e.g., "Methods to Transfer Foreign Genes to Plants," Y Narusaka, et al., cdn.intechopen.com/pdfs-wm/30876.pdf).

Although preferred embodiments of the present invention have been shown and described herein, it will be obvious to those skilled in the art that such embodiments are provided by way of example only. From the above description and the following Examples, one skilled in the art can ascertain essential characteristics of this invention, and without departing from the spirit and scope thereof, can make changes, substitutions, variations, and modifications of the invention to adapt it to various usages and conditions. Such changes, substitutions, variations, and modifications are also intended to fall within the scope of the present disclosure.

EXPERIMENTAL

Aspects of the present invention are further illustrated in the following Examples. Efforts have been made to ensure accuracy with respect to numbers used (e.g., amounts, concentrations, percent changes, etc.) but some experimental errors and deviations should be accounted for. Unless indicated otherwise, temperature is in degrees Centigrade and pressure is at or near atmospheric. It should be understood that these Examples, although indicating some embodiments of the invention, are given by way of illustration only.

The following examples are not intended to limit the scope of what the inventors regard as various aspects of the present invention.

Materials and Methods

Cas9 and sgRNAs

Recombinant *Streptococcus pyogenes* (Spy) Cas9 and in vitro transcribed single-guide RNAs (sgRNAs) were generated as described by Briner et al., "Guide RNA Functional Modules Direct Cas9 Activity and Orthogonality," Molecular Cell (2014) 56:333-339). Oligonucleotides used in the generation of sgRNA templates are listed in Table 1, Table 3 and Table 5. Transcription reactions were digested with 2 Units RNAse-free DNAse I (NEB) at 37° C. for 15 minutes; the reaction was stopped by adding EDTA to final concentration of 5 mM and incubating at 75° C. for 10 minutes.

sgRNP Formation and Nucleofection

A single set of single-guide ribonucleoproteins (sgRNPs) was prepared for three independent nucleofection reactions. sgRNA was denatured by incubating at 98° C. for 2 minutes and then allowed to cool at room temperature for 10 minutes. 2.9 µl of denatured sgRNA was placed in a 96-well plate (average concentration 4 µg/ml) and combined with 3.1 µl of Cas9/CCE mix (1.9 µL of Cas9 protein at 10 mg/mL+1.2 µl 5×CCE buffer (100 mM HEPES, pH 7.4, 500 mM KCl, 25 mM MgCl$_2$, 5 mM DTT, 25% Glycerol). The sgRNA and Cas9 mixture was gently vortexed and incubated at 37° C. for 10 mins to form sgRNPs. 60 µl of cell suspension (10,000 cells/µl) was added to each well and mixed. 20 µl was transferred from the cell/sgRNP mixture into three 96-well nucleofection plates. Cells were nucleofected using the 96-well shuttle amaxa nucleofector II (Lonza) using the program recommended by the manufacturer for each cell line. HEK293 and K562 cell lines were nucleofected using the SF cell line kit (Lonza V4SC-2960). HCT116 cell line was nucleofected using the SE cell line kit (Lonza V4SC-1960). Hematopoietic stem cells (HSCs) were nucleofected using the P3 primary cell kit (Lonza V4SP-3960).

Cell Culture

HEK293 and HCT116 cell lines were cultured in DMEM Glutamax (Gibco, 10569-010) with 10% Fetal Bovine Serum (FBS; Gibco, 16000-044) and 1% Antibiotic-Antimytotic (Gibco, 15240-062). K562 cell line was cultured in IMDM Glutamax (Gibco, 31980-097)+10% FBS (Gibco, 16000-044)+1% Antibiotic-Antimytotic (Gibco, 15240-062). All cell lines were cultured at 37° C. and 5% $CO_2$. HEK293 and HCT116 cell lines were split when they reached 90% confluence and trypsinized with TrypLE Express (Gibco, 12604-021). K562 cell line was split before reaching a density of 1×10$^6$ cells/ml. The three cell lines were plated 48 hours prior to nucleofection and were at 70-80% of confluence (HEK293 and HCT116) before harvesting. Cells were counted using the Countess II FL system (Life Technologies). All cell lines were cultured in 96-well tissue culture plates post-nucleofection (Santa Cruz Biotechnologies, sc-204447). Adherent cell lines (HEK293 and HCT116) were plated on collagen coated 96-well plates post-nucleofection (Corning, 354236). All cell lines were authenticated using Geneprint 10 from Promega and the ATCC STR database. For each cell line, a wild type (WT) control plate was created by plating 200,000 cells/well. The cells were cultured for 48 hours and genomic lysate was prepared as described below.

Mobilized peripheral blood hematopoietic stem cells (HSCs) (AllCells #mPB018F) were thawed the day prior to nucleofection in DMEM/F12 Glutamax (Dulbecco Minimum Essential Medium, 10565-018, Gibco) supplemented with 100×MNEAA solution (Minimum Essential Medium Non Essential Amino Acids, 11140-050, Gibco) and 1000× 2-mercaptoethanol (21985-023, Gibco). HSCs were counted with a hemocytometer and plated at 1.5×10$^5$/ml in the same media with 100× StemSpan™ CC100 (02690, StemCell technologies), 1000× human recombinant TPO (Thrombo-POetin, 02522, StemCell Technologies) and 10,000× human recombinant GM-CSF (Granulocyte-Macrophage Colony-Stimulating factor, PHC6025, Gibco). 40 min after nucleofection, an equal volume of 2×Antibiotic-Antimytotic (Gibco, 15240-062) containing media was added to cells. The HSCs were incubated at 37° C. and 5% $CO_2$ and harvested 48 hours post nucleofection.

Compound Treatments

For compound treatments, sgRNP formation and nucleofection of 293T cells was performed as described above and cells were plated in 150 µl of culture medium. One hour after plating, 50 µl of media containing compound at 4× the final concentration were delivered to the cells. The DNA-PK inhibitor NU7441 (Leahy et al., "Identification of a highly potent and selective DNA-dependent protein kinase (DNA-PK) inhibitor (NU7441) by screening of chromenone libraries" Bioorg. Med. Chem. Lett. (2004) 14:6083-6087) delivered in a five point dose response across a concentration range from 25 µM-1.56 µM (1:2 dilutions). 48 hours after compound addition, cells were harvested and processed for genomic DNA preparation as described below.

Genomic Lysate

K562 cells and HSCs were transferred to a thermal cycler compatible plate and pelleted by centrifugation. After the media was gently aspirated, 50 µl EpiBio QuickExtract DNA extraction solution (Epicentre, QE09050) was added into each well and the plate was incubated at 37° C. for 15 minutes. For HEK293 and HCT116 cells, media was gently aspirated from 96-well culture plates and cells were gently rinsed with 1×Phosphate Buffered Saline (PBS). 50 µl of EpiBio QuickExtract DNA extraction solution was added to each well and the plates were incubated at 37° C. for 15 minutes. For all cell types, molecular biology grade water (Teknova) was added to each well to attain a concentration of 1000 genomic copies/µl for subsequent PCR reactions.

After addition of water, adherent cells were then transferred to thermal cycler compatible plates. All cell types were lysed (75° C. 10 min, 95° C. 5 min) and the lysate was stored at −80° C.

Lentivirus Cloning

For Cas9 expression, a *Streptococcus pyogenes* Cas9 cDNA codon optimized for expression in human cells including an N-terminal 3×FLAG tag as well as both an N- and C-terminal NLS signal as previously described (Smurnyy et al., "DNA sequencing and CRISPR-Cas9 gene editing for target validation in mammalian cells" Nat. Chem. Biol. (2014) 10:623-625), was synthesized as a gBlock and ligated into pLenti6 (Thermo Scientific). The Cas9 construct is expressed under a constitutive CMV promoter and expresses a blasticidin resistance marker co-transcriptionally with Cas9 using a T2A sequence. sgRNAs were cloned by synthesizing an oligo corresponding to the spacer sequence into a modified version of the pRSI16 lentiviral plasmid (Cellecta) containing a modified tracrRNA sequence modified as previous described including an RFP and puromycin expression cassette (Chen et al., "Dynamic imaging of genomic loci in living human cells by an optimized CRISPR/Cas system" Cell (2013) 155:1479-1491).

Lentivirus Cell Culture

Lentiviral particles were generated according to previously described methods (Hoffman et al., "Functional epigenetics approach identifies BRM/SMARCA2 as a critical synthetic lethal target in BRG1-deficient cancers" Proc. Natl. Acad. Sci. U.S.A. (2014) 111:3128-3133). 0.75×10$^6$ 293 T cells were plated in well of a 6-well plates 24 hours prior to transfection. For each well, cells were transfected using 1.5 µl of TransIT reagent diluted 55.1 µl of OPTI-MEM that was combined with 0.23 µg of the lentiviral plasmid and 0.28 µg of the Cellecta packaging mix (containing the psPAX2 and pMD2 plasmids that encode Gag/Pol and VSV-G respectively). Virus was harvested at 72 hours post transfection, aliquoted, and frozen at −80 C for later use. Viral titer was measured using the LentiX qPCR kit and was typically in the range of 5×106 TU/mL using this procedure. Stable Cas9 expression was established via lentiviral transduction at an MOI of approximately 1.0 followed by treatment with blasticidin for 96 hours to select for Cas9 expressing cells. Cas9 expression was confirmed by Western blot and by IF using a mouse monoclonal anti-Flag M2 antibody (Sigma). For sgRNA expression cells were transduced at an MOI of approximately 1 and treated with puromycin for 72 hours to select for sgRNA expressing cells.

Sequencing Library Generation for sgRNP Delivery

For sequencing sites of DNA repair following RNP delivery of sgRNA, PCR primers were designed to amplify uniquely a 180-220 base pair region of genomic DNA surrounding the target site using the Primer3 software package (Untergasser et al., "Primer3—new capabilities and interfaces" Nucleic Acids Res. (2012) 40:e115). Sequences were appended to the PCR primers such that the Illumina P5 adapter (CACTCTTTCCCTACACGACGCTCTTCCGATCT; SEQ ID NO: 643) would be on the 5' end of the amplicon and the P7 adapter (GGAGTTCAGACGTGTGCTCTTCCGATCT; SEQ ID NO:644) would be on the 3' end of the amplicon (sequencing primers are listed in Table 6 and Table 7).

In the first PCR 8,000 copies of genomic template were used in a 25 µl reaction with Q5 Master Mix (NEB, M0494L) and 500 nM final concentration of forward and reverse primers (each). The thermal cycler program for the first PCR is as follows: 1 cycle×1 min at 98° C., 35 cycles×10 sec at 98° C., 20 sec at 60° C., 30 sec at 72° C., 1 cycle×2 min at 72° C.

A second PCR was performed to add index barcodes to each sample. For this PCR, the product of the first PCR was diluted 100× and 8 µl of this dilution was used as template in a 25 µl reaction with Q5 Master Mix and 500 nM final concentration of each of the forward (i5, see Table 6) and reverse (i7, see Table 7) primers. The thermal cycler program for PCR2 is as follows: 1 cycle×1 min at 98° C., 12 cycles×10 sec at 98° C., 20 sec at 60° C., 30 sec at 72° C., 1 cycle×2 min at 72° C.

All wells were pooled after the second PCR and mixed by vortexing to form an Indexed Sample Pool (ISP). 450 µl of SPRISelect beads were added (Beckman Coulter, B24965AA) to a new microcentrifuge tube. 500 µl of the ISP were added to the beads. The mixture of beads and ISP was incubated for 10 minutes at room temperature. The tube was transferred to a magnetic separator and incubated for 4 minutes until the solution cleared. The beads were then rinsed carefully (so as to not disturb the pellet) with 1 ml 85% ethanol, and incubated for 30 seconds before removing the ethanol. Beads were air-dried on the magnetic separator for 10 minutes. The library was then eluted from the beads by adding 500 µl low EDTA TE buffer (10 mM Tris, 0.5 mM EDTA, pH 8.0). Sequencing libraries were evaluated by high sensitivity gel electrophoresis (Fragment Analyzer (Advanced Analytical Technologies)). Sequencing libraries were then quantified using the KAPA Library Quantification Kit for Illumina Systems (Kapa Biosystems, KK4824) and were sequenced on a MiSeq sequencer (Illumina). MiSeq Reagent Kit v2 (300 cycles) (Illumina MS-102-2002) was used for paired-end sequencing (2×151), yielding 4,000-20,000 reads/sample depending on level of multiplexing.

Sequencing Library Generation for Lentiviral sgRNA Delivery

Protocols for library generation and sequencing of DNA repair structures following lentiviral delivery of the sgRNA were similar to those described above with the following minor modifications. For PCR1 primers were appended with partial 'Nextera' Illumina P5 adapter (TCGTCGGCAGCGTCAGATGTGTATAAGAGACAG; SEQ ID NO: 645) and P7 adapter (GTCTCGTGGGCTCGGAGATGTGTATAAGAGACAG; SEQ ID NO: 646) sequences (sequencing primers are listed in Tables 6 and 7). For PCR2, standard Nextera v2 index and sequencing primers were used such that the adapter TCGTCGGCAGCGTC (SEQ ID NO: 647) would be on the 5' end and GTCTCGTGGGCTCGG (SEQ ID NO: 648) would be on the 3' end of the amplicon. Libraries were quantified using an in-house SYBR green qPCR protocol using primers to P5 and P7, and subsequently sequenced with 2×250b reads using MiSeq Reagent Kit v2 (500 cycles) (Illumina MS-102-2003).

Multiple Target Single Spacer

Approximately 16,000 target sequences were identified that exist with at least one exact copy of the target sequence in the hg38 reference genome yielding 192,955 sites with an average of 12 sites per target sequence. A filter was applied to this list to extract the target sequences where at least 50% of the sites could be uniquely amplified resulting in 51 targets covering 494 sites in the genome with an average of 10 sites per target sequence. From this group, 29 targets were tested experimentally covering 179 sites with an average of 6 sites that could be amplified uniquely per target and their DNA repair outcomes were profiled. A filter was placed on the resulting data to exclude sites with a cleavage efficiency of less than 1% yielding a final group of 21 targets covering 127 sites in the genome.

Amplicon Sequencing Pipeline and Repair Classification

FASTQ read pairs generated by the Illumina MiSeq were first processed using cutAdapter to trim adapter sequences. Read pairs were then stitched into a single contig using FLASH (Maga' and Salzberg, "FLASH: fast length adjustment of short reads to improve genome assemblies" Bioinformatics (2011) 27:2957-2963).

The contigs were aligned to the reference genome using the "mem" algorithm of bwa. The resulting SAM files were subsequently filtered to only retain reads that overlap with the on-target amplicon location using a relational database of the known on-target amplicon location. The location of an indel within a given read was determined from the CIGAR string (Li et al., "The Sequence Alignment/Map format and SAMtools" Bioinformatics (2009) 25:2078-2079).

When an aligner such as bwa attempts to align a read containing an indel to a reference genome and discovers multiple, equally good local alignments of the indel, the aligner arbitrarily selects one of the local indel alignments. To eliminate this ambiguity and attain a consistent indel justification, a "secondary alignment" of the indel in each mutant read was then performed. This secondary aligner is a custom-written Python function that re-discovers the multiple, equally good local alignments for each indel and then selects a local indel alignment deterministically using the following algorithm. First, it identifies the start and end of each possible indel relative to the cut site. Second, for each possible local alignment, it calculates its "edge distance," i.e., the minimum of the distance of the indel start to the cut site and the distance of the indel end to the cut site. Third, it selects the local indel alignment with the smallest edge distance. If two local indel alignments have the same edge distance, it chooses the one with the smaller start site. Practically speaking, the secondary aligner chooses the alignment that is closest to the cut-site as is most biologically plausible.

Following secondary alignment, reads were then categorized as "mutant" if they contained an indel within ±5 base pairs of the cut site; otherwise, they were categorized as "wild type". Each mutant read was assigned to an "indel class" based on the indel type (insertion or deletion), start site, and length.

Heat Maps

Heat maps were generated from the processed sequencing data as follows. For a given target site, the frequencies of insertions and deletions were tallied by length (for 1 nucleotide insertions, the four nucleotides were tallied separately). Each column in the heat map represents a different target site. The color intensities in the cells correspond to frequency as a fraction of mutant reads, with the color scale ranging from 0 to 0.2 (saturation). The editing efficiency of each target site is indicated in the orange bar plot above the heat map.

MH Mask

A stringent mask for microhomology deletions was applied (FIG. 12D). For deletions with multiple possible local alignments (see above), a predicted microhomology score was first computed for each of the local alignments and then the maximum (most conservative) across all of these was retained. Deletions with a maximum microhomology score >3 (i.e., deletions with more than one basepair of microhomology are masked) were then masked (Bae et al. "Microhomology-based choice of Cas9 nuclease target sites" (2014) Nat. Methods 11:705-706).

Clustering

Cluster analysis was applied to the repair outcomes at different genomic loci as follows. First, a binary vector, or bit string, was used as per Willett et al., "Implementation of Nearest-Neighbor Searching in an Online Chemical Structure Search System" Journal of Chemical Information and Computer Sciences (1986) 26:36-41, to encode the indels observed at each locus. All possible insertions (based on start site and length) that start within +5 bp of the cut site and with length ≤10 were considered (there were 110 possibilities); all possible deletions (based on start site and length) fully enclosed in ±25 bp of the cut site and with at least 1 bp present in ±5 bp of the cut site were considered (there were 906 possibilities). For a given genomic locus, this vector of possible indels was scored as follows: any indel among the 10 most frequent by fraction of mutant reads for that locus was assigned a value 1, otherwise 0. Genomic loci that had less than 500 aligned read contigs or that had less than 10 observed indel classes were filtered out to avoid biasing downstream clustering performance metrics.

Next, given these bit strings for the genomic loci, a similarity matrix was computed using the Jaccard/Tanimoto similarity coefficient (Jaccard, P, "The distribution of flora in the alpine zone" New Phytologist (1912) 11:37-50); Rogers and Tanimoto, "A computer program for classifying plants" Science (1960) 132:1115-1118), which is the ratio of the number of elements in the intersection of two bit strings to the number of elements in their union:

$$J = M_{11}/(M_{10} + M_{01} + M_{11})$$

where $M_{11}$ is the number of elements for which both bit strings have a value of 1, $M_{10}$ is the number of elements for which the first bit string (but not the second) has a value of 1, and $M_{01}$ is the number of elements for which the second bit string (but not the first) has a value of 1. This similarity matrix was used as the input to Affinity Propagation (AP) clustering (Jaccard, P, "The distribution of flora in the alpine zone" New Phytologist (1912) 11:37-50), an algorithm for which the number of clusters is optimized internally, rather than being specified as a parameter. The AP algorithm identifies "exemplars"—data points that are representative of other data points—by iteratively updating one of two matrices based on values in the other matrix: a "responsibility" matrix, wherein r(i, k) indicates how representative a potential exemplar k is of data point i compared to other potential exemplars, and an "availability" matrix, wherein a(i, k) indicates how "appropriate" it would be for data point i to choose potential exemplar k based on the evidence that k could also be an exemplar for other data points (Frey and Dueck, "Clustering by passing messages between data points" Science (2007) 315:972-976). The number of exemplars identified then becomes the number of clusters, and each non-exemplar data point is assigned to an exemplar.

To determine if clustering based on repair outcomes led to partitions that were similar to those corresponding to spacer sequence labels, the Adjusted Rand Index (ARI) was employed (Hubert and Arabie, "Comparing partitions" Journal of Classification (1985) 2:193-218.). Given a "ground truth" partitioning U of a set of labeled data points and an observed partitioning V, the Rand Index (RI) (Rand, "Objective criteria for the evaluation of clustering methods" Journal of the American Statistical Association 66:846-850) is the fraction of pairs of data points that are concordant across U and V (i.e., partitioned together in U and partitioned together in V, or in different partitions in U and in different partitions in V). The ARI is a version of the RI that is corrected for the expectation under randomness, such that an ARI of 0 indicates that the partition membership of V is random and an ARI of 1 indicates that the partition membership of V perfectly matches that of U. For a detailed explanation and demonstration, see the Supplementary Information of (Yeung and Ruzzo, "Principal component analysis for clustering gene expression data" Bioinformatics (2001) 17:763-774).

Figures 1B, 1C:
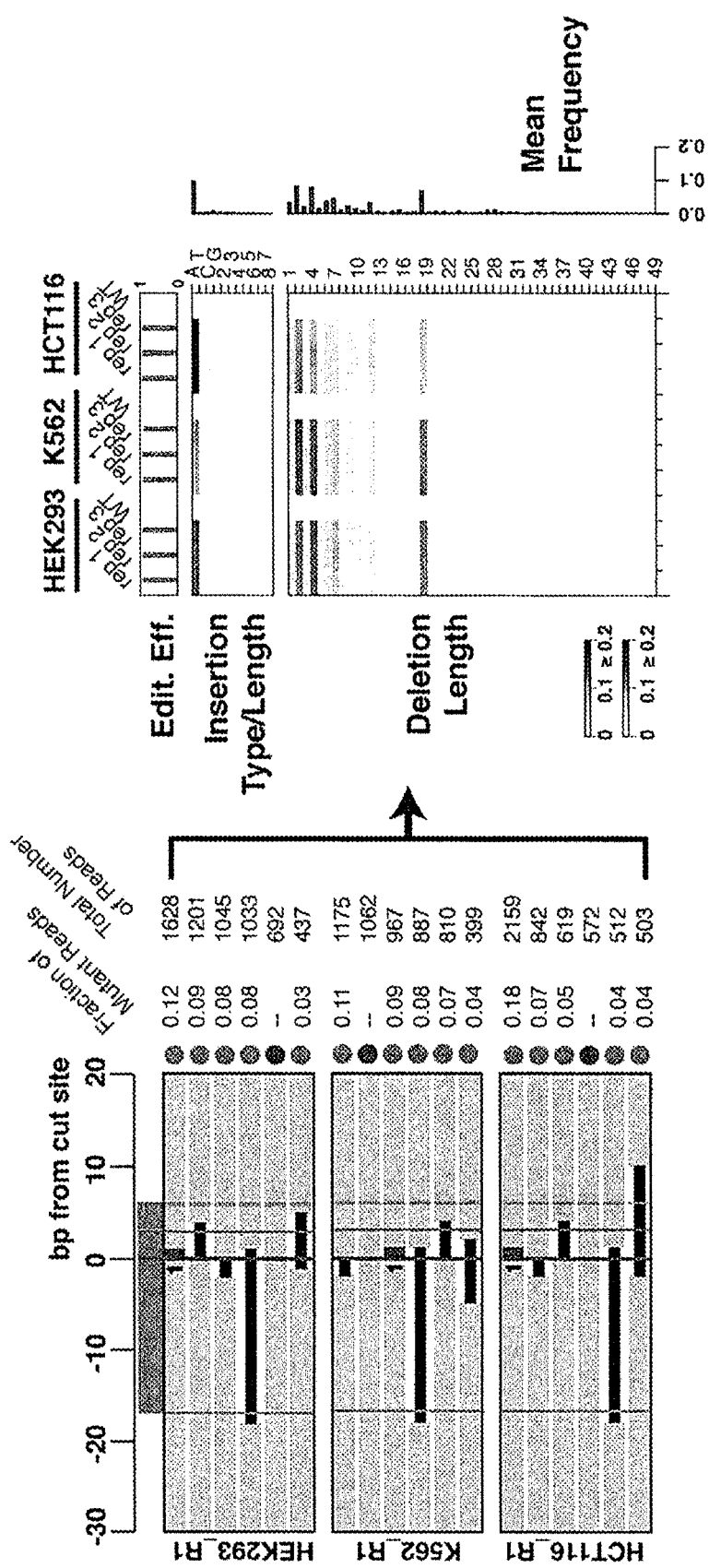

The following figures display data and outcomes from the examples herein:

FIGS. 1A-1C depict the profiling of DNA repair outcomes after Cas9 cleavage. FIG. 1A: (i), Cell editing workflow. (ii) Sequencing library steps. (iii) Indel class visualization following Cas9 cleavage at a target (SEQ ID NO: 624) in JAK1 (Spacer 54, Table 1). The position of each insertion class and deletion class is plotted relative to the cut site. Throughout the text, indel visualizations are annotated as follows: (right) each class is annotated with frequency (fraction of total reads and fraction of mutant reads) and the number of reads observed. Classes are ranked by frequency (classes with frequency <0.01 (fraction of mutant reads) are not displayed). FIG. 1B: Visualization of the five most frequent indel classes and wild-type (WT) at the same target in three cell lines (the first replicate (R1) of each is displayed). FIG. 1C: An indel frequency heat map by length for each cell line (three replicates and WT control shown). Throughout the text, heat maps are annotated as follows: insertions of 1 to 8 nucleotides are displayed. Single base insertions are separated by nucleotide (A, T, C, G). Deletion lengths of 1 to 50 nucleotides are displayed. The color intensity scales with frequency as a fraction of mutant reads up to 0.2. The bar graph on the right displays the mean frequency of each indel 1. The bar graph above displays editing efficiency ("Edit. Elf.") as a fraction of total reads.

FIGS. 2A-2C show that DNA repair profiles are unique to each spacer sequence. FIGS. 2A and 2B: A matrix of the (Jaccard/Tanimoto) similarity of the top ten indel classes across pairs of 69 target sites in HEK293, K562, and HCT116 cell lines comparing sgRNP-only delivery of reagents (FIG. 2A) and sgRNP and constitutive delivery of reagents (FIG. 2B). Targets with the same spacer label (within the ticks) are different experimental replicates of each cell type targeted by the same sgRNA. A similarity score of 1 represents complete overlap of the top ten indel classes between two sites, whereas 0 represents no overlap of the top ten indel classes between two sites. FIG. 2C: Adjusted Rand Index (ARI) values from cluster analysis (see Examples) of FIG. 2A and FIG. 2B.

Figure 3B:
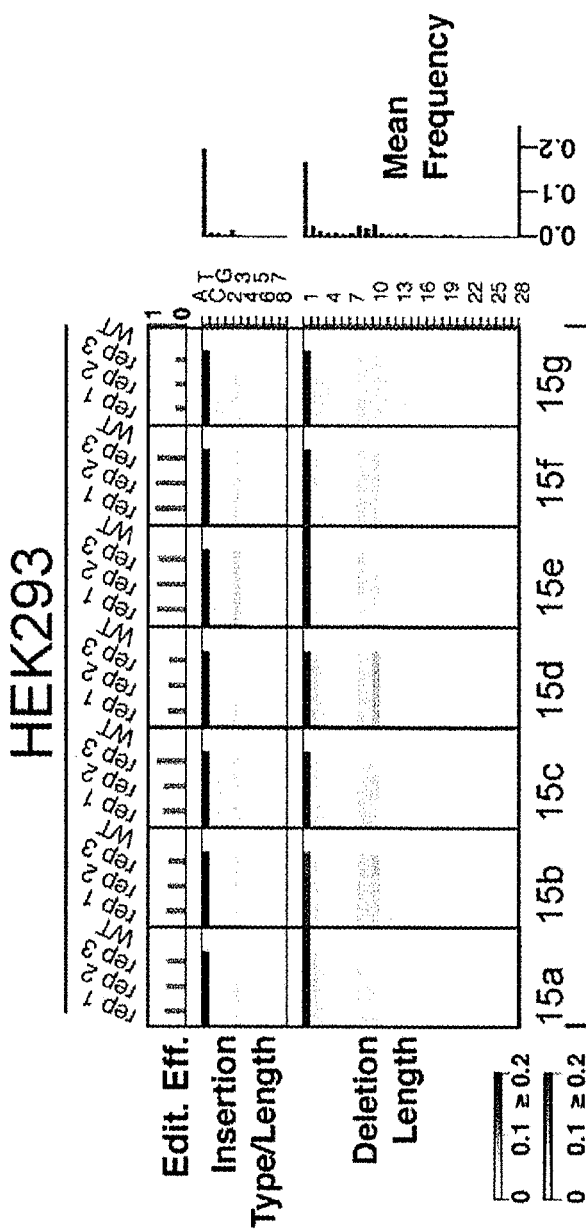
Figure 3C:
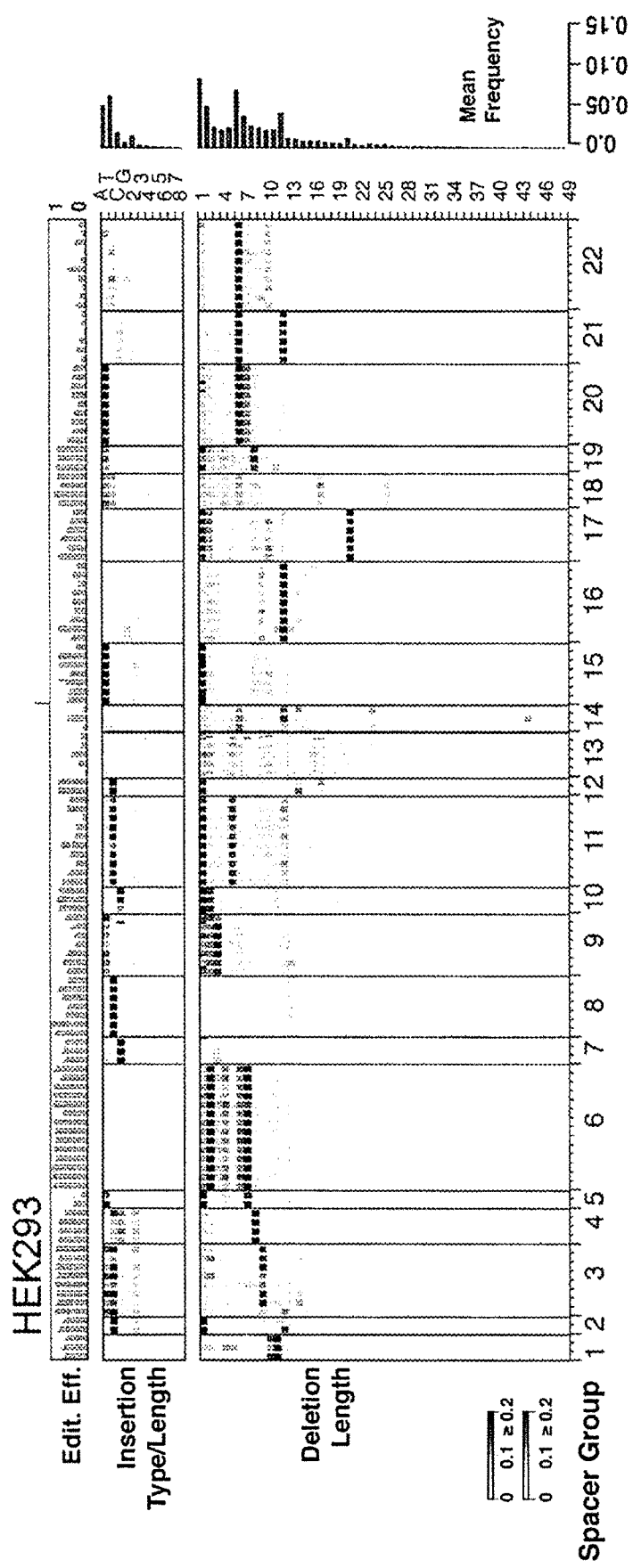
Figure 3D:
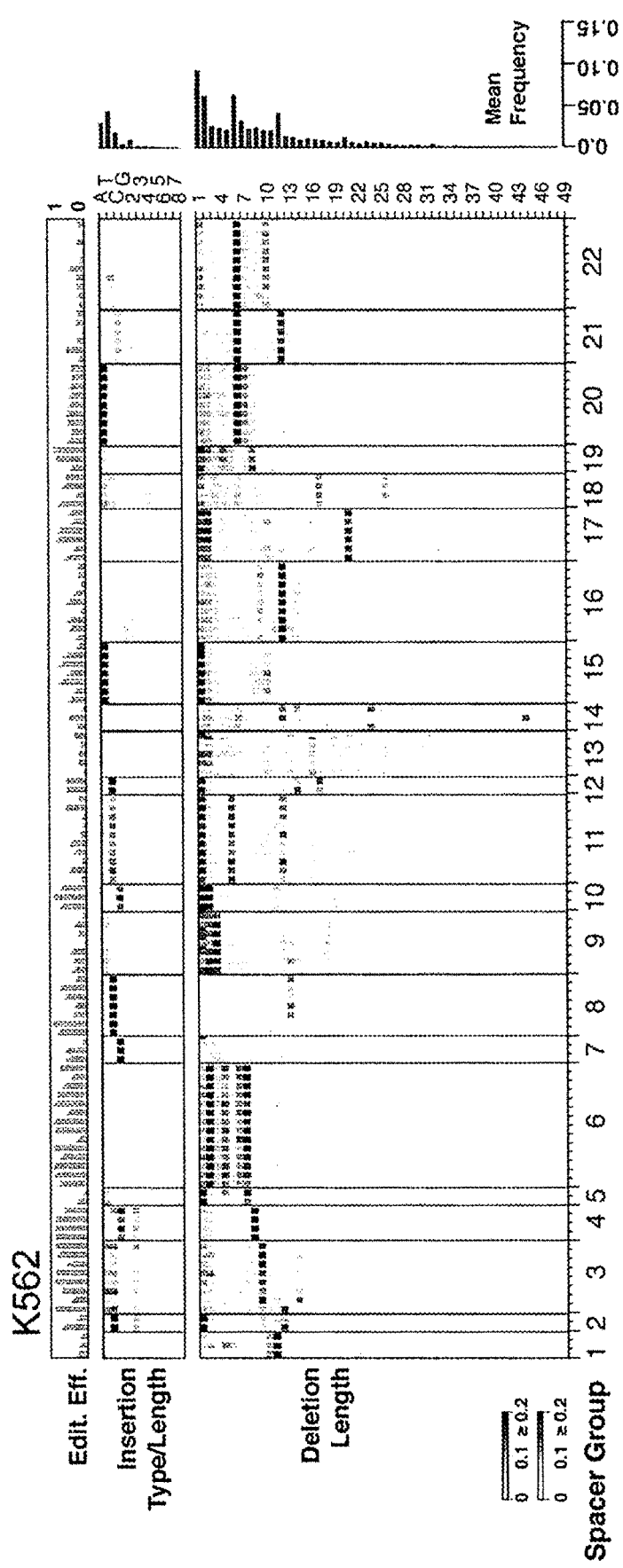
Figure 3F:
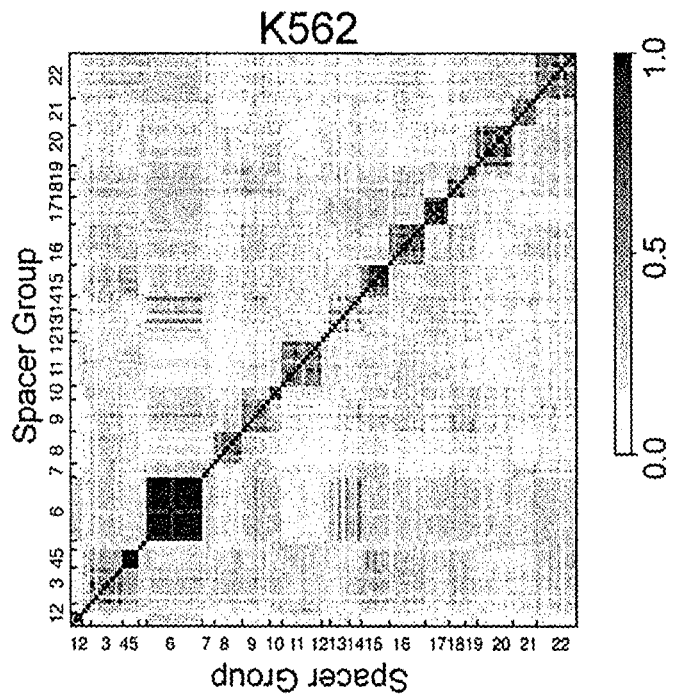
Figure 3E:
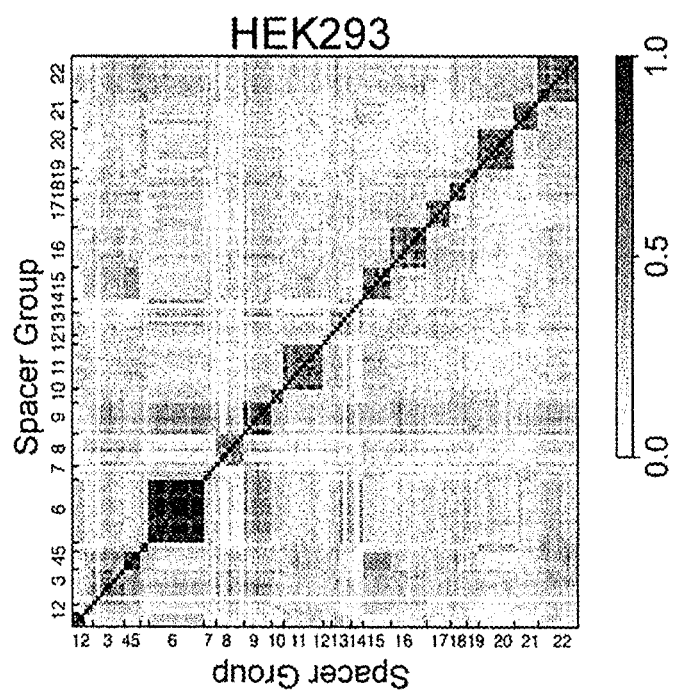

FIGS. 3A-3F show the results of an experiment using multiple target single spacer (MTSS) sequences and display that DNA repair outcomes at Cas9-mediated DSBs are sequence-dependent. FIG. 3A: Genomic coordinates (hg38) that contain exact copies of the spacer 15 sequence (SEQ ID NO: 649). FIG. 3B: A heat map of the frequencies of indels by length for the seven targets listed in FIG. 3A from replicate experiments plus wild-type (WT) controls 48 hours after nucleofection into HEK293 cells. FIG. 3C: A heat map of the frequencies of indels by length in HEK293 cells for 22 different spacer groups (outlined in grey boxes). Each target sequence occurs at 2-14 times in the genome. For each target site within each spacer group, three experimental replicates and a WT control are displayed (within the minor ticks). FIG. 3D: A heat map of the frequencies of indels by length in K562 cells for the same 22 spacer groups (outlined in grey boxes) as described for FIG. 3C. FIGS. 3E and 3F: A matrix of the (Jaccard/Tanimoto) similarity of the top ten indel classes across pairs of target sites in HEK293 cells (FIG. 3E) and K562 cells (FIG. 3F). Targets with the same spacer label (within the ticks) are different genomic loci targeted by the same sgRNA. ARI values from subsequent cluster analysis are displayed.

Figure 4A:
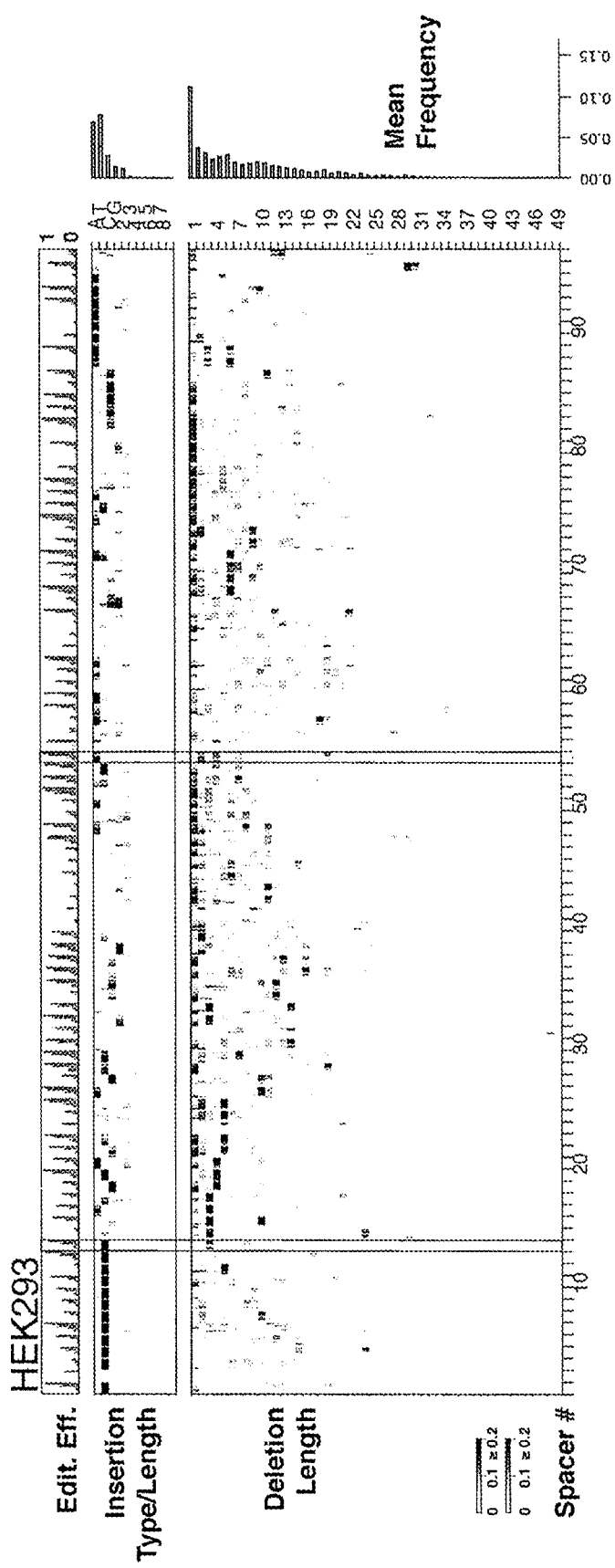
Figures 4B, 4C:
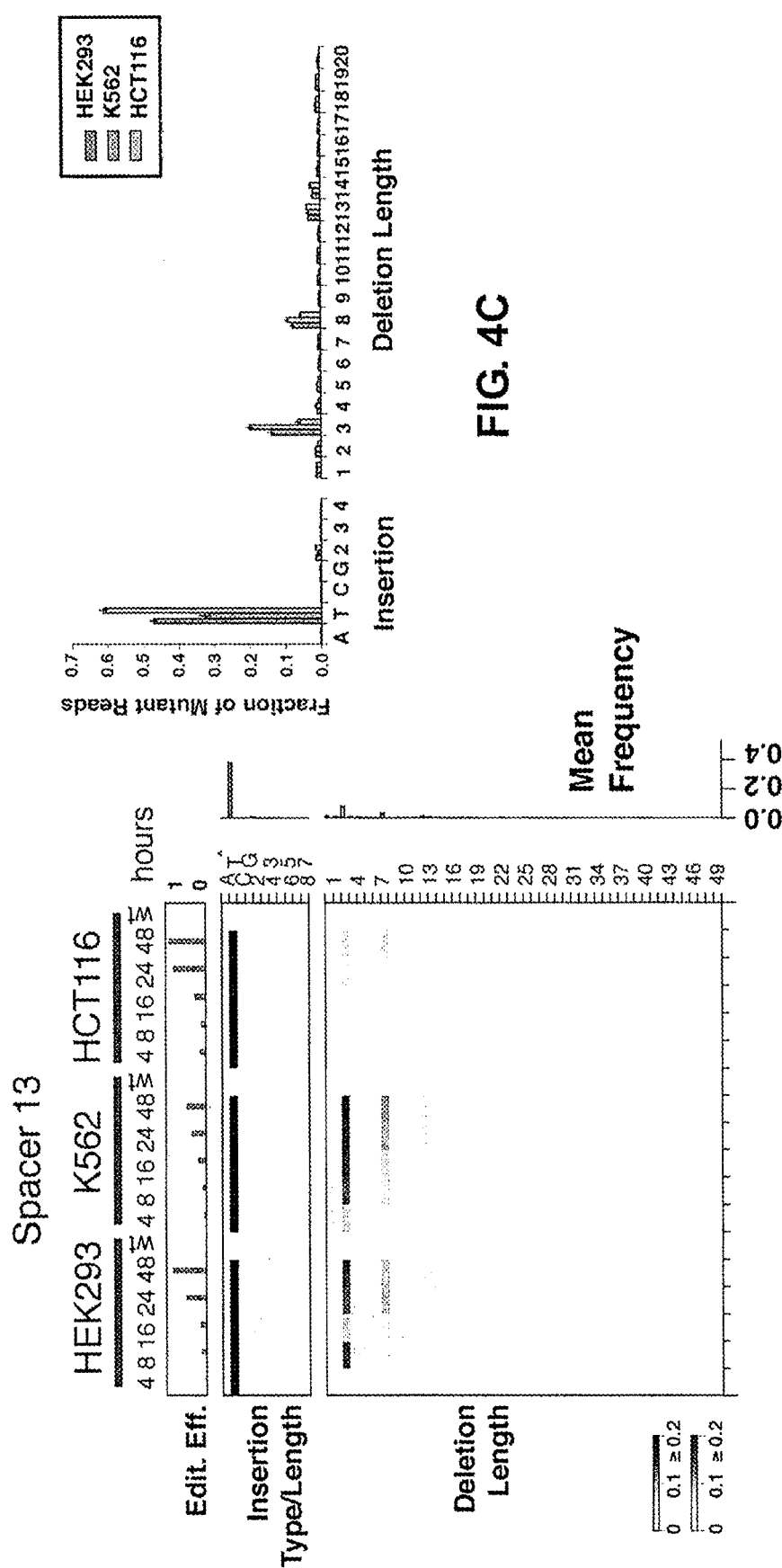
Figures 4D, 4E:
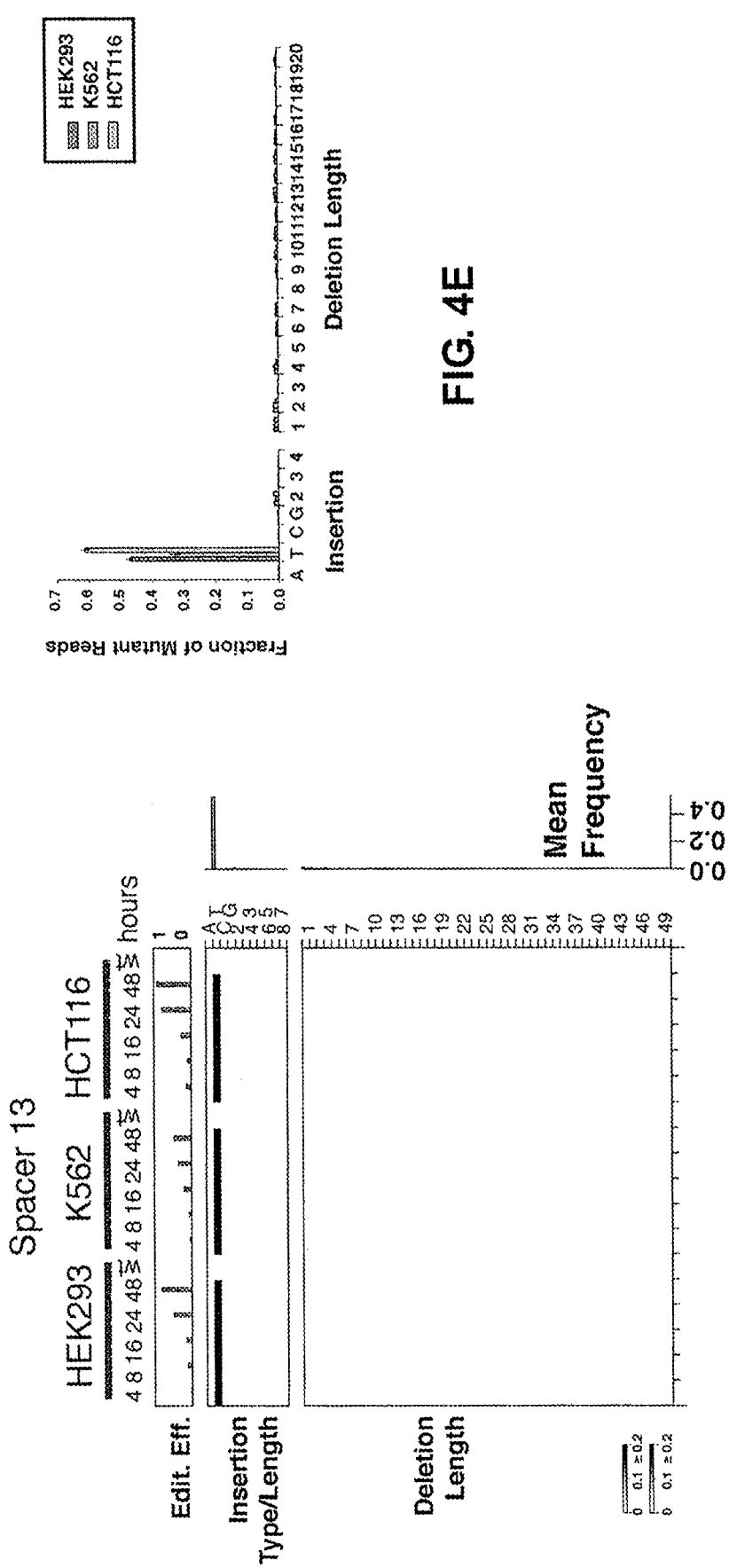
Figure 4G:
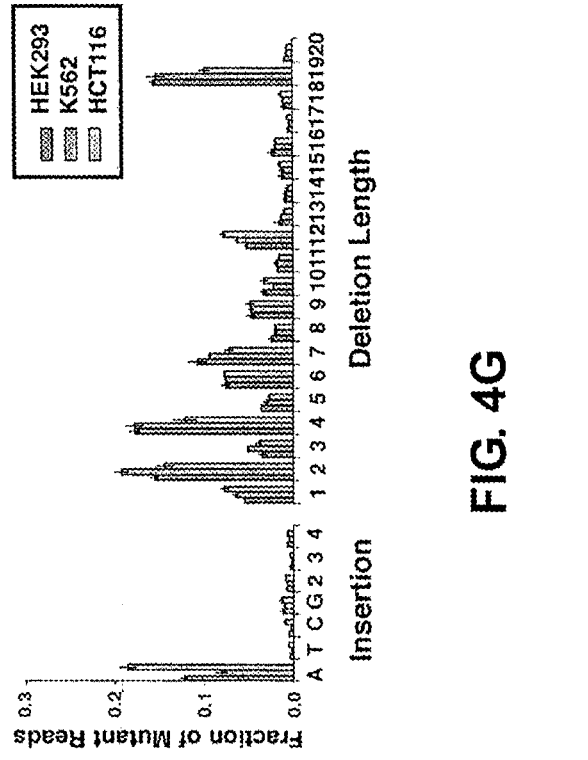
Figure 4F:
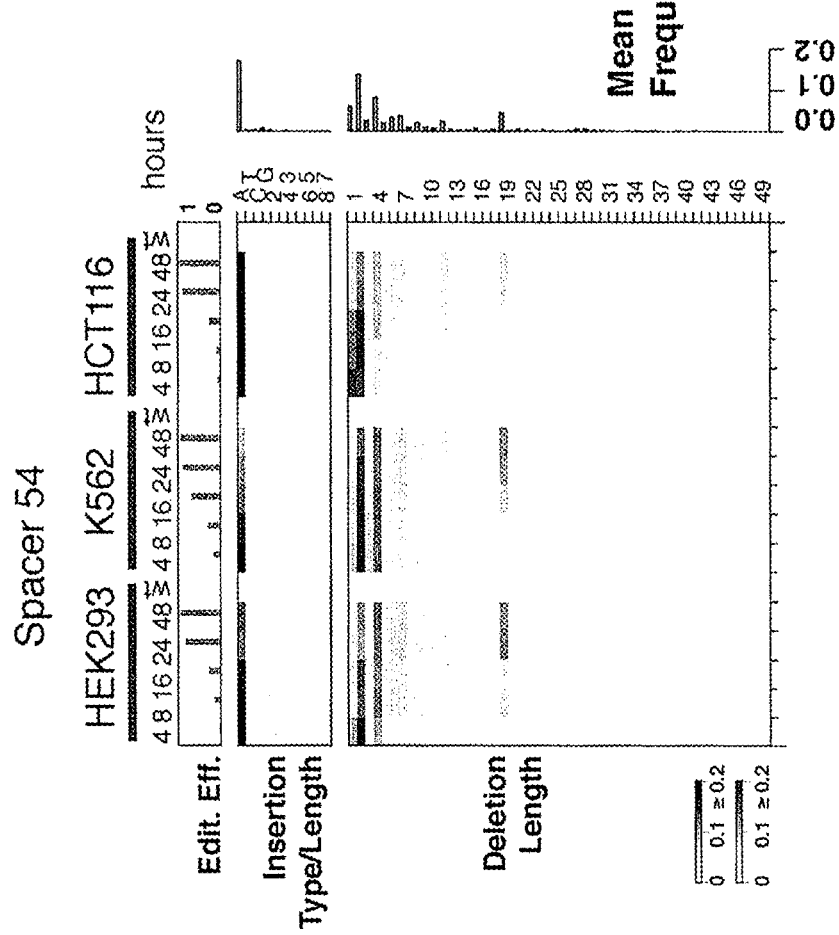

FIGS. 4A-4I show that the distribution of DNA repair outcomes after Cas9 cleavage changes over time. FIG. 4A: Heat map of DNA repair outcomes in HEK293 cells for 96 different spacers, each of with three experimental replicates for multiple time points (4, 8, 16, 24 and 48 hours) and a wild type control (within the minor ticks). FIGS. 4B and 4F: Heat maps for the indicated spacer (FIG. 4B: spacer 13; FIG. 4F: spacer 54) showing single experiments at each time point for three cell lines. FIGS. 4C and 4G: Bar graphs of indel frequencies by length for the indicated spacer (FIG. 4C: spacer 13; FIG. 4G: spacer 54) displayed as a fraction of mutant reads (mean and standard deviation across triplicates) in three cell lines at the 48 hour time point. FIGS. 4D and 4H: A heat map of spacer 13 (FIG. 4D) or spacer 54 (FIG. 4H) showing single experiments at each time point for three cell lines after applying a stringent microhomology mask (MH_score >3, see FIG. 12D). FIGS. 4E and 4I: Bar graph of indel frequencies by length displayed as a fraction of mutant reads (mean and standard deviation across triplicates) at the 48 hour time point for spacer 13 (FIG. 4E) or spacer 54 (FIG. 4I) after applying a stringent microhomology mask (MH_score >3).

Figure 5A:
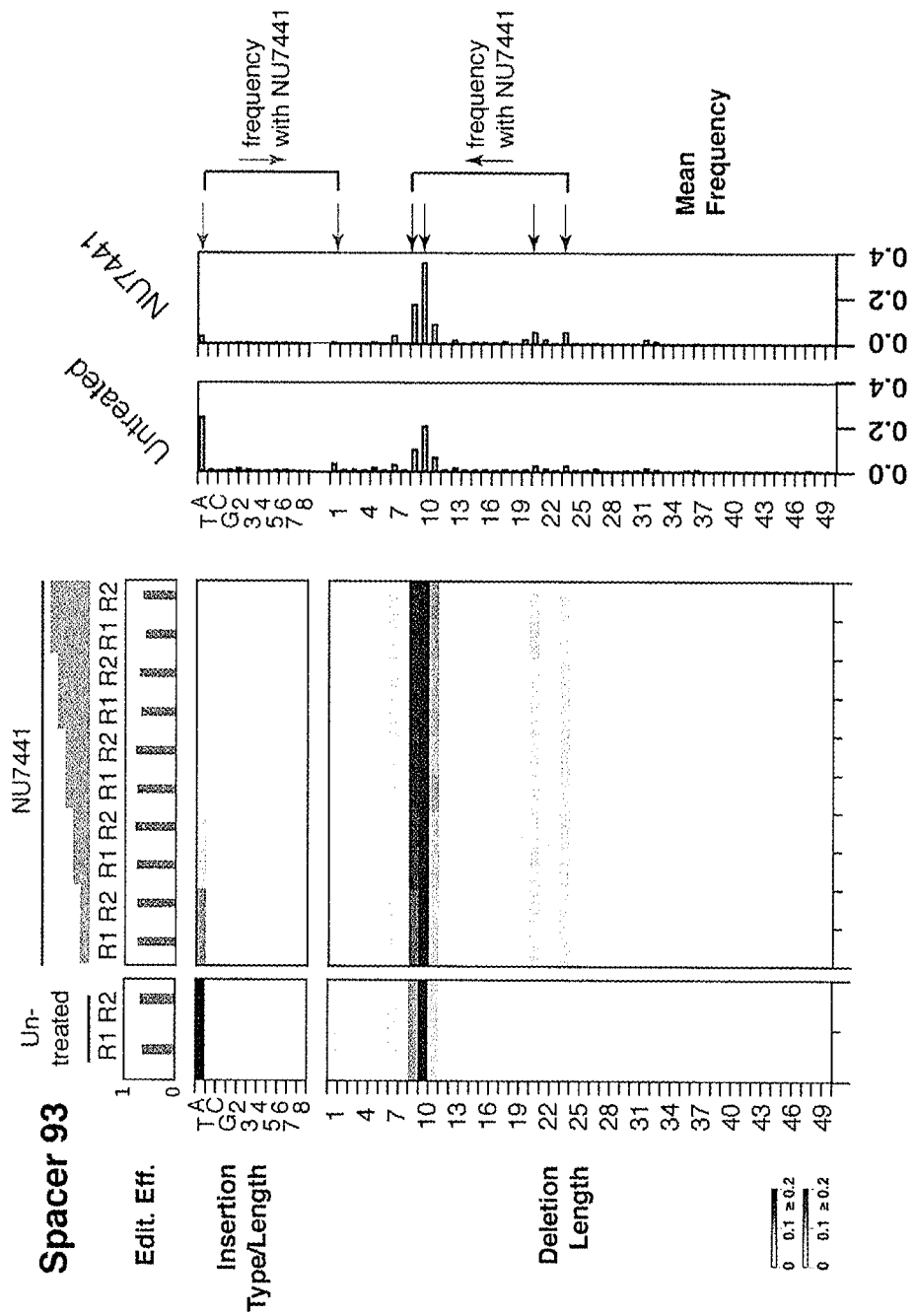
FIGS. 5A-5D show that chemical perturbation of c-NHEJ promotes a subset of DNA repair outcomes after Cas9 cleavage.
Figure 5B:
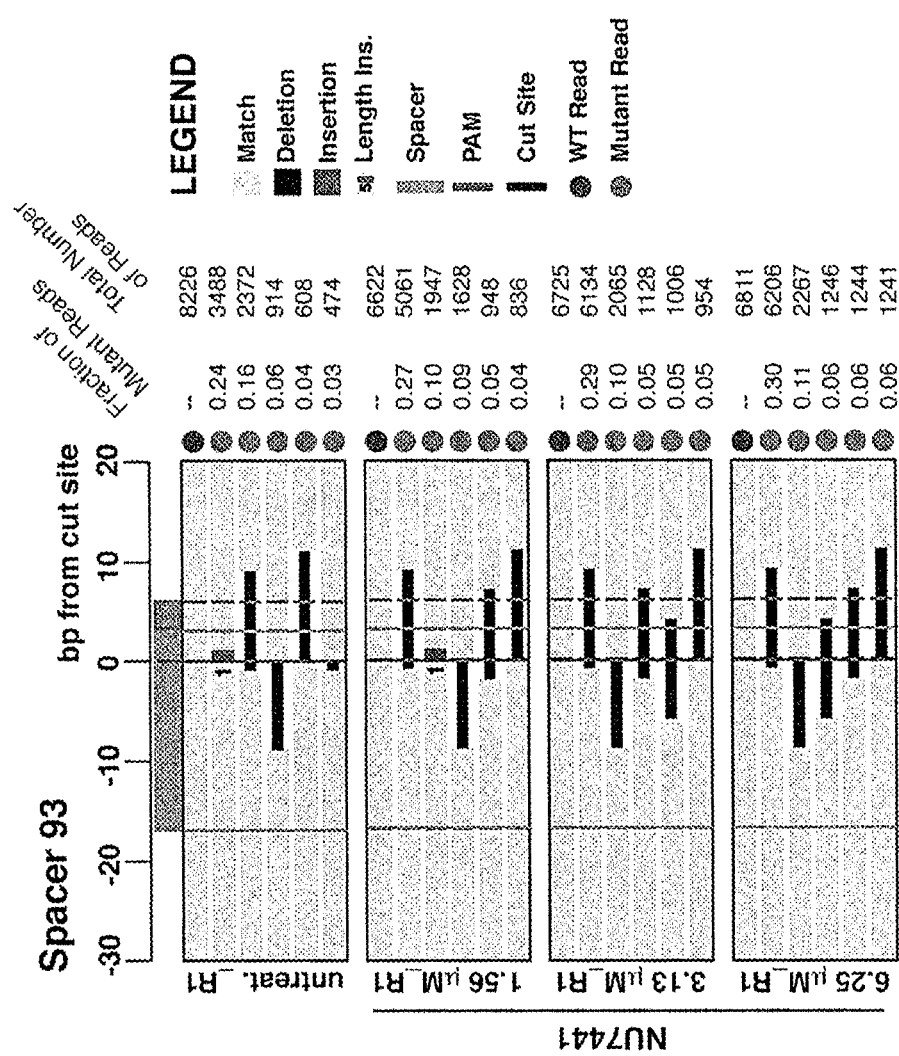
Figure 5C:
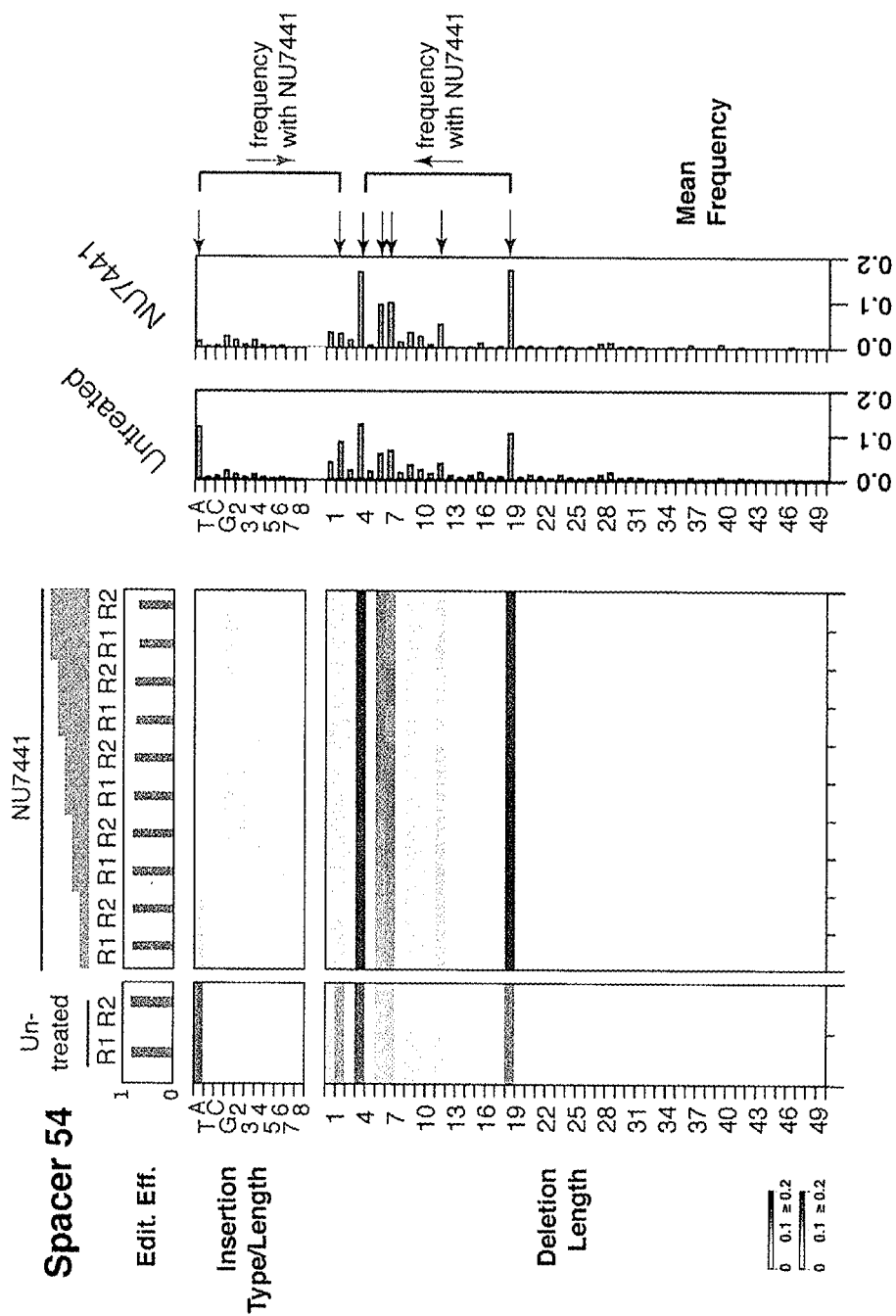
Figure 5D:
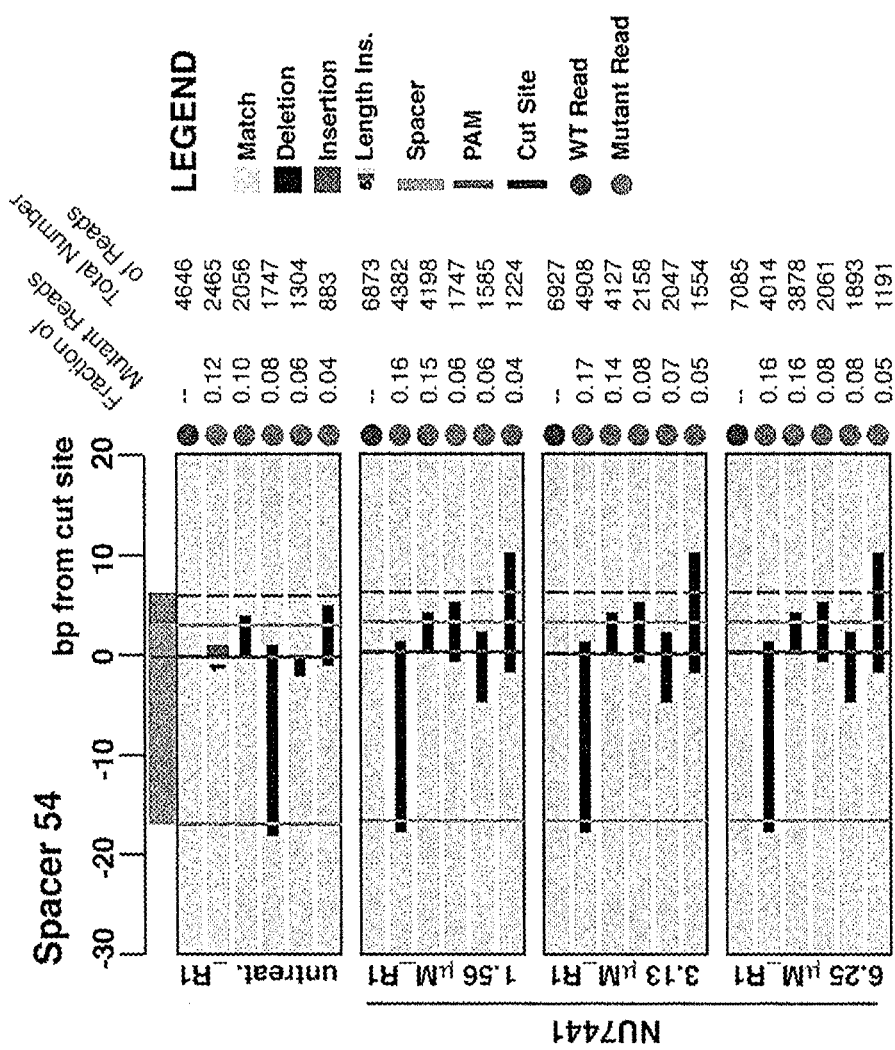

FIGS. 5A-5D show that chemical perturbation of c-NHEJ promotes a subset of DNA repair outcomes after Cas9 cleavage. FIG. 5A: Heat map representing DNA repair classes present 48 hours after sgRNP introduction into HEK293T cells (Spacer 93, Table 1). Cells were treated with the DNA-PK inhibitor NU7441 (Leahy et al., "Identification of a highly potent and selective DNA-dependent protein kinase (DNA-PK) inhibitor (NU7441) by screening of chromenone libraries" Bioorg. Med. Chem. Lett. (2004) 14:6083-6087) in a 2 fold dilution series ranging from 1.56 μM to 25 μM. Each concentration was performed in duplicate. Untreated control replicates are shown on the right. Mean frequency plots are shown on the left comparing untreated samples with samples treated with DNA-PK inhibitor NU7441 (average mean frequency of entire dilution series 1.56 μM-25 μM displayed). Arrows indicate the repair classes that change frequency after treatment with NU7441 (down arrow indicates a decrease in mean frequency in the presence of inhibitor, up arrow indicates an increase in mean frequency in the presence of inhibitor). FIG. 5B: Visualization of the five most frequent indel classes and wild-type (WT) of the same target shown in FIG. 5A (the first replicate (R1) of each is displayed). NU7441 inhibitor concentrations 1.56, 3.13 and 6.25 μM are shown. FIG. 5C: Same as in FIG. 5A for target spacer 54 (Table 1). FIG. 5D: Same as in FIG. 5B for target spacer 54.

Figure 6A:
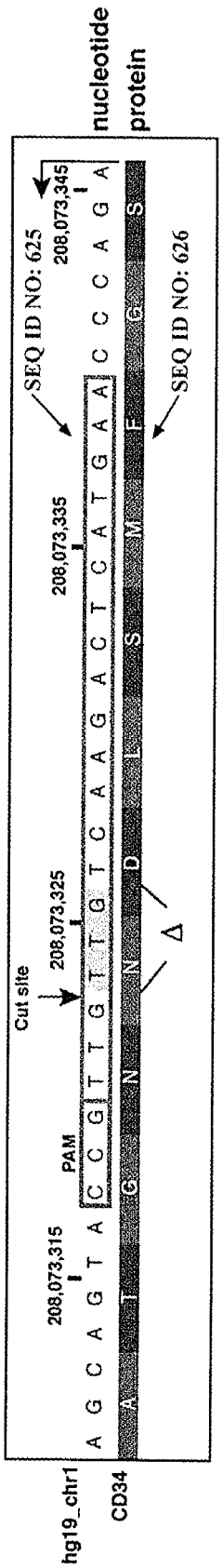
FIGS. 6A-6E show high frequency in-frame mutation after Cas9 cleavage of a target in CD34.
Figure 6B:
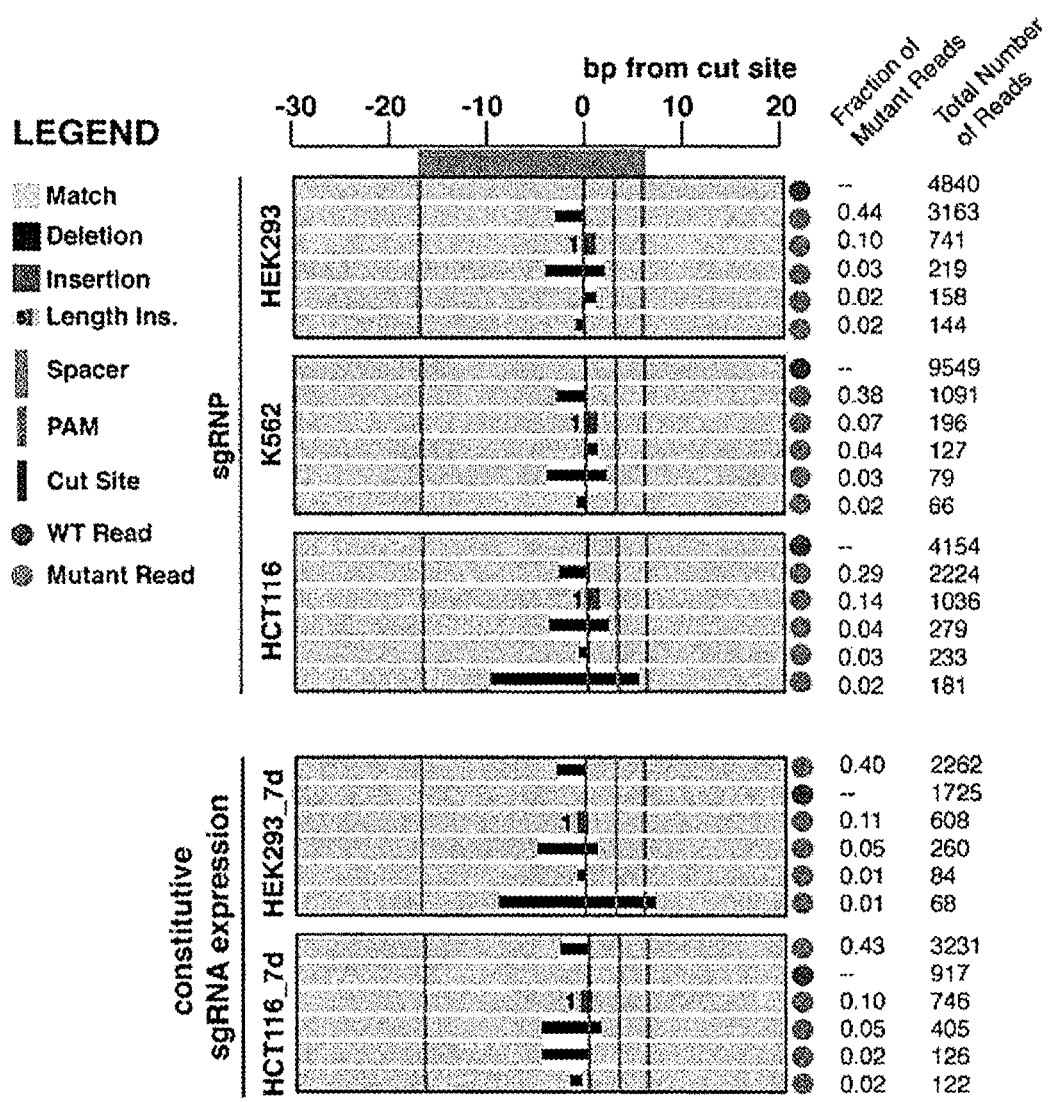
Figure 6C:
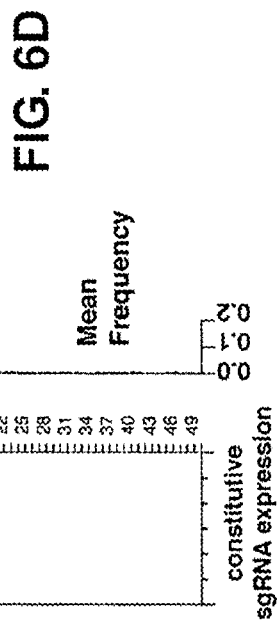
Figure 6D:
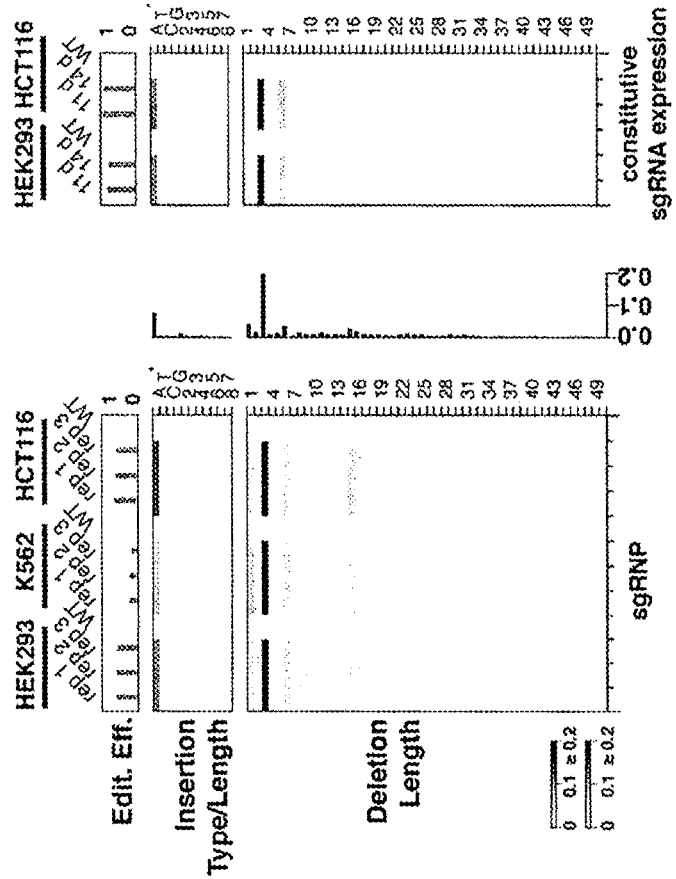
Figure 6E:
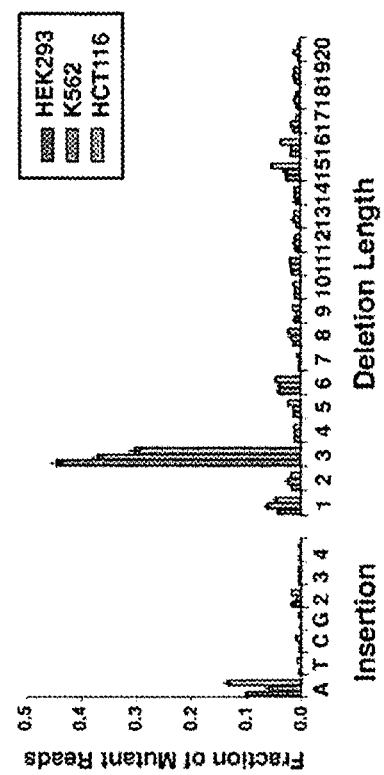

FIGS. 6A-6E show high frequency in-frame mutation after Cas9 cleavage of a target in CD34. FIG. 6A: Genomic location (hg19 coordinates; SEQ ID NOS: 625 and 626) of a target in the CD34 gene with the protospacer adjacent motif (PAM) and Cas9 cut site indicated by an arrow. The entire protospacer sequence is boxed (Spacer 16 in Table 1). Deletion of the three nucleotide sequence, TTG, shaded, is the most frequent indel after either sgRNP delivery or constitutive expression of sgRNA to direct Cas9 cleavage activity to this site. FIG. 6B: A visualization of a subset of the indel classes (the five most frequent) and wild-type (WT) at the CD34 target in three different cell lines using sgRNP delivery and in two different cell lines for constitutive expression of Cas9/sgRNA as indicated on the left (a single replicate of each is displayed). FIG. 6C: A heat map of the frequencies of indels by length at the CD34 target in HEK293, K562 and HCT116 cell lines (three experimental replicates of each and a WT control) 48 hours post-sgRNP delivery. FIG. 6D: A heat map of the frequencies of indels by length at the CD34 target in HEK293 and HCT116 cell lines 11 and 14 days post constitutive expression of Cas9/sgRNA (single replicate of two different time points and a WT control (Cas9-only)). FIG. 6E: Bar graph of indel frequencies by length displayed as a fraction of mutant reads (mean and standard deviation across three experimental replicates) in three cell lines 48 hours post sgRNP delivery.

Figure 7A:
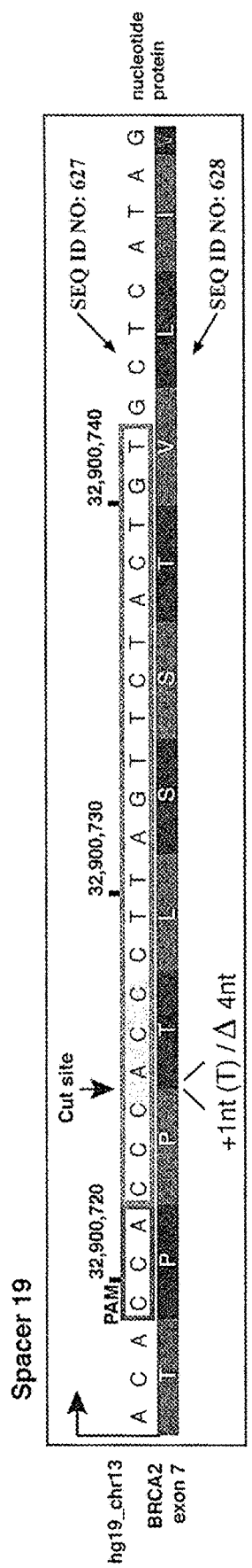
Figure 7B:
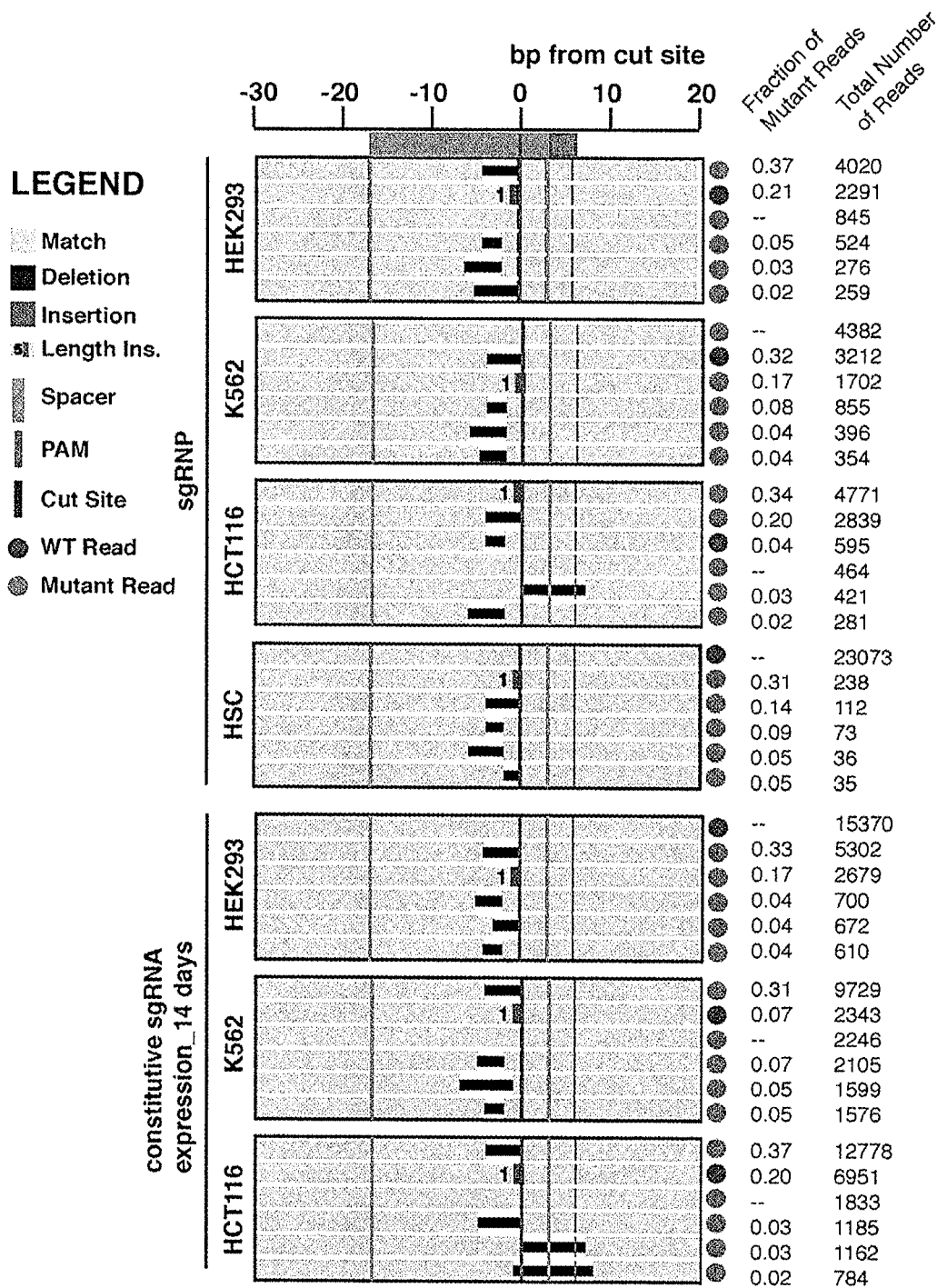
Figure 7E:
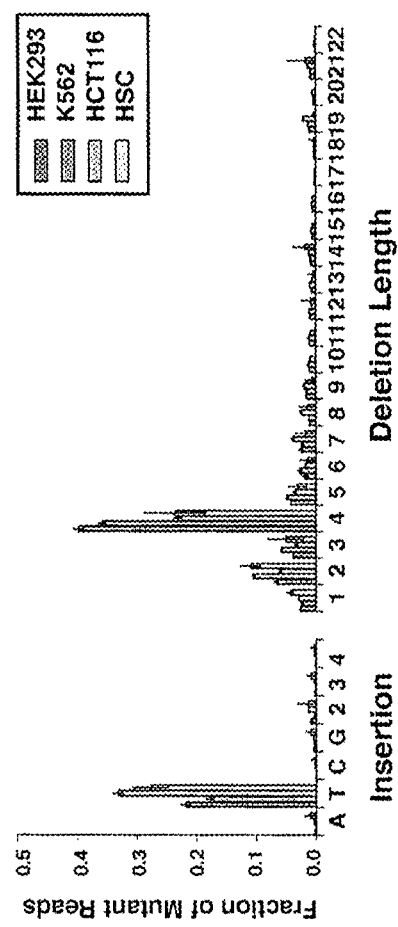
Figure 7F:
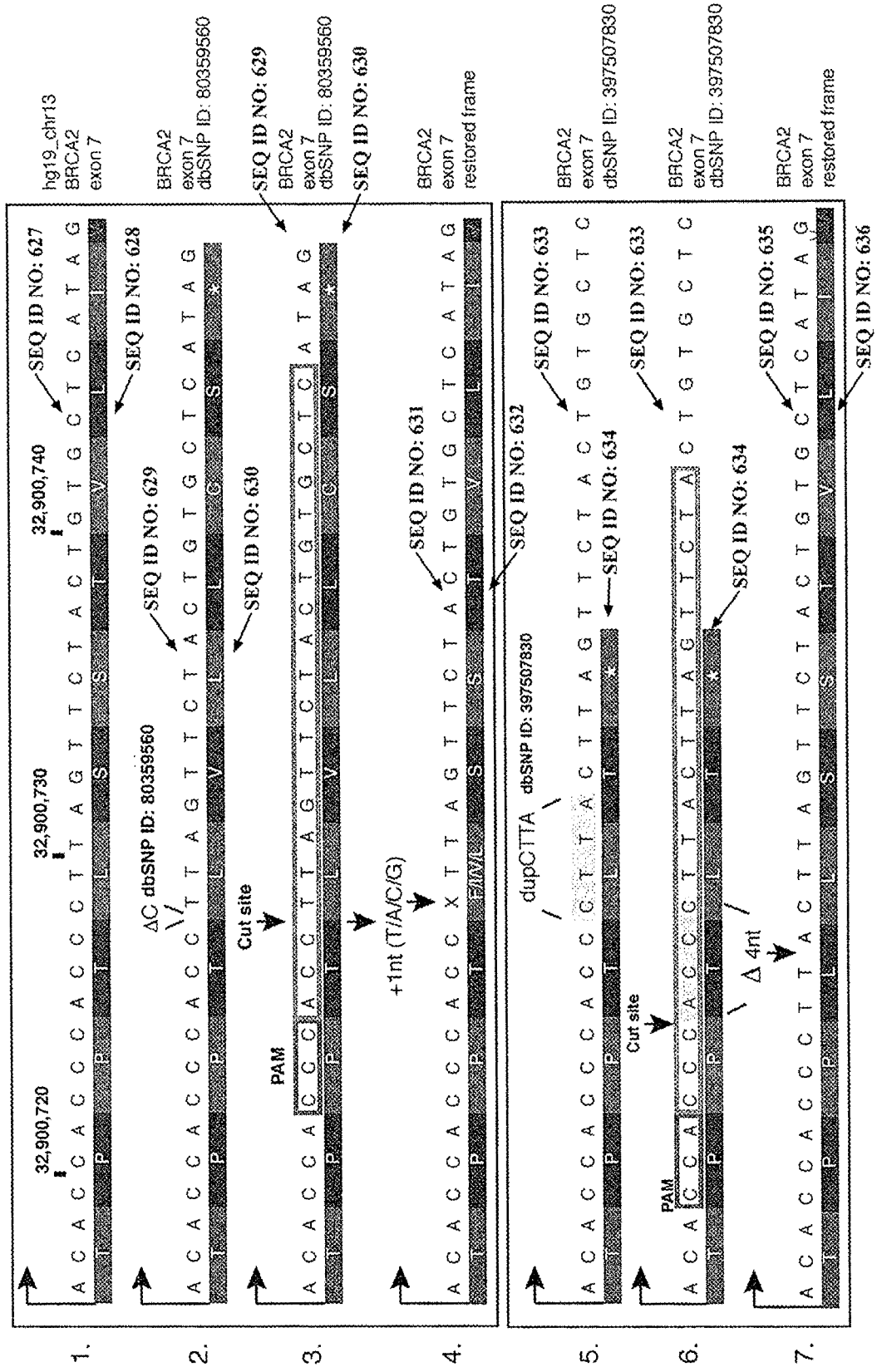

FIGS. 7A-7F show that DNA repair outcome profiling in cell lines is predictive for human primary cells. DNA repair outcome after cleavage of a BRCA2 target results in two dominant products. FIG. 7A: Genomic location (hg19 coordinates) of a target in the BRCA2 gene (SEQ ID NOS: 627 and 628); PAM, boxed in light grey; protospacer, grey box. Cas9 cut site is indicated by an arrow. The entire protospacer sequence is boxed in grey (Spacer 19 in Table 1). Deletion of the four-nucleotide sequence, shaded, and a single nucleotide insertion represent the most frequent indels after Cas9 cleavage. FIG. 7B: Visualization of a subset (the five most frequent) of the indel classes and wild-type (WT) at the BRCA2 target in three different cell lines and hematopoietic stem cells (HSCs) for sgRNP and three different cell lines for constitutive expression of Cas9/sgRNA as indicated on the left (a single replicate of each is displayed). FIGS. 7C and 7D: Heat maps of the frequencies of indels by length at the BRCA2 target in various cell types (three experimental replicates and a WT control) 48 hours post-sgRNP delivery (FIG. 7C) or 11 and 14 days post constitutive expression of Cas9/sgRNA (FIG. 7D). FIG. 7E: Bar graph of indel frequencies by length displayed as a fraction of mutant reads (mean and standard deviation across three experimental replicates) in three cell lines and HSCs 48 hours post sgRNP delivery. FIG. 7F: Use of DNA repair profiles to restore the reading frame of specific mutant alleles of BRCA2. 1. Wild type BRCA2 locus (hg19 coordinates; (SEQ ID NOS: 627 and 628). 2. Sequence of BRCA2 mutant allele (dbSNP ID: 80359550; (SEQ ID NOS: 629 and 630) missing a "C" nucleotide shifting the frame of BRCA2 resulting in a premature stop codon (box with asterisk). 3. Genomic location of a target site on the BRCA2 mutant allele shown in (2) with the protospacer adjacent motif (PAM) boxed in light grey and Cas9 cut site indicated by an arrow. The entire protospacer sequence is boxed in grey. 4. An insertion of a single nucleotide after Cas9-cleavage (SEQ ID NOS: 631 and 632) at the target site shown in (3) would restore the frame of the BRCA2 mutant allele. Depending on the nucleotide that was inserted during the DNA repair reaction, the fifth amino acid from the left would be a Phenylalanine, Isoleucine, Valine, or Leucine (WT). 5. Sequence of a BRCA2 mutant allele (dbSNP ID: 397507830; SEQ ID NOS: 633 and 634) containing a duplication of "CTTA" resulting in a frame shift and a premature stop codon (box with asterisk). 6. Genomic location of a target site on the BRCA2 mutant allele shown in (5) with the protospacer adjacent motif (PAM) boxed in light grey and Cas9 cut site indicated by an arrow. The entire protospacer sequence is boxed in grey. 7. A four base deletion after Cas9-cleavage at the target site shown in (6) would restore the frame of the BRCA2 mutant allele (SEQ ID NOS: 635 and 636). The resulting allele would differ from the WT allele by a single amino acid (Leucine instead of a Threonine, fourth amino acid from the left).

Figure 8A:
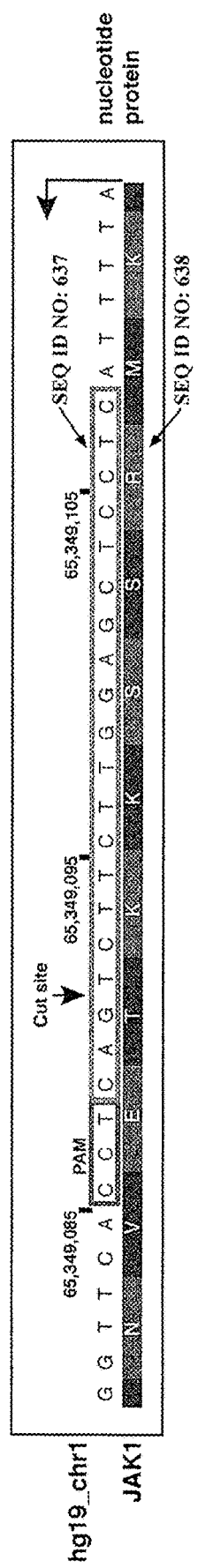
FIGS. 8A-8E show DNA repair outcomes are similar comparing across replicates and reagent delivery methods at a JAK1 target.
Figure 8B:
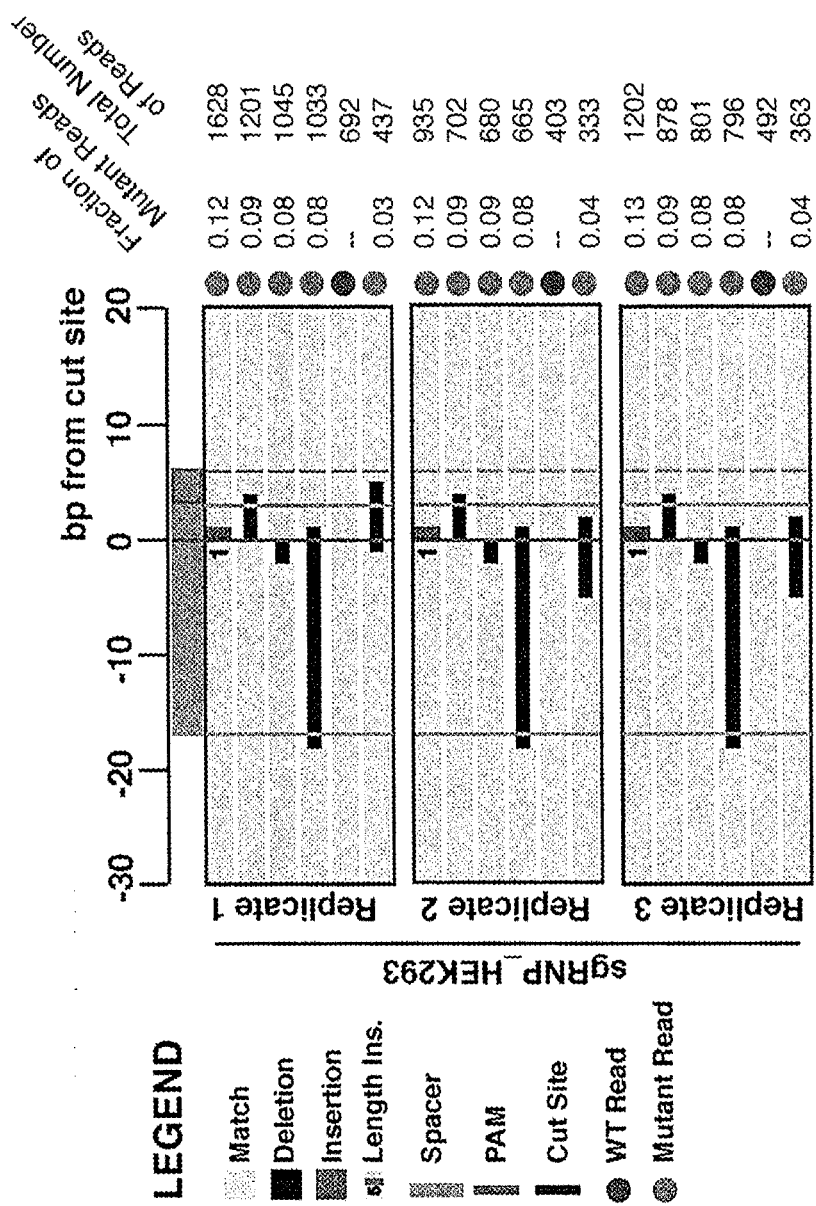
Figure 8C:
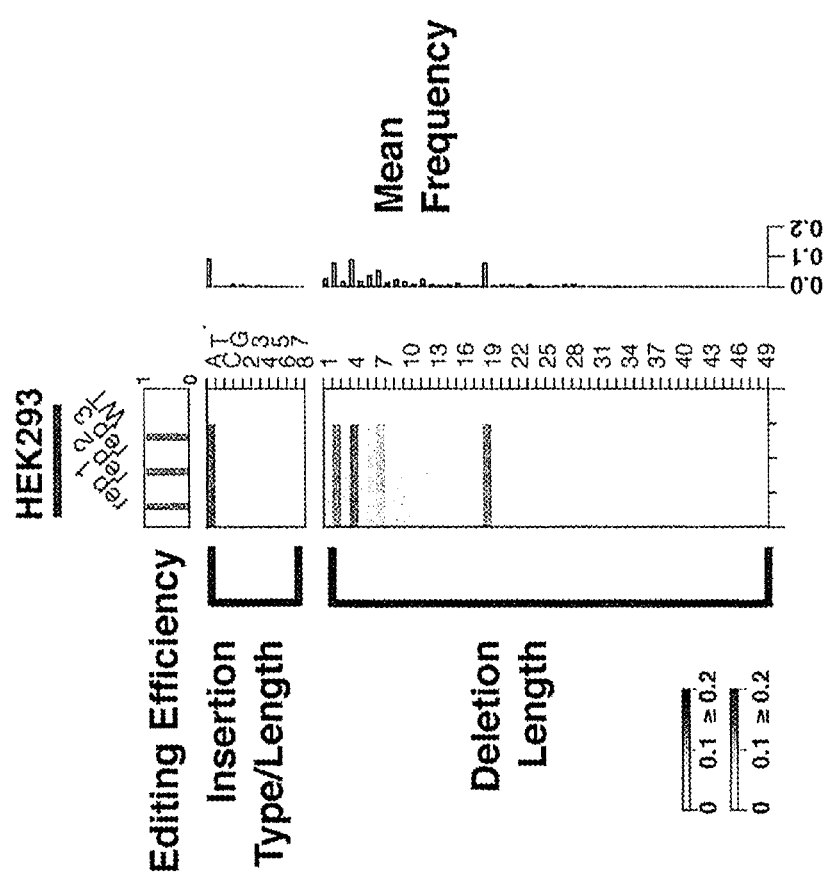
Figure 8D:
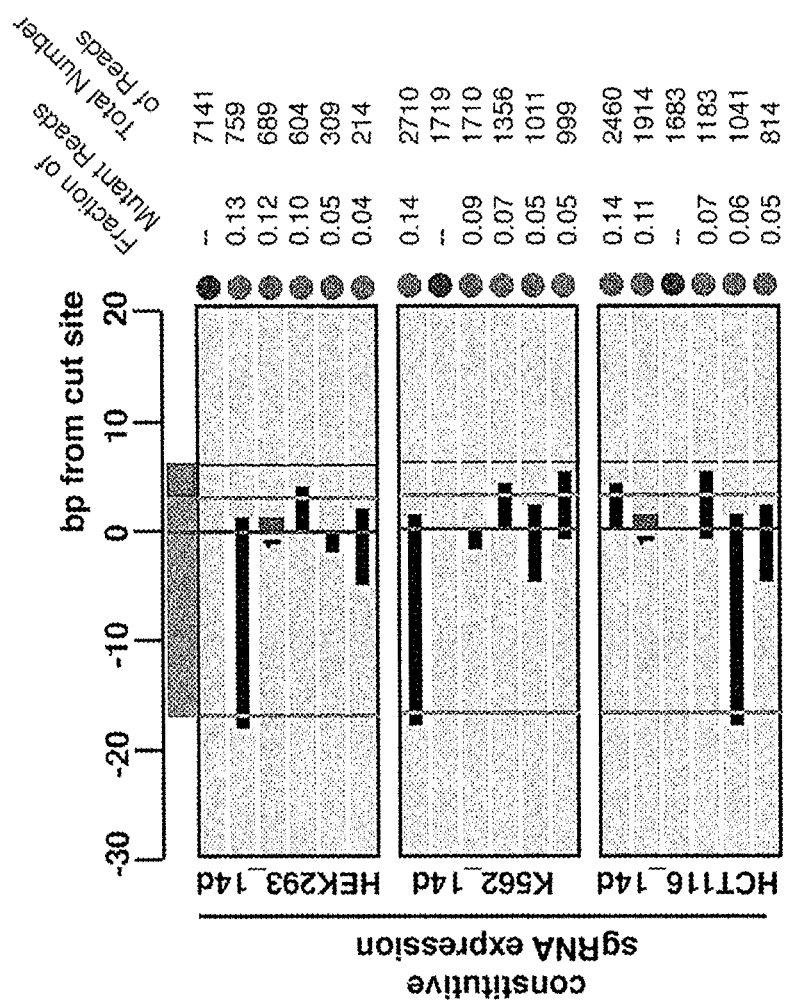
Figure 8E:
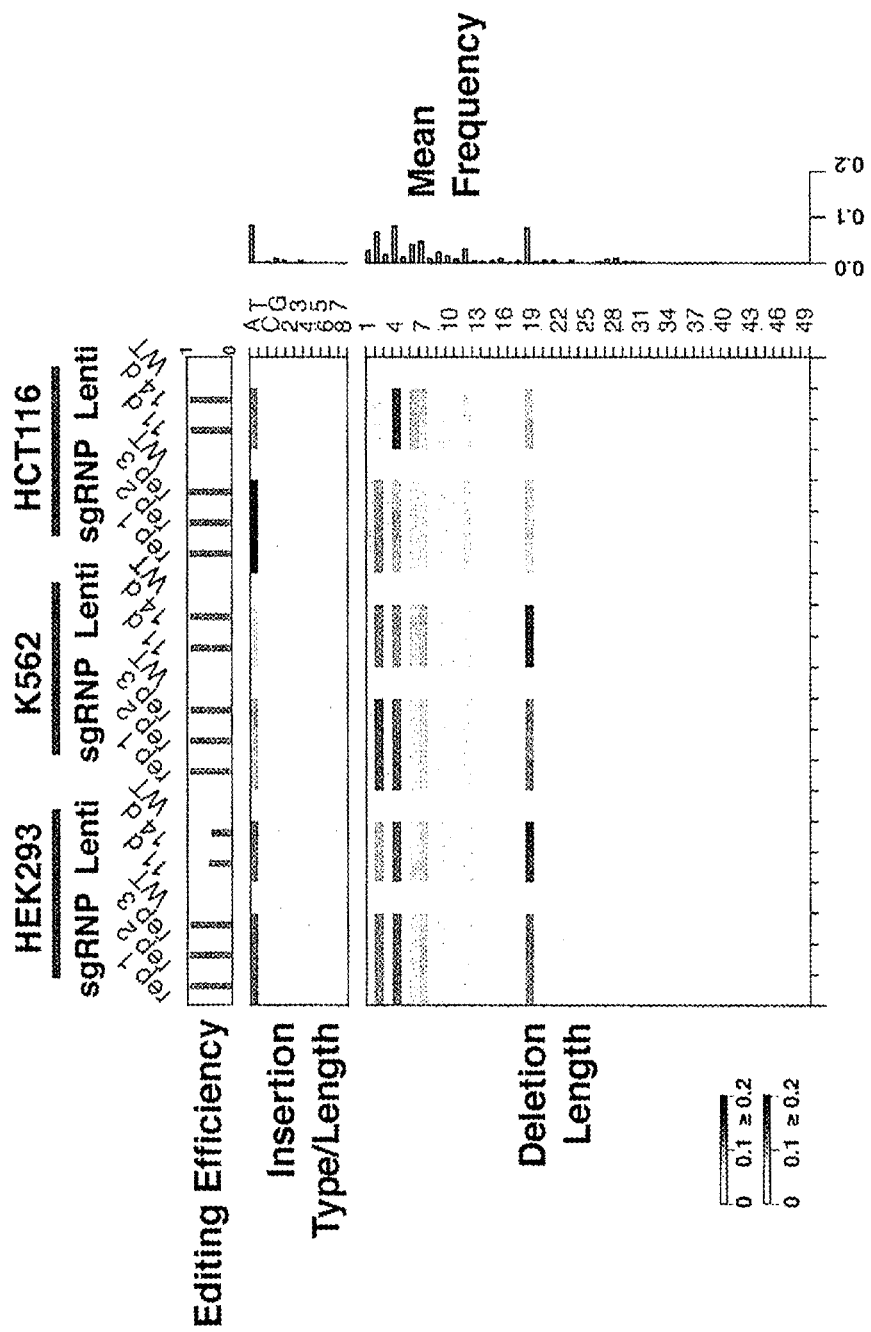

FIGS. 8A-8E show DNA repair outcomes are similar comparing across replicates and reagent delivery methods at a JAK1 target. FIG. 8A: Genomic location (hg19 coordinates; SEQ ID NOS: 637 and 638) of a target in the JAK1 gene with the protospacer adjacent motif (PAM) boxed in light grey and Cas9 cut site indicated by an arrow. The entire protospacer sequence is boxed in grey. This is the same target shown in FIG. 1 (Spacer 54 in Table 1). FIG. 8B: A visualization of a subset of the indel classes (the five most frequent) and wild-type (WT) at the JAK1 target comparing three experimental replicates in HEK293 cells, as indicated on the left, 48 hours after sgRNP delivery. FIG. 8C: A heat map of the frequencies of indels by length at the JAK1 target of the same three experimental replicates and a WT control in HEK293. FIG. 8D: A visualization of a subset of the indel classes (the five most frequent) and wild-type (WT) at a JAK1 target comparing HEK293, K562 and HCT116 cell lines, as indicated on the left, 14 days after constitutive expression of Cas9/sgRNA. FIG. 8E: A heat map of the frequencies of indels by length at the JAK1 target (three replicates and a WT control) in HEK293, K562, and HCT116 cell lines 48 hours after sgRNP delivery compared with 11 and 14 days after constitutive expression of Cas9/sgRNA in the same parental cell lines (plus WT control (Cas9-only)).

Figure 9A:
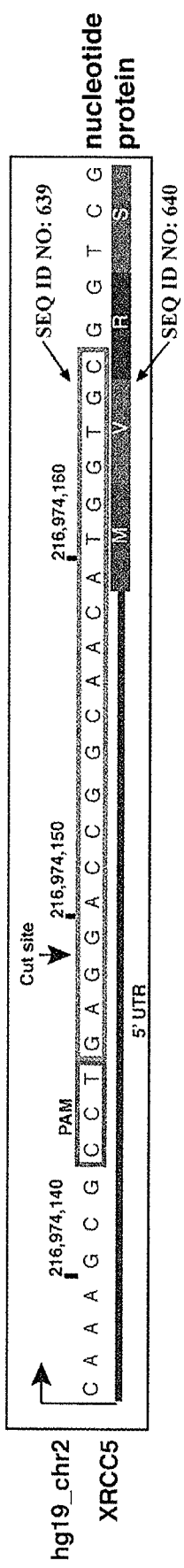
FIGS. 9A-9F show that DNA repair profiles are unique to each target.
Figure 9B:
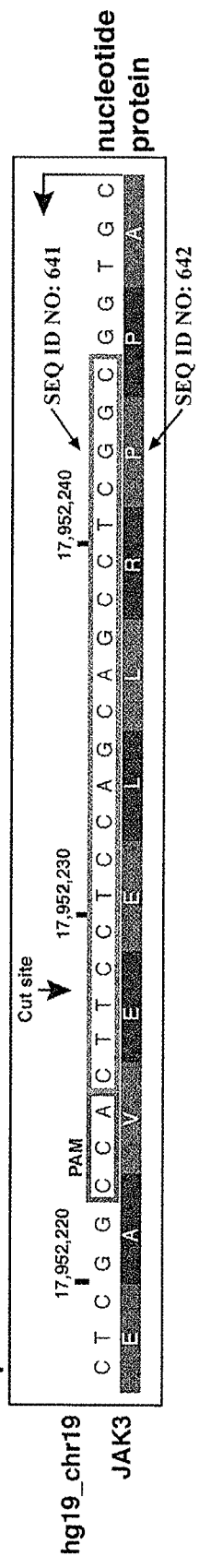
Figure 9C:
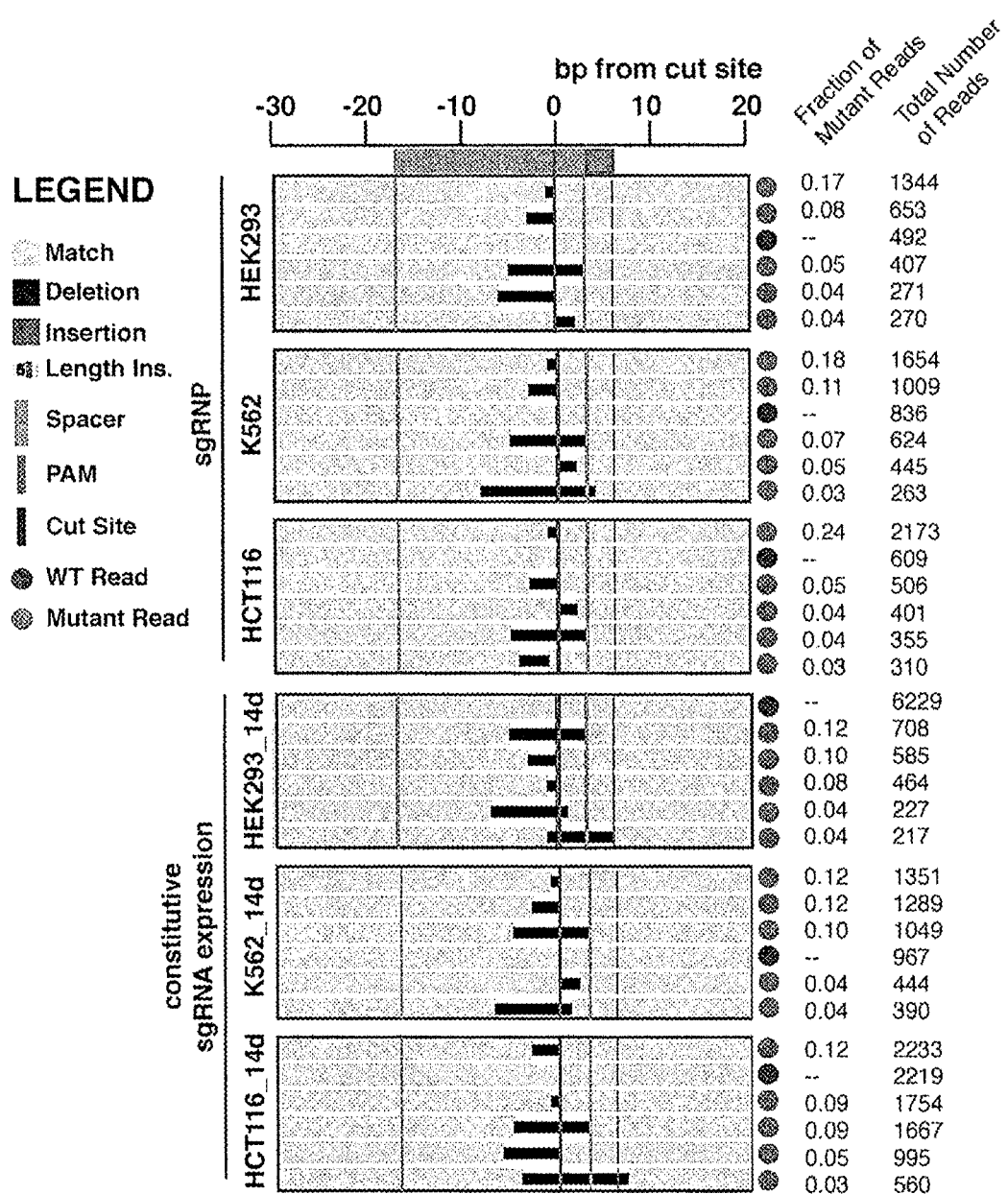
Figure 9D:
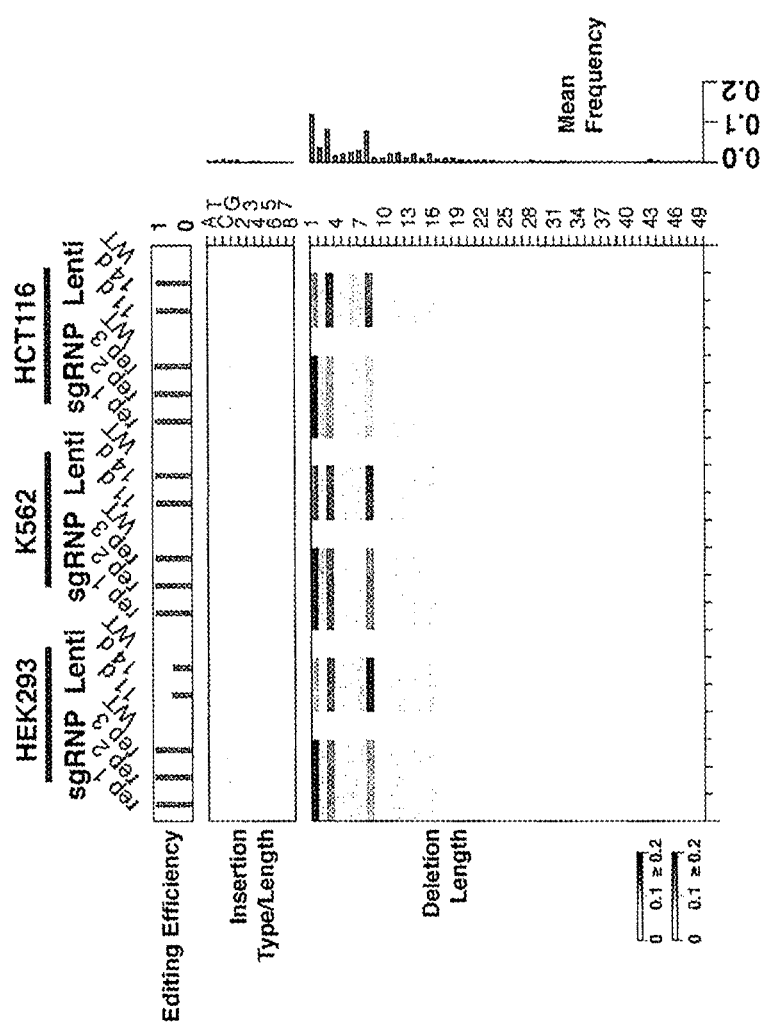
Figure 9E:
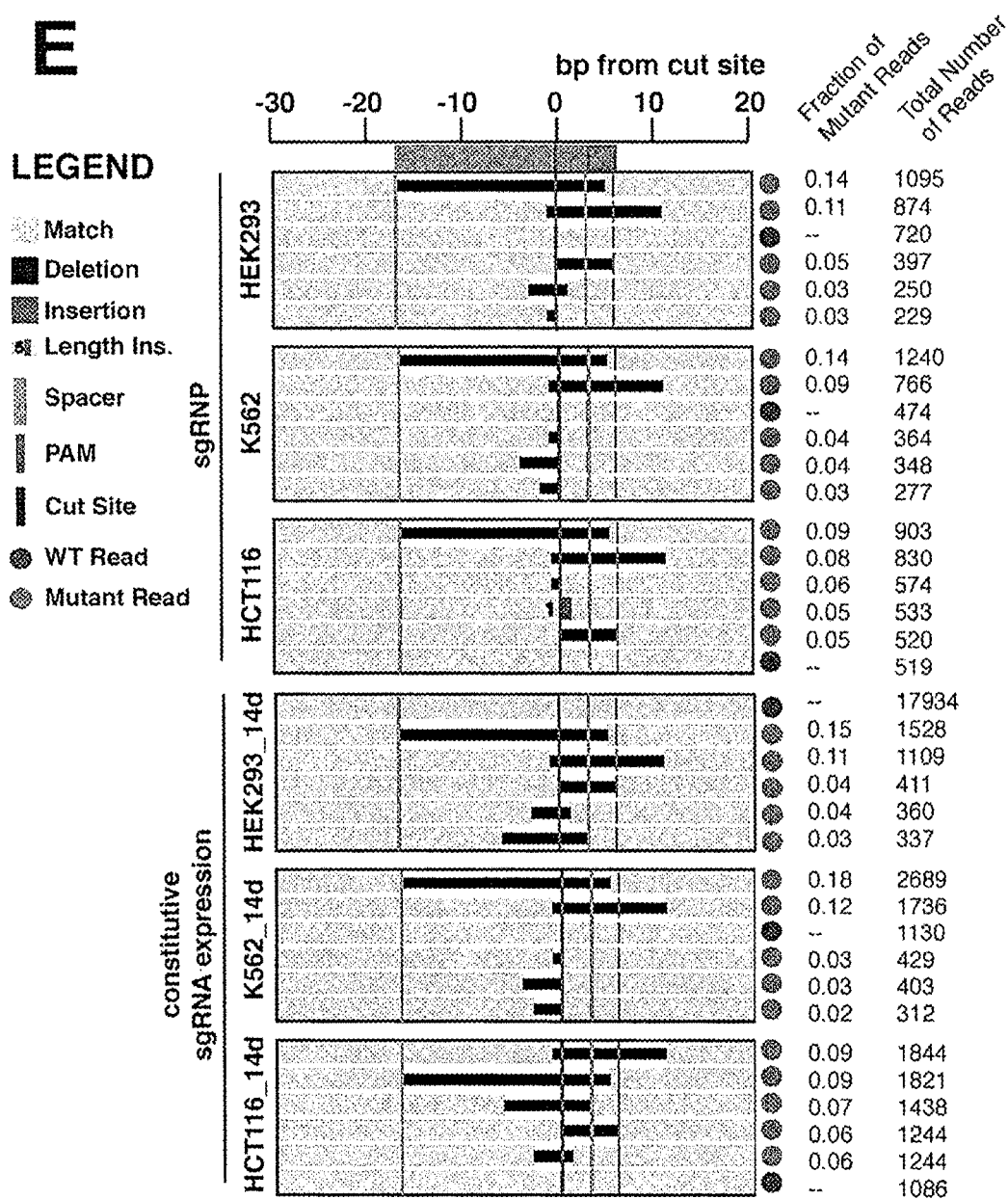
Figure 9F:
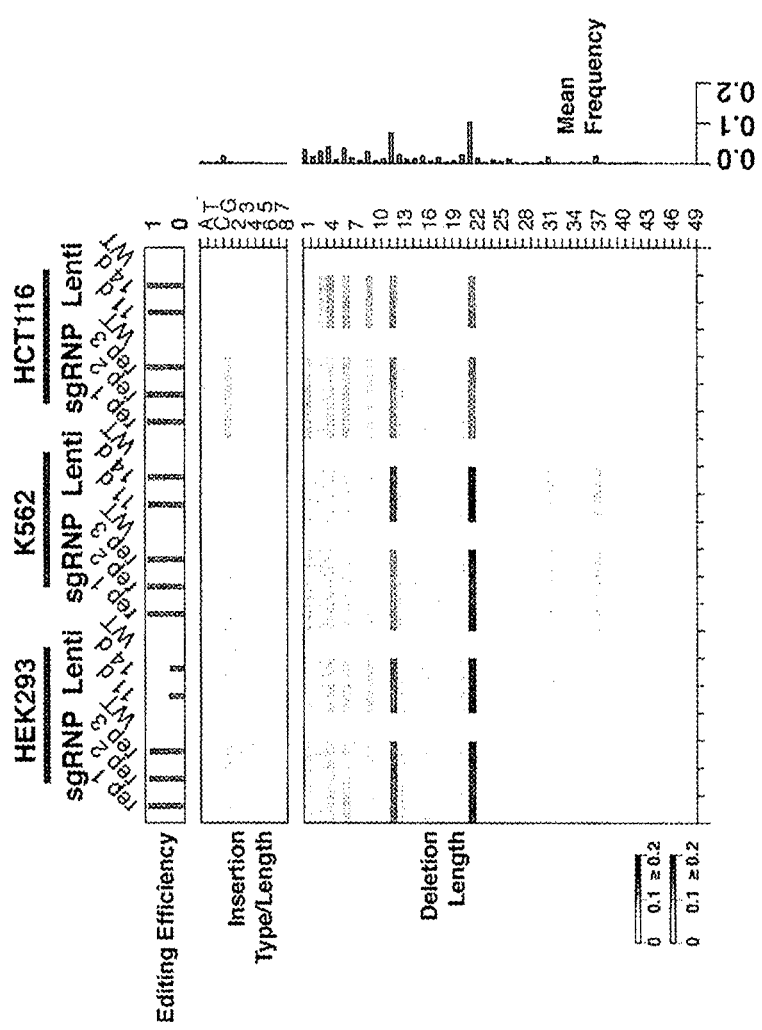

FIGS. 9A-9F show that DNA repair profiles are unique to each target. FIG. 9A: Genomic location of a target in the XRCC5 gene (SEQ ID NOS: 639 and 640) with the protospacer adjacent motif (PAM) boxed in light grey and Cas9 cut site indicated by an arrow (Spacer 51 in Table 1). FIG. 9B: Genomic location of a target in the JAK3 gene (SEQ ID NOS: 641 and 642); (Spacer 66 in Table 1). FIG. 9C: Visualization of a subset of the indel classes (the five most frequent) and wild-type (WT) at the XRCC5 target comparing HEK293, K562 and HCT116 cell lines for both sgRNP and 14 days after constitutive expression of Cas9/sgRNA, as indicated on the left (a single replicate of each is displayed). FIG. 9D: A heat map of the frequencies of indels by length at the XRCC5 target (three experimental replicates and a WT control) in HEK293, K562, and HCT116 cell lines 48 hours after sgRNP delivery compared with 11 and 14 days after constitutive expression of Cas9/sgRNA in the same parental cell lines (Lenti) plus WT control (Cas9-only)). FIGS. 9E and 9F: same as FIGS. 9C and 9D at the JAK3 target.

Figure 10A:
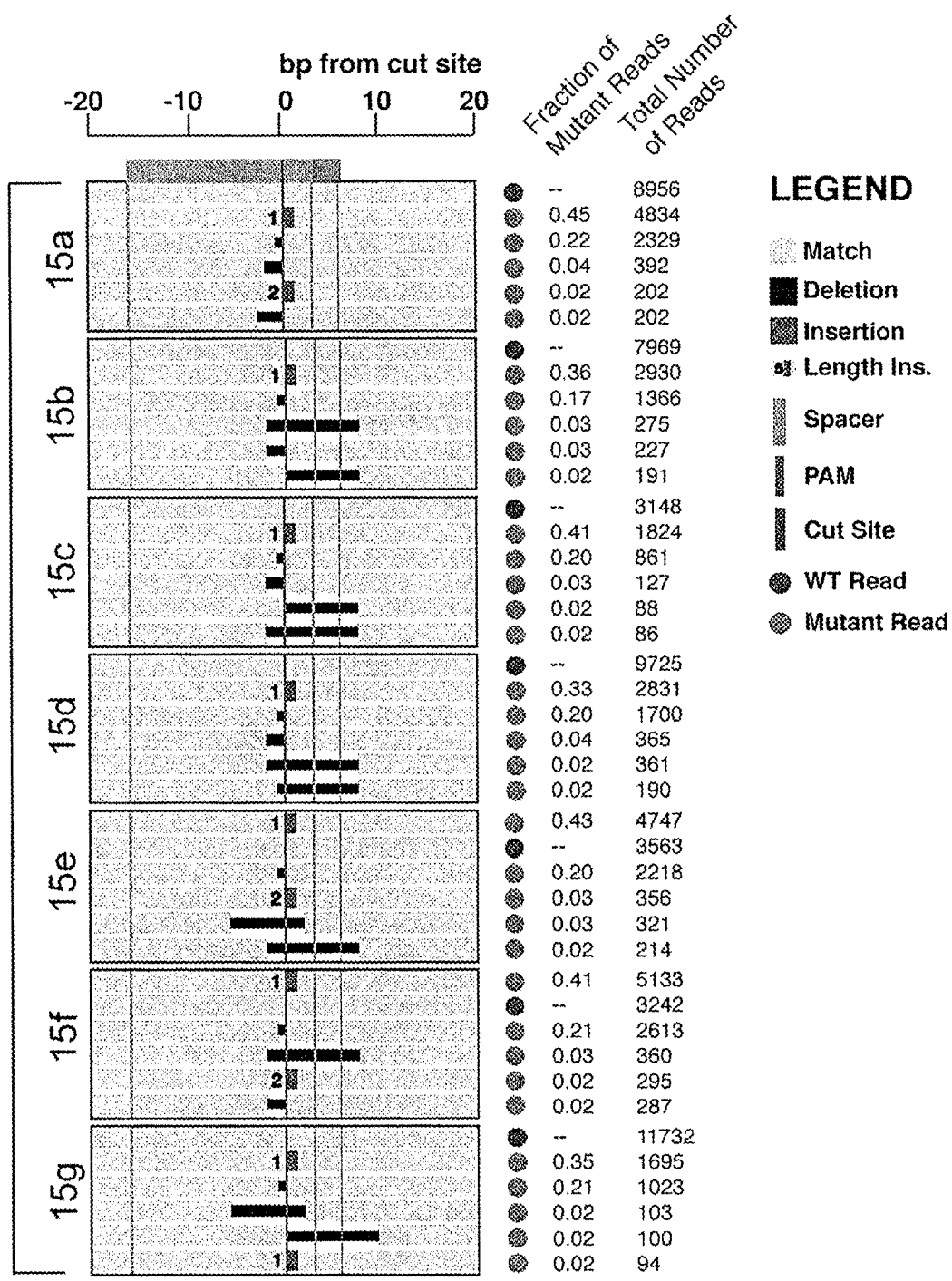
FIGS. 10A and 10B show visualizations of DNA repair outcomes at seven sites in the human genome with the same spacer sequence.
Figure 10B:
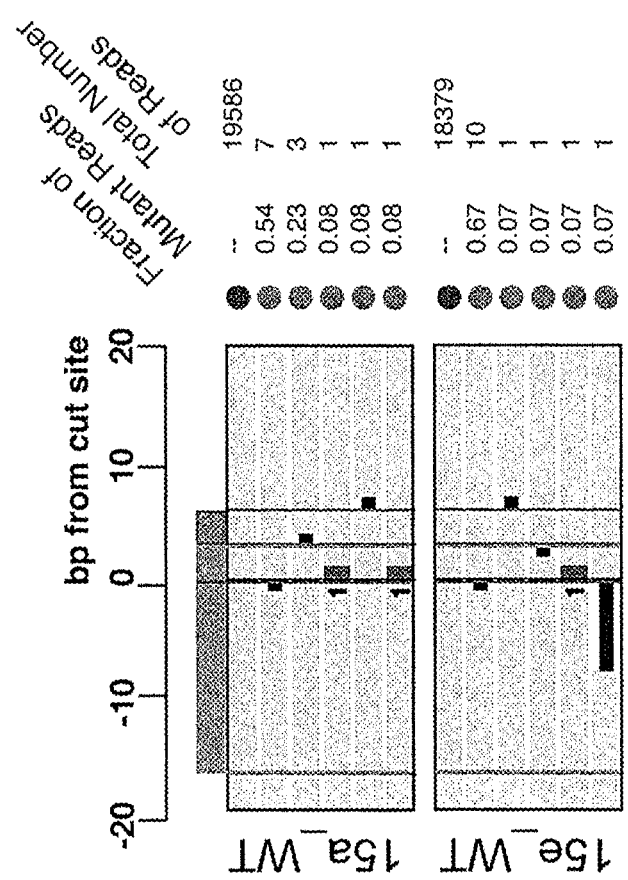

FIGS. 10A and 10B show visualizations of DNA repair outcomes at seven sites in the human genome with the same spacer sequence. FIG. 10A: Visualization of a subset (the five most frequent) of the indel and wild-type (WT) classes for seven sites in spacer group 15 in HEK293 (15a-15g), as indicated on the left (a single replicate of each is displayed). Genomic coordinates for each site are described in FIG. 3A. Corresponding heat map visualization of indel distribution for each site is shown in FIG. 3B. FIG. 10B: Visualization of the top five most frequent indel classes for spacer 15 WT controls (unedited) at sites a and e in HEK293 (related to FIGS. 3A and 3B). Each class expressed as a fraction of mutant reads. The number of reads attributed to each class is shown in the second column on the right. The small number of reads that contain indels in WT controls are attributed to sequencing errors.

Figure 11A:
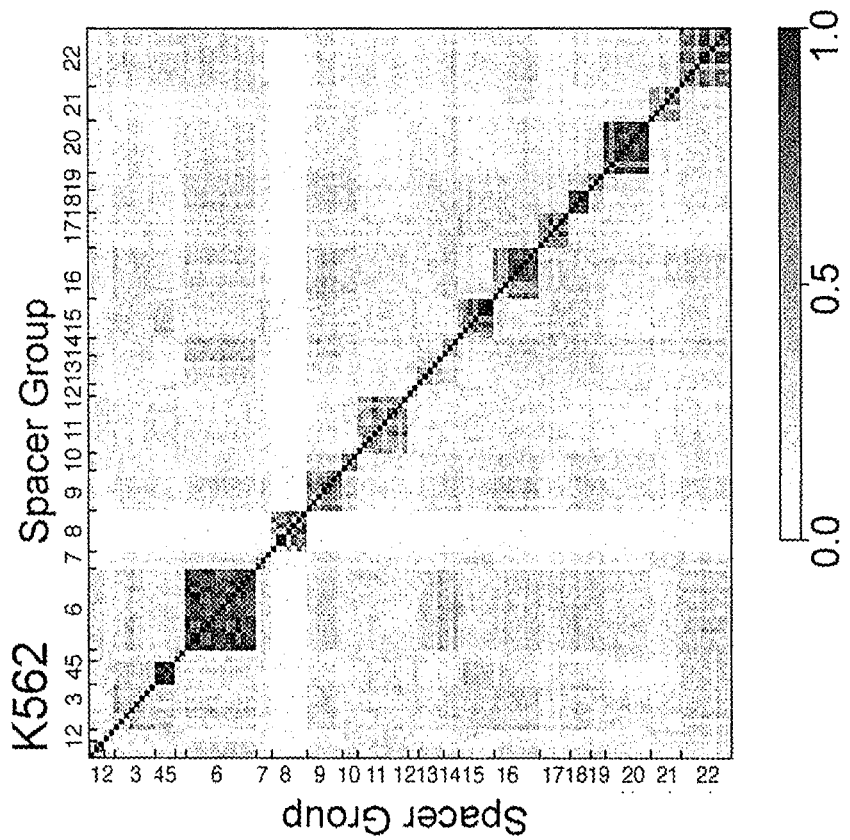
Figure 11B:
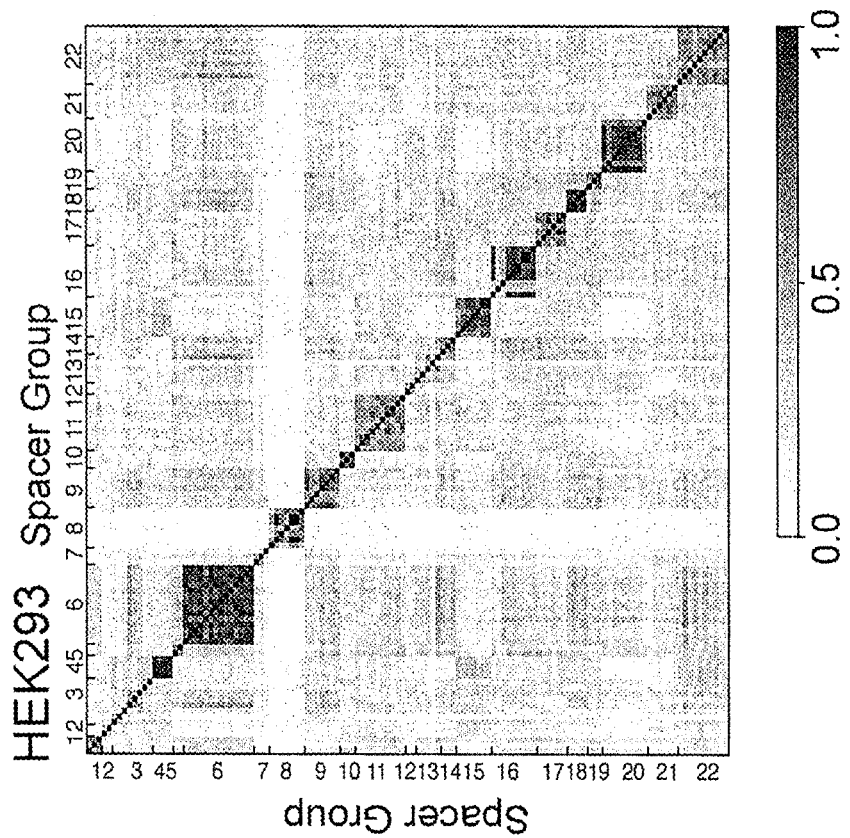

FIGS. 11A-11D show that DNA repair outcomes are more similar within spacer groups than between spacer groups. FIGS. 11A and 11B: A matrix of the (Jaccard/Tanimoto) similarity of indel classes with a frequency ≥0.01 (as a fraction of mutant reads) across pairs of target sites in HEK293 cells (FIG. 11A) and K562 cells (FIG. 11B). Spacer group labels are indicated on the horizontal and vertical axes. Targets with the same spacer label (within the minor ticks) indicate different genomic loci targeted by the same sgRNA (Multiple Target Single Spacer (MTSS)). A value of 1 represents complete overlap of the top ten indel classes between two sites. A value of 0 represents no overlap of the top ten indel classes between two sites. FIG. 11C: Cluster analysis of the 127 target sites by DNA repair outcomes using the Jaccard similarity matrix as input to Affinity Propagation (AP) clustering. The "ground truth" cluster membership, where targets are simply arranged by spacer group label, is shown in the left column. The cluster membership resulting from clustering analysis of DNA repair outcomes for HEK293 and K562 cells is shown in the center and right columns, respectively. Each target site is displayed as its spacer label (1-22). The number of sites per spacer group is the number of points in each cell of the ground truth column. FIG. 11D: ARI scores calculated based on pairwise overlap and clustering of top 10 indels or ranked by frequency for all 127 spacer sites.

Figure 12A:
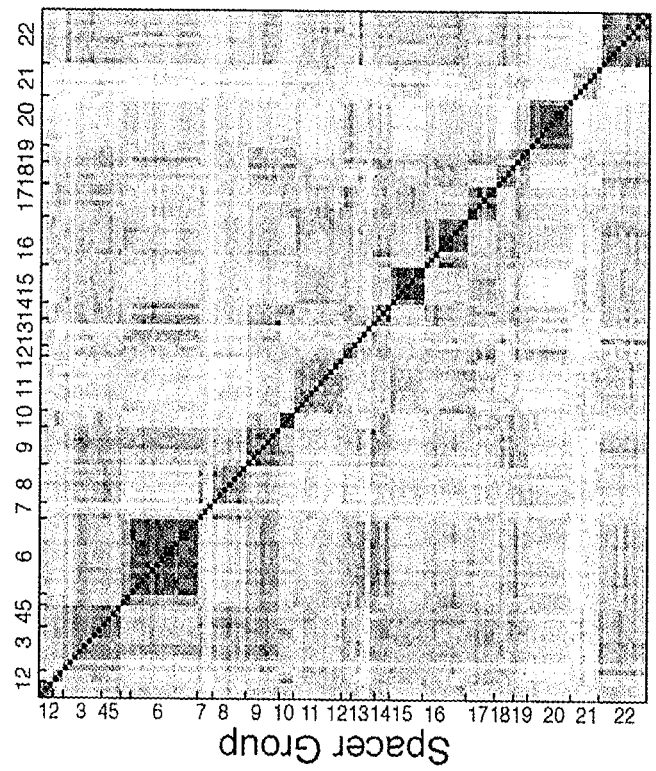
Figure 12A:
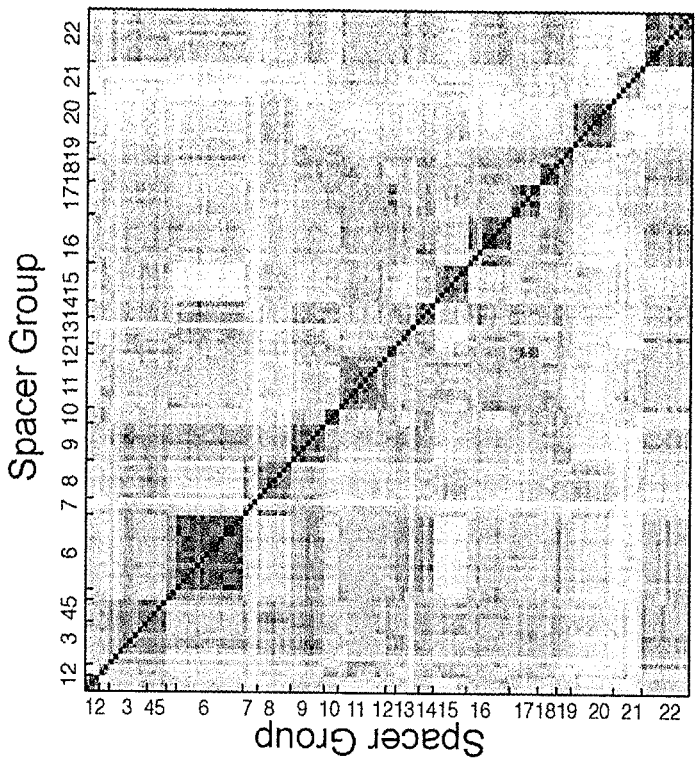
Figure 12B:
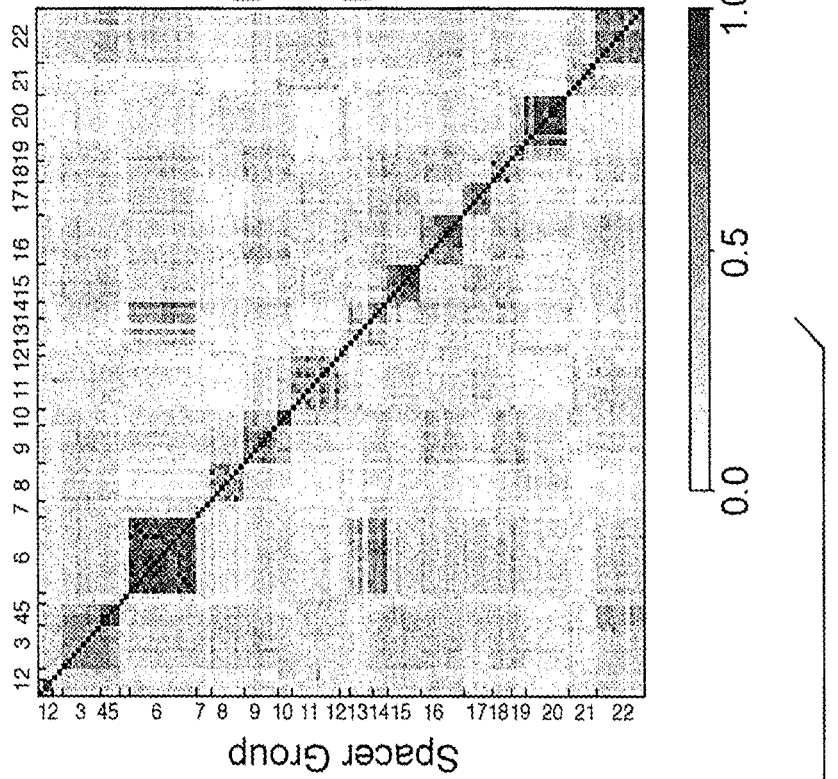
Figure 12B:
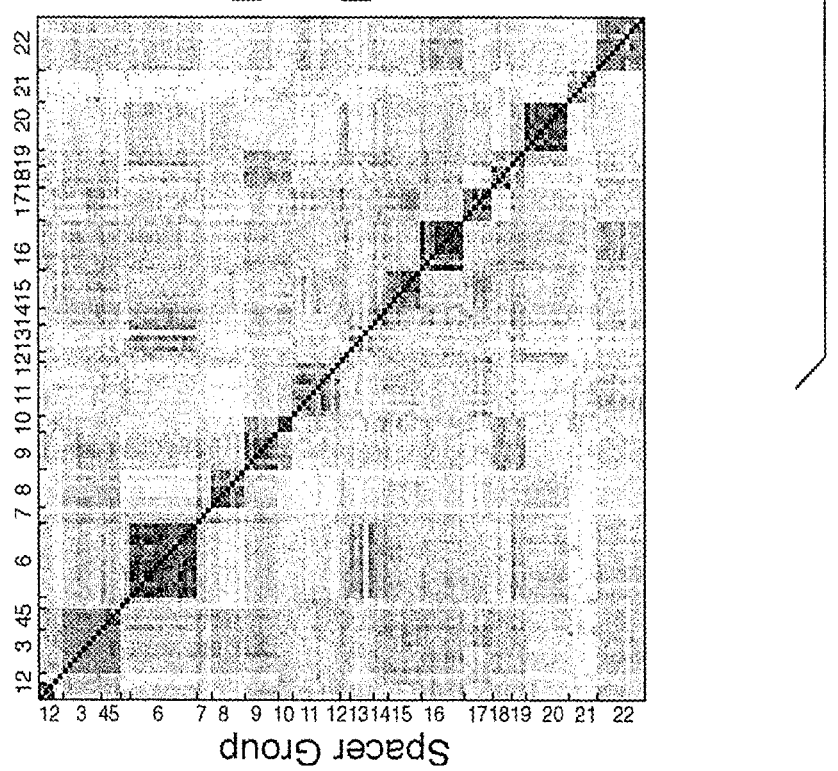

FIGS. 12A-12D show that similarity of DNA repair outcomes within spacer groups is not fully explained by microhomology. FIG. 12A: A matrix of the (Jaccard/Tanimoto) similarity of top ten indel classes across pairs of target sites in HEK293 cells. Spacer group labels are indicated on the top and left axes. Targets with the same spacer label (within the minor ticks) indicate different genomic loci targeted by the same sgRNA (Multiple Target Single Spacer (MTSS)). A value of 1 represents complete overlap of the top ten indel classes between two sites. A value of 0 represents no overlap of the top ten indel classes between two sites. Microhomology masks were applied with varying stringencies as indicated on the right of each matrix (see FIG. 12D) for details). FIG. 12B: same as in FIG. 12A for K562. FIG. 12C: ARI scores calculated based on pairwise overlap and clustering of top 10 indels for all 127 spacer sites with and without microhomology masking (see FIG. 12D). FIG. 12D: Definition of microhomology masks.

Figure 13A:
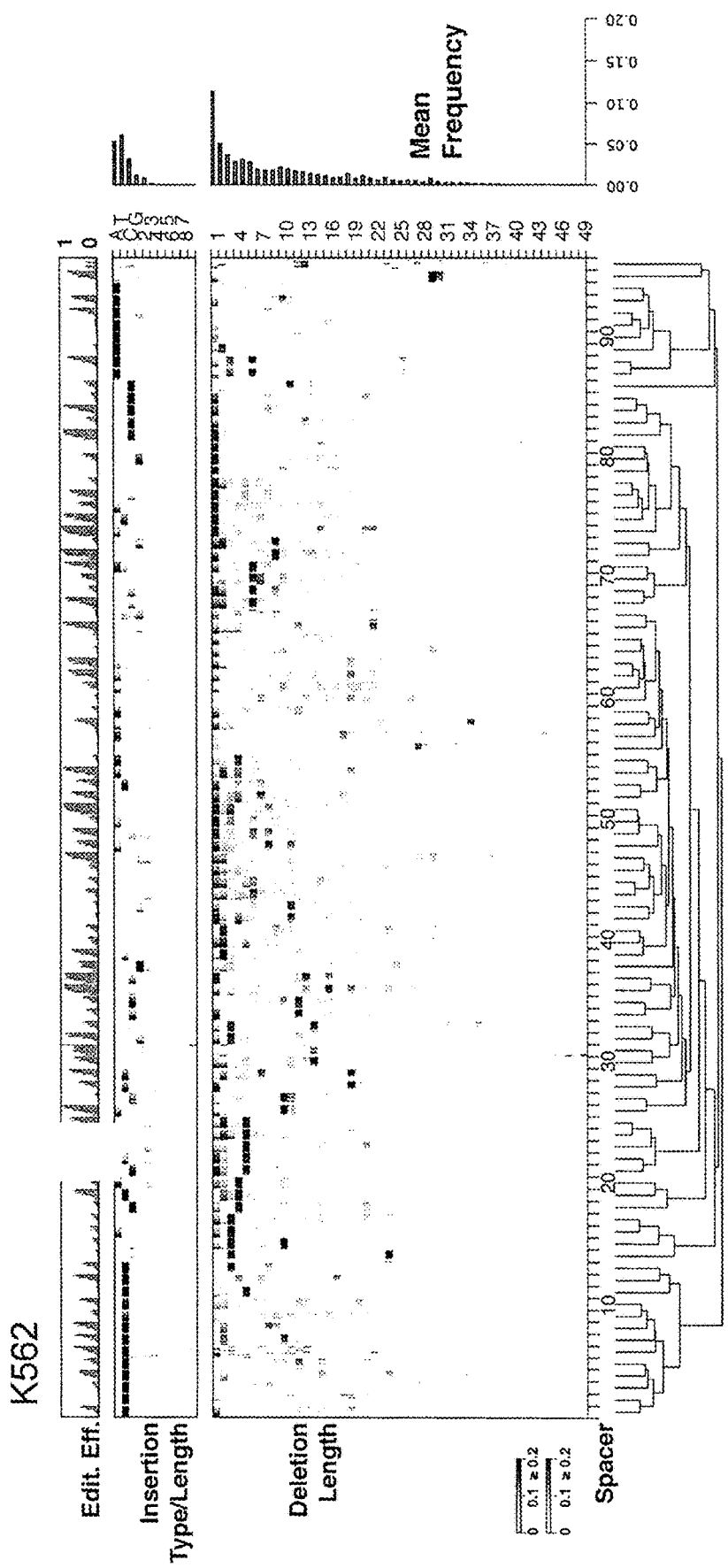
FIGS. 13A-13B show sgRNP time course data from K562 and HCT116 cells for 96 target sites.
Figure 13B:
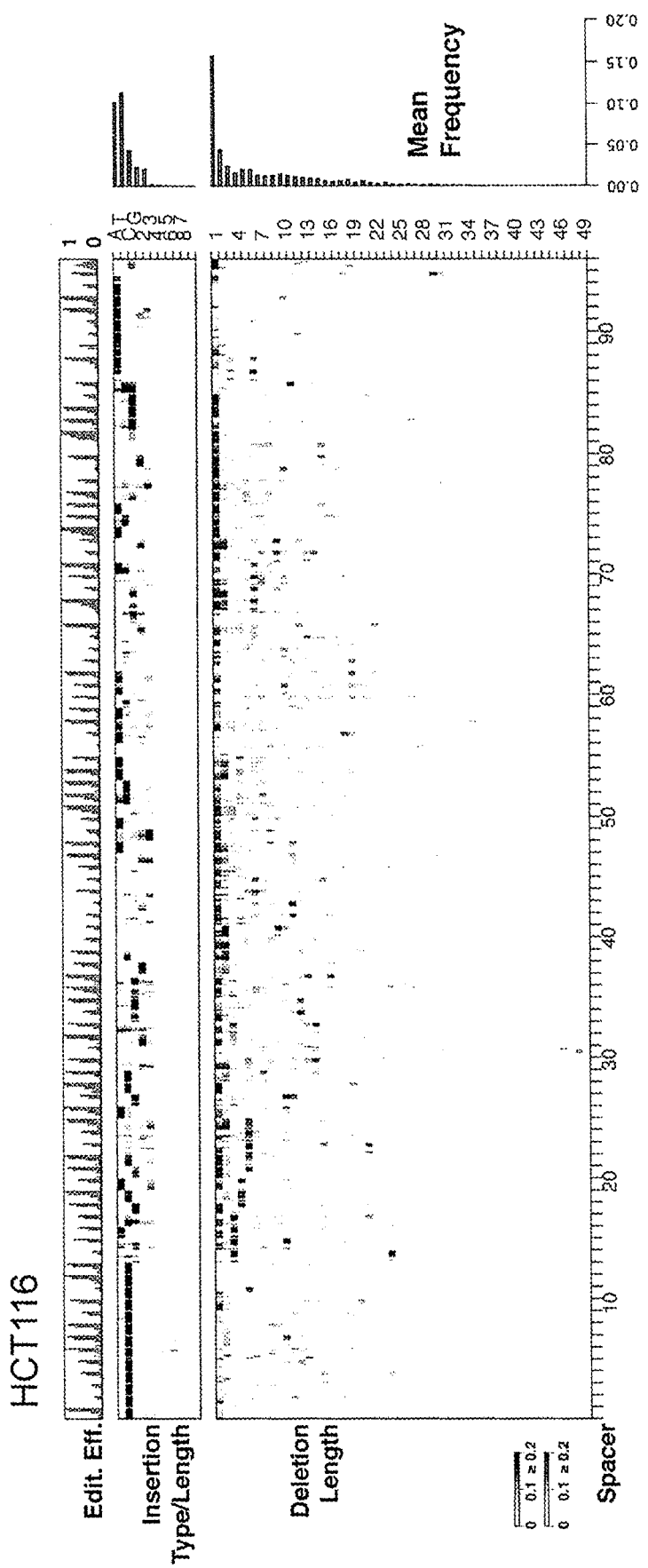

FIGS. 13A-13B show sgRNP time course data from K562 and HCT116 cells for 96 target sites. FIG. 13A: Heat map of DNA repair outcomes in K562 cells for 96 different spacers. For each spacer, five time points in each of three experimental replicates and a wild type control are displayed (4, 8, 16, 24 and 48 hours) for a total of 16 data points per spacer (within the minor ticks). Target sites are arranged based on the results of hierarchical clustering (Target sites shown for HEK293 in FIG. 4A are arranged in the same order). FIG. 13B: Same as in FIG. 13A for HCT116. Target sites are arranged in the same order as in FIGS. 13A and 4A. Zooms of individual spacers in this series are shown in FIGS. 4 and 14.

Figures 14A, 14B:
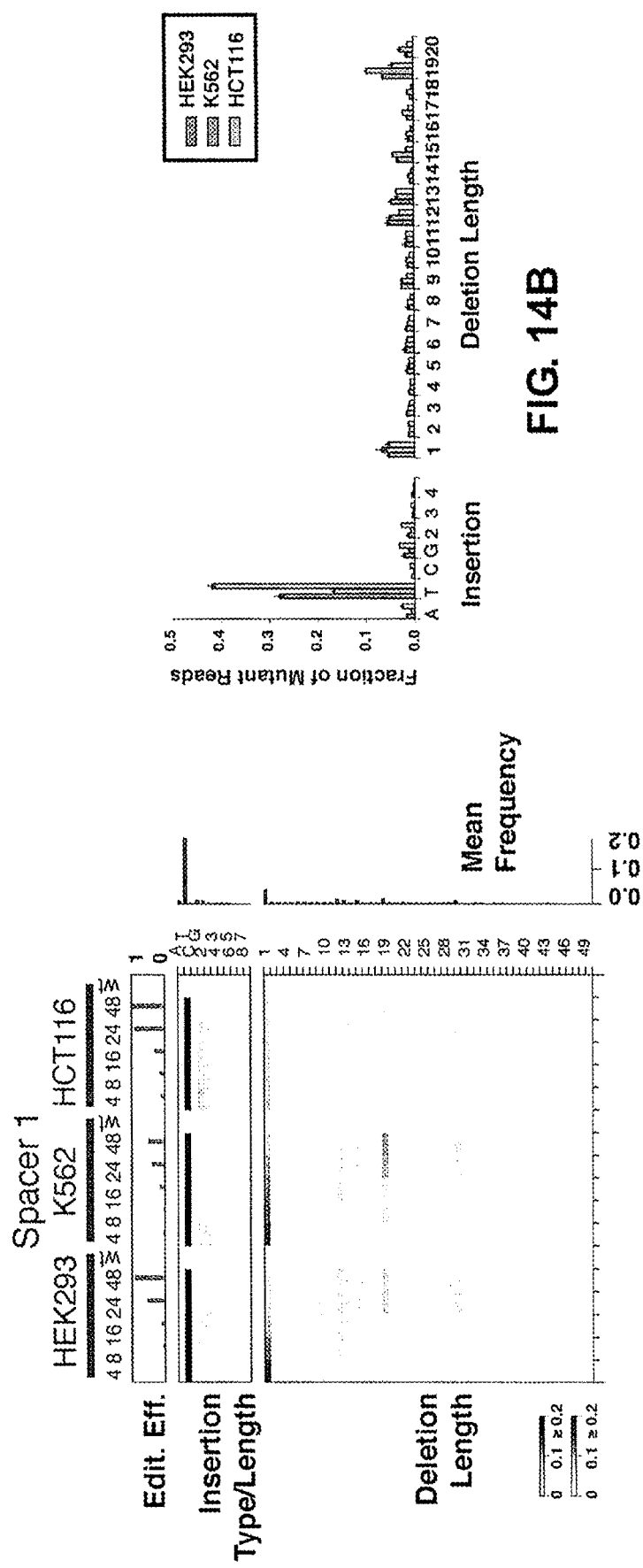
FIGS. 14A-14L show that the distribution of DNA repair outcomes after Cas9 cleavage changes over time in a cell type-dependent manner.
Figures 14C, 14D:
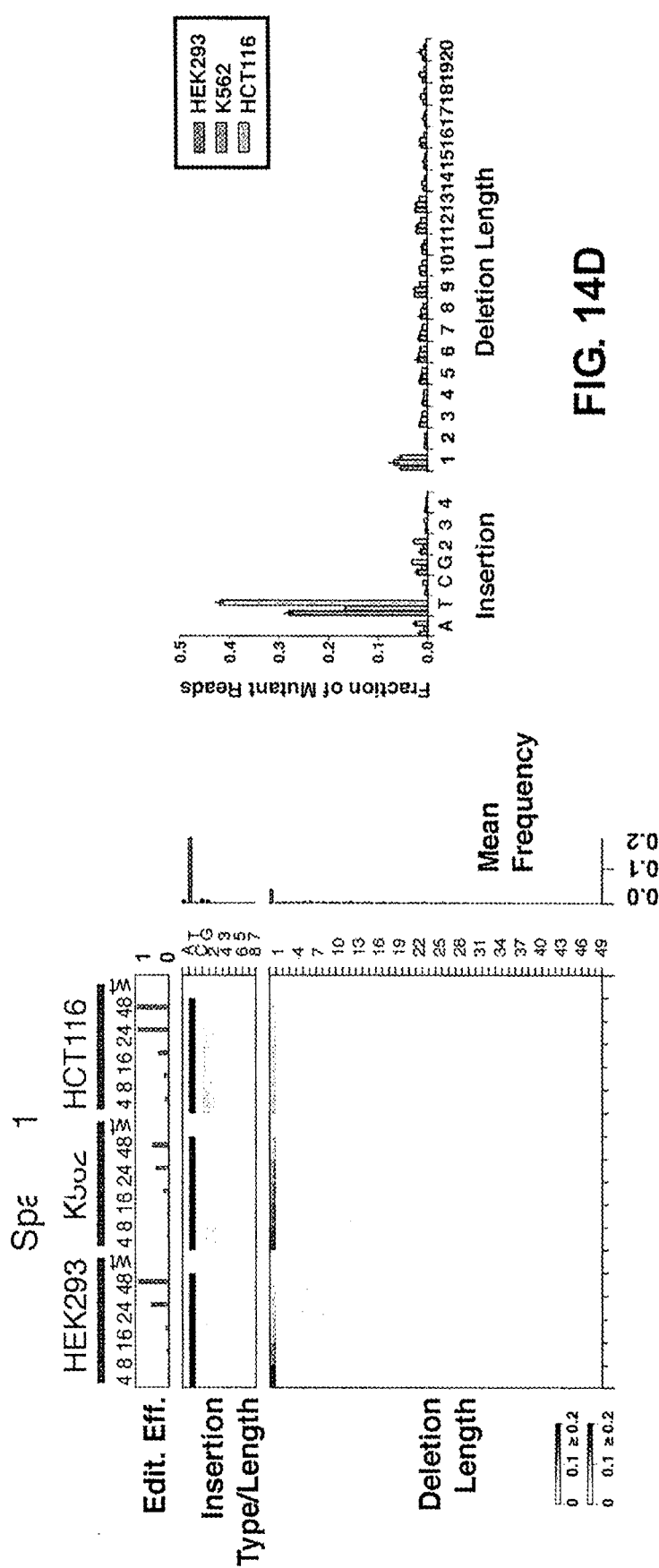
Figures 14E, 14F:
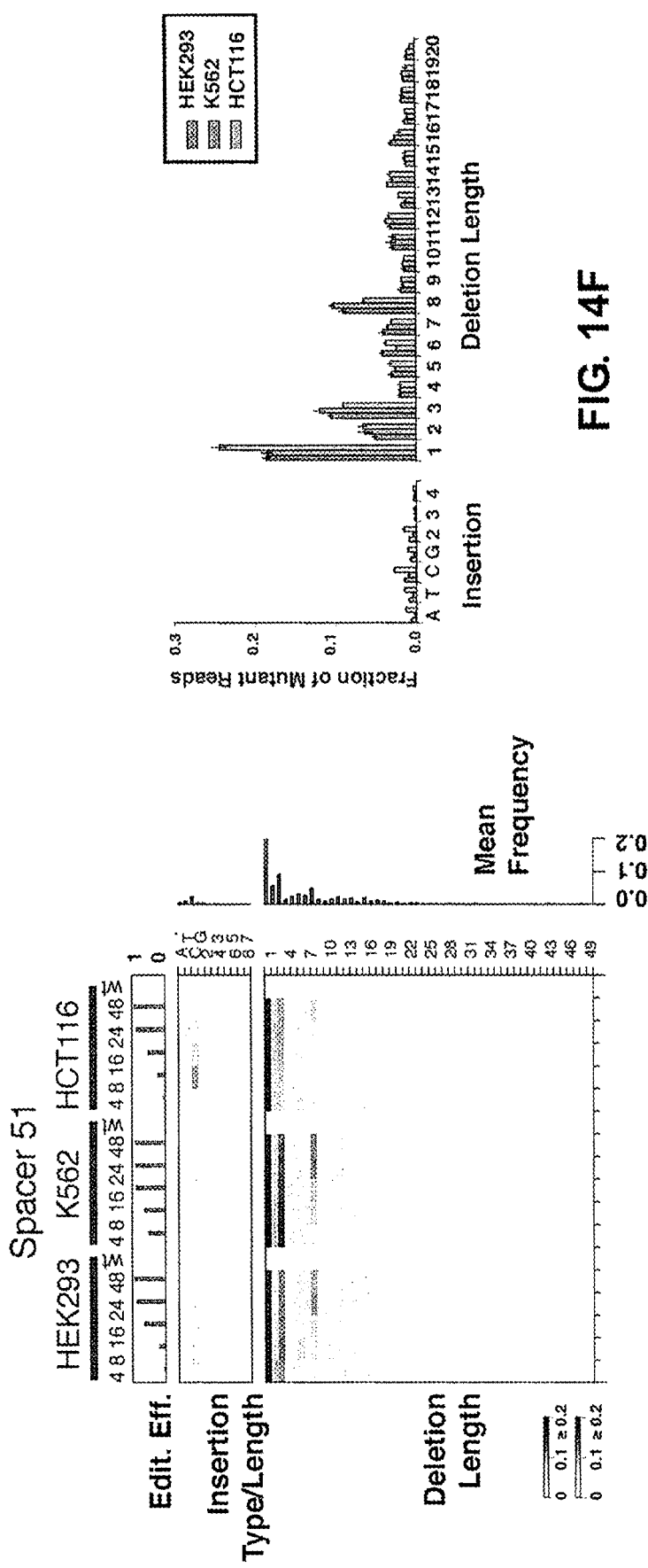
Figures 14G, 14H:
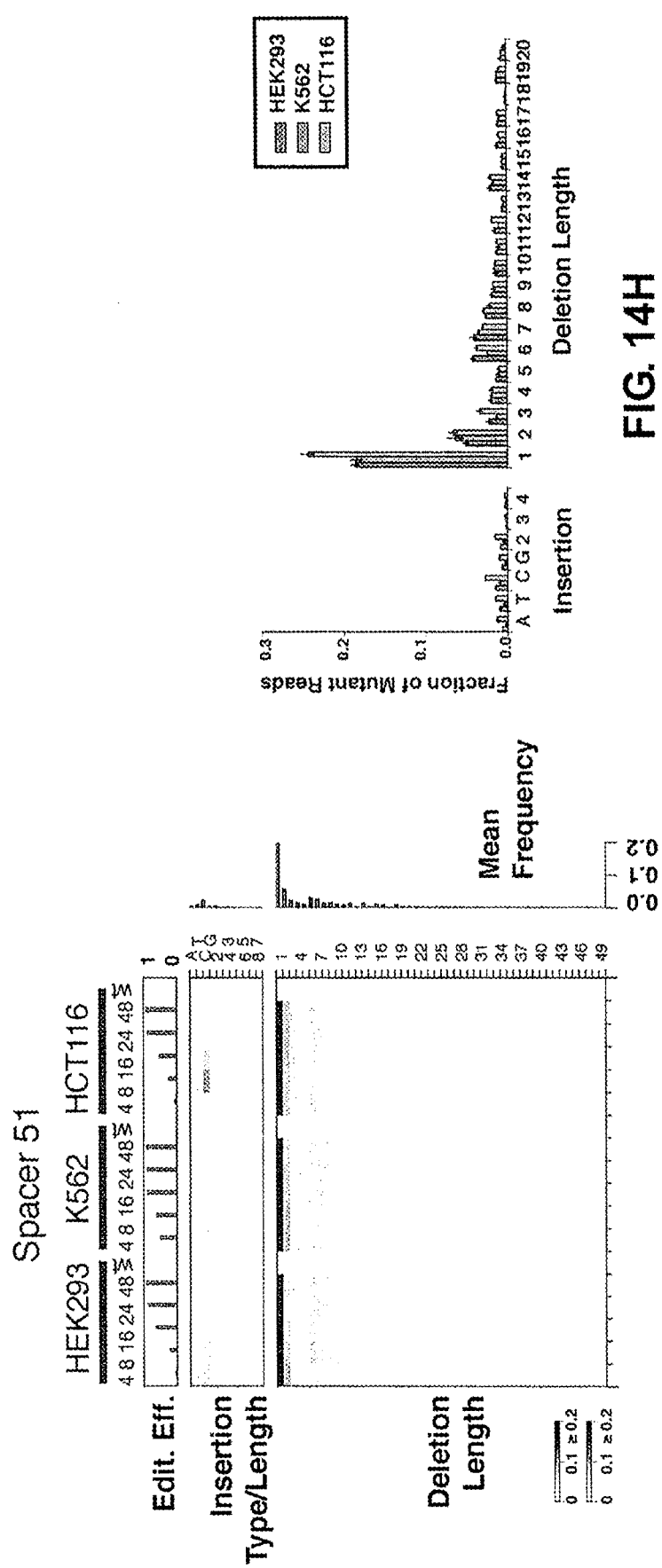
Figures 14I, 14J:
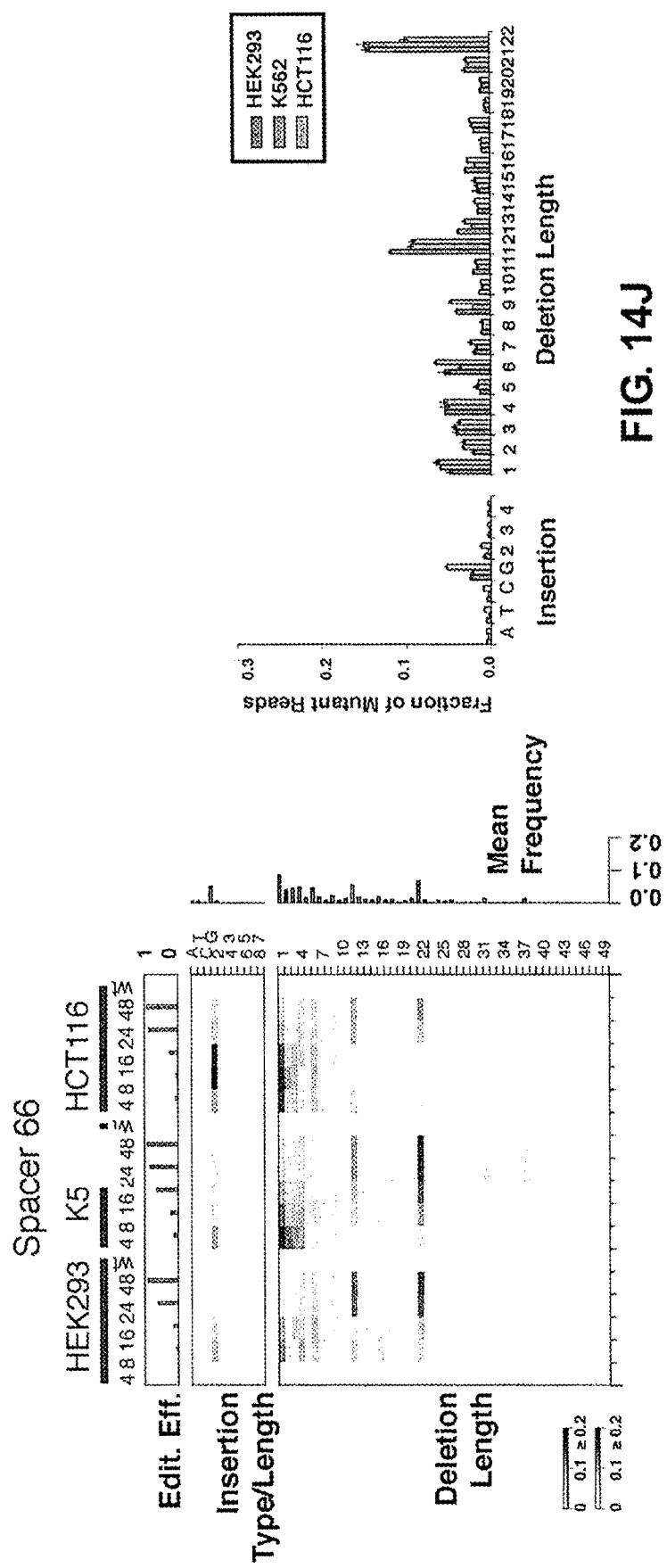
Figures 14K, 14L:
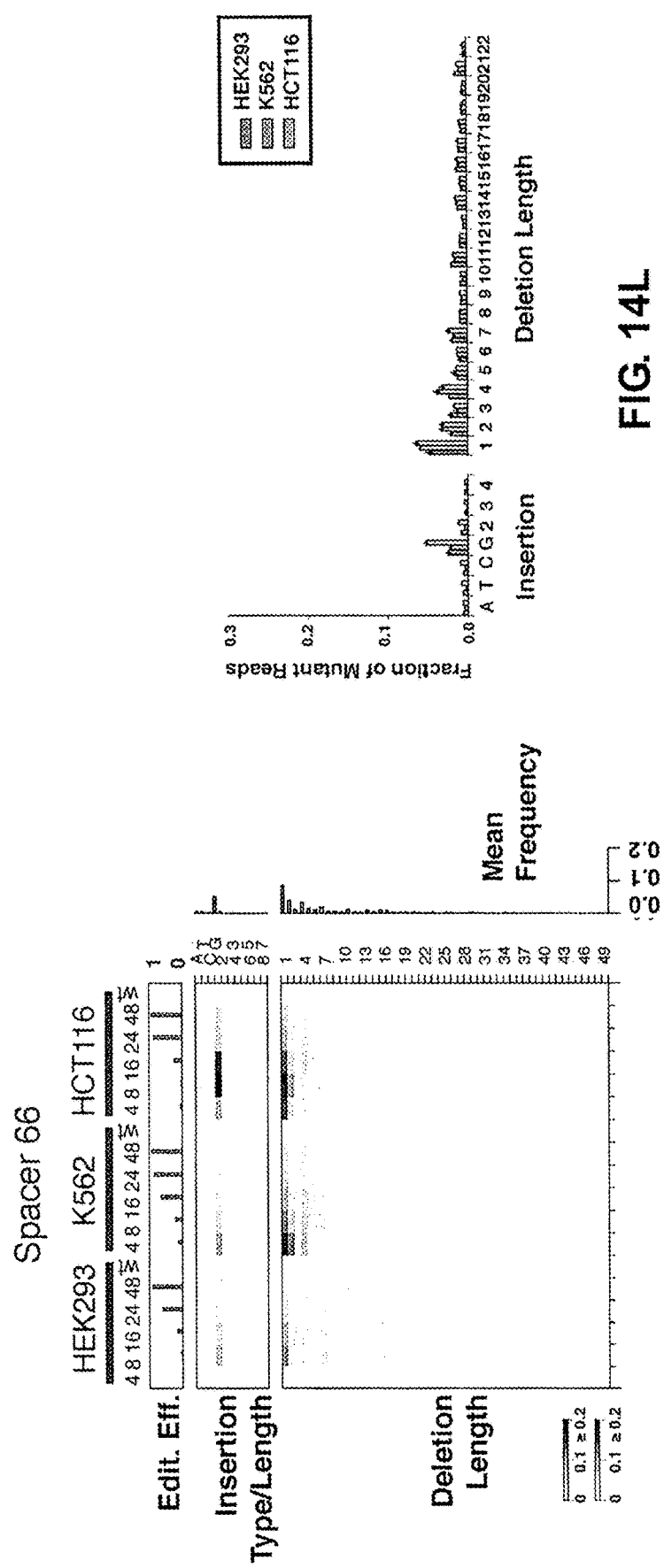

FIGS. 14A-14L show that the distribution of DNA repair outcomes after Cas9 cleavage changes over time in a cell type-dependent manner. FIGS. 14A, 14E and 14I: Heat map zooms of the indicated spacer (FIG. 14A: spacer 1; FIG. 14E: spacer 51; FIG. 14I: spacer 66) showing single replicates of each time point comparing three cell lines. (FIGS. 14B, 14F and 14J) Bar graphs of indel frequencies by length for the indicated spacer (FIG. 14B: spacer 1; FIG. 14F: spacer 51; FIG. 14J: spacer 66) displayed as a fraction of mutant reads (mean and standard deviation across triplicates) in three cell lines at the 48 hour time point. DNA repair outcomes for three spacers with a computational mask of microhomology deletions (FIGS. 14C and 14D; FIGS. 14G and 14H; FIGS. 14K and 14L) (see FIG. 12D). FIGS. 14C, 14G and 14K: Heat map zooms of the indicated spacer (FIG. 14C: spacer 1; FIG. 14G: spacer 51; FIG. 14K: spacer 66) showing single replicates of each time point comparing three cell types after applying a stringent computational mask of microhomology deletions (MH_score >3). FIGS. 14D, 14H and 14L: Bar graphs of indel frequencies by length for the indicated spacer (FIG. 14D: spacer 1; FIG. 14H: spacer 51; FIG. 14L: spacer 66) displayed as a fraction of mutant reads (mean and standard deviation across triplicates) in three cell lines at the 48 hour time point after applying a stringent computational mask of microhomology deletions (MH_score >3).

Figure 15:
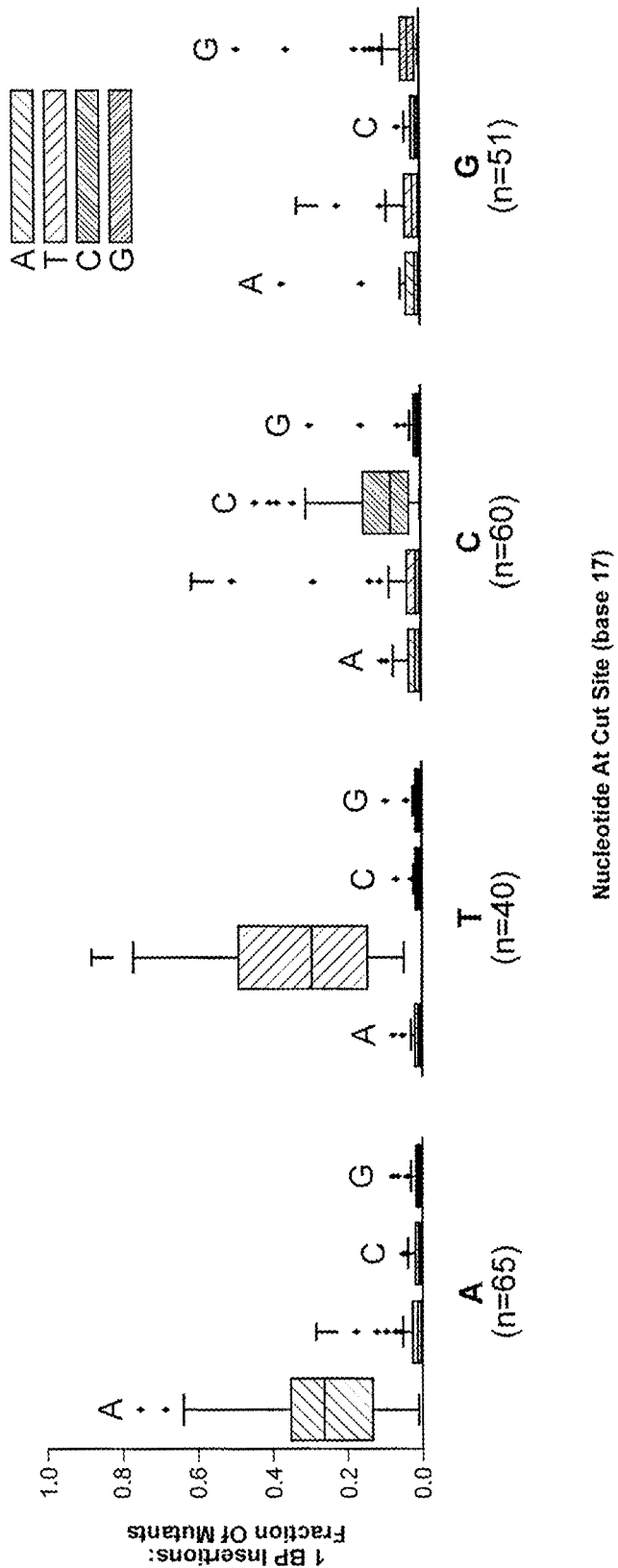
FIG. 15 displays the frequencies of nucleotide insertions as a function of the position-17 nucleotide in the protospacer.

FIG. 15 displays the frequencies of nucleotide insertions as a function of the position-17 nucleotide in the protospacer.

Example 1

DNA Repair Outcomes at Cas9 Breaks

The repair outcomes following Cas9 cleavage of double-stranded DNA, which result in blunt end products (Gasiunas et al., "Cas9-crRNA ribonucleoprotein complex mediates specific DNA cleavage for adaptive immunity in bacteria" Proc. Natl. Acad. Sci. U.S.A. (2012) 109:E2579-86; Jinek et al., "A programmable dual-RNA-guided DNA endonuclease in adaptive bacterial immunity," Science (2012) 337:816-821), were profiled using computational tools developed to categorize indels from our cell-based assay. Results are shown in FIGS. 1A-1C.

To this end, HEK293 cells were transfected with pre-assembled complexes of Cas9 protein and sgRNA (single-guide RNA ribonucleoprotein complexes (sgRNPs)) (Lin et al., "Enhanced homology-directed human genome engineering by controlled timing of CRISPR/Cas9 delivery" Elife (2014) 3:e04766.2014; Schumann et al., "Generation of knock-in primary human T cells using Cas9 ribonucleoproteins" Proc. Natl. Acad. Sci. U.S.A. (2015) 112:10437-10442). DNA repair patterns following Cas9 cleavage were analyzed by amplicon sequencing (FIG. 1A). Sequencing reads were assigned to a specific indel class based on the indel type (insertion or deletion), start site, and length (or to the wild type class), and then the frequency of each class was calculated as a fraction of aligned reads or as a fraction of mutant reads (see, FIG. 1A). A window of 50 base pairs on either side of the Cas9 cut site was captured for all targets, which defines the range within which the distribution of DNA repair outcomes was monitored. Surprisingly, the identities and frequencies of specific indel classes were similar between independent experimental replicates, and this reproducibility extended to the specific start and end coordinates for each class (FIGS. 8B, 8C). Furthermore, the highest frequency indel classes were also preserved when the same site was cut in three different cell lines (HCT116, HEK293, K562; FIG. 1B). However, the relative frequencies of those classes were not identical between cell lines. HCT116 cells showed a higher frequency of insertion of a single adenine base and a lower frequency of a 19-base pair deletion compared to either HEK293 or K562 cell lines as a fraction of total edits. HCT116 is a mismatch repair-deficient cell line and this attribute might contribute to the observed pattern, potentially through lack of recruitment of Exo1 at DSBs (De las Alas et al., "Loss of DNA mismatch repair: effects on the rate of mutation to drug resistance" J. Natl. Cancer Inst. (1997) 89:1537-1541; Goellner et al., "Exonuclease 1-dependent and independent mismatch repair" DNA Repair (2015) 32:24-32).

Next, DNA repair outcomes at the same spacer target sites were assessed by delivering sgRNAs via lentiviral transduction into cells that express Cas9 constitutively (Zhou et al., "High-throughput screening of a CRISPR/Cas9 library for functional genomics in human cells" Nature (2014) 509: 487-491; Wang et al., "Genetic screens in human cells using the CRISPR-Cas9 system" Science (2014) 343:80-84). DNA repair outcomes were measured at a later time point in lentiviral delivery experiments than in sgRNP delivery experiments (11 and 14 days post-delivery compared to 48 hours post-delivery) to gauge what constituted a mature DNA repair profile and when this profile was achieved in each delivery method. sgRNPs are transient and are metabolized by the cell; whereas constitutive expression of Cas9 and sgRNA provides an environment where a target site can be re-cleaved until an editing outcome is achieved that prevents further cutting of the target.

The repair outcomes were quantified to determine whether those resulting from one spacer target (across all replicates, cell types, and reagent delivery methods) were more similar to each other than to the repair outcomes of samples corresponding to a different spacer target from a set of 69 spacers. First, a matrix of the similarity in DNA repair outcomes between all pairs of samples was generated, using Jaccard/Tanimoto similarity (FIGS. 2A-2C). The top 10 indels were scored for each of the 69 genomic loci (in a binary list of possible indels) and the overlap in this list was then compared pair-wise across all loci (FIGS. 2A-2C). The landscape of indel classes was consistent at an individual site when compared across replicates, cell types and reagent delivery methods (mean Jaccard/Tanimoto similarity score of 0.70+/−0.06 (see, FIGS. 6-9). In contrast, when DNA repair outcomes were compared across different spacer target sites, the landscapes of indel classes were not consistent (mean similarity score of 0.09+/−0.03) (FIGS. 5, 6, 8 and 9). Samples corresponding to the same target sequence had higher similarity scores, indicating more overlap in indel landscapes, than samples corresponding to different target sequences (FIGS. 2A, 2B, along the diagonal). Additionally, cluster analysis (via Affinity Propagation clustering) was applied to the indel similarity matrix to partition the samples by repair outcome similarity (without referencing spacer labels) and the resulting cluster membership was then compared to the "ground truth" where samples were simply grouped by spacer label. An ARI (Adjusted Rand Index) value of 0.92 was attained for sgRNP-only delivery and an ARI value of 0.76 was attained when sgRNP and lentivirus delivery were combined (FIG. 2C) (An ARI value of 1 indicates that the observed clustering perfectly matches the ground truth, while an ARI value of 0 indicates a random distribution of labels in the observed clustering.) These statistics of similarity strongly corroborate the heat map visualizations and indicate that each target sequence has a characteristic DNA repair indel landscape.

Thus, DNA repair outcomes at Cas9 breaks are nonrandom and unique to each target.

Example 2

DNA Repair Signatures after Cas9 Cleavage

The characteristic patterns of DNA repair outcomes observed for different target sequences could be the consequence of either sequence-dependent or genomic context-dependent factors. To distinguish between sequence and context dependence, a series of sgRNAs were designed such that the spacer sequence of each sgRNA perfectly matched multiple locations in the human genome (multiple target single spacer; MTSS), whereas the sequences flanking the protospacer ensured that each of these sites could be amplified uniquely by PCR (Tables 3; 4A; and 4B). Twenty-two spacer sequences were selected that met these criteria; the targeted sequences each occur 2-14 times in the genome, providing a total of 127 sites for analysis (FIGS. 3A-3F). Consistent with the initial observations, distinct patterns of the highest frequency indel classes were conserved across experimental replicates at each of the individual sites (FIGS. 3B, 10A). Furthermore, the DNA repair patterns at each of the sites targeted by the same spacer sequence were strikingly similar to each other. For example, "spacer 15" targets seven sites in the genome that can be uniquely amplified; for each of these sites, two dominant repair outcomes, a single insertion of "A" and a single base deletion, comprise 53-67% of the total observed repair events. In addition, less frequent yet reproducible repair events resulting in 8- and 10-base pair deletions and a 2 base pair insertion were observed (FIGS. 3B, 10A). Furthermore, for all of the target sites for a given spacer sequence, the same pattern was also observed in different cell types (FIGS. 3C-3D). The relative editing efficiencies were different between sites of the same spacer group and between the same site comparing between cell types; however, the overall pattern of DNA repair outcomes was the same. The distribution of the mean indel frequencies by length across all samples in the twenty-two spacer groups was nearly identical when compared across different cell types (FIGS. 3C-3D (right distributions)). The same methods described above were used to assess whether the repair outcomes of the genomic target sites of one spacer group were more similar to each other than to the repair outcomes of the genomic target sites of the other 21 spacer groups (FIGS. 3E, 3F, 11A, 11B). Genomic loci corresponding to the same spacer sequence had higher similarity scores, indicating more overlap in indel landscapes, than genomic target sites corresponding to different spacer sequences (FIGS. 3E-3F, along the diagonal).

Cluster analysis was applied to the indel similarity matrix to partition the 127 loci by repair outcome similarity, and an ARI value of 0.87 was attained for both HEK293 and K562 cell lines from this analysis indicating that the repair outcomes at sites with the same target sequence located in diverse regions of the genome are more similar to each other than to the repair outcomes resulting from different sgRNAs (FIG. 11D). Comparable results were obtained when an indel frequency-based threshold was used rather than a rank-based threshold for scoring indels (FIGS. 11A-11B, 11D). These computational analyses demonstrate that repair outcomes at target sites primarily cluster within spacer groups. There were a small number of cases where samples corresponding to the same spacer group were split into multiple clusters or were clustered with samples corresponding to other spacer groups (e.g., HEK293 groups 12 and 14, and K562 groups 2 and 5 (FIG. 11C)). In the case of spacer group 2, there were sequence differences 5' of the target sequence such that a region of microhomology was present at site 1 but not site 2, coincident with a 12-base pair deletion at site 1 but not site 2. Taken together, these findings strongly evidence that the DNA repair patterns observed after sgRNP cleavage are nonrandom and are dependent on DNA sequence rather than functional genomic context.

It has been proposed that a subset of deletion outcomes after Cas9 cleavage are due to MMEJ where a reproducible deletion occurs between regions of microhomology (Nakade et al., "Microhomology-mediated end-joining-dependent integration of donor DNA in cells and animals using TALENs and CRISPR/Cas9" Nat Commun (2014) 5:5560; Bae et al. "Microhomology-based choice of Cas9 nuclease target sites" Nat. Methods (2014) 11:705-706). DNA repair patterns from the MTSS experiment were analyzed to determine whether microhomology could be a driver of the non-random patterns. A microhomology (MH) score was predicted for each repair class at each target site (FIG. 12D). MH scores were used to filter potential MH-dependent sites from the repair patterns at various stringencies. After MH masking, ARI values dropped to a range of 0.66-0.74 depending on the MH-mask stringency, yet strong clustering of all 127 loci remained indicating that c-NHEJ repair outcomes are a substantial portion of each repair landscape (FIG. 12C). Furthermore, similarity matrices generated after MH-masking revealed less indel class overlap between loci with the same spacer sequence, but a strong pattern remained (FIGS. 12A-12B). Examination of the change in overall indel pattern after MH masking showed that large deletions were masked, supporting the hypothesis that large deletion formation may rely on MH (FIGS. 4, 14). The pattern that remains after the most stringent MH mask (score >3, FIG. 12D) contains all insertions and primarily small deletions that are specific to a particular spacer sequence and are most probably the result of DSB repair by the c-NHEJ machinery; whereas, larger deletions are more likely the result of microhomology and MMEJ-dependent repair. However, even the most stringent computational MH-mask, where only 1-2 nucleotides of homology are required, likely provides only an approximation of the MMEJ-dependent repair landscape. It should also be noted that, although larger deletions were filtered out using the MH mask, MH scores were not predictive for the highest frequency deletions observed for a given target site.

Example 3

Distribution of DNA Repair Outcomes after Cas9 Cleavage

Genome editing outcomes are determined by the DNA repair pathway that is engaged. These pathways are, in turn, influenced by cell cycle stage. MMEJ initiates with end resection at a DSB (Truong et al., "Microhomology-mediated End Joining and Homologous Recombination share the initial end resection step to repair DNA double-strand breaks in mammalian cells" Proc. Natl. Acad. Sci. U.S.A. (2013) 110:7720-7725), an activity that is dependent on CDK levels (Huertas et al., "CDK targets Sae2 to control DNA-end resection and homologous recombination" Nature (2008) 455:689-692; Huertas and Jackson, "Human CtIP mediates cell cycle control of DNA end resection and double strand break repair" J. Biol. Chem. (2009) 284:9558-9565). c-NHEJ, however, can operate throughout the cell cycle (Aylon et al., "The CDK regulates repair of double-strand breaks by homologous recombination during the cell cycle." (2004) EMBO J. 23:4868-4875; Ira et al., "DNA end resection, homologous recombination and DNA damage checkpoint activation require CDK1" Nature (2004) 431:1011-1017). Given that heat map profiling and MH masking could distinguish between c-NHEJ-dependent small indels and MH-dependent deletions, the evolution of repair outcomes over a 48-hour period of time was investigated. Genomic DNA was harvested 4, 8, 16, 24 and 48 hours post nucleofection from HEK293, K562 and HCT116 cell lines edited with 96 different sgRNPs (FIGS. 4A, 13A, 13B). The overall distribution of repair classes was similar for HEK293 and K562 cell lines at each time point, whereas the frequencies of insertions and smaller deletions were relatively higher in HCT116 cells (FIGS. 4A, 13A, 13B, right distribution of mean frequencies). For example, when the distribution of indel frequencies by length for spacer 13 was compared between different cell lines harvested at 48 hours, HCT116 cells had a lower frequency of 3 and 8 base pair deletions and a higher frequency of single base pair insertions (FIGS. 4B-4C). Similarly, with spacer 54, HCT116 cells had a lower frequency of 4 and 19 base pair deletions compared to HEK293 and K562 cells; however, other deletion classes were at similar frequencies as observed in HEK293 and K562 cells (FIGS. 4F, 4G). When the MH-mask was applied to these sites, the deletion lengths with dissimilar frequency in HCT116 cells disappeared (FIGS. 4D, 4E, 4H, 4I).

Analysis of the full set of 96 spacers at each time point revealed a consistent pattern where single base pair insertions and small deletions (1-2 base pairs) were dominant at early time points (expressed as a fraction of the total classes) and larger deletions became more prominent at later time points (FIGS. 4, 13, 14). However, large deletions (>5 base pairs) were generally less prominent in HCT116 cells throughout the time course as a fraction of total repair classes, consistent with the overall pattern (FIGS. 4, 13, 14). When a stringent MH mask was applied to the time course data, the larger deletions that appear at later time points were filtered out, indicating that at least a subset of deletions are likely dependent on MH and that the reduced level of large deletions in HCT116 is potentially due to a deficiency in MMEJ (FIGS. 4D, 4E, 4H, 4I, 14C, 14D, 14G, 14H, 14K, 14L).

Thus, the distribution of DNA repair outcomes after Cas9 cleavage changes over time.

Example 4

Effect of Chemical Perturbation of c-NHEJ after Cas9 Cleavage

To test the hypothesis that suppression of c-NHEJ would alter the DNA repair landscapes, favoring MMEJ repair outcomes, a chemical inhibitor of DNA-PK, NU7441, was added to HEK293T cells one hour post nucleofection in a five point dose response (Leahy et al., "Identification of a highly potent and selective DNA-dependent protein kinase (DNA-PK) inhibitor (NU7441) by screening of chromenone libraries" Bioorg. Med. Chem. Lett. (2004) 14:6083-6087; Robert et al., "Pharmacological inhibition of DNA-PK stimulates Cas9-mediated genome editing" Genome Med (2015) 7:93). Genomic lysate was harvested 48 hours post nucleofection and processed as in previous experiments (see, description of FIG. 5A). Chemical inhibitors of the c-NHEJ pathway have been used in conjunction with delivery of Cas9/sgRNA before (Maruyama et al., "Increasing the efficiency of precise genome editing with CRISPR-Cas9 by inhibition of nonhomologous end joining" Nat. Biotechnol. (2015) 33:538-542; Chu et al., "Increasing the efficiency of homology-directed repair for CRISPR-Cas9-induced precise gene editing in mammalian cells" Nat. Biotechnol. (2015) 33:543-548; Robert et al., "Pharmacological inhibition of DNA-PK stimulates Cas9-mediated genome editing" Genome Med (2015) 7:93); however, this was in the context of using an exogenous donor template and attempting to promote HDR by suppressing indel formation by c-NHEJ.

At the lowest concentration of inhibitor (1.56 µM), a change of the DNA repair patterns at 12 different target sites compared with untreated samples was apparent (FIG. 5). As inhibitor concentration increased, the mean frequency of single base insertions and small deletions (<3 base pairs) decreased, whereas the mean frequency of a subset of large deletions (>3 base pairs) present in the DNA repair profiles increased (FIGS. 5A, 5C). This experiment evidences that the suppression of c-NHEJ enhances DNA repair by MMEJ pathways after DSB formation by Cas9. These data also indicate that we can effectively segregate DNA editing events produced by different DNA repair machineries by DNA repair profiling and that individual repair profiles can be modulated by suppressing or enhancing individual components of these pathways. The ability to promote a subset of editing outcomes by chemical perturbation, as has already been described for HDR, can be applied to correct a mutant allele in the absence of a donor template (e.g. FIG. 7E).

Thus, chemical perturbation of c-NHEJ alters DNA repair profiles after Cas9 cleavage.

Example 5

Prediction of the Most Frequently Inserted Nucleotide at Cas9 Target Sites

One of the more common DNA repair outcomes following Cas9 cleavage of targets is a single base pair insertion. Furthermore, the frequencies with which each nucleotide is inserted (A, T, C, or G) vary widely across targets. To test the hypothesis that the cut-site nucleotides of the protospacer sequence may be predictive of which nucleotide is most frequently inserted (Cas9 cleaves between positions 17 and 18 in the protospacer) the following experiment was conducted.

A data set of repair outcome data for 216 Cas9 target sites in K562 cells was generated. A multiclass classifier was performed using linear discriminant analysis (James et al., An Introduction to Statistical Learning, First Edition, 2013, Springer, ISBN 978-1461471370) via the Python Scikit-learn library (Pedregosa et al., "Sckit-learn: Machine Learning in Python" J. Mach. Learn Res. (2011) 12:2825-2830). For each target site, the cut-site nucleotide of interest (spacer position 17 or 18) was represented in a feature vector with three indicator variables. Predictive performance was assessed using the stratified, five-fold cross-validated accuracy (percentage of predictions that were true positives or true negatives). The baseline accuracy was determined by permuting the outcome labels and assessing performance.

Using the above methods, it was determined that the PAM-proximal, cut-site nucleotide (protospacer position 18) was not predictive of which nucleotide was most frequently inserted at Cas9 targets. Cross-validated accuracy was 33%±6% (compared to a baseline of 29%±7% when labels were permuted). However, the PAM-distal, cut-site nucleotide (protospacer position 17) was highly predictive of which nucleotide was most frequently inserted. Cross-validated accuracy was 83%±4%. FIG. 15 displays the frequencies of nucleotide insertions as a function of the position-17 nucleotide in the protospacer.

Next, linear regression was used to evaluate the performance of using the position-17 nucleotide to predict the frequencies with which each nucleotide was inserted. Linear regression was performed via the Python Scikit-learn library (Pedregosa et al., "Sckit-learn: Machine Learning in Python" J. Mach. Learn Res. (2011) 12:2825-2830). Predictive performance was assessed using the stratified, five-fold cross-validated $R^2$. The cross-validated $R^2$ values were 0.52±0.12 for insertion of A; 0.54±0.13 for insertion of T; 0.30±0.10 for insertion of C; and not significantly different than 0 for insertion of G.

In summary, the protospacer position-17 nucleotide accurately predicts which nucleotide is most frequently inserted at Cas9 targets and also explains substantial portions of the variance in the frequencies of insertion of A and insertion of T.

Although preferred embodiments of the subject methods have been described in some detail, it is understood that obvious variations can be made without departing from the spirit and the scope of the methods as defined by the appended claims.

TABLE 1

Genomic coordinates and sgRNA primer sequences for Spacers 1-96

| Spacer | Genomic location of spacer | sgRNA primer | SEQ ID NO.: |
|---|---|---|---|
| 1 | chr11: 836293-836316 | TAATACGACTCACTATAGGCTGATGTAGTCACTCTTGAGTTTTAGAGCTAGAAATAGC | 1 |
| 2 | chr4: 145041692-145041714 | TAATACGACTCACTATAGAGTGTGCATTGCCACCTCAGGTTTTAGAGCTAGAAATAGC | 2 |
| 3 | chr15: 90348654-90348677 | TAATACGACTCACTATAGAGATGCAGGCTGCAGATGCCGTTTTAGAGCTAGAAATAGC | 3 |
| 4 | chr17: 40440261-40440283 | TAATACGACTCACTATAGGGCCCTCGGCGGCGGCTCCCGTTTTAGAGCTAGAAATAGC | 4 |
| 5 | chrX: 138644010-138644032 | TAATACGACTCACTATAGACAGAACATGTTGTTATAGAGTTTTAGAGCTAGAAATAGC | 5 |
| 6 | chrX: 66765045-66765067 | TAATACGACTCACTATAGACAGATTCTGGAAAGCTCCTGTTTTAGAGCTAGAAATAGC | 6 |
| 7 | chrX: 138643957-138643979 | TAATACGACTCACTATAGGGTCAACAAGTGGAACTCTAGTTTTAGAGCTAGAAATAGC | 7 |
| 8 | chr8: 39871134-39871156 | TAATACGACTCACTATAGGGAGTATTTCAGGGGCTCTTGTTTTAGAGCTAGAAATAGC | 8 |
| 9 | chr1: 183218409-183218431 | TAATACGACTCACTATAGGGGAGGGCTGTGCTGCTAGTGTTTTAGAGCTAGAAATAGC | 9 |
| 10 | chr7: 50526196-50526218 | TAATACGACTCACTATAGGCAACTTGAAATTATATCTGGTTTTAGAGCTAGAAATAGC | 10 |
| 11 | chr8: 39845460-39845482 | TAATACGACTCACTATAGGTAGAGAAAGAAGCAGTGCCGTTTTAGAGCTAGAAATAGC | 11 |
| 12 | chr1: 208072333-208072356 | TAATACGACTCACTATAGATAGGAGAAGATGATGTATAGTTTTAGAGCTAGAAATAGC | 12 |
| 13 | chr10: 89506437-89506459 | TAATACGACTCACTATAGGCATACAGTGATTTGATGAAGTTTTAGAGCTAGAAATAGC | 13 |
| 14 | chr7: 55240709-55240731 | TAATACGACTCACTATAGGGGGCCCTCCTCTTGCTGCGTTTTAGAGCTAGAAATAGC | 14 |
| 15 | chr1: 183220487-183220509 | TAATACGACTCACTATAGGAAAATCATCAGTTATCATCGTTTTAGAGCTAGAAATAGC | 15 |

TABLE 1-continued

Genomic coordinates and sgRNA primer sequences for Spacers 1-96

| Spacer | Genomic location of spacer | sgRNA primer | SEQ ID NO.: |
|---|---|---|---|
| 16 | chr1: 208073317-208073340 | TAATACGACTCACTATAGTTCATGAGTCTTGACAACAAGTTTTAGAGCTAGAAATAGC | 16 |
| 17 | chr11: 836360-836383 | TAATACGACTCACTATAGGGTGGCGGGCACTGTCGTCAGTTTTAGAGCTAGAAATAGC | 17 |
| 18 | chr22: 42032717-42032740 | TAATACGACTCACTATAGATGACAGTGCCAAAGCCAGCGTTTTAGAGCTAGAAATAGC | 18 |
| 19 | chr13: 32900719-32900742 | TAATACGACTCACTATAGACAGTAGAACTAAGGGTGGGGTTTTAGAGCTAGAAATAGC | 19 |
| 20 | chrX: 66765028-66765050 | TAATACGACTCACTATAGCCGCCGTCCAAGACCTACCGTTTTAGAGCTAGAAATAGC | 20 |
| 21 | chr15: 90348584-90348607 | TAATACGACTCACTATAGCATCACGCTTATCCACCCCAGTTTTAGAGCTAGAAATAGC | 21 |
| 22 | chr2: 216977771-216977794 | TAATACGACTCACTATAGACCATGAGTAACTCCATTCCGTTTTAGAGCTAGAAATAGC | 22 |
| 23 | chrX: 138644048-138644070 | TAATACGACTCACTATAGGGAGGTAGAGATTCATGTCAGTTTTAGAGCTAGAAATAGC | 23 |
| 24 | chr13: 108863525-108863547 | TAATACGACTCACTATAGGAACGAATACAGAAAAGTAAGTTTTAGAGCTAGAAATAGC | 24 |
| 25 | chr22: 42032577-42032600 | TAATACGACTCACTATAGATCCGTGGCCCATCATGTCTGTTTTAGAGCTAGAAATAGC | 25 |
| 26 | chr2: 216974068-216974091 | TAATACGACTCACTATAGGGTGGACAAGCGGCAGATAGGTTTTAGAGCTAGAAATAGC | 26 |
| 27 | chr4: 156826243-156826265 | TAATACGACTCACTATAGGAACTGCAAAGTGAAACAAGTTTTAGAGCTAGAAATAGC | 27 |
| 28 | chr1: 198668757-198668780 | TAATACGACTCACTATAGACTGACACGCAGACATTCAGGTTTTAGAGCTAGAAATAGC | 28 |
| 29 | chr22: 37461708-37461730 | TAATACGACTCACTATAGCGAAGCTGGAATCTGCTCTCGTTTTAGAGCTAGAAATAGC | 29 |
| 30 | chr10: 6104130-6104152 | TAATACGACTCACTATAGGACCAGCCGGGGCAGTGAAGGTTTTAGAGCTAGAAATAGC | 30 |
| 31 | chr15: 90358013-90358036 | TAATACGACTCACTATAGGGGCGCTGGAACCTGGACCCGTTTTAGAGCTAGAAATAGC | 31 |
| 32 | chr17: 37883173-37883195 | TAATACGACTCACTATAGGGACAGAAGAAGCCCTGCTGGTTTTAGAGCTAGAAATAGC | 32 |
| 33 | chr3: 169482616-169482638 | TAATACGACTCACTATAGCTGGGCAGGCGACCCGCCGCGTTTTAGAGCTAGAAATAGC | 33 |
| 34 | chr17: 37884086-37884108 | TAATACGACTCACTATAGGTTCTCCACGGCACCCCCAAGTTTTAGAGCTAGAAATAGC | 34 |
| 35 | chr7: 55259538-55259560 | TAATACGACTCACTATAGGAGAAAGAATACCATGCAGAGTTTTAGAGCTAGAAATAGC | 35 |
| 36 | chrX: 133594274-133594296 | TAATACGACTCACTATAGCTCCTCCTCTGCTCCGCCACGTTTTAGAGCTAGAAATAGC | 36 |
| 37 | chrX: 133594290-133594312 | TAATACGACTCACTATAGGCTCAGGAGGAGGAAGCCGGGTTTTAGAGCTAGAAATAGC | 37 |
| 38 | chr1: 65432129-65432151 | TAATACGACTCACTATAGGCTGAGGAGGGTCGCGGCGGTTTTAGAGCTAGAAATAGC | 38 |
| 39 | chr16: 29708698-29708720 | TAATACGACTCACTATAGGGGCACTGGAGCCACCTCTTGTTTTAGAGCTAGAAATAGC | 39 |
| 40 | chr19: 17942176-17942198 | TAATACGACTCACTATAGGCACGCAGCGGCGGGAGCCCGTTTTAGAGCTAGAAATAGC | 40 |
| 41 | chr19: 17945473-17945495 | TAATACGACTCACTATAGGGCCCCCAAGTGGACAGAGCGTTTTAGAGCTAGAAATAGC | 41 |
| 42 | chr13: 32893320-32893343 | TAATACGACTCACTATAGTGTGGAGTTTTAAATAGGTTGTTTTAGAGCTAGAAATAGC | 42 |
| 43 | chr2: 191878760-191878782 | TAATACGACTCACTATAGGGAAGGGCTAGGCGGGGCGGTTTTAGAGCTAGAAATAGC | 43 |
| 44 | chr12: 72425547-72425569 | TAATACGACTCACTATAGGCAAATAACCTTCTGTGTCAGTTTTAGAGCTAGAAATAGC | 44 |
| 45 | chr8: 39840236-39840258 | TAATACGACTCACTATAGGCACCAAGTCTGAGTGGACCGTTTTAGAGCTAGAAATAGC | 45 |
| 46 | chr12: 72416242-72416264 | TAATACGACTCACTATAGGCAGGACTCCTTTCCTCCATGTTTTAGAGCTAGAAATAGC | 46 |
| 47 | chr13: 32889667-32889690 | TAATACGACTCACTATAGGCTGCGCCTCTGCTGCGCCTGTTTTAGAGCTAGAAATAGC | 47 |
| 48 | chr13: 32893350-32893373 | TAATACGACTCACTATAGGAAGCCAGCTGATTATAAGAGTTTTAGAGCTAGAAATAGC | 48 |
| 49 | chr13: 32889776-32889799 | TAATACGACTCACTATAGCCAAAAAGAACTGCACCTCGTTTTAGAGCTAGAAATAGC | 49 |
| 50 | chr15: 90348325-90348348 | TAATACGACTCACTATAGGTTCGACTACGTGGAGAAGCGTTTTAGAGCTAGAAATAGC | 50 |
| 51 | chr2: 216974143-216974166 | TAATACGACTCACTATAGGCACCATGTTGCCGGTCCTCGTTTTAGAGCTAGAAATAGC | 51 |
| 52 | chr11: 836347-836370 | TAATACGACTCACTATAGGCCCGCCACCACCAGGATGTGTTTTAGAGCTAGAAATAGC | 52 |

TABLE 1-continued

Genomic coordinates and sgRNA primer sequences for Spacers 1-96

| Spacer | Genomic location of spacer | sgRNA primer | SEQ ID NO.: |
|---|---|---|---|
| 53 | chr2: 216981432-216981455 | TAATACGACTCACTATAGGGCACTGACAATCCCCTTTCGTTTTAGAGCTAGAAATAGC | 53 |
| 54 | chr1: 65349086-65349108 | TAATACGACTCACTATAGGAGGAGCTCCAAGAAGACTGGTTTTAGAGCTAGAAATAGC | 54 |
| 55 | chr4: 156825204-156825226 | TAATACGACTCACTATAGGAAGAAGACAAATCACAAACGTTTTAGAGCTAGAAATAGC | 55 |
| 56 | chr1: 208084481-208084504 | TAATACGACTCACTATAGGGGCGGGAAGAGCGCGTCCGTTTTAGAGCTAGAAATAGC | 56 |
| 57 | chr16: 29708389-29708411 | TAATACGACTCACTATAGGCCGTGCAGGCAGCTGAGGCGTTTTAGAGCTAGAAATAGC | 57 |
| 58 | chr1: 198608241-198608264 | TAATACGACTCACTATAGCTCGTCTGATAAGACAACAGGTTTTAGAGCTAGAAATAGC | 58 |
| 59 | chr4: 156825228-156825250 | TAATACGACTCACTATAGGTGAATAGAGCCAGCAAAGGGTTTTAGAGCTAGAAATAGC | 59 |
| 60 | chr1: 198668733-198668756 | TAATACGACTCACTATAGGACTCGCAGACGCCCTCTGCGTTTTAGAGCTAGAAATAGC | 60 |
| 61 | chr22: 42017307-42017330 | TAATACGACTCACTATAGTTGTCGTCTTCTGTCCAAGTGTTTTAGAGCTAGAAATAGC | 61 |
| 62 | chr13: 32889654-32889677 | TAATACGACTCACTATAGGAGGCGCAGCAGTGCCACAGGTTTTAGAGCTAGAAATAGC | 62 |
| 63 | chr17: 40441426-40441448 | TAATACGACTCACTATAGGGCCATGGCGGGCTGGATCCGTTTTAGAGCTAGAAATAGC | 63 |
| 64 | chr22: 37539598-37539620 | TAATACGACTCACTATAGGAGCCAAGATGGGGCTCTGCGTTTTAGAGCTAGAAATAGC | 64 |
| 65 | chr6: 43737291-43737313 | TAATACGACTCACTATAGGGTGGGGGAGTTTGCTCCGTTTTAGAGCTAGAAATAGC | 65 |
| 66 | chr19: 17952223-17952245 | TAATACGACTCACTATAGGCCGAGGCTGCTGGAGGAAGGTTTTAGAGCTAGAAATAGC | 66 |
| 67 | chrX: 66765119-66765141 | TAATACGACTCACTATAGGCCGGGAGGTGCTGCGCTCGTTTTAGAGCTAGAAATAGC | 67 |
| 68 | chr1: 198668793-198668816 | TAATACGACTCACTATAGGCAAAACTCAACCCTACCCCGTTTTAGAGCTAGAAATAGC | 68 |
| 69 | chr10: 6104107-6104129 | TAATACGACTCACTATAGGAATCCATCTTCCTGACCCTGTTTTAGAGCTAGAAATAGC | 69 |
| 70 | chr1: 198608161-198608184 | TAATACGACTCACTATAGCTAGGTGATGATGTCAGATTGTTTTAGAGCTAGAAATAGC | 70 |
| 71 | chr17: 40481444-40481466 | TAATACGACTCACTATAGGAGCAGAGATGTGGGAATGGGTTTTAGAGCTAGAAATAGC | 71 |
| 72 | chr17: 40466486-40466508 | TAATACGACTCACTATAGGGGACTGGGGTCGGGAGGGTGTTTTAGAGCTAGAAATAGC | 72 |
| 73 | chr7: 50605568-50605590 | TAATACGACTCACTATAGGAGAAAGCTGGAGAAGGGGGGTTTTAGAGCTAGAAATAGC | 73 |
| 74 | chr22: 42017321-42017344 | TAATACGACTCACTATAGGCGCAGGGAAGCGACCAACTGTTTTAGAGCTAGAAATAGC | 74 |
| 75 | chr17: 40466373-40466395 | TAATACGACTCACTATAGGAAGAGGGGAGAGAGTTACGTTTTAGAGCTAGAAATAGC | 75 |
| 76 | chr1: 65311293-65311315 | TAATACGACTCACTATAGGTGGAAGAGTTTGTGGAAGGGTTTTAGAGCTAGAAATAGC | 76 |
| 77 | chr15: 40987440-40987463 | TAATACGACTCACTATAGAGTTCCCAGCTGCACGCCTCGTTTTAGAGCTAGAAATAGC | 77 |
| 78 | chr7: 50633109-50633131 | TAATACGACTCACTATAGGAAGAGGGAAACGTGTGGCTGTTTTAGAGCTAGAAATAGC | 78 |
| 79 | chr17: 37863274-37863296 | TAATACGACTCACTATAGGGTGGGTCTCGGGACTGGCAGTTTTAGAGCTAGAAATAGC | 79 |
| 80 | chr2: 191835123-191835145 | TAATACGACTCACTATAGGAATGAGGGTCCTTTGGGAAGTTTTAGAGCTAGAAATAGC | 80 |
| 81 | chr2: 191878928-191878950 | TAATACGACTCACTATAGGGTGGGGCGGAAGGGGGCCGTTTTAGAGCTAGAAATAGC | 81 |
| 82 | chr15: 40987403-40987426 | TAATACGACTCACTATAGCGGCCAGAGACCGAGCCCTAGTTTTAGAGCTAGAAATAGC | 82 |
| 83 | chr7: 55220290-55220312 | TAATACGACTCACTATAGGTTGTGGCAGCAGTCACTGGGTTTTAGAGCTAGAAATAGC | 83 |
| 84 | chr17: 40458414-40458436 | TAATACGACTCACTATAGGGCCACTGTAGTCCTCCAGGGTTTTAGAGCTAGAAATAGC | 84 |
| 85 | chr22: 37532281-37532303 | TAATACGACTCACTATAGGGAGCCAGCCCCTGGCCTTCGTTTTAGAGCTAGAAATAGC | 85 |
| 86 | chr1: 208084623-208084646 | TAATACGACTCACTATAGTCCCAAAGGCGGAGGGCGTTGTTTTAGAGCTAGAAATAGC | 86 |
| 87 | chr2: 73160981-73161003 | TAATACGACTCACTATAGTGAGTCCGAGCAGAAGAAGAGTTTTAGAGCTAGAAATAGC | 87 |
| 88 | chr2: 73160982-73161004 | TAATACGACTCACTATAGGAGTCCGAGCAGAAGAAGAAGTTTTAGAGCTAGAAATAGC | 88 |
| 89 | chr1: 65312386-65312408 | TAATACGACTCACTATAGGGCAGCCAGCATGATGAGACGTTTTAGAGCTAGAAATAGC | 89 |
| 90 | chr2: 216977802-216977825 | TAATACGACTCACTATAGCTTCTTTGCTTGTTCAAATGGTTTTAGAGCTAGAAATAGC | 90 |

TABLE 1-continued

Genomic coordinates and sgRNA primer sequences for Spacers 1-96

| Spacer | Genomic location of spacer | sgRNA primer | SEQ ID NO.: |
|---|---|---|---|
| 91 | chr19: 17953906-17953928 | TAATACGACTCACTATAGGCAGGGTGAGTGTCTCAGCCGTTTTAGAGCTAGAAATAGC | 91 |
| 92 | chr22: 37523901-37523923 | TAATACGACTCACTATAGGAACTGTGTGTGTTGCAGGGGTTTTAGAGCTAGAAATAGC | 92 |
| 93 | chr1: 55529322-55529344 | TAATACGACTCACTATAGGGGCTGAGAGAGGGACAAGTGTTTTAGAGCTAGAAATAGC | 93 |
| 94 | chr22: 42032568-42032591 | TAATACGACTCACTATAGAAAACGTTTCCAAGACATGAGTTTTAGAGCTAGAAATAGC | 94 |
| 95 | chr15: 40987560-40987583 | TAATACGACTCACTATAGCCACGCCCGCGGGGTGAAGTGTTTTAGAGCTAGAAATAGC | 95 |
| 96 | chrX: 133594214-133594236 | TAATACGACTCACTATAGGAGCCCTCAGGCGAACCTCTGTTTTAGAGCTAGAAATAGC | 96 |

TABLE 2

Sequencing library primers for Spacers 1-96 (PCR1)

| Spacer | ILMN primer sequence | SEQ ID NO.: |
|---|---|---|
| 1 | CACTCTTTCCCTACACGACGCTCTTCCGATCTCAGATGCGATGACCTTTGTG | 97 |
| 1 | GGAGTTCAGACGTGTGCTCTTCCGATCTAGTCACCATGACGACAGTGC | 98 |
| 2 | CACTCTTTCCCTACACGACGCTCTTCCGATCTCAGGTCCCCTAAAATGGGTT | 99 |
| 2 | GGAGTTCAGACGTGTGCTCTTCCGATCTGCTTTATGGTCCGCTCAGTC | 100 |
| 3 | CACTCTTTCCCTACACGACGCTCTTCCGATCTCTCACCTTTGGGAAGCATGT | 101 |
| 3 | GGAGTTCAGACGTGTGCTCTTCCGATCTAGCTCTGGCACACCCTCTAA | 102 |
| 4 | CACTCTTTCCCTACACGACGCTCTTCCGATCTcagGTTTGGGATTTCCAGAG | 103 |
| 4 | GGAGTTCAGACGTGTGCTCTTCCGATCTCCTGCAAGTGCGCAACAG | 104 |
| 5 | CACTCTTTCCCTACACGACGCTCTTCCGATCTTCCTCAAATTTGGATCTGGC | 105 |
| 5 | GGAGTTCAGACGTGTGCTCTTCCGATCTCCCCCACTATCTCCTTGACA | 106 |
| 6 | CACTCTTTCCCTACACGACGCTCTTCCGATCTTTCTGAGCAAGAGAAGGGGA | 107 |
| 6 | GGAGTTCAGACGTGTGCTCTTCCGATCTctgcAGCAGCAGCAAACT | 108 |
| 7 | CACTCTTTCCCTACACGACGCTCTTCCGATCTTCCTCAAATTTGGATCTGGC | 105 |
| 7 | GGAGTTCAGACGTGTGCTCTTCCGATCTCCCCCACTATCTCCTTGACA | 106 |
| 8 | CACTCTTTCCCTACACGACGCTCTTCCGATCTTGCACCCCTTTCATCTCTCT | 109 |
| 8 | GGAGTTCAGACGTGTGCTCTTCCGATCTCACCTCTCCTCTTCCTCCCT | 110 |
| 9 | CACTCTTTCCCTACACGACGCTCTTCCGATCTGAGACTTTCCCCCTTGTTCC | 111 |
| 9 | GGAGTTCAGACGTGTGCTCTTCCGATCTACAGGCAGAAGGAAAACCCT | 112 |
| 10 | CACTCTTTCCCTACACGACGCTCTTCCGATCTtGCCGTTTAAAAACATCCAA | 113 |
| 10 | GGAGTTCAGACGTGTGCTCTTCCGATCTAAGTGGTAGGAAAGCCTCACTG | 114 |
| 11 | CACTCTTTCCCTACACGACGCTCTTCCGATCTAAGGAACCTGGAGACCATCA | 115 |
| 11 | GGAGTTCAGACGTGTGCTCTTCCGATCTGAAAGGCACTGAGTGGGAAG | 116 |
| 12 | CACTCTTTCCCTACACGACGCTCTTCCGATCTGGAAAGAAACAGCTTGCCTG | 117 |
| 12 | GGAGTTCAGACGTGTGCTCTTCCGATCTGAAGCCTAGCCTGTCACCTG | 118 |
| 13 | CACTCTTTCCCTACACGACGCTCTTCCGATCTCGTGTTGAAGACCTGACTGG | 119 |
| 13 | GGAGTTCAGACGTGTGCTCTTCCGATCTCAATGACCACAGCAAAGAGC | 120 |
| 14 | CACTCTTTCCCTACACGACGCTCTTCCGATCTATCTGTCAGCAACCTCACCC | 121 |

TABLE 2-continued

Sequencing library primers for Spacers 1-96 (PCR1)

| Spacer | ILMN primer sequence | SEQ ID NO.: |
|---|---|---|
| 14 | GGAGTTCAGACGTGTGCTCTTCCGATCTACTGGCACTCACCTCCCTC | 122 |
| 15 | CACTCTTTCCCTACACGACGCTCTTCCGATCTAACAAGACCAAGGCACTGCT | 123 |
| 15 | GGAGTTCAGACGTGTGCTCTTCCGATCTCTCAACCCTGGAGGTCTTTG | 124 |
| 16 | CACTCTTTCCCTACACGACGCTCTTCCGATCTCCATGTTGAGACACAGGGTG | 125 |
| 16 | GGAGTTCAGACGTGTGCTCTTCCGATCTTCAGGAAATTGCATCAGGTG | 126 |
| 17 | CACTCTTTCCCTACACGACGCTCTTCCGATCTCAGATGCGATGACCTTTGTG | 97 |
| 17 | GGAGTTCAGACGTGTGCTCTTCCGATCTGTTCCGACGCTCCTTGAA | 127 |
| 18 | CACTCTTTCCCTACACGACGCTCTTCCGATCTTCAGTGAAGTGCTGTGGGTC | 128 |
| 18 | GGAGTTCAGACGTGTGCTCTTCCGATCTTGCCAATTTAAGAGAACGGG | 129 |
| 19 | CACTCTTTCCCTACACGACGCTCTTCCGATCTGGGTCGTCAGACACCAAAAC | 130 |
| 19 | GGAGTTCAGACGTGTGCTCTTCCGATCTCAACCTCATCTGCTCTTTCTTG | 131 |
| 20 | CACTCTTTCCCTACACGACGCTCTTCCGATCTTTCTGAGCAAGAGAAGGGGA | 107 |
| 20 | GGAGTTCAGACGTGTGCTCTTCCGATCTCCGGGTTCTGGATCACTTC | 132 |
| 21 | CACTCTTTCCCTACACGACGCTCTTCCGATCTAGGGAGCATGTGTGTGAG | 133 |
| 21 | GGAGTTCAGACGTGTGCTCTTCCGATCTGGAAGTCCTTCCCATGCTTC | 134 |
| 22 | CACTCTTTCCCTACACGACGCTCTTCCGATCTTCCCTTTTTCACACCTTTCC | 135 |
| 22 | GGAGTTCAGACGTGTGCTCTTCCGATCTCTGTCGCTGTACAAACATGG | 136 |
| 23 | CACTCTTTCCCTACACGACGCTCTTCCGATCTTTCCACAAAGGGAGATCAGC | 137 |
| 23 | GGAGTTCAGACGTGTGCTCTTCCGATCTTTGCCTTTCATTGCACACTC | 138 |
| 24 | CACTCTTTCCCTACACGACGCTCTTCCGATCTTTCCATAGGCCATTCTCTCTC | 139 |
| 24 | GGAGTTCAGACGTGTGCTCTTCCGATCTGCTGCCTCACAAACTTCACA | 140 |
| 25 | CACTCTTTCCCTACACGACGCTCTTCCGATCTAGGCAGCCACTGACATTCTT | 141 |
| 25 | GGAGTTCAGACGTGTGCTCTTCCGATCTGGGGTTGTCTTCATTGGTGA | 142 |
| 26 | CACTCTTTCCCTACACGACGCTCTTCCGATCTTGCGCATGCTCAGAGTTC | 143 |
| 26 | GGAGTTCAGACGTGTGCTCTTCCGATCTCCAAGTCCATGGCTTTCTTT | 144 |
| 27 | CACTCTTTCCCTACACGACGCTCTTCCGATCTTGAGTTTGGAGGAGCATTTG | 145 |
| 27 | GGAGTTCAGACGTGTGCTCTTCCGATCTCAATGAGAAATGCCTGTGGA | 146 |
| 28 | CACTCTTTCCCTACACGACGCTCTTCCGATCTCAGTGGGGAAGACTGATGT | 147 |
| 28 | GGAGTTCAGACGTGTGCTCTTCCGATCTCCGCAAACCTGAGATAGCAT | 148 |
| 29 | CACTCTTTCCCTACACGACGCTCTTCCGATCTAGTCAGGACTTCCCCACCTT | 149 |
| 29 | GGAGTTCAGACGTGTGCTCTTCCGATCTTGGTTCTACATCCCGAGGAG | 150 |
| 30 | CACTCTTTCCCTACACGACGCTCTTCCGATCTGACTCCCTCTGGTTCTGTGG | 151 |
| 30 | GGAGTTCAGACGTGTGCTCTTCCGATCTGATGCCAAAAAGAGGCTGAC | 152 |
| 31 | CACTCTTTCCCTACACGACGCTCTTCCGATCTAGAAGTCCAGCTCCGCAC | 153 |
| 31 | GGAGTTCAGACGTGTGCTCTTCCGATCTAAAAAGACGGGAAAGGAGGA | 154 |
| 32 | CACTCTTTCCCTACACGACGCTCTTCCGATCTGACAGCACCTTCTACCGCTC | 155 |
| 32 | GGAGTTCAGACGTGTGCTCTTCCGATCTGGTAAGCAGACAGCCACACA | 156 |
| 33 | CACTCTTTCCCTACACGACGCTCTTCCGATCTGCTGACAGAGCCCAACTCTT | 157 |

TABLE 2-continued

Sequencing library primers for Spacers 1-96 (PCR1)

| Spacer | ILMN primer sequence | SEQ ID NO.: |
|---|---|---|
| 33 | GGAGTTCAGACGTGTGCTCTTCCGATCTGCCTTCCACCGTTCATTCTA | 158 |
| 34 | CACTCTTTCCCTACACGACGCTCTTCCGATCTCTGGTGCCACTCTGGAAAG | 159 |
| 34 | GGAGTTCAGACGTGTGCTCTTCCGATCTGTTCTCTGCCGTAGGTGTCC | 160 |
| 35 | CACTCTTTCCCTACACGACGCTCTTCCGATCTCCTCACAGCAGGGTCTTCTC | 161 |
| 35 | GGAGTTCAGACGTGTGCTCTTCCGATCTCCTGGTGTCAGGAAAATGCT | 162 |
| 36 | CACTCTTTCCCTACACGACGCTCTTCCGATCTcCTGCTTCTCCTCAGCTTCA | 163 |
| 36 | GGAGTTCAGACGTGTGCTCTTCCGATCTGAGCTGCTCACCACGACG | 164 |
| 37 | CACTCTTTCCCTACACGACGCTCTTCCGATCTcCTGCTTCTCCTCAGCTTCA | 163 |
| 37 | GGAGTTCAGACGTGTGCTCTTCCGATCTGAGCTGCTCACCACGACG | 164 |
| 38 | CACTCTTTCCCTACACGACGCTCTTCCGATCTACACTCACCACTTCCGTGTG | 165 |
| 38 | GGAGTTCAGACGTGTGCTCTTCCGATCTGCGGAGTATCCTGGAGCTG | 166 |
| 39 | CACTCTTTCCCTACACGACGCTCTTCCGATCTATCACCCTGGACAACCTCC | 167 |
| 39 | GGAGTTCAGACGTGTGCTCTTCCGATCTAAGATGTGTGACCCAGAGGG | 168 |
| 40 | CACTCTTTCCCTACACGACGCTCTTCCGATCTGCTTAGCTAGGCCGAAGTCA | 169 |
| 40 | GGAGTTCAGACGTGTGCTCTTCCGATCTGCTCGGGGTAGGGTTATAG | 170 |
| 41 | CACTCTTTCCCTACACGACGCTCTTCCGATCTGCACCTGAAGAGATGAGGCT | 171 |
| 41 | GGAGTTCAGACGTGTGCTCTTCCGATCTGGAGATTGGGGTGGGTCTAT | 172 |
| 42 | CACTCTTTCCCTACACGACGCTCTTCCGATCTTTTTCTTCAGAAGCTCCACCC | 173 |
| 42 | GGAGTTCAGACGTGTGCTCTTCCGATCTTCAGCCCTTGCTCTTTGAAT | 174 |
| 43 | CACTCTTTCCCTACACGACGCTCTTCCGATCTCCCGAGGACTCTGTCCCT | 175 |
| 43 | GGAGTTCAGACGTGTGCTCTTCCGATCTCTTTTCTCCTGCCGGGTAGT | 176 |
| 44 | CACTCTTTCCCTACACGACGCTCTTCCGATCTTATCTGGGGATTTGATGCCT | 177 |
| 44 | GGAGTTCAGACGTGTGCTCTTCCGATCTGAGTGGTTATCTGCCATTGGA | 178 |
| 45 | CACTCTTTCCCTACACGACGCTCTTCCGATCTGAAAGGTCCTGCCAAGGAAT | 179 |
| 45 | GGAGTTCAGACGTGTGCTCTTCCGATCTGTGTTTCCTGGGGAAAGTT | 180 |
| 46 | CACTCTTTCCCTACACGACGCTCTTCCGATCTTTTTGTTTTGGGTGCCATTT | 181 |
| 46 | GGAGTTCAGACGTGTGCTCTTCCGATCTTTTCCCTGACCTTGAACCAG | 182 |
| 47 | CACTCTTTCCCTACACGACGCTCTTCCGATCTAATTTCCTTTCGCCACACTG | 183 |
| 47 | GGAGTTCAGACGTGTGCTCTTCCGATCTGGTCACAAATCTGTCCCCTC | 184 |
| 48 | CACTCTTTCCCTACACGACGCTCTTCCGATCTTTTCTTCAGAAGCTCCACCC | 173 |
| 48 | GGAGTTCAGACGTGTGCTCTTCCGATCTACAGGAGATTGGTACAGCGG | 185 |
| 49 | CACTCTTTCCCTACACGACGCTCTTCCGATCTCTTCTGAAACTAGGCGGCAG | 186 |
| 49 | GGAGTTCAGACGTGTGCTCTTCCGATCTGACTGGGACTGCGGAAGAC | 187 |
| 50 | CACTCTTTCCCTACACGACGCTCTTCCGATCTccctggcctAACAATTCAGA | 188 |
| 50 | GGAGTTCAGACGTGTGCTCTTCCGATCTGACCCCAACTGGAATGTCAC | 189 |
| 51 | CACTCTTTCCCTACACGACGCTCTTCCGATCTTTTCAGGCCTAGCAGGAAAC | 190 |
| 51 | GGAGTTCAGACGTGTGCTCTTCCGATCTCCCATTCTTTGTCTTGACCG | 191 |
| 52 | CACTCTTTCCCTACACGACGCTCTTCCGATCTCAGATGCGATGACCTTTGTG | 97 |

TABLE 2-continued

Sequencing library primers for Spacers 1-96 (PCR1)

| Spacer | ILMN primer sequence | SEQ ID NO.: |
|---|---|---|
| 52 | GGAGTTCAGACGTGTGCTCTTCCGATCTGTTCCGACGCTCCTTGAA | 127 |
| 53 | CACTCTTTCCCTACACGACGCTCTTCCGATCTGAGGTCTGGTTGTCCTGCTC | 192 |
| 53 | GGAGTTCAGACGTGTGCTCTTCCGATCTCAATGTCCTCCAGCAAATCA | 193 |
| 54 | CACTCTTTCCCTACACGACGCTCTTCCGATCTTGTGTACTCTCCACTGCCCA | 194 |
| 54 | GGAGTTCAGACGTGTGCTCTTCCGATCTTCAGAACACTCCCTTTTGCC | 195 |
| 55 | CACTCTTTCCCTACACGACGCTCTTCCGATCTGCAATGAGAATTTTAATCACCC | 196 |
| 55 | GGAGTTCAGACGTGTGCTCTTCCGATCTTGCCTAACAATGGACACCAA | 197 |
| 56 | CACTCTTTCCCTACACGACGCTCTTCCGATCTCAGCAAACTCAGCAAGCAAA | 198 |
| 56 | GGAGTTCAGACGTGTGCTCTTCCGATCTGGAGGGGAGAAGAGAGGAAA | 199 |
| 57 | CACTCTTTCCCTACACGACGCTCTTCCGATCTCAGTCCTCACCCTTGTCCTC | 200 |
| 57 | GGAGTTCAGACGTGTGCTCTTCCGATCTTAAGAGCCCACCACAGATCC | 201 |
| 58 | CACTCTTTCCCTACACGACGCTCTTCCGATCTTCCTGCAAAGAGGACCCTTA | 202 |
| 58 | GGAGTTCAGACGTGTGCTCTTCCGATCTGCGTCCTTCTGAAAAGCAAA | 203 |
| 59 | CACTCTTTCCCTACACGACGCTCTTCCGATCTGCAATGAGAATTTTAATCACCC | 196 |
| 59 | GGAGTTCAGACGTGTGCTCTTCCGATCTTGCCTAACAATGGACACCAA | 197 |
| 60 | CACTCTTTCCCTACACGACGCTCTTCCGATCTCAGTGGGGAAGACTGATGT | 147 |
| 60 | GGAGTTCAGACGTGTGCTCTTCCGATCTAGGGTTGAGTTTTGCATTGG | 204 |
| 61 | CACTCTTTCCCTACACGACGCTCTTCCGATCTTAGAAGCTGGTTGGGGAGTG | 205 |
| 61 | GGAGTTCAGACGTGTGCTCTTCCGATCTCTAGCTGGCGAACAACACAA | 206 |
| 62 | CACTCTTTCCCTACACGACGCTCTTCCGATCTAATTTCCTTTCGCCACACTG | 183 |
| 62 | GGAGTTCAGACGTGTGCTCTTCCGATCTGGTCACAAATCTGTCCCCTC | 184 |
| 63 | CACTCTTTCCCTACACGACGCTCTTCCGATCTGGATAGGTAGGCATGGCAAG | 207 |
| 63 | GGAGTTCAGACGTGTGCTCTTCCGATCTTACCATGGCTGGCTCTCAAT | 208 |
| 64 | CACTCTTTCCCTACACGACGCTCTTCCGATCTCTCCTTGGAGTCCAGTGCAT | 209 |
| 64 | GGAGTTCAGACGTGTGCTCTTCCGATCTACTCACACCTCATCTTGCCC | 210 |
| 65 | CACTCTTTCCCTACACGACGCTCTTCCGATCTCCAGATGGCACATTGTCAGA | 211 |
| 65 | GGAGTTCAGACGTGTGCTCTTCCGATCTCCTAGTGACTGCCGTCTGC | 212 |
| 66 | CACTCTTTCCCTACACGACGCTCTTCCGATCTGAAAACTTGACCCCTGTCCA | 213 |
| 66 | GGAGTTCAGACGTGTGCTCTTCCGATCTCTCGTGGACGGCTACTTCC | 214 |
| 67 | CACTCTTTCCCTACACGACGCTCTTCCGATCTACCGAGGAGCTTTCCAGAAT | 215 |
| 67 | GGAGTTCAGACGTGTGCTCTTCCGATCTGGGGAGAACCATCCTCAC | 216 |
| 68 | CACTCTTTCCCTACACGACGCTCTTCCGATCTGTACAGACGCCTCACCTTCC | 217 |
| 68 | GGAGTTCAGACGTGTGCTCTTCCGATCTGCTGCACATTGAATAAGTGGTT | 218 |
| 69 | CACTCTTTCCCTACACGACGCTCTTCCGATCTGACTCCCTCTGGTTCTGTGG | 151 |
| 69 | GGAGTTCAGACGTGTGCTCTTCCGATCTGATGCCAAAAAGAGGCTGAC | 152 |
| 70 | CACTCTTTCCCTACACGACGCTCTTCCGATCTAACATCTTCCTTGATGGGAAAA | 219 |
| 70 | GGAGTTCAGACGTGTGCTCTTCCGATCTCAATTTCCTCCTCTGTTACCC | 220 |
| 71 | CACTCTTTCCCTACACGACGCTCTTCCGATCTTCATGTCACTTTGGCCTGAA | 221 |

TABLE 2-continued

Sequencing library primers for Spacers 1-96 (PCR1)

| Spacer | ILMN primer sequence | SEQ ID NO.: |
|---|---|---|
| 71 | GGAGTTCAGACGTGTGCTCTTCCGATCTCTAGGGAGAGCCTCACAGGA | 222 |
| 72 | CACTCTTTCCCTACACGACGCTCTTCCGATCTCTCTCCCCCTCTTCTTCCAT | 223 |
| 72 | GGAGTTCAGACGTGTGCTCTTCCGATCTGTTGTTTCTGTGGGTGCCTT | 224 |
| 73 | CACTCTTTCCCTACACGACGCTCTTCCGATCTAAGCATGAGTGCCTCTTTCC | 225 |
| 73 | GGAGTTCAGACGTGTGCTCTTCCGATCTTCGGTTAATCCCTTCCCTTC | 226 |
| 74 | CACTCTTTCCCTACACGACGCTCTTCCGATCTCATGCGTGATGACGTAGAGG | 227 |
| 74 | GGAGTTCAGACGTGTGCTCTTCCGATCTTCGCACACTTAAGGCTAACG | 228 |
| 75 | CACTCTTTCCCTACACGACGCTCTTCCGATCTAAGACGCCATTACAAGTGCC | 229 |
| 75 | GGAGTTCAGACGTGTGCTCTTCCGATCTGCGTGTCTAAAGGTCCCTCA | 230 |
| 76 | CACTCTTTCCCTACACGACGCTCTTCCGATCTCTCACCAAGTAGCTCAGGGC | 231 |
| 76 | GGAGTTCAGACGTGTGCTCTTCCGATCTGGACTGTCGTAAGGGGATGA | 232 |
| 77 | CACTCTTTCCCTACACGACGCTCTTCCGATCTGAATTCTGAAAGCCGCTGG | 233 |
| 77 | GGAGTTCAGACGTGTGCTCTTCCGATCTCGCTCCACTTCTCTACTCGC | 234 |
| 78 | CACTCTTTCCCTACACGACGCTCTTCCGATCTCCAACTTTGGGGACTGAAGA | 235 |
| 78 | GGAGTTCAGACGTGTGCTCTTCCGATCTGCTTCCAGGATTTGGAATGA | 236 |
| 79 | CACTCTTTCCCTACACGACGCTCTTCCGATCTGCTTCTCCCTGTCTGAGGTG | 237 |
| 79 | GGAGTTCAGACGTGTGCTCTTCCGATCTGCAGGTAGGTGAGTTCCAGG | 238 |
| 80 | CACTCTTTCCCTACACGACGCTCTTCCGATCTTCCTACGTCAAGCAGTTCCC | 239 |
| 80 | GGAGTTCAGACGTGTGCTCTTCCGATCTGGCATTCTCTGAAGAGTGGG | 240 |
| 81 | CACTCTTTCCCTACACGACGCTCTTCCGATCTCTGCTCGGTCTGGGGTCT | 241 |
| 81 | GGAGTTCAGACGTGTGCTCTTCCGATCTGAAGCCGGCGGAAATACC | 242 |
| 82 | CACTCTTTCCCTACACGACGCTCTTCCGATCTAGTCTGTAAACTCGCGCAGG | 243 |
| 82 | GGAGTTCAGACGTGTGCTCTTCCGATCTCAGATGAGTTGCAGTTCCCA | 244 |
| 83 | CACTCTTTCCCTACACGACGCTCTTCCGATCTTCACAGGGAACCTTTGCTCT | 245 |
| 83 | GGAGTTCAGACGTGTGCTCTTCCGATCTCTTACCAGGCAGTCGCTCTC | 246 |
| 84 | CACTCTTTCCCTACACGACGCTCTTCCGATCTACATGAAATTCAAGGCCGAA | 247 |
| 84 | GGAGTTCAGACGTGTGCTCTTCCGATCTACCTGTCTGTGAGGTGGAGG | 248 |
| 85 | CACTCTTTCCCTACACGACGCTCTTCCGATCTAGGGATGGAGCTGACTGCTA | 249 |
| 85 | GGAGTTCAGACGTGTGCTCTTCCGATCTACCCCAGACACCCAGTATGA | 250 |
| 86 | CACTCTTTCCCTACACGACGCTCTTCCGATCTTTTCCTCTCTTCTCCCCTCC | 251 |
| 86 | GGAGTTCAGACGTGTGCTCTTCCGATCTCTGCCACAAAGGGGTTAAAA | 252 |
| 87 | CACTCTTTCCCTACACGACGCTCTTCCGATCTGTTTCTCATCTGTGCCCCTC | 253 |
| 87 | GGAGTTCAGACGTGTGCTCTTCCGATCTGTTGCCCACCCTAGTCATTG | 254 |
| 88 | CACTCTTTCCCTACACGACGCTCTTCCGATCTGTTTCTCATCTGTGCCCCTC | 253 |
| 88 | GGAGTTCAGACGTGTGCTCTTCCGATCTGTTGCCCACCCTAGTCATTG | 254 |
| 89 | CACTCTTTCCCTACACGACGCTCTTCCGATCTaagaaaggCAAGAAGCCTGG | 255 |
| 89 | GGAGTTCAGACGTGTGCTCTTCCGATCTGCTGGCCTGAGACATTCCTA | 256 |
| 90 | CACTCTTTCCCTACACGACGCTCTTCCGATCTTTGGAACTTTGTTTCCAGGC | 257 |

TABLE 2-continued

Sequencing library primers for Spacers 1-96 (PCR1)

| Spacer | ILMN primer sequence | SEQ ID NO.: |
|---|---|---|
| 90 | GGAGTTCAGACGTGTGCTCTTCCGATCTGGCAACAAGCAGTTCAAACA | 258 |
| 91 | CACTCTTTCCCTACACGACGCTCTTCCGATCTTGGCTCTCACCTGACAGTCTT | 259 |
| 91 | GGAGTTCAGACGTGTGCTCTTCCGATCTACAACAGGGCTTGAAGTTGG | 260 |
| 92 | CACTCTTTCCCTACACGACGCTCTTCCGATCTagaggagcgatgcttctgAG | 261 |
| 92 | GGAGTTCAGACGTGTGCTCTTCCGATCTACTTGGTCCATCCATTTCCA | 262 |
| 93 | CACTCTTTCCCTACACGACGCTCTTCCGATCTCAGGAGCTCCAGTGACAGC | 263 |
| 93 | GGAGTTCAGACGTGTGCTCTTCCGATCTGGCACCCAGAGTGAGTGAGT | 264 |
| 94 | CACTCTTTCCCTACACGACGCTCTTCCGATCTAGGCAGCCACTGACATTCTT | 141 |
| 94 | GGAGTTCAGACGTGTGCTCTTCCGATCTGGGGTTGTCTTCATTGGTGA | 142 |
| 95 | CACTCTTTCCCTACACGACGCTCTTCCGATCTAGAGACCGAGCCCTAAGGAG | 265 |
| 95 | GGAGTTCAGACGTGTGCTCTTCCGATCTCTCACACACTCACCTCGGTC | 266 |
| 96 | CACTCTTTCCCTACACGACGCTCTTCCGATCTAGAAAATTCCCACGGCTACC | 267 |
| 96 | GGAGTTCAGACGTGTGCTCTTCCGATCTGACTGCTCAGGAGGAGGAAG | 268 |

TABLE 3

Multiple Target Single Spacer (MTSS) genomic coordinates and sgRNA primer sequences

| Spacer | Genomic location (hg38) | sgRNA primer | SEQ ID NO.: |
|---|---|---|---|
| 1a | chr1: 58056377-58056400 | TAATACGACTCACTATAGCCTTGTCCTTGGGCACGCATGTTTTAGAGCTAGAAATAGC | 269 |
| 1b | chr2: 171375175-171375198 | TAATACGACTCACTATAGCCTTGTCCTTGGGCACGCATGTTTTAGAGCTAGAAATAGC | 270 |
| 1c | chr4: 113214290-113214313 | TAATACGACTCACTATAGCCTTGTCCTTGGGCACGCATGTTTTAGAGCTAGAAATAGC | 270 |
| 2a | chr5: 41951514-41951537 | TAATACGACTCACTATAGGTGACCAAGGAGGAATTTCAGTTTTAGAGCTAGAAATAGC | 271 |
| 2b | chr10: 14723370-14723393 | TAATACGACTCACTATAGGTGACCAAGGAGGAATTTCAGTTTTAGAGCTAGAAATAGC | 271 |
| 3a | chr12: 124927891-124927914 | TAATACGACTCACTATAGctctcccaactgagctatttGTTTTAGAGCTAGAAATAGC | 272 |
| 3b | chr12: 19613825-19613848 | TAATACGACTCACTATAGctctcccaactgagctatttGTTTTAGAGCTAGAAATAGC | 272 |
| 3c | chr19: 1383410-1383433 | TAATACGACTCACTATAGctctcccaactgagctatttGTTTTAGAGCTAGAAATAGC | 272 |
| 3d | chr13: 94549698-94549721 | TAATACGACTCACTATAGctctcccaactgagctatttGTTTTAGAGCTAGAAATAGC | 272 |
| 3e | chr6: 28790770-28790793 | TAATACGACTCACTATAGctctcccaactgagctatttGTTTTAGAGCTAGAAATAGC | 272 |
| 3f | chr6: 28823365-28823388 | TAATACGACTCACTATAGctctcccaactgagctatttGTTTTAGAGCTAGAAATAGC | 272 |
| 3g | chr6: 28981720-28981743 | TAATACGACTCACTATAGctctcccaactgagctatttGTTTTAGAGCTAGAAATAGC | 272 |
| 3h | chr11: 59566428-59566451 | TAATACGACTCACTATAGctctcccaactgagctatttGTTTTAGAGCTAGAAATAGC | 272 |
| 4a | chr12: 124927869-124927892 | TAATACGACTCACTATAGgcgttagactgaagatctaaGTTTTAGAGCTAGAAATAGC | 273 |
| 4b | chr19: 1383388-1383411 | TAATACGACTCACTATAGgcgttagactgaagatctaaGTTTTAGAGCTAGAAATAGC | 273 |
| 4c | chr13: 94549676-94549699 | TAATACGACTCACTATAGgcgttagactgaagatctaaGTTTTAGAGCTAGAAATAGC | 273 |
| 4d | chr6: 28764409-28764432 | TAATACGACTCACTATAGgcgttagactgaagatctaaGTTTTAGAGCTAGAAATAGC | 273 |
| 5a | chr1: 229431555-229431578 | TAATACGACTCACTATAGGATCCACATCTGCTGGAAGGGTTTTAGAGCTAGAAATAGC | 274 |
| 5b | chr6: 101430419-101430442 | TAATACGACTCACTATAGGATCCACATCTGCTGGAAGGGTTTTAGAGCTAGAAATAGC | 274 |
| 6a | chr9: 92006517-92006540 | TAATACGACTCACTATAGGCCATGAATTCATAGGGAATGTTTTAGAGCTAGAAATAGC | 275 |

TABLE 3-continued

Multiple Target Single Spacer (MTSS) genomic coordinates and sgRNA primer sequences

| Spacer | Genomic location (hg38) | sgRNA primer | SEQ ID NO.: |
|---|---|---|---|
| 6b | chr12: 122365605-122365628 | TAATACGACTCACTATAGGCCATGAATTCATAGGGAATGTTTTAGAGCTAGAAATAGC | 275 |
| 6c | chr12: 12155745-12155768 | TAATACGACTCACTATAGGCCATGAATTCATAGGGAATGTTTTAGAGCTAGAAATAGC | 275 |
| 6d | chr2: 171587547-171587570 | TAATACGACTCACTATAGGCCATGAATTCATAGGGAATGTTTTAGAGCTAGAAATAGC | 275 |
| 6e | chr13: 27256498-27256521 | TAATACGACTCACTATAGGCCATGAATTCATAGGGAATGTTTTAGAGCTAGAAATAGC | 275 |
| 6f | chr4: 19814204-19814227 | TAATACGACTCACTATAGGCCATGAATTCATAGGGAATGTTTTAGAGCTAGAAATAGC | 275 |
| 6g | chr17: 3665675-3665698 | TAATACGACTCACTATAGGCCATGAATTCATAGGGAATGTTTTAGAGCTAGAAATAGC | 275 |
| 6h | chr17: 43079753-43079776 | TAATACGACTCACTATAGGCCATGAATTCATAGGGAATGTTTTAGAGCTAGAAATAGC | 275 |
| 6i | chr7: 20003220-20003243 | TAATACGACTCACTATAGGCCATGAATTCATAGGGAATGTTTTAGAGCTAGAAATAGC | 275 |
| 6j | chr5: 177265214-177265237 | TAATACGACTCACTATAGGCCATGAATTCATAGGGAATGTTTTAGAGCTAGAAATAGC | 275 |
| 6k | chr10: 67794223-67794246 | TAATACGACTCACTATAGGCCATGAATTCATAGGGAATGTTTTAGAGCTAGAAATAGC | 275 |
| 6l | chr3: 154024271-154024294 | TAATACGACTCACTATAGGCCATGAATTCATAGGGAATGTTTTAGAGCTAGAAATAGC | 275 |
| 6m | chr3: 147277225-147277248 | TAATACGACTCACTATAGGCCATGAATTCATAGGGAATGTTTTAGAGCTAGAAATAGC | 275 |
| 6n | chr3: 32030651-32030674 | TAATACGACTCACTATAGGCCATGAATTCATAGGGAATGTTTTAGAGCTAGAAATAGC | 275 |
| 7a | chr1: 39963383-39963406 | TAATACGACTCACTATAGCCAGCTGTGGCTACAACATAGTTTTAGAGCTAGAAATAGC | 276 |
| 7b | chr6: 43364273-43364296 | TAATACGACTCACTATAGCCAGCTGTGGCTACAACATAGTTTTAGAGCTAGAAATAGC | 276 |
| 7c | chr10: 106455788-106455811 | TAATACGACTCACTATAGCCAGCTGTGGCTACAACATAGTTTTAGAGCTAGAAATAGC | 276 |
| 8a | chr15: 64593305-64593328 | TAATACGACTCACTATAGCCCCCACCAAAGCCCATGTAGTTTTAGAGCTAGAAATAGC | 277 |
| 8b | chr12: 56044133-56044156 | TAATACGACTCACTATAGCCCCCACCAAAGCCCATGTAGTTTTAGAGCTAGAAATAGC | 277 |
| 8c | chr12: 3469275-3469298 | TAATACGACTCACTATAGCCCCCACCAAAGCCCATGTAGTTTTAGAGCTAGAAATAGC | 277 |
| 8d | chr1: 51980799-51980822 | TAATACGACTCACTATAGCCCCCACCAAAGCCCATGTAGTTTTAGAGCTAGAAATAGC | 277 |
| 8e | chrX: 72044871-72044894 | TAATACGACTCACTATAGCCCCCACCAAAGCCCATGTAGTTTTAGAGCTAGAAATAGC | 277 |
| 8f | chr5: 75374788-75374811 | TAATACGACTCACTATAGCCCCCACCAAAGCCCATGTAGTTTTAGAGCTAGAAATAGC | 277 |
| 8g | chr18: 59761884-59761907 | TAATACGACTCACTATAGCCCCCACCAAAGCCCATGTAGTTTTAGAGCTAGAAATAGC | 277 |
| 9a | chr12: 118246943-118246966 | TAATACGACTCACTATAGTCCAGCTGTGGCTACAACATGTTTTAGAGCTAGAAATAGC | 278 |
| 9b | chr19: 12285163-12285186 | TAATACGACTCACTATAGTCCAGCTGTGGCTACAACATGTTTTAGAGCTAGAAATAGC | 278 |
| 9c | chr19: 16413554-16413577 | TAATACGACTCACTATAGTCCAGCTGTGGCTACAACATGTTTTAGAGCTAGAAATAGC | 278 |
| 9d | chr1: 198949783-198949806 | TAATACGACTCACTATAGTCCAGCTGTGGCTACAACATGTTTTAGAGCTAGAAATAGC | 278 |
| 9e | chr1: 39963382-39963405 | TAATACGACTCACTATAGTCCAGCTGTGGCTACAACATGTTTTAGAGCTAGAAATAGC | 278 |
| 9f | chr6: 43364272-43364295 | TAATACGACTCACTATAGTCCAGCTGTGGCTACAACATGTTTTAGAGCTAGAAATAGC | 278 |
| 9g | chr10: 106455787-106455810 | TAATACGACTCACTATAGTCCAGCTGTGGCTACAACATGTTTTAGAGCTAGAAATAGC | 278 |
| 10a | chr22: 19258809-19258832 | TAATACGACTCACTATAGAGCAGAAGCAGGGTACCCTTGTTTTAGAGCTAGAAATAGC | 279 |
| 10b | chr12: 52952845-52952868 | TAATACGACTCACTATAGAGCAGAAGCAGGGTACCCTTGTTTTAGAGCTAGAAATAGC | 279 |
| 10c | chr6: 34191085-34191108 | TAATACGACTCACTATAGAGCAGAAGCAGGGTACCCTTGTTTTAGAGCTAGAAATAGC | 279 |
| 11a | chr9: 106978769-106978792 | TAATACGACTCACTATAGGTACATTTAACCCAGTTTAGGTTTTAGAGCTAGAAATAGC | 280 |
| 11b | chr9: 133351349-133351372 | TAATACGACTCACTATAGGTACATTTAACCCAGTTTAGGTTTTAGAGCTAGAAATAGC | 280 |
| 11c | chr14: 69885333-69885356 | TAATACGACTCACTATAGGTACATTTAACCCAGTTTAGGTTTTAGAGCTAGAAATAGC | 280 |
| 11d | chr1: 147224336-147224359 | TAATACGACTCACTATAGGTACATTTAACCCAGTTTAGGTTTTAGAGCTAGAAATAGC | 280 |
| 11e | chr2: 158549207-158549230 | TAATACGACTCACTATAGGTACATTTAACCCAGTTTAGGTTTTAGAGCTAGAAATAGC | 280 |

TABLE 3-continued

Multiple Target Single Spacer (MTSS) genomic coordinates and sgRNA primer sequences

| Spacer | Genomic location (hg38) | sgRNA primer | SEQ ID NO.: |
|---|---|---|---|
| 11f | chr16: 22379779-22379802 | TAATACGACTCACTATAGGTACATTTAACCCAGTTTAGGTTTTAGAGCTAGAAATAGC | 280 |
| 11g | chr8: 39860514-39860537 | TAATACGACTCACTATAGGTACATTTAACCCAGTTTAGGTTTTAGAGCTAGAAATAGC | 280 |
| 11h | chr10: 63902437-63902460 | TAATACGACTCACTATAGGTACATTTAACCCAGTTTAGGTTTTAGAGCTAGAAATAGC | 280 |
| 11i | chr10: 33057602-33057625 | TAATACGACTCACTATAGGTACATTTAACCCAGTTTAGGTTTTAGAGCTAGAAATAGC | 280 |
| 11j | chr3: 121494891-121494914 | TAATACGACTCACTATAGGTACATTTAACCCAGTTTAGGTTTTAGAGCTAGAAATAGC | 280 |
| 12a | chr15: 99285519-99285542 | TAATACGACTCACTATAGCTGAGGAAGCTCTTCATTGGGTTTTAGAGCTAGAAATAGC | 281 |
| 12b | chr1: 115857760-115857783 | TAATACGACTCACTATAGCTGAGGAAGCTCTTCATTGGGTTTTAGAGCTAGAAATAGC | 281 |
| 13a | chr19: 21233591-21233614 | TAATACGACTCACTATAGAAGATGCAAGCATTTTGAACGTTTTAGAGCTAGAAATAGC | 282 |
| 13b | chr4: 112171466-112171489 | TAATACGACTCACTATAGAAGATGCAAGCATTTTGAACGTTTTAGAGCTAGAAATAGC | 282 |
| 13c | chr17: 67224980-67225003 | TAATACGACTCACTATAGAAGATGCAAGCATTTTGAACGTTTTAGAGCTAGAAATAGC | 282 |
| 13d | chr8: 95403830-95403853 | TAATACGACTCACTATAGAAGATGCAAGCATTTTGAACGTTTTAGAGCTAGAAATAGC | 282 |
| 13e | chrX: 101395414-101395437 | TAATACGACTCACTATAGAAGATGCAAGCATTTTGAACGTTTTAGAGCTAGAAATAGC | 282 |
| 14a | chr15: 43989501-43989524 | TAATACGACTCACTATAGCCATCTCCTGCTCGAAGTCCGTTTTAGAGCTAGAAATAGC | 283 |
| 14b | chr17: 81511307-81511330 | TAATACGACTCACTATAGCCATCTCCTGCTCGAAGTCCGTTTTAGAGCTAGAAATAGC | 283 |
| 14c | chrX: 53143241-53143264 | TAATACGACTCACTATAGCCATCTCCTGCTCGAAGTCCGTTTTAGAGCTAGAAATAGC | 283 |
| 15a | chr12: 30862020-30862043 | TAATACGACTCACTATAGGGCAGTGCAGATGAAAAACTGTTTTAGAGCTAGAAATAGC | 284 |
| 15b | chr2: 129496621-129496644 | TAATACGACTCACTATAGGGCAGTGCAGATGAAAAACTGTTTTAGAGCTAGAAATAGC | 284 |
| 15c | chr2: 68125583-68125606 | TAATACGACTCACTATAGGGCAGTGCAGATGAAAAACTGTTTTAGAGCTAGAAATAGC | 284 |
| 15d | chr20: 53421489-53421512 | TAATACGACTCACTATAGGGCAGTGCAGATGAAAAACTGTTTTAGAGCTAGAAATAGC | 284 |
| 15e | chr7: 76361951-76361974 | TAATACGACTCACTATAGGGCAGTGCAGATGAAAAACTGTTTTAGAGCTAGAAATAGC | 284 |
| 15f | chr7: 44799840-44799863 | TAATACGACTCACTATAGGGCAGTGCAGATGAAAAACTGTTTTAGAGCTAGAAATAGC | 284 |
| 15g | chr11: 43466710-43466733 | TAATACGACTCACTATAGGGCAGTGCAGATGAAAAACTGTTTTAGAGCTAGAAATAGC | 284 |
| 16a | chr14: 76634801-76634824 | TAATACGACTCACTATAGCCATTCAGTGGCCTGAGCAGGTTTTAGAGCTAGAAATAGC | 285 |
| 16b | chr12: 65758144-65758167 | TAATACGACTCACTATAGCCATTCAGTGGCCTGAGCAGGTTTTAGAGCTAGAAATAGC | 285 |
| 16c | chr1: 154378226-154378249 | TAATACGACTCACTATAGCCATTCAGTGGCCTGAGCAGGTTTTAGAGCTAGAAATAGC | 285 |
| 16d | chr1: 101786362-101786385 | TAATACGACTCACTATAGCCATTCAGTGGCCTGAGCAGGTTTTAGAGCTAGAAATAGC | 285 |
| 16e | chr1: 160266365-160266388 | TAATACGACTCACTATAGCCATTCAGTGGCCTGAGCAGGTTTTAGAGCTAGAAATAGC | 285 |
| 16f | chr13: 67266858-67266881 | TAATACGACTCACTATAGCCATTCAGTGGCCTGAGCAGGTTTTAGAGCTAGAAATAGC | 285 |
| 16g | chrX: 87703369-87703392 | TAATACGACTCACTATAGCCATTCAGTGGCCTGAGCAGGTTTTAGAGCTAGAAATAGC | 285 |
| 16h | chr10: 14723194-14723217 | TAATACGACTCACTATAGCCATTCAGTGGCCTGAGCAGGTTTTAGAGCTAGAAATAGC | 285 |
| 16i | chr3: 110682312-110682335 | TAATACGACTCACTATAGCCATTCAGTGGCCTGAGCAGGTTTTAGAGCTAGAAATAGC | 285 |
| 17a | chr12: 65758139-65758162 | TAATACGACTCACTATAGGCTCAGGCCACTGAATGGGTGTTTTAGAGCTAGAAATAGC | 286 |
| 17b | chr1: 101786357-101786380 | TAATACGACTCACTATAGGCTCAGGCCACTGAATGGGTGTTTTAGAGCTAGAAATAGC | 286 |
| 17c | chr1: 154378221-154378244 | TAATACGACTCACTATAGGCTCAGGCCACTGAATGGGTGTTTTAGAGCTAGAAATAGC | 286 |
| 17d | chr1: 160266360-160266383 | TAATACGACTCACTATAGGCTCAGGCCACTGAATGGGTGTTTTAGAGCTAGAAATAGC | 286 |
| 17e | chrX: 87703364-87703387 | TAATACGACTCACTATAGGCTCAGGCCACTGAATGGGTGTTTTAGAGCTAGAAATAGC | 286 |
| 17f | chr3: 110682307-110682330 | TAATACGACTCACTATAGGCTCAGGCCACTGAATGGGTGTTTTAGAGCTAGAAATAGC | 286 |
| 18a | chr22: 40106287-40106310 | TAATACGACTCACTATAGCCAGCTTAGAAAAATAATCAGTTTTAGAGCTAGAAATAGC | 287 |

TABLE 3-continued

Multiple Target Single Spacer (MTSS) genomic coordinates and sgRNA primer sequences

| Spacer | Genomic location (hg38) | sgRNA primer | SEQ ID NO.: |
|---|---|---|---|
| 18b | chr1: 81098229-81098252 | TAATACGACTCACTATAGCCAGCTTAGAAAAATAATCAGTTTTAGAGCTAGAAATAGC | 287 |
| 18c | chr13: 76981140-76981163 | TAATACGACTCACTATAGCCAGCTTAGAAAAATAATCAGTTTTAGAGCTAGAAATAGC | 287 |
| 18d | chr6: 17530862-17530885 | TAATACGACTCACTATAGCCAGCTTAGAAAAATAATCAGTTTTAGAGCTAGAAATAGC | 287 |
| 19a | chr2: 36299490-36299513 | TAATACGACTCACTATAGAGCCAAAGAGAAAGGTACCTGTTTTAGAGCTAGAAATAGC | 288 |
| 19b | chr13: 110762776-110762799 | TAATACGACTCACTATAGAGCCAAAGAGAAAGGTACCTGTTTTAGAGCTAGAAATAGC | 288 |
| 19c | chr17: 29716286-29716309 | TAATACGACTCACTATAGAGCCAAAGAGAAAGGTACCTGTTTTAGAGCTAGAAATAGC | 288 |
| 20a | chr15: 78863705-78863728 | TAATACGACTCACTATAGTGACGAACACAAAGGGAAAGGTTTTAGAGCTAGAAATAGC | 289 |
| 20b | chr14: 55414035-55414058 | TAATACGACTCACTATAGTGACGAACACAAAGGGAAAGGTTTTAGAGCTAGAAATAGC | 289 |
| 20c | chr14: 90367155-90367178 | TAATACGACTCACTATAGTGACGAACACAAAGGGAAAGGTTTTAGAGCTAGAAATAGC | 289 |
| 20d | chr14: 65267666-65267689 | TAATACGACTCACTATAGTGACGAACACAAAGGGAAAGGTTTTAGAGCTAGAAATAGC | 289 |
| 20e | chr6: 159526504-159526527 | TAATACGACTCACTATAGTGACGAACACAAAGGGAAAGGTTTTAGAGCTAGAAATAGC | 289 |
| 20f | chr4: 127813176-127813199 | TAATACGACTCACTATAGTGACGAACACAAAGGGAAAGGTTTTAGAGCTAGAAATAGC | 289 |
| 20g | chr4: 13632574-13632597 | TAATACGACTCACTATAGTGACGAACACAAAGGGAAAGGTTTTAGAGCTAGAAATAGC | 289 |
| 20h | chr10: 120355159-120355182 | TAATACGACTCACTATAGTGACGAACACAAAGGGAAAGGTTTTAGAGCTAGAAATAGC | 289 |
| 20i | chr18: 21119637-21119660 | TAATACGACTCACTATAGTGACGAACACAAAGGGAAAGGTTTTAGAGCTAGAAATAGC | 289 |
| 21a | chr1: 56619406-56619429 | TAATACGACTCACTATAGCCCTATGTTGTAGCCACAGCGTTTTAGAGCTAGAAATAGC | 290 |
| 21b | chr16: 1962095-1962118 | TAATACGACTCACTATAGCCCTATGTTGTAGCCACAGCGTTTTAGAGCTAGAAATAGC | 290 |
| 21c | chr17: 47159188-47159211 | TAATACGACTCACTATAGCCCTATGTTGTAGCCACAGCGTTTTAGAGCTAGAAATAGC | 290 |
| 21d | chr17: 53756986-53757009 | TAATACGACTCACTATAGCCCTATGTTGTAGCCACAGCGTTTTAGAGCTAGAAATAGC | 290 |
| 21e | chrX: 40934979-40935002 | TAATACGACTCACTATAGCCCTATGTTGTAGCCACAGCGTTTTAGAGCTAGAAATAGC | 290 |
| 21f | chr20: 47160835-47160858 | TAATACGACTCACTATAGCCCTATGTTGTAGCCACAGCGTTTTAGAGCTAGAAATAGC | 290 |
| 22a | chr14: 70595829-70595852 | TAATACGACTCACTATAGAAAGGGTACCCTGCTTCTGCGTTTTAGAGCTAGAAATAGC | 291 |
| 22b | chr22: 19258807-19258830 | TAATACGACTCACTATAGAAAGGGTACCCTGCTTCTGCGTTTTAGAGCTAGAAATAGC | 291 |
| 22c | chr12: 52952843-52952866 | TAATACGACTCACTATAGAAAGGGTACCCTGCTTCTGCGTTTTAGAGCTAGAAATAGC | 291 |
| 22d | chr1: 111648262-111648285 | TAATACGACTCACTATAGAAAGGGTACCCTGCTTCTGCGTTTTAGAGCTAGAAATAGC | 291 |
| 22e | chr16: 72729906-72729929 | TAATACGACTCACTATAGAAAGGGTACCCTGCTTCTGCGTTTTAGAGCTAGAAATAGC | 291 |
| 22f | chr4: 144572204-144572227 | TAATACGACTCACTATAGAAAGGGTACCCTGCTTCTGCGTTTTAGAGCTAGAAATAGC | 291 |
| 22g | chr4: 135371152-135371175 | TAATACGACTCACTATAGAAAGGGTACCCTGCTTCTGCGTTTTAGAGCTAGAAATAGC | 291 |
| 22h | chr20: 49958033-49958056 | TAATACGACTCACTATAGAAAGGGTACCCTGCTTCTGCGTTTTAGAGCTAGAAATAGC | 291 |
| 22i | chr3: 12787365-12787388 | TAATACGACTCACTATAGAAAGGGTACCCTGCTTCTGCGTTTTAGAGCTAGAAATAGC | 291 |
| 22j | chr3: 32260231-32260254 | TAATACGACTCACTATAGAAAGGGTACCCTGCTTCTGCGTTTTAGAGCTAGAAATAGC | 291 |

TABLE 4A

Multiple Target Single Spacer (MTSS) sequencing library ILMN_P5 primers (PCR1)

| Spacer group* | ILMN_P5 | SEQ ID NO.: |
|---|---|---|
| 1a | CACTCTTTCCCTACACGACGCTCTTCCGATCTACATAGGCATCGAAGACGCT | 292 |
| 1b | CACTCTTTCCCTACACGACGCTCTTCCGATCTAGGCATTGAAGACGCTCACT | 293 |
| 1c | CACTCTTTCCCTACACGACGCTCTTCCGATCTCTTGGGAAGCACATAGGCAT | 294 |

TABLE 4A-continued

Multiple Target Single Spacer (MTSS) sequencing library ILMN_P5 primers (PCR1)

| Spacer group* | ILMN_P5 | SEQ ID NO.: |
|---|---|---|
| 2a | CACTCTTTCCCTACACGACGCTCTTCCGATCTACAAAGCACACATGCAACCT | 295 |
| 2b | CACTCTTTCCCTACACGACGCTCTTCCGATCTTCTGCACACCTTCAGACCAG | 296 |
| 3a | CACTCTTTCCCTACACGACGCTCTTCCGATCTAATCGGCTTCGTCTATGCAC | 297 |
| 3b | CACTCTTTCCCTACACGACGCTCTTCCGATCTTTGGAAATGACAGATTTGGGA | 298 |
| 3c | CACTCTTTCCCTACACGACGCTCTTCCGATCTGGACCAATCCTGAACGAAAG | 299 |
| 3d | CACTCTTTCCCTACACGACGCTCTTCCGATCTGGTATCGTGGACGGAGAGTC | 300 |
| 3e | CACTCTTTCCCTACACGACGCTCTTCCGATCTcaaaaTAAGGGTTCTATTAGGCAAA | 301 |
| 3f | CACTCTTTCCCTACACGACGCTCTTCCGATCTGGATTGGTGTGCAAGTGTTG | 302 |
| 3g | CACTCTTTCCCTACACGACGCTCTTCCGATCTATATTTGTATTGCCGTGGGC | 303 |
| 3h | CACTCTTTCCCTACACGACGCTCTTCCGATCTCTAACGCCTAAAACGGAAGC | 304 |
| 4a | CACTCTTTCCCTACACGACGCTCTTCCGATCTAATCGGCTTCGTCTATGCAC | 297 |
| 4b | CACTCTTTCCCTACACGACGCTCTTCCGATCTGGACCAATCCTGAACGAAAG | 299 |
| 4c | CACTCTTTCCCTACACGACGCTCTTCCGATCTGGTATCGTGGACGGAGAGTC | 300 |
| 4d | CACTCTTTCCCTACACGACGCTCTTCCGATCTAGGCATTAGGAAATACGCCC | 305 |
| 5a | CACTCTTTCCCTACACGACGCTCTTCCGATCTGCTGGAGGTGGAGTGTGTCT | 306 |
| 5b | CACTCTTTCCCTACACGACGCTCTTCCGATCTTCAGATACAAGCTTCTGGGACA | 307 |
| 6a | CACTCTTTCCCTACACGACGCTCTTCCGATCTaagagaaagGTGCCTGGGTT | 308 |
| 6b | CACTCTTTCCCTACACGACGCTCTTCCGATCTAAGAAGCCAAAGAGCAAGGG | 309 |
| 6c | CACTCTTTCCCTACACGACGCTCTTCCGATCTGGTTCAACTGAAGCGCCA | 310 |
| 6d | CACTCTTTCCCTACACGACGCTCTTCCGATCTAGAAAGCTACCCGGGTTCA | 311 |
| 6e | CACTCTTTCCCTACACGACGCTCTTCCGATCTTTAATAGCCTGCTCCACCCA | 312 |
| 6f | CACTCTTTCCCTACACGACGCTCTTCCGATCTACCTGGGTTCAACTAAAGCG | 313 |
| 6g | CACTCTTTCCCTACACGACGCTCTTCCGATCTACTAAAGCACCAGCCTGCTC | 314 |
| 6h | CACTCTTTCCCTACACGACGCTCTTCCGATCTGTTCAACTGAAGCACCAGCC | 315 |
| 6i | CACTCTTTCCCTACACGACGCTCTTCCGATCTCAACTAAAGCGCCAGCCTAC | 316 |
| 6j | CACTCTTTCCCTACACGACGCTCTTCCGATCTGCACTAGCTTGCTCCACTCA | 317 |
| 6k | CACTCTTTCCCTACACGACGCTCTTCCGATCTGCCAATGAGAAAGGTTCCTG | 318 |
| 6l | CACTCTTTCCCTACACGACGCTCTTCCGATCTGGTACTTGGTGTCAGCCAGC | 319 |
| 6m | CACTCTTTCCCTACACGACGCTCTTCCGATCTAACTGAAGCTCCAGCCTGC | 320 |
| 6n | CACTCTTTCCCTACACGACGCTCTTCCGATCTGACAAACGTACCTGGGTTCAA | 321 |
| 7a | CACTCTTTCCCTACACGACGCTCTTCCGATCTCGACCTCTGGAAGGAGACTG | 322 |
| 7b | CACTCTTTCCCTACACGACGCTCTTCCGATCTCGACCTCTGGAAGGAGACAG | 323 |
| 7c | CACTCTTTCCCTACACGACGCTCTTCCGATCTTGTGGCTACAACATAGGGG | 324 |
| 8a | CACTCTTTCCCTACACGACGCTCTTCCGATCTAGGAATCGATCTCGTGAAGC | 325 |
| 8b | CACTCTTTCCCTACACGACGCTCTTCCGATCTTGTGAGAGGATGGTGGTCAA | 326 |
| 8c | CACTCTTTCCCTACACGACGCTCTTCCGATCTGAGTGTGCAATTCACAGCAAA | 327 |
| 8d | CACTCTTTCCCTACACGACGCTCTTCCGATCTGAATCGATCTCATGAAGCCC | 328 |
| 8e | CACTCTTTCCCTACACGACGCTCTTCCGATCTAATCGATCTCGTGAAGCCTG | 329 |

TABLE 4A-continued

Multiple Target Single Spacer (MTSS) sequencing library ILMN_P5 primers (PCR1)

| Spacer group* | ILMN_P5 | SEQ ID NO.: |
|---|---|---|
| 8f | CACTCTTTCCCTACACGACGCTCTTCCGATCTCAGGAATCGATCTCATGAAGG | 330 |
| 8g | CACTCTTTCCCTACACGACGCTCTTCCGATCTATCAATCTTGTGTAGCCCGC | 331 |
| 9a | CACTCTTTCCCTACACGACGCTCTTCCGATCTCGACCTCTGGAAGGAGACTG | 322 |
| 9b | CACTCTTTCCCTACACGACGCTCTTCCGATCTTAACCCCTGACCTCTGGAAG | 332 |
| 9c | CACTCTTTCCCTACACGACGCTCTTCCGATCTCTGACTCCCAACCTCTGGAA | 333 |
| 9d | CACTCTTTCCCTACACGACGCTCTTCCGATCTGACCTACAGCTACCTGACCCC | 334 |
| 9e | CACTCTTTCCCTACACGACGCTCTTCCGATCTCGACCTCTGGAAGGAGACTG | 322 |
| 9f | CACTCTTTCCCTACACGACGCTCTTCCGATCTCGACCTCTGGAAGGAGACAG | 323 |
| 9g | CACTCTTTCCCTACACGACGCTCTTCCGATCTCTTGTGGCTACAACATAGGGG | 324 |
| 10a | CACTCTTTCCCTACACGACGCTCTTCCGATCTCCCTAGACAGCAGCAACTCC | 335 |
| 10b | CACTCTTTCCCTACACGACGCTCTTCCGATCTAACCATCCAAAAGACCACCA | 336 |
| 10c | CACTCTTTCCCTACACGACGCTCTTCCGATCTCCGCCAGGATAGTGGATG | 337 |
| 11a | CACTCTTTCCCTACACGACGCTCTTCCGATCTAAGCCCTGAACTTCTCTTTCAA | 338 |
| 11b | CACTCTTTCCCTACACGACGCTCTTCCGATCTTTTGTCTTTTCAGATCCGCC | 339 |
| 11c | CACTCTTTCCCTACACGACGCTCTTCCGATCTCCTTCAAAACCCAGTTCCAA | 340 |
| 11d | CACTCTTTCCCTACACGACGCTCTTCCGATCTGCAATGTCCTGGGTCCTAAA | 341 |
| 11e | CACTCTTTCCCTACACGACGCTCTTCCGATCTATGATGAGATCCGCCATCAC | 342 |
| 11f | CACTCTTTCCCTACACGACGCTCTTCCGATCTTTGTAAGTGGTGATTTTCAGTTTGA | 343 |
| 11g | CACTCTTTCCCTACACGACGCTCTTCCGATCTGGTGGAAGCTATCAGGACCA | 344 |
| 11h | CACTCTTTCCCTACACGACGCTCTTCCGATCTGTGACAAAAGGTGACCTGGG | 345 |
| 11i | CACTCTTTCCCTACACGACGCTCTTCCGATCTttcttcatccctttactttcttTTT | 346 |
| 11j | CACTCTTTCCCTACACGACGCTCTTCCGATCTTGGCTAAGCTGGTGGAAGTT | 347 |
| 12a | CACTCTTTCCCTACACGACGCTCTTCCGATCTTAGTGACAAACCCAAAGCCC | 348 |
| 12b | CACTCTTTCCCTACACGACGCTCTTCCGATCTCATTAACACTCAGCCCGTGA | 349 |
| 13a | CACTCTTTCCCTACACGACGCTCTTCCGATCTAGCAGAATGGCTATGATGGG | 350 |
| 13b | CACTCTTTCCCTACACGACGCTCTTCCGATCTGGGACAAGCTAAGCCAATTTT | 351 |
| 13c | CACTCTTTCCCTACACGACGCTCTTCCGATCTTTCCGGAAGAAGGCTAAAACT | 352 |
| 13d | CACTCTTTCCCTACACGACGCTCTTCCGATCTTGCATGCATTCACACACAAT | 353 |
| 13e | CACTCTTTCCCTACACGACGCTCTTCCGATCTTTTGCAATGCTTTGCTTTAAATA | 354 |
| 14a | CACTCTTTCCCTACACGACGCTCTTCCGATCTAGGTAGTTTCATGGATGCCG | 355 |
| 14b | CACTCTTTCCCTACACGACGCTCTTCCGATCTGCTCACAACACCTACCCAGG | 356 |
| 14c | CACTCTTTCCCTACACGACGCTCTTCCGATCTCAAGAAGGAAGGCTGGAACA | 357 |
| 15a | CACTCTTTCCCTACACGACGCTCTTCCGATCTATCCTGGAATTCGGTGAGG | 358 |
| 15b | CACTCTTTCCCTACACGACGCTCTTCCGATCTCACCATAACAGCACTGGTGG | 359 |
| 15c | CACTCTTTCCCTACACGACGCTCTTCCGATCTCTGGTCCATCTATGGGGAGA | 360 |
| 15d | CACTCTTTCCCTACACGACGCTCTTCCGATCTCAGTGGTGGTAAGCCCATCT | 361 |
| 15e | CACTCTTTCCCTACACGACGCTCTTCCGATCTTGGGGAGAAAATTCGATGAAG | 362 |
| 15f | CACTCTTTCCCTACACGACGCTCTTCCGATCTGGTGACTTCACACGCCATAA | 363 |

TABLE 4A-continued

Multiple Target Single Spacer (MTSS) sequencing library ILMN_P5 primers (PCR1)

| Spacer group* | ILMN_P5 | SEQ ID NO.: |
|---|---|---|
| 15g | CACTCTTTCCCTACACGACGCTCTTCCGATCTTCCGGAGTTTATATGCCAGG | 364 |
| 16a | CACTCTTTCCCTACACGACGCTCTTCCGATCTTGCTCTACAAGGTCACATGCTT | 365 |
| 16b | CACTCTTTCCCTACACGACGCTCTTCCGATCTTGCCATGGACTTAGGATGACT | 366 |
| 16c | CACTCTTTCCCTACACGACGCTCTTCCGATCTGGCCAAAGGCTGTTCACTAA | 367 |
| 16d | CACTCTTTCCCTACACGACGCTCTTCCGATCTttcTGCACATGTATCCCGTG | 368 |
| 16e | CACTCTTTCCCTACACGACGCTCTTCCGATCTTCCACGTAATGATGACTTCCAA | 369 |
| 16f | CACTCTTTCCCTACACGACGCTCTTCCGATCTtgtaaaggtgctcaacatTTCTTT | 370 |
| 16g | CACTCTTTCCCTACACGACGCTCTTCCGATCTAAACAATGCTAAATGATGGCAA | 371 |
| 16h | CACTCTTTCCCTACACGACGCTCTTCCGATCTCCATCAGACTTGTGTCCACG | 372 |
| 16i | CACTCTTTCCCTACACGACGCTCTTCCGATCTGGGCTTATGCCCAAGACTTT | 373 |
| 17a | CACTCTTTCCCTACACGACGCTCTTCCGATCTTGCCATGGACTTAGGATGACT | 366 |
| 17b | CACTCTTTCCCTACACGACGCTCTTCCGATCTttcTGCACATGTATCCCGTG | 368 |
| 17c | CACTCTTTCCCTACACGACGCTCTTCCGATCTGGCCAAAGGCTGTTCACTAA | 367 |
| 17d | CACTCTTTCCCTACACGACGCTCTTCCGATCTTCCACGTAATGATGACTTCCAA | 369 |
| 17e | CACTCTTTCCCTACACGACGCTCTTCCGATCTAAACAATGCTAAATGATGGCAA | 371 |
| 17f | CACTCTTTCCCTACACGACGCTCTTCCGATCTGGGCTTATGCCCAAGACTTT | 373 |
| 18a | CACTCTTTCCCTACACGACGCTCTTCCGATCTTGGTTTTATGTTGCCTGCTTT | 374 |
| 18b | CACTCTTTCCCTACACGACGCTCTTCCGATCTTGGCCATACACTCCAATGAA | 375 |
| 18c | CACTCTTTCCCTACACGACGCTCTTCCGATCTGGATGCTCCCTGAGTTTCTTC | 376 |
| 18d | CACTCTTTCCCTACACGACGCTCTTCCGATCTTCCACCTGTTCCAAGAGACTG | 377 |
| 19a | CACTCTTTCCCTACACGACGCTCTTCCGATCTGCAATGACTCCAGAGGGAAG | 378 |
| 19b | CACTCTTTCCCTACACGACGCTCTTCCGATCTATTCACAGGGAAAAGGTCCC | 379 |
| 19c | CACTCTTTCCCTACACGACGCTCTTCCGATCTTCTCCTCAGCCTGGAAACAT | 380 |
| 20a | CACTCTTTCCCTACACGACGCTCTTCCGATCTGGTAACACTTGTGGGGCATT | 381 |
| 20b | CACTCTTTCCCTACACGACGCTCTTCCGATCTCAGCCATTCCCTTGATGTCT | 382 |
| 20c | CACTCTTTCCCTACACGACGCTCTTCCGATCTGGTAACACTTGTGGGGCATT | 381 |
| 20d | CACTCTTTCCCTACACGACGCTCTTCCGATCTcggccGATATCAACTTTCTT | 383 |
| 20e | CACTCTTTCCCTACACGACGCTCTTCCGATCTGCATATACGTGGCCAAAGGA | 384 |
| 20f | CACTCTTTCCCTACACGACGCTCTTCCGATCTTTTGAACAGTACCCGTTCCC | 385 |
| 20g | CACTCTTTCCCTACACGACGCTCTTCCGATCTaagcctggccTCACCTTT | 386 |
| 20h | CACTCTTTCCCTACACGACGCTCTTCCGATCTGGTAACACTTGTGGGGCATT | 381 |
| 20i | CACTCTTTCCCTACACGACGCTCTTCCGATCTCTCTTCCAGTTTTGCCAAGG | 387 |
| 21a | CACTCTTTCCCTACACGACGCTCTTCCGATCTAAAGTGCTCCCGTTCTGCTA | 388 |
| 21b | CACTCTTTCCCTACACGACGCTCTTCCGATCTCACTAACCATGCAGGACACG | 389 |
| 21c | CACTCTTTCCCTACACGACGCTCTTCCGATCTaccacgcttggccTTAATTT | 390 |
| 21d | CACTCTTTCCCTACACGACGCTCTTCCGATCTCTTCTGCATTTTCACATTAGCAA | 391 |
| 21e | CACTCTTTCCCTACACGACGCTCTTCCGATCTccacacctggcTCAGAGG | 392 |
| 21f | CACTCTTTCCCTACACGACGCTCTTCCGATCTgatttcatccttgaagcctcC | 393 |

TABLE 4A-continued

Multiple Target Single Spacer (MTSS) sequencing library ILMN_P5 primers (PCR1)

| Spacer group* | ILMN_P5 | SEQ ID NO.: |
|---|---|---|
| 22a | CACTCTTTCCCTACACGACGCTCTTCCGATCTGGAAGACAGCCAGGACTTCA | 394 |
| 22b | CACTCTTTCCCTACACGACGCTCTTCCGATCTCCCTAGACAGCAGCAACTCC | 335 |
| 22c | CACTCTTTCCCTACACGACGCTCTTCCGATCTAACCATCCAAAAGACCACCA | 336 |
| 22d | CACTCTTTCCCTACACGACGCTCTTCCGATCTgcctcccaggttcaaacA | 395 |
| 22e | CACTCTTTCCCTACACGACGCTCTTCCGATCTTCCATGCAAACCATTCAAAA | 396 |
| 22f | CACTCTTTCCCTACACGACGCTCTTCCGATCTGAAATTACCTATTAACAGATGCTGACA | 397 |
| 22g | CACTCTTTCCCTACACGACGCTCTTCCGATCTcaagccagggttaagttacacaG | 398 |
| 22h | CACTCTTTCCCTACACGACGCTCTTCCGATCTAACCATCCAAAAGACCACCA | 336 |
| 22i | CACTCTTTCCCTACACGACGCTCTTCCGATCTcaggagaccataTGTTTATTTATTGATT | 399 |
| 22j | CACTCTTTCCCTACACGACGCTCTTCCGATCTATCCAAAAGACCACCACCTG | 400 |

*Spacer group subsets indicated by lower case letters; genomic location of spacer group subsets are provided in Table 3.

TABLE 4B

Multiple Target Single Spacer (MTSS) sequencing library ILMN_P7 primers (PCR1)

| Spacer group* | ILMN_P7 | SEQ ID NO.: |
|---|---|---|
| 1a | GGAGTTCAGACGTGTGCTCTTCCGATCTTGCACATGAGCTCTCTCTGG | 401 |
| 1b | GGAGTTCAGACGTGTGCTCTTCCGATCTGCTAACGAGGAACTTGGCAG | 402 |
| 1c | GGAGTTCAGACGTGTGCTCTTCCGATCTCAGCATTTTGGCTCCTCTCT | 403 |
| 2a | GGAGTTCAGACGTGTGCTCTTCCGATCTGGATGGTGGCCAAGAAGTTA | 404 |
| 2b | GGAGTTCAGACGTGTGCTCTTCCGATCTTCCTGTAAACACCCGTGACA | 405 |
| 3a | GGAGTTCAGACGTGTGCTCTTCCGATCTGCAAAACGACCAGGAGGAT | 406 |
| 3b | GGAGTTCAGACGTGTGCTCTTCCGATCTAGCATTCCTACACAATTACTGCTG | 407 |
| 3c | GGAGTTCAGACGTGTGCTCTTCCGATCTGCCCTGGGAGACCTTACAA | 408 |
| 3d | GGAGTTCAGACGTGTGCTCTTCCGATCTGGAAAAGACAAGCAAGCCAG | 409 |
| 3e | GGAGTTCAGACGTGTGCTCTTCCGATCTAGGGGTGAGTGAATGACAGG | 410 |
| 3f | GGAGTTCAGACGTGTGCTCTTCCGATCTGAAGACAACCGAATTAGGCG | 411 |
| 3g | GGAGTTCAGACGTGTGCTCTTCCGATCTTTTGTCTTTGGTTCCTTCGG | 412 |
| 3h | GGAGTTCAGACGTGTGCTCTTCCGATCTGCCTTGCCTTATCACCTTTG | 413 |
| 4a | GGAGTTCAGACGTGTGCTCTTCCGATCTGCAAAACGACCAGGAGGATA | 414 |
| 4b | GGAGTTCAGACGTGTGCTCTTCCGATCTGCCCTGGGAGACCTTACAA | 408 |
| 4c | GGAGTTCAGACGTGTGCTCTTCCGATCTGGAAAAGACAAGCAAGCCAG | 409 |
| 4d | GGAGTTCAGACGTGTGCTCTTCCGATCTATACACTTCTGGGATTGGCG | 415 |
| 5a | GGAGTTCAGACGTGTGCTCTTCCGATCTGAAGATCAAGGTGGGTGGTG | 416 |
| 5b | GGAGTTCAGACGTGTGCTCTTCCGATCTACCCCAACACCACGAAGAT | 417 |
| 6a | GGAGTTCAGACGTGTGCTCTTCCGATCTACAACCCCTTTGTTCCCCTA | 418 |
| 6b | GGAGTTCAGACGTGTGCTCTTCCGATCTcccagccACAAGTTTGTTTT | 419 |
| 6c | GGAGTTCAGACGTGTGCTCTTCCGATCTtGAAGAAACAAGGCAAGGCT | 420 |

TABLE 4B-continued

Multiple Target Single Spacer (MTSS) sequencing
library ILMN_P7 primers (PCR1)

| Spacer group* | ILMN_P7 | SEQ ID NO.: |
|---|---|---|
| 6d | GGAGTTCAGACGTGTGCTCTTCCGATCTTGTGGGAGATGACACCACAC | 421 |
| 6e | GGAGTTCAGACGTGTGCTCTTCCGATCTGGGAGAGGACACCACACTTC | 422 |
| 6f | GGAGTTCAGACGTGTGCTCTTCCGATCTactgtgcctggccTGAAATA | 423 |
| 6g | GGAGTTCAGACGTGTGCTCTTCCGATCTCTCACGAACACGTATCCACG | 424 |
| 6h | GGAGTTCAGACGTGTGCTCTTCCGATCTGCATGAGGCCCATTGTAGTAA | 425 |
| 6i | GGAGTTCAGACGTGTGCTCTTCCGATCTACTCATCTTCTGTGATTTTGTTTCA | 426 |
| 6j | GGAGTTCAGACGTGTGCTCTTCCGATCTATTCCCATGCTGACTTTTGC | 427 |
| 6k | GGAGTTCAGACGTGTGCTCTTCCGATCTGGAAGGGACACCACACTTCT | 428 |
| 6l | GGAGTTCAGACGTGTGCTCTTCCGATCTTGCCCTTTATGTGTGTGTGTG | 429 |
| 6m | GGAGTTCAGACGTGTGCTCTTCCGATCTggacacttatgttgattccagtGT | 430 |
| 6n | GGAGTTCAGACGTGTGCTCTTCCGATCTTGCTGTTGGAGAAAATGTGTTT | 431 |
| 7a | GGAGTTCAGACGTGTGCTCTTCCGATCTgcaagactctgtctcgtaaaCATT | 432 |
| 7b | GGAGTTCAGACGTGTGCTCTTCCGATCTAAAAGTTCCATTGGCTGTGG | 433 |
| 7c | GGAGTTCAGACGTGTGCTCTTCCGATCTGGTGCTAAAACAAACGTTATCAAA | 434 |
| 8a | GGAGTTCAGACGTGTGCTCTTCCGATCTTCAGAATTTCACTGCATCGTG | 435 |
| 8b | GGAGTTCAGACGTGTGCTCTTCCGATCTAAATCCCCACCTTATCTGGC | 436 |
| 8c | GGAGTTCAGACGTGTGCTCTTCCGATCTccagcactGGAAGCTCTTTT | 437 |
| 8d | GGAGTTCAGACGTGTGCTCTTCCGATCTAGGATATGCTTGAATTATTTTCCG | 438 |
| 8e | GGAGTTCAGACGTGTGCTCTTCCGATCTACCTTGGGCCACTCTTCTTT | 439 |
| 8f | GGAGTTCAGACGTGTGCTCTTCCGATCTTCACCCTAGGTGGCACAGAT | 440 |
| 8g | GGAGTTCAGACGTGTGCTCTTCCGATCTgcacttcgctaagaactgtcttC | 441 |
| 9a | GGAGTTCAGACGTGTGCTCTTCCGATCTgatagcactgCTCCAGGGAT | 442 |
| 9b | GGAGTTCAGACGTGTGCTCTTCCGATCTaaacaaacaaacaaaCAATGCATAC | 443 |
| 9c | GGAGTTCAGACGTGTGCTCTTCCGATCTGTCTGCCCTGGATGGAAAC | 444 |
| 9d | GGAGTTCAGACGTGTGCTCTTCCGATCTATCATCCCTAATGCCAAAGC | 445 |
| 9e | GGAGTTCAGACGTGTGCTCTTCCGATCTgcaagactctgtctcgtaaaCATT | 432 |
| 9f | GGAGTTCAGACGTGTGCTCTTCCGATCTAAAAGTTCCATTGGCTGTGG | 433 |
| 9g | GGAGTTCAGACGTGTGCTCTTCCGATCTGGTGCTAAAACAAACGTTATCAAA | 434 |
| 10a | GGAGTTCAGACGTGTGCTCTTCCGATCTcattttatgattttaattgttGGGG | 446 |
| 10b | GGAGTTCAGACGTGTGCTCTTCCGATCTGTTGGGTTAGGGCATTTGTG | 447 |
| 10c | GGAGTTCAGACGTGTGCTCTTCCGATCTattgcacctggcCTATGTCT | 448 |
| 11a | GGAGTTCAGACGTGTGCTCTTCCGATCTTCCAAAATCTGTGGCTTGTG | 449 |
| 11b | GGAGTTCAGACGTGTGCTCTTCCGATCTCAACAGACACTGGCTGAAGG | 450 |
| 11c | GGAGTTCAGACGTGTGCTCTTCCGATCTGGTCCTAAGTCTGTGGCTCG | 451 |
| 11d | GGAGTTCAGACGTGTGCTCTTCCGATCTTCCAAAGAATACCAGCCACC | 452 |
| 11e | GGAGTTCAGACGTGTGCTCTTCCGATCTTCCACCCCTGTAAAAGTACCA | 453 |
| 11f | GGAGTTCAGACGTGTGCTCTTCCGATCTGGTCCTAAGTCTGTGGCTCG | 451 |
| 11g | GGAGTTCAGACGTGTGCTCTTCCGATCTtgtggttctctttctagattcctTTT | 454 |

TABLE 4B-continued

Multiple Target Single Spacer (MTSS) sequencing
library ILMN_P7 primers (PCR1)

| Spacer group* | ILMN_P7 | SEQ ID NO.: |
|---|---|---|
| 11h | GGAGTTCAGACGTGTGCTCTTCCGATCTGGTGGAAGCTATCAGGACCA | 455 |
| 11i | GGAGTTCAGACGTGTGCTCTTCCGATCTAGATATGATGAGATCCGCCG | 456 |
| 11j | GGAGTTCAGACGTGTGCTCTTCCGATCTcccagcATCTTTACATGCTTTT | 457 |
| 12a | GGAGTTCAGACGTGTGCTCTTCCGATCTAGTACACAGTGGCTGCCCAT | 458 |
| 12b | GGAGTTCAGACGTGTGCTCTTCCGATCTGCCGAGGAAGCATTGTAAAG | 459 |
| 13a | GGAGTTCAGACGTGTGCTCTTCCGATCTAATAAAGGATGACACTTTAGAACTGGA | 460 |
| 13b | GGAGTTCAGACGTGTGCTCTTCCGATCTacccggccATAAACTCAAG | 461 |
| 13c | GGAGTTCAGACGTGTGCTCTTCCGATCTGTTAAAACAAATGCTTTGGGCT | 462 |
| 13d | GGAGTTCAGACGTGTGCTCTTCCGATCTCCTTGTCTCCAACTCCCAAA | 463 |
| 13e | GGAGTTCAGACGTGTGCTCTTCCGATCTTTGCACCTTCCACCCATAAT | 464 |
| 14a | GGAGTTCAGACGTGTGCTCTTCCGATCTAGCTACATCTTCACCGCCAC | 465 |
| 14b | GGAGTTCAGACGTGTGCTCTTCCGATCTGAGGCTACAGCTTCACCACC | 466 |
| 14c | GGAGTTCAGACGTGTGCTCTTCCGATCTCTCACCAAGCTTCACCATCA | 467 |
| 15a | GGAGTTCAGACGTGTGCTCTTCCGATCTGCCTCCACAATATTCATGCC | 468 |
| 15b | GGAGTTCAGACGTGTGCTCTTCCGATCTTGTGGCCTCCACAATATTCA | 469 |
| 15c | GGAGTTCAGACGTGTGCTCTTCCGATCTTGGTGATCTTGCTGGTCTTG | 470 |
| 15d | GGAGTTCAGACGTGTGCTCTTCCGATCTATTGATTCATGCCCTCTTGC | 471 |
| 15e | GGAGTTCAGACGTGTGCTCTTCCGATCTggccATAGCAATGGTGATCT | 472 |
| 15f | GGAGTTCAGACGTGTGCTCTTCCGATCTTAGTGTTTGTTCCGTTCCCC | 473 |
| 15g | GGAGTTCAGACGTGTGCTCTTCCGATCTTTCACCCTGCCAAAGATCA | 474 |
| 16a | GGAGTTCAGACGTGTGCTCTTCCGATCTCCCTACTGAAGACTGGAGCG | 475 |
| 16b | GGAGTTCAGACGTGTGCTCTTCCGATCTCCTCTGTGCCTATTCAGCAGT | 476 |
| 16c | GGAGTTCAGACGTGTGCTCTTCCGATCTCCCTACTGAAGACTGGAGCG | 475 |
| 16d | GGAGTTCAGACGTGTGCTCTTCCGATCTCCCTACTGAAGACTGGAGCG | 475 |
| 16e | GGAGTTCAGACGTGTGCTCTTCCGATCTGAACAATGGAGCACTCAGC | 477 |
| 16f | GGAGTTCAGACGTGTGCTCTTCCGATCTCAGACTGGTCTGAAAGCGTG | 478 |
| 16g | GGAGTTCAGACGTGTGCTCTTCCGATCTGAAGACTGGAGCACTCAGC | 479 |
| 16h | GGAGTTCAGACGTGTGCTCTTCCGATCTCCAGCACCTGAGTTCACTG | 480 |
| 16i | GGAGTTCAGACGTGTGCTCTTCCGATCTGCCTATTCAGCAGTTCCCT | 481 |
| 17a | GGAGTTCAGACGTGTGCTCTTCCGATCTCCTCTGTGCCTATTCAGCAGT | 476 |
| 17b | GGAGTTCAGACGTGTGCTCTTCCGATCTCCCTACTGAAGACTGGAGCG | 475 |
| 17c | GGAGTTCAGACGTGTGCTCTTCCGATCTCCCTACTGAAGACTGGAGCG | 475 |
| 17d | GGAGTTCAGACGTGTGCTCTTCCGATCTGAACAATGGAGCACTCAGC | 477 |
| 17e | GGAGTTCAGACGTGTGCTCTTCCGATCTAAGACTGGAGCACTCAGCGT | 482 |
| 17f | GGAGTTCAGACGTGTGCTCTTCCGATCTGCCTATTCAGCAGTTCCCT | 481 |
| 18a | GGAGTTCAGACGTGTGCTCTTCCGATCTTAGAAGGTGGAGATGCTGGC | 483 |
| 18b | GGAGTTCAGACGTGTGCTCTTCCGATCTGGCAACAGACAGGACCAGAT | 484 |

TABLE 4B-continued

Multiple Target Single Spacer (MTSS) sequencing library ILMN_P7 primers (PCR1)

| Spacer group* | ILMN_P7 | SEQ ID NO.: |
|---|---|---|
| 18c | GGAGTTCAGACGTGTGCTCTTCCGATCTTAGAAGGTGGAGATGCTGGC | 483 |
| 18d | GGAGTTCAGACGTGTGCTCTTCCGATCTTAGAAGGTGGAGATGCTGGC | 483 |
| 19a | GGAGTTCAGACGTGTGCTCTTCCGATCTTTGTGCACGTTAAGCACTCTG | 485 |
| 19b | GGAGTTCAGACGTGTGCTCTTCCGATCTAAGAGAGCTTCCTGACACGC | 486 |
| 19c | GGAGTTCAGACGTGTGCTCTTCCGATCTTCTAAGAGCCAAGACAGCTTCC | 487 |
| 20a | GGAGTTCAGACGTGTGCTCTTCCGATCTAGCTTGTTCCTTTCAGCCG | 488 |
| 20b | GGAGTTCAGACGTGTGCTCTTCCGATCTCAATGCGTTTCCTTTTAGCC | 489 |
| 20c | GGAGTTCAGACGTGTGCTCTTCCGATCTAGTATTCTTTTGCCTTTCGGC | 490 |
| 20d | GGAGTTCAGACGTGTGCTCTTCCGATCTTATCCATTTCTGCCTCTGCC | 491 |
| 20e | GGAGTTCAGACGTGTGCTCTTCCGATCTCCCTTTTCTTTTCCCAGAGG | 492 |
| 20f | GGAGTTCAGACGTGTGCTCTTCCGATCTAAAAGAAAATCGCCTTTCGG | 493 |
| 20g | GGAGTTCAGACGTGTGCTCTTCCGATCTtcttTTCCTTTCAGCCGGA | 494 |
| 20h | GGAGTTCAGACGTGTGCTCTTCCGATCTTTGTCTGCCTCAGCTCAAGA | 495 |
| 20i | GGAGTTCAGACGTGTGCTCTTCCGATCTaaaacTCCCTTCCTTTTGGC | 496 |
| 21a | GGAGTTCAGACGTGTGCTCTTCCGATCTCGACCTCTGGAAGGAGACTG | 497 |
| 21b | GGAGTTCAGACGTGTGCTCTTCCGATCTCGACCTCTGGAAGGAGACTG | 497 |
| 21c | GGAGTTCAGACGTGTGCTCTTCCGATCTCACTGACCACCTCGTCAAGA | 498 |
| 21d | GGAGTTCAGACGTGTGCTCTTCCGATCTCACTGACCACCTCGTCAAGA | 498 |
| 21e | GGAGTTCAGACGTGTGCTCTTCCGATCTCGACCTCTGGAAGGAGACTG | 497 |
| 21f | GGAGTTCAGACGTGTGCTCTTCCGATCTGACCTACAGCTACCCGACCC | 499 |
| 22a | GGAGTTCAGACGTGTGCTCTTCCGATCTGAACGTCAAGCATCCCAAGT | 500 |
| 22b | GGAGTTCAGACGTGTGCTCTTCCGATCTcattttatgattttaattgttGGGG | 446 |
| 22c | GGAGTTCAGACGTGTGCTCTTCCGATCTGTTGGGTTAGGGCATTTGTG | 447 |
| 22d | GGAGTTCAGACGTGTGCTCTTCCGATCTAAAAGACGACCATCCACCAG | 501 |
| 22e | GGAGTTCAGACGTGTGCTCTTCCGATCTatgatgctcacccagaGACC | 502 |
| 22f | GGAGTTCAGACGTGTGCTCTTCCGATCTGAGCAGCTCCTCCTTGAGAG | 503 |
| 22g | GGAGTTCAGACGTGTGCTCTTCCGATCTAGCAAAGTGGGGTGTGAGAC | 504 |
| 22h | GGAGTTCAGACGTGTGCTCTTCCGATCTtgccagtgggatgataagaaA | 505 |
| 22i | GGAGTTCAGACGTGTGCTCTTCCGATCTCGGATAGTGGATGGCAAAGT | 506 |
| 22j | GGAGTTCAGACGTGTGCTCTTCCGATCTTCATTATATTTAGCTTTGTTAGCGAGA | 507 |

*Spacer group subsets indicated by lower case letters; genomic location of spacer group subsets are provided in Table 3.

TABLE 5 sgRNA assembly primers for sgRNPs

Primer 1: AGTAATAATACGACTCACTATAG (SEQ ID NO: 508)

Primer 2: AAAAAAAGCACCGACTCGGTGCCACTTTTTCAAGTTGATAACGGACTAGC (SEQ ID NO: 509)

Primer 3: Unique to sgRNA and listed in Table 1 as SEQ ID NOS: 1-4, respectively TABLE 5-continued sgRNA assembly primers for sgRNPs Primer 4: GTTTTAGAGCTAGAAATAGCAAGTTAAAATAAGGCTAGTCCGTTATCAAC (SEQ ID NO: 510)

Primer 5: AAAAAAAGCACCGACTCGGTGCC (SEQ ID NO: 511)

TABLE 6

Illumina sequencing index primers (i5) for PCR2 (i5 index sequences are bolded)

| Well position | Name | Sequence | SEQ ID NO.: |
|---|---|---|---|
| A1 | ILMN_AMP_FORi5_BC1 | AATGATACGGCGACCACCGAGATCTACACTAGATCGCACACTCTTTCCCTACACGACG | 512 |
| B1 | ILMN_AMP_FORi5_BC2 | AATGATACGGCGACCACCGAGATCTACACCTCTCTATACACTCTTTCCCTACACGACG | 513 |
| C1 | ILMN_AMP_FORi5_BC3 | AATGATACGGCGACCACCGAGATCTACACTATCCTCTACACTCTTTCCCTACACGACG | 514 |
| D1 | ILMN_AMP_FORi5_BC4 | AATGATACGGCGACCACCGAGATCTACACAGAGTAGAACACTCTTTCCCTACACGACG | 515 |
| E1 | ILMN_AMP_FORi5_BC5 | AATGATACGGCGACCACCGAGATCTACACGTAAGGAGACACTCTTTCCCTACACGACG | 516 |
| F1 | ILMN_AMP_FORi5_BC6 | AATGATACGGCGACCACCGAGATCTACACACTGCATAACACTCTTTCCCTACACGACG | 517 |
| G1 | ILMN_AMP_FORi5_BC7 | AATGATACGGCGACCACCGAGATCTACACAAGGAGTAACACTCTTTCCCTACACGACG | 518 |
| H1 | ILMN_AMP_FORi5_BC8 | AATGATACGGCGACCACCGAGATCTACACCTAAGCCTACACTCTTTCCCTACACGACG | 519 |
| A2 | ILMN_AMP_FORi5_BC9 | AATGATACGGCGACCACCGAGATCTACACTGAACCTTACACTCTTTCCCTACACGACG | 520 |
| B2 | ILMN_AMP_FORi5_BC10 | AATGATACGGCGACCACCGAGATCTACACTGCTAAGTACACTCTTTCCCTACACGACG | 521 |
| C2 | ILMN_AMP_FORi5_BC11 | AATGATACGGCGACCACCGAGATCTACACTAAGTTCCACACTCTTTCCCTACACGACG | 522 |
| D2 | ILMN_AMP_FORi5_BC12 | AATGATACGGCGACCACCGAGATCTACACATAGAGGCACACTCTTTCCCTACACGACG | 523 |
| E2 | ILMN_AMP_FORi5_BC13 | AATGATACGGCGACCACCGAGATCTACACGGCTCTGAACACTCTTTCCCTACACGACG | 524 |
| F2 | ILMN_AMP_FORi5_BC14 | AATGATACGGCGACCACCGAGATCTACACAGGCGAAGACACTCTTTCCCTACACGACG | 525 |
| G2 | ILMN_AMP_FORi5_BC15 | AATGATACGGCGACCACCGAGATCTACACTAATCTTAACACTCTTTCCCTACACGACG | 526 |
| H2 | ILMN_AMP_FORi5_BC16 | AATGATACGGCGACCACCGAGATCTACACCAGGACGTACACTCTTTCCCTACACGACG | 527 |

TABLE 7

Illumina sequencing index primers (i7) for PCR2 (i7 index sequences are bolded)

| Well position | Name | Sequence | SEQ ID NO.: |
|---|---|---|---|
| A1 | ILMN_AMP_REVi7_BC1 | CAAGCAGAAGACGGCATACGAGATATTGGTCAGTGACTGGAGTTCAGACGTGTGCTC | 528 |
| B1 | ILMN_AMP_REVi7_BC2 | CAAGCAGAAGACGGCATACGAGATTAAAAATGGTGACTGGAGTTCAGACGTGTGCTC | 529 |
| C1 | ILMN_AMP_REVi7_BC3 | CAAGCAGAAGACGGCATACGAGATATCACTGTGTGACTGGAGTTCAGACGTGTGCTC | 530 |
| D1 | ILMN_AMP_REVi7_BC4 | CAAGCAGAAGACGGCATACGAGATTATTTCACGTGACTGGAGTTCAGACGTGTGCTC | 531 |
| E1 | ILMN_AMP_REVi7_BC5 | CAAGCAGAAGACGGCATACGAGATATATTGGCGTGACTGGAGTTCAGACGTGTGCTC | 532 |
| F1 | ILMN_AMP_REVi7_BC6 | CAAGCAGAAGACGGCATACGAGATTATACAAGGTGACTGGAGTTCAGACGTGTGCTC | 533 |
| G1 | ILMN_AMP_REVi7_BC7 | CAAGCAGAAGACGGCATACGAGATATGATCTGGTGACTGGAGTTCAGACGTGTGCTC | 534 |
| H1 | ILMN_AMP_REVi7_BC8 | CAAGCAGAAGACGGCATACGAGATTACTCTACGTGACTGGAGTTCAGACGTGTGCTC | 535 |
| A2 | ILMN_AMP_REVi7_BC9 | CAAGCAGAAGACGGCATACGAGATATAAGCTAGTGACTGGAGTTCAGACGTGTGCTC | 536 |
| B2 | ILMN_AMP_REVi7_BC10 | CAAGCAGAAGACGGCATACGAGATTAGTATAGGTGACTGGAGTTCAGACGTGTGCTC | 537 |

TABLE 7-continued

Illumina sequencing index primers (i7) for PCR2 (i7 index sequences are bolded)

| Well position | Name | Sequence | SEQ ID NO.: |
|---|---|---|---|
| C2 | ILMN_AMP_REVi7_BC11 | CAAGCAGAAGACGGCATACGAGATATTACAAGGTGACTGGAGTTCAGACGTGTGCTC | 538 |
| D2 | ILMN_AMP_REVi7_BC12 | CAAGCAGAAGACGGCATACGAGATTAATTGGCGTGACTGGAGTTCAGACGTGTGCTC | 539 |
| E2 | ILMN_AMP_REVi7_BC13 | CAAGCAGAAGACGGCATACGAGATATCTCTACGTGACTGGAGTTCAGACGTGTGCTC | 540 |
| F2 | ILMN_AMP_REVi7_BC14 | CAAGCAGAAGACGGCATACGAGATTAGATCTGGTGACTGGAGTTCAGACGTGTGCTC | 541 |
| G2 | ILMN_AMP_REVi7_BC15 | CAAGCAGAAGACGGCATACGAGATATGCGGAGTGACTGGAGTTCAGACGTGTGCTC | 542 |
| H2 | ILMN_AMP_REVi7_BC16 | CAAGCAGAAGACGGCATACGAGATTAATCAGTGTGACTGGAGTTCAGACGTGTGCTC | 543 |
| A3 | ILMN_AMP_REVi7_BC17 | CAAGCAGAAGACGGCATACGAGATATTTTCACGTGACTGGAGTTCAGACGTGTGCTC | 544 |
| B3 | ILMN_AMP_REVi7_BC18 | CAAGCAGAAGACGGCATACGAGATTACACTGTGTGACTGGAGTTCAGACGTGTGCTC | 545 |
| C3 | ILMN_AMP_REVi7_BC19 | CAAGCAGAAGACGGCATACGAGATATGGCCACGTGACTGGAGTTCAGACGTGTGCTC | 546 |
| D3 | ILMN_AMP_REVi7_BC20 | CAAGCAGAAGACGGCATACGAGATTACCGGTGGTGACTGGAGTTCAGACGTGTGCTC | 547 |
| E3 | ILMN_AMP_REVi7_BC21 | CAAGCAGAAGACGGCATACGAGATATCGAAACGTGACTGGAGTTCAGACGTGTGCTC | 548 |
| F3 | ILMN_AMP_REVi7_BC22 | CAAGCAGAAGACGGCATACGAGATTATAGTTGGTGACTGGAGTTCAGACGTGTGCTC | 549 |
| G3 | ILMN_AMP_REVi7_BC23 | CAAGCAGAAGACGGCATACGAGATATCGTACGGTGACTGGAGTTCAGACGTGTGCTC | 550 |
| H3 | ILMN_AMP_REVi7_BC24 | CAAGCAGAAGACGGCATACGAGATTAGAATGAGTGACTGGAGTTCAGACGTGTGCTC | 551 |
| A4 | ILMN_AMP_REVi7_BC25 | CAAGCAGAAGACGGCATACGAGATATGCTACCGTGACTGGAGTTCAGACGTGTGCTC | 552 |
| B4 | ILMN_AMP_REVi7_BC26 | CAAGCAGAAGACGGCATACGAGATTAATCGTGGTGACTGGAGTTCAGACGTGTGCTC | 553 |
| C4 | ILMN_AMP_REVi7_BC27 | CAAGCAGAAGACGGCATACGAGATATATCAGTGTGACTGGAGTTCAGACGTGTGCTC | 554 |
| D4 | ILMN_AMP_REVi7_BC28 | CAAGCAGAAGACGGCATACGAGATTAGCGGACGTGACTGGAGTTCAGACGTGTGCTC | 555 |
| E4 | ILMN_AMP_REVi7_BC29 | CAAGCAGAAGACGGCATACGAGATATGCTCATGTGACTGGAGTTCAGACGTGTGCTC | 556 |
| F4 | ILMN_AMP_REVi7_BC30 | CAAGCAGAAGACGGCATACGAGATTACGATTAGTGACTGGAGTTCAGACGTGTGCTC | 557 |
| G4 | ILMN_AMP_REVi7_BC31 | CAAGCAGAAGACGGCATACGAGATATAGGAATGTGACTGGAGTTCAGACGTGTGCTC | 558 |
| H4 | ILMN_AMP_REVi7_BC32 | CAAGCAGAAGACGGCATACGAGATATTAGTTGGTGACTGGAGTTCAGACGTGTGCTC | 559 |
| A5 | ILMN_AMP_REVi7_BC33 | CAAGCAGAAGACGGCATACGAGATTACGAAACGTGACTGGAGTTCAGACGTGTGCTC | 560 |
| B5 | ILMN_AMP_REVi7_BC34 | CAAGCAGAAGACGGCATACGAGATATCCGGTGGTGACTGGAGTTCAGACGTGTGCTC | 561 |
| C5 | ILMN_AMP_REVi7_BC35 | CAAGCAGAAGACGGCATACGAGATTAGGCCACGTGACTGGAGTTCAGACGTGTGCTC | 562 |
| D5 | ILMN_AMP_REVi7_BC36 | CAAGCAGAAGACGGCATACGAGATATATCGTGGTGACTGGAGTTCAGACGTGTGCTC | 563 |
| E5 | ILMN_AMP_REVi7_BC37 | CAAGCAGAAGACGGCATACGAGATTAGCTACCGTGACTGGAGTTCAGACGTGTGCTC | 564 |
| F5 | ILMN_AMP_REVi7_BC38 | CAAGCAGAAGACGGCATACGAGATATCGCCTGGTGACTGGAGTTCAGACGTGTGCTC | 565 |
| G5 | ILMN_AMP_REVi7_BC39 | CAAGCAGAAGACGGCATACGAGATATAAAATGGTGACTGGAGTTCAGACGTGTGCTC | 566 |
| H5 | ILMN_AMP_REVi7_BC40 | CAAGCAGAAGACGGCATACGAGATTATGGTCAGTGACTGGAGTTCAGACGTGTGCTC | 567 |
| A6 | ILMN_AMP_REVi7_BC41 | CAAGCAGAAGACGGCATACGAGATATATTCCGGTGACTGGAGTTCAGACGTGTGCTC | 568 |
| B6 | ILMN_AMP_REVi7_BC42 | CAAGCAGAAGACGGCATACGAGATATGTATAGGTGACTGGAGTTCAGACGTGTGCTC | 569 |
| C6 | ILMN_AMP_REVi7_BC43 | CAAGCAGAAGACGGCATACGAGATTAAAGCTAGTGACTGGAGTTCAGACGTGTGCTC | 570 |
| D6 | ILMN_AMP_REVi7_BC44 | CAAGCAGAAGACGGCATACGAGATATCGATTAGTGACTGGAGTTCAGACGTGTGCTC | 571 |
| E6 | ILMN_AMP_REVi7_BC45 | CAAGCAGAAGACGGCATACGAGATTAGCTCATGTGACTGGAGTTCAGACGTGTGCTC | 572 |
| F6 | ILMN_AMP_REVi7_BC46 | CAAGCAGAAGACGGCATACGAGATATGAATGAGTGACTGGAGTTCAGACGTGTGCTC | 573 |
| G6 | ILMN_AMP_REVi7_BC47 | CAAGCAGAAGACGGCATACGAGATTACGTACGGTGACTGGAGTTCAGACGTGTGCTC | 574 |
| H6 | ILMN_AMP_REVi7_BC48 | CAAGCAGAAGACGGCATACGAGATATCGTGATGTGACTGGAGTTCAGACGTGTGCTC | 575 |

TABLE 7-continued

Illumina sequencing index primers (i7) for PCR2 (i7 index sequences are bolded)

| Well position | Name | Sequence | SEQ ID NO.: |
|---|---|---|---|
| A7 | ILMN_AMP_REVi7_BC49 | CAAGCAGAAGACGGCATACGAGATATACATCGGTGACTGGAGTTCAGACGTGTGCTC | 576 |
| B7 | ILMN_AMP_REVi7_BC50 | CAAGCAGAAGACGGCATACGAGATATGCCTAAGTGACTGGAGTTCAGACGTGTGCTC | 577 |
| C7 | ILMN_AMP_REVi7_BC51 | CAAGCAGAAGACGGCATACGAGATATTCAAGTGTGACTGGAGTTCAGACGTGTGCTC | 578 |
| D7 | ILMN_AMP_REVi7_BC52 | CAAGCAGAAGACGGCATACGAGATATCTGATCGTGACTGGAGTTCAGACGTGTGCTC | 579 |
| E7 | ILMN_AMP_REVi7_BC53 | CAAGCAGAAGACGGCATACGAGATATGTAGCCGTGACTGGAGTTCAGACGTGTGCTC | 580 |
| F7 | ILMN_AMP_REVi7_BC54 | CAAGCAGAAGACGGCATACGAGATATTTGACTGTGACTGGAGTTCAGACGTGTGCTC | 581 |
| G7 | ILMN_AMP_REVi7_BC55 | CAAGCAGAAGACGGCATACGAGATATGGAACTGTGACTGGAGTTCAGACGTGTGCTC | 582 |
| H7 | ILMN_AMP_REVi7_BC56 | CAAGCAGAAGACGGCATACGAGATATTGACATGTGACTGGAGTTCAGACGTGTGCTC | 583 |
| A8 | ILMN_AMP_REVi7_BC57 | CAAGCAGAAGACGGCATACGAGATATGGACGGGTGACTGGAGTTCAGACGTGTGCTC | 584 |
| B8 | ILMN_AMP_REVi7_BC58 | CAAGCAGAAGACGGCATACGAGATATCCACTCGTGACTGGAGTTCAGACGTGTGCTC | 585 |
| C8 | ILMN_AMP_REVi7_BC59 | CAAGCAGAAGACGGCATACGAGATATCTTTTGGTGACTGGAGTTCAGACGTGTGCTC | 586 |
| D8 | ILMN_AMP_REVi7_BC60 | CAAGCAGAAGACGGCATACGAGATATTGAGTGGTGACTGGAGTTCAGACGTGTGCTC | 587 |
| E8 | ILMN_AMP_REVi7_BC61 | CAAGCAGAAGACGGCATACGAGATATGCCATGGTGACTGGAGTTCAGACGTGTGCTC | 588 |
| F8 | ILMN_AMP_REVi7_BC62 | CAAGCAGAAGACGGCATACGAGATATTGTTGGGTGACTGGAGTTCAGACGTGTGCTC | 589 |
| G8 | ILMN_AMP_REVi7_BC63 | CAAGCAGAAGACGGCATACGAGATATAGCTAGGTGACTGGAGTTCAGACGTGTGCTC | 590 |
| H8 | ILMN_AMP_REVi7_BC64 | CAAGCAGAAGACGGCATACGAGATATTCTGAGGTGACTGGAGTTCAGACGTGTGCTC | 591 |
| A9 | ILMN_AMP_REVi7_BC65 | CAAGCAGAAGACGGCATACGAGATATGTCGTCGTGACTGGAGTTCAGACGTGTGCTC | 592 |
| B9 | ILMN_AMP_REVi7_BC66 | CAAGCAGAAGACGGCATACGAGATATGCTGTAGTGACTGGAGTTCAGACGTGTGCTC | 593 |
| C9 | ILMN_AMP_REVi7_BC67 | CAAGCAGAAGACGGCATACGAGATATATTATAGTGACTGGAGTTCAGACGTGTGCTC | 594 |
| D9 | ILMN_AMP_REVi7_BC68 | CAAGCAGAAGACGGCATACGAGATATTCGGGAGTGACTGGAGTTCAGACGTGTGCTC | 595 |
| E9 | ILMN_AMP_REVi7_BC69 | CAAGCAGAAGACGGCATACGAGATATCTTCGAGTGACTGGAGTTCAGACGTGTGCTC | 596 |
| F9 | ILMN_AMP_REVi7_BC70 | CAAGCAGAAGACGGCATACGAGATATTGCCGAGTGACTGGAGTTCAGACGTGTGCTC | 597 |
| G9 | ILMN_AMP_REVi7_BC71 | CAAGCAGAAGACGGCATACGAGATTACGTGATGTGACTGGAGTTCAGACGTGTGCTC | 598 |
| H9 | ILMN_AMP_REVi7_BC72 | CAAGCAGAAGACGGCATACGAGATTAACATCGGTGACTGGAGTTCAGACGTGTGCTC | 599 |
| A10 | ILMN_AMP_REVi7_BC73 | CAAGCAGAAGACGGCATACGAGATTAGCCTAAGTGACTGGAGTTCAGACGTGTGCTC | 600 |
| B10 | ILMN_AMP_REVi7_BC74 | CAAGCAGAAGACGGCATACGAGATTATCAAGTGTGACTGGAGTTCAGACGTGTGCTC | 601 |
| C10 | ILMN_AMP_REVi7_BC75 | CAAGCAGAAGACGGCATACGAGATTACTGATCGTGACTGGAGTTCAGACGTGTGCTC | 602 |
| D10 | ILMN_AMP_REVi7_BC76 | CAAGCAGAAGACGGCATACGAGATTAGTAGCCGTGACTGGAGTTCAGACGTGTGCTC | 603 |
| E10 | ILMN_AMP_REVi7_BC77 | CAAGCAGAAGACGGCATACGAGATTATTGACTGTGACTGGAGTTCAGACGTGTGCTC | 604 |
| F10 | ILMN_AMP_REVi7_BC78 | CAAGCAGAAGACGGCATACGAGATTAGGAACTGTGACTGGAGTTCAGACGTGTGCTC | 605 |
| G10 | ILMN_AMP_REVi7_BC79 | CAAGCAGAAGACGGCATACGAGATTATGACATGTGACTGGAGTTCAGACGTGTGCTC | 606 |
| H10 | ILMN_AMP_REVi7_BC80 | CAAGCAGAAGACGGCATACGAGATTAGGACGGGTGACTGGAGTTCAGACGTGTGCTC | 607 |
| A11 | ILMN_AMP_REVi7_BC81 | CAAGCAGAAGACGGCATACGAGATTACCACTCGTGACTGGAGTTCAGACGTGTGCTC | 608 |
| B11 | ILMN_AMP_REVi7_BC82 | CAAGCAGAAGACGGCATACGAGATTAAGGAATGTGACTGGAGTTCAGACGTGTGCTC | 609 |
| C11 | ILMN_AMP_REVi7_BC83 | CAAGCAGAAGACGGCATACGAGATTACTTTTGGTGACTGGAGTTCAGACGTGTGCTC | 610 |
| D11 | ILMN_AMP_REVi7_BC84 | CAAGCAGAAGACGGCATACGAGATTATGAGTGGTGACTGGAGTTCAGACGTGTGCTC | 611 |
| E11 | ILMN_AMP_REVi7_BC85 | CAAGCAGAAGACGGCATACGAGATTACGCCTGGTGACTGGAGTTCAGACGTGTGCTC | 612 |

TABLE 7-continued

Illumina sequencing index primers (i7) for PCR2 (i7 index sequences are bolded)

| Well position | Name | Sequence | SEQ ID NO.: |
|---|---|---|---|
| F11 | ILMN_AMP_REVi7_BC86 | CAAGCAGAAGACGGCATACGAGATTAGCCATGGTGACTGGAGTTCAGACGTGTGCTC | 613 |
| G11 | ILMN_AMP_REVi7_BC87 | CAAGCAGAAGACGGCATACGAGATTATGTTGGGTGACTGGAGTTCAGACGTGTGCTC | 614 |
| H11 | ILMN_AMP_REVi7_BC88 | CAAGCAGAAGACGGCATACGAGATTAATTCCGGTGACTGGAGTTCAGACGTGTGCTC | 615 |
| A12 | ILMN_AMP_REVi7_BC89 | CAAGCAGAAGACGGCATACGAGATTAAGCTAGGTGACTGGAGTTCAGACGTGTGCTC | 616 |
| B12 | ILMN_AMP_REVi7_BC90 | CAAGCAGAAGACGGCATACGAGATTATCTGAGGTGACTGGAGTTCAGACGTGTGCTC | 617 |
| C12 | ILMN_AMP_REVi7_BC91 | CAAGCAGAAGACGGCATACGAGATTAGTCGTCGTGACTGGAGTTCAGACGTGTGCTC | 618 |
| D12 | ILMN_AMP_REVi7_BC92 | CAAGCAGAAGACGGCATACGAGATTAGCTGTAGTGACTGGAGTTCAGACGTGTGCTC | 619 |
| E12 | ILMN_AMP_REVi7_BC93 | CAAGCAGAAGACGGCATACGAGATTAATTATAGTGACTGGAGTTCAGACGTGTGCTC | 620 |
| F12 | ILMN_AMP_REVi7_BC94 | CAAGCAGAAGACGGCATACGAGATTATCGGGAGTGACTGGAGTTCAGACGTGTGCTC | 621 |
| G12 | ILMN_AMP_REVi7_BC95 | CAAGCAGAAGACGGCATACGAGATTACTTCGAGTGACTGGAGTTCAGACGTGTGCTC | 622 |
| H12 | ILMN_AMP_REVi7_BC96 | CAAGCAGAAGACGGCATACGAGATTATGCCGAGTGACTGGAGTTCAGACGTGTGCTC | 623 |

The invention claimed is:

1. A method of engineering genomic DNA in a cell, the method comprising:
   selecting a target region in the genomic DNA of the cell; and
   introducing into the cell a complex comprising a catalytically active CRISPR Class 2 Type II Cas9 protein and a guide polynucleotide complementary to a 20 nucleotide protospacer in the target region in the DNA, wherein the nucleotide at position 17 of the protospacer is an adenine (A); and
   selecting for cells comprising a single insertion of an adenine (A) nucleotide between position 17 and 18 of the protospacer.

2. The method of claim 1, wherein the target region in the DNA comprises a gene encoding a gene product.

3. The method of claim 2, further comprising:
   reducing or restoring function of the gene product.

4. The method of claim 1, wherein the Cas9 protein comprises a *Streptococcus pyogenes* Cas9 protein.

5. The method of claim 1, wherein the guide polynucleotide comprises a single-guide RNA.

6. The method of claim 1, wherein the cell comprises a mammalian cell.

7. The method of claim 6, wherein the mammalian cell comprises a cell selected from the group consisting of a pig cell, a cow cell, a goat cell, a sheep cell, a rodent cell, a rat cell, a mouse cell, a non-human primate cell, and a human cell.

8. The method of claim 7, wherein the mammalian cell comprises a human cell.

9. The method of claim 8, wherein the human cell comprises a stem cell.

* * * * *

SEQUENCE LISTING

```
<160> NUMBER OF SEQ ID NOS: 649

<210> SEQ ID NO 1
<211> LENGTH: 58
<212> TYPE: DNA
<213> ORGANISM: Artificial Sequence
<220> FEATURE:
<223> OTHER INFORMATION: Synthetic

<400> SEQUENCE: 1
taatacgact cactataggc tgatgtagtc actcttgagt tttagagcta gaaatagc     58

<210> SEQ ID NO 2
<211> LENGTH: 58
<212> TYPE: DNA
<213> ORGANISM: Artificial Sequence
<220> FEATURE:
<223> OTHER INFORMATION: Synthetic

<400> SEQUENCE: 2
taatacgact cactatagag tgtgcattgc cacctcaggt tttagagcta gaaatagc     58

<210> SEQ ID NO 3
<211> LENGTH: 58
<212> TYPE: DNA
<213> ORGANISM: Artificial Sequence
<220> FEATURE:
<223> OTHER INFORMATION: Synthetic

<400> SEQUENCE: 3
taatacgact cactatagag atgcaggctg cagatgccgt tttagagcta gaaatagc     58

<210> SEQ ID NO 4
<211> LENGTH: 58
<212> TYPE: DNA
<213> ORGANISM: Artificial Sequence
<220> FEATURE:
<223> OTHER INFORMATION: Synthetic

<400> SEQUENCE: 4
```
taatacgact cactataggg ccctcggcgg cggctcccgt tttagagcta gaaatagc    58

<210> SEQ ID NO 5
<211> LENGTH: 58
<212> TYPE: DNA
<213> ORGANISM: Artificial Sequence
<220> FEATURE:
<223> OTHER INFORMATION: Synthetic

<400> SEQUENCE: 5
taatacgact cactatagac agaacatgtt gttatagagt tttagagcta gaaatagc    58

<210> SEQ ID NO 6
<211> LENGTH: 58
<212> TYPE: DNA
<213> ORGANISM: Artificial Sequence
<220> FEATURE:
<223> OTHER INFORMATION: Synthetic

<400> SEQUENCE: 6
taatacgact cactatagac agattctgga aagctcctgt tttagagcta gaaatagc    58

<210> SEQ ID NO 7
<211> LENGTH: 58
<212> TYPE: DNA
<213> ORGANISM: Artificial Sequence
<220> FEATURE:
<223> OTHER INFORMATION: Synthetic

<400> SEQUENCE: 7
taatacgact cactataggg tcaacaagtg gaactctagt tttagagcta gaaatagc    58

<210> SEQ ID NO 8
<211> LENGTH: 58
<212> TYPE: DNA
<213> ORGANISM: Artificial Sequence
<220> FEATURE:
<223> OTHER INFORMATION: Synthetic

<400> SEQUENCE: 8
taatacgact cactataggg agtatttcag gggctcttgt tttagagcta gaaatagc    58

<210> SEQ ID NO 9
<211> LENGTH: 58
<212> TYPE: DNA
<213> ORGANISM: Artificial Sequence
<220> FEATURE:
<223> OTHER INFORMATION: Synthetic

<400> SEQUENCE: 9
taatacgact cactataggg gagggctgtg ctgctagtgt tttagagcta gaaatagc    58

<210> SEQ ID NO 10
<211> LENGTH: 58
<212> TYPE: DNA
<213> ORGANISM: Artificial Sequence
<220> FEATURE:
<223> OTHER INFORMATION: Synthetic

<400> SEQUENCE: 10
taatacgact cactataggc aacttgaaat tatatctggt tttagagcta gaaatagc    58

<210> SEQ ID NO 11
<211> LENGTH: 58
<212> TYPE: DNA

<213> ORGANISM: Artificial Sequence
<220> FEATURE:
<223> OTHER INFORMATION: Synthetic

<400> SEQUENCE: 11
taatacgact cactataggt agagaaagaa gcagtgccgt tttagagcta gaaatagc    58

<210> SEQ ID NO 12
<211> LENGTH: 58
<212> TYPE: DNA
<213> ORGANISM: Artificial Sequence
<220> FEATURE:
<223> OTHER INFORMATION: Synthetic

<400> SEQUENCE: 12
taatacgact cactatagat aggagaagat gatgtatagt tttagagcta gaaatagc    58

<210> SEQ ID NO 13
<211> LENGTH: 58
<212> TYPE: DNA
<213> ORGANISM: Artificial Sequence
<220> FEATURE:
<223> OTHER INFORMATION: Synthetic

<400> SEQUENCE: 13
taatacgact cactataggc atacagtgat ttgatgaagt tttagagcta gaaatagc    58

<210> SEQ ID NO 14
<211> LENGTH: 58
<212> TYPE: DNA
<213> ORGANISM: Artificial Sequence
<220> FEATURE:
<223> OTHER INFORMATION: Synthetic

<400> SEQUENCE: 14
taatacgact cactataggg gggccctcct cttgctgcgt tttagagcta gaaatagc    58

<210> SEQ ID NO 15
<211> LENGTH: 58
<212> TYPE: DNA
<213> ORGANISM: Artificial Sequence
<220> FEATURE:
<223> OTHER INFORMATION: Synthetic

<400> SEQUENCE: 15
taatacgact cactatagga aaatcatcag ttatcatcgt tttagagcta gaaatagc    58

<210> SEQ ID NO 16
<211> LENGTH: 58
<212> TYPE: DNA
<213> ORGANISM: Artificial Sequence
<220> FEATURE:
<223> OTHER INFORMATION: Synthetic

<400> SEQUENCE: 16
taatacgact cactatagtt catgagtctt gacaacaagt tttagagcta gaaatagc    58

<210> SEQ ID NO 17
<211> LENGTH: 58
<212> TYPE: DNA
<213> ORGANISM: Artificial Sequence
<220> FEATURE:
<223> OTHER INFORMATION: Synthetic

<400> SEQUENCE: 17
taatacgact cactataggg tggcgggcac tgtcgtcagt tttagagcta gaaatagc    58

```
<210> SEQ ID NO 18
<211> LENGTH: 58
<212> TYPE: DNA
<213> ORGANISM: Artificial Sequence
<220> FEATURE:
<223> OTHER INFORMATION: Synthetic

<400> SEQUENCE: 18
taatacgact cactatagat gacagtgcca aagccagcgt tttagagcta gaaatagc        58

<210> SEQ ID NO 19
<211> LENGTH: 58
<212> TYPE: DNA
<213> ORGANISM: Artificial Sequence
<220> FEATURE:
<223> OTHER INFORMATION: Synthetic

<400> SEQUENCE: 19
taatacgact cactatagac agtagaacta agggtggggt tttagagcta gaaatagc        58

<210> SEQ ID NO 20
<211> LENGTH: 58
<212> TYPE: DNA
<213> ORGANISM: Artificial Sequence
<220> FEATURE:
<223> OTHER INFORMATION: Synthetic

<400> SEQUENCE: 20
taatacgact cactatagcc gccgtccaag acctaccggt tttagagcta gaaatagc        58

<210> SEQ ID NO 21
<211> LENGTH: 58
<212> TYPE: DNA
<213> ORGANISM: Artificial Sequence
<220> FEATURE:
<223> OTHER INFORMATION: Synthetic

<400> SEQUENCE: 21
taatacgact cactatagca tcacgcttat ccaccccagt tttagagcta gaaatagc        58

<210> SEQ ID NO 22
<211> LENGTH: 58
<212> TYPE: DNA
<213> ORGANISM: Artificial Sequence
<220> FEATURE:
<223> OTHER INFORMATION: Synthetic

<400> SEQUENCE: 22
taatacgact cactatagac catgagtaac tccattccgt tttagagcta gaaatagc        58

<210> SEQ ID NO 23
<211> LENGTH: 58
<212> TYPE: DNA
<213> ORGANISM: Artificial Sequence
<220> FEATURE:
<223> OTHER INFORMATION: Synthetic

<400> SEQUENCE: 23
taatacgact cactataggg aggtagagat tcatgtcagt tttagagcta gaaatagc        58

<210> SEQ ID NO 24
<211> LENGTH: 58
<212> TYPE: DNA
<213> ORGANISM: Artificial Sequence
<220> FEATURE:
```

<223> OTHER INFORMATION: Synthetic

<400> SEQUENCE: 24
taatacgact cactatagga acgaatacag aaaagtaagt tttagagcta gaaatagc    58

<210> SEQ ID NO 25
<211> LENGTH: 58
<212> TYPE: DNA
<213> ORGANISM: Artificial Sequence
<220> FEATURE:
<223> OTHER INFORMATION: Synthetic

<400> SEQUENCE: 25
taatacgact cactatagat ccgtggccca tcatgtctgt tttagagcta gaaatagc    58

<210> SEQ ID NO 26
<211> LENGTH: 58
<212> TYPE: DNA
<213> ORGANISM: Artificial Sequence
<220> FEATURE:
<223> OTHER INFORMATION: Synthetic

<400> SEQUENCE: 26
taatacgact cactataggg tggacaagcg gcagataggt tttagagcta gaaatagc    58

<210> SEQ ID NO 27
<211> LENGTH: 58
<212> TYPE: DNA
<213> ORGANISM: Artificial Sequence
<220> FEATURE:
<223> OTHER INFORMATION: Synthetic

<400> SEQUENCE: 27
taatacgact cactatagga actgcaaagt gaaacaaagt tttagagcta gaaatagc    58

<210> SEQ ID NO 28
<211> LENGTH: 58
<212> TYPE: DNA
<213> ORGANISM: Artificial Sequence
<220> FEATURE:
<223> OTHER INFORMATION: Synthetic

<400> SEQUENCE: 28
taatacgact cactatagac tgacacgcag acattcaggt tttagagcta gaaatagc    58

<210> SEQ ID NO 29
<211> LENGTH: 58
<212> TYPE: DNA
<213> ORGANISM: Artificial Sequence
<220> FEATURE:
<223> OTHER INFORMATION: Synthetic

<400> SEQUENCE: 29
taatacgact cactatagcg aagctggaat ctgctctcgt tttagagcta gaaatagc    58

<210> SEQ ID NO 30
<211> LENGTH: 58
<212> TYPE: DNA
<213> ORGANISM: Artificial Sequence
<220> FEATURE:
<223> OTHER INFORMATION: Synthetic

<400> SEQUENCE: 30
taatacgact cactatagga ccagccgggg cagtgaaggt tttagagcta gaaatagc    58

```
<210> SEQ ID NO 31
<211> LENGTH: 58
<212> TYPE: DNA
<213> ORGANISM: Artificial Sequence
<220> FEATURE:
<223> OTHER INFORMATION: Synthetic

<400> SEQUENCE: 31
taatacgact cactataggg gcgctggaac ctggacccgt tttagagcta gaaatagc      58

<210> SEQ ID NO 32
<211> LENGTH: 58
<212> TYPE: DNA
<213> ORGANISM: Artificial Sequence
<220> FEATURE:
<223> OTHER INFORMATION: Synthetic

<400> SEQUENCE: 32
taatacgact cactataggg acagaagaag ccctgctggt tttagagcta gaaatagc      58

<210> SEQ ID NO 33
<211> LENGTH: 58
<212> TYPE: DNA
<213> ORGANISM: Artificial Sequence
<220> FEATURE:
<223> OTHER INFORMATION: Synthetic

<400> SEQUENCE: 33
taatacgact cactatagct gggcaggcga cccgccgcgt tttagagcta gaaatagc      58

<210> SEQ ID NO 34
<211> LENGTH: 58
<212> TYPE: DNA
<213> ORGANISM: Artificial Sequence
<220> FEATURE:
<223> OTHER INFORMATION: Synthetic

<400> SEQUENCE: 34
taatacgact cactataggt tctccacggc accccaagt tttagagcta gaaatagc       58

<210> SEQ ID NO 35
<211> LENGTH: 58
<212> TYPE: DNA
<213> ORGANISM: Artificial Sequence
<220> FEATURE:
<223> OTHER INFORMATION: Synthetic

<400> SEQUENCE: 35
taatacgact cactatagga gaaagaatac catgcagagt tttagagcta gaaatagc      58

<210> SEQ ID NO 36
<211> LENGTH: 58
<212> TYPE: DNA
<213> ORGANISM: Artificial Sequence
<220> FEATURE:
<223> OTHER INFORMATION: Synthetic

<400> SEQUENCE: 36
taatacgact cactatagct cctcctctgc tccgccacgt tttagagcta gaaatagc      58

<210> SEQ ID NO 37
<211> LENGTH: 58
<212> TYPE: DNA
<213> ORGANISM: Artificial Sequence
<220> FEATURE:
<223> OTHER INFORMATION: Synthetic
```

<400> SEQUENCE: 37
taatacgact cactataggc tcaggaggag gaagccgggt tttagagcta gaaatagc    58

<210> SEQ ID NO 38
<211> LENGTH: 58
<212> TYPE: DNA
<213> ORGANISM: Artificial Sequence
<220> FEATURE:
<223> OTHER INFORMATION: Synthetic

<400> SEQUENCE: 38
taatacgact cactataggc tgaggagggg tcgcggcggt tttagagcta gaaatagc    58

<210> SEQ ID NO 39
<211> LENGTH: 58
<212> TYPE: DNA
<213> ORGANISM: Artificial Sequence
<220> FEATURE:
<223> OTHER INFORMATION: Synthetic

<400> SEQUENCE: 39
taatacgact cactataggg gcactggagc cacctcttgt tttagagcta gaaatagc    58

<210> SEQ ID NO 40
<211> LENGTH: 58
<212> TYPE: DNA
<213> ORGANISM: Artificial Sequence
<220> FEATURE:
<223> OTHER INFORMATION: Synthetic

<400> SEQUENCE: 40
taatacgact cactataggc acgcagcggc gggagcccgt tttagagcta gaaatagc    58

<210> SEQ ID NO 41
<211> LENGTH: 58
<212> TYPE: DNA
<213> ORGANISM: Artificial Sequence
<220> FEATURE:
<223> OTHER INFORMATION: Synthetic

<400> SEQUENCE: 41
taatacgact cactataggg cccccaagtg gacagagcgt tttagagcta gaaatagc    58

<210> SEQ ID NO 42
<211> LENGTH: 58
<212> TYPE: DNA
<213> ORGANISM: Artificial Sequence
<220> FEATURE:
<223> OTHER INFORMATION: Synthetic

<400> SEQUENCE: 42
taatacgact cactatagtg tggagtttta ataggttgt tttagagcta gaaatagc    58

<210> SEQ ID NO 43
<211> LENGTH: 58
<212> TYPE: DNA
<213> ORGANISM: Artificial Sequence
<220> FEATURE:
<223> OTHER INFORMATION: Synthetic

<400> SEQUENCE: 43
taatacgact cactataggg aagggctagg cggggcggt tttagagcta gaaatagc    58

<210> SEQ ID NO 44
<211> LENGTH: 58

<210> SEQ ID NO 44
<211> LENGTH: 58
<212> TYPE: DNA
<213> ORGANISM: Artificial Sequence
<220> FEATURE:
<223> OTHER INFORMATION: Synthetic

<400> SEQUENCE: 44
taatacgact cactataggc aaataacctt ctgtgtcagt tttagagcta gaaatagc    58

<210> SEQ ID NO 45
<211> LENGTH: 58
<212> TYPE: DNA
<213> ORGANISM: Artificial Sequence
<220> FEATURE:
<223> OTHER INFORMATION: Synthetic

<400> SEQUENCE: 45
taatacgact cactataggc accaagtctg agtggaccgt tttagagcta gaaatagc    58

<210> SEQ ID NO 46
<211> LENGTH: 58
<212> TYPE: DNA
<213> ORGANISM: Artificial Sequence
<220> FEATURE:
<223> OTHER INFORMATION: Synthetic

<400> SEQUENCE: 46
taatacgact cactataggc aggactcctt tcctccatgt tttagagcta gaaatagc    58

<210> SEQ ID NO 47
<211> LENGTH: 58
<212> TYPE: DNA
<213> ORGANISM: Artificial Sequence
<220> FEATURE:
<223> OTHER INFORMATION: Synthetic

<400> SEQUENCE: 47
taatacgact cactataggc tgcgcctctg ctgcgcctgt tttagagcta gaaatagc    58

<210> SEQ ID NO 48
<211> LENGTH: 58
<212> TYPE: DNA
<213> ORGANISM: Artificial Sequence
<220> FEATURE:
<223> OTHER INFORMATION: Synthetic

<400> SEQUENCE: 48
taatacgact cactatagga agccagctga ttataagagt tttagagcta gaaatagc    58

<210> SEQ ID NO 49
<211> LENGTH: 58
<212> TYPE: DNA
<213> ORGANISM: Artificial Sequence
<220> FEATURE:
<223> OTHER INFORMATION: Synthetic

<400> SEQUENCE: 49
taatacgact cactatagcc aaaaaagaac tgcacctcgt tttagagcta gaaatagc    58

<210> SEQ ID NO 50
<211> LENGTH: 58
<212> TYPE: DNA
<213> ORGANISM: Artificial Sequence
<220> FEATURE:
<223> OTHER INFORMATION: Synthetic

<400> SEQUENCE: 50

```
taatacgact cactataggt tcgactacgt ggagaagcgt tttagagcta gaaatagc      58
```

<210> SEQ ID NO 51
<211> LENGTH: 58
<212> TYPE: DNA
<213> ORGANISM: Artificial Sequence
<220> FEATURE:
<223> OTHER INFORMATION: Synthetic

<400> SEQUENCE: 51

```
taatacgact cactataggc accatgttgc cggtcctcgt tttagagcta gaaatagc      58
```

<210> SEQ ID NO 52
<211> LENGTH: 58
<212> TYPE: DNA
<213> ORGANISM: Artificial Sequence
<220> FEATURE:
<223> OTHER INFORMATION: Synthetic

<400> SEQUENCE: 52

```
taatacgact cactataggc ccgccaccac caggatgtgt tttagagcta gaaatagc      58
```

<210> SEQ ID NO 53
<211> LENGTH: 58
<212> TYPE: DNA
<213> ORGANISM: Artificial Sequence
<220> FEATURE:
<223> OTHER INFORMATION: Synthetic

<400> SEQUENCE: 53

```
taatacgact cactataggg cactgacaat cccctttcgt tttagagcta gaaatagc      58
```

<210> SEQ ID NO 54
<211> LENGTH: 58
<212> TYPE: DNA
<213> ORGANISM: Artificial Sequence
<220> FEATURE:
<223> OTHER INFORMATION: Synthetic

<400> SEQUENCE: 54

```
taatacgact cactatagga ggagctccaa gaagactggt tttagagcta gaaatagc      58
```

<210> SEQ ID NO 55
<211> LENGTH: 58
<212> TYPE: DNA
<213> ORGANISM: Artificial Sequence
<220> FEATURE:
<223> OTHER INFORMATION: Synthetic

<400> SEQUENCE: 55

```
taatacgact cactatagga agaagacaaa tcacaaacgt tttagagcta gaaatagc      58
```

<210> SEQ ID NO 56
<211> LENGTH: 58
<212> TYPE: DNA
<213> ORGANISM: Artificial Sequence
<220> FEATURE:
<223> OTHER INFORMATION: Synthetic

<400> SEQUENCE: 56

```
taatacgact cactataggg ggcgggaaga gcgcgtccgt tttagagcta gaaatagc      58
```

<210> SEQ ID NO 57
<211> LENGTH: 58
<212> TYPE: DNA
<213> ORGANISM: Artificial Sequence

```
<220> FEATURE:
<223> OTHER INFORMATION: Synthetic

<400> SEQUENCE: 57
taatacgact cactataggc cgtgcaggca gctgaggcgt tttagagcta gaaatagc        58

<210> SEQ ID NO 58
<211> LENGTH: 58
<212> TYPE: DNA
<213> ORGANISM: Artificial Sequence
<220> FEATURE:
<223> OTHER INFORMATION: Synthetic

<400> SEQUENCE: 58
taatacgact cactatagct cgtctgataa gacaacaggt tttagagcta gaaatagc        58

<210> SEQ ID NO 59
<211> LENGTH: 58
<212> TYPE: DNA
<213> ORGANISM: Artificial Sequence
<220> FEATURE:
<223> OTHER INFORMATION: Synthetic

<400> SEQUENCE: 59
taatacgact cactataggt gaatagagcc agcaaagggt tttagagcta gaaatagc        58

<210> SEQ ID NO 60
<211> LENGTH: 58
<212> TYPE: DNA
<213> ORGANISM: Artificial Sequence
<220> FEATURE:
<223> OTHER INFORMATION: Synthetic

<400> SEQUENCE: 60
taatacgact cactatagga ctcgcagacg ccctctgcgt tttagagcta gaaatagc        58

<210> SEQ ID NO 61
<211> LENGTH: 58
<212> TYPE: DNA
<213> ORGANISM: Artificial Sequence
<220> FEATURE:
<223> OTHER INFORMATION: Synthetic

<400> SEQUENCE: 61
taatacgact cactatagtt gtcgtcttct gtccaagtgt tttagagcta gaaatagc        58

<210> SEQ ID NO 62
<211> LENGTH: 58
<212> TYPE: DNA
<213> ORGANISM: Artificial Sequence
<220> FEATURE:
<223> OTHER INFORMATION: Synthetic

<400> SEQUENCE: 62
taatacgact cactatagga ggcgcagcag tgccacaggt tttagagcta gaaatagc        58

<210> SEQ ID NO 63
<211> LENGTH: 58
<212> TYPE: DNA
<213> ORGANISM: Artificial Sequence
<220> FEATURE:
<223> OTHER INFORMATION: Synthetic

<400> SEQUENCE: 63
taatacgact cactataggg ccatggcggg ctggatccgt tttagagcta gaaatagc        58
```

```
<210> SEQ ID NO 64
<211> LENGTH: 58
<212> TYPE: DNA
<213> ORGANISM: Artificial Sequence
<220> FEATURE:
<223> OTHER INFORMATION: Synthetic

<400> SEQUENCE: 64
taatacgact cactatagga gccaagatgg ggctctgcgt tttagagcta gaaatagc        58

<210> SEQ ID NO 65
<211> LENGTH: 58
<212> TYPE: DNA
<213> ORGANISM: Artificial Sequence
<220> FEATURE:
<223> OTHER INFORMATION: Synthetic

<400> SEQUENCE: 65
taatacgact cactataggg gtggggggag tttgctccgt tttagagcta gaaatagc        58

<210> SEQ ID NO 66
<211> LENGTH: 58
<212> TYPE: DNA
<213> ORGANISM: Artificial Sequence
<220> FEATURE:
<223> OTHER INFORMATION: Synthetic

<400> SEQUENCE: 66
taatacgact cactataggc cgaggctgct ggaggaaggt tttagagcta gaaatagc        58

<210> SEQ ID NO 67
<211> LENGTH: 58
<212> TYPE: DNA
<213> ORGANISM: Artificial Sequence
<220> FEATURE:
<223> OTHER INFORMATION: Synthetic

<400> SEQUENCE: 67
taatacgact cactataggc cgggaggtgc tgcgctcggt tttagagcta gaaatagc        58

<210> SEQ ID NO 68
<211> LENGTH: 58
<212> TYPE: DNA
<213> ORGANISM: Artificial Sequence
<220> FEATURE:
<223> OTHER INFORMATION: Synthetic

<400> SEQUENCE: 68
taatacgact cactataggc aaaactcaac cctaccccgt tttagagcta gaaatagc        58

<210> SEQ ID NO 69
<211> LENGTH: 58
<212> TYPE: DNA
<213> ORGANISM: Artificial Sequence
<220> FEATURE:
<223> OTHER INFORMATION: Synthetic

<400> SEQUENCE: 69
taatacgact cactatagga atccatcttc ctgaccctgt tttagagcta gaaatagc        58

<210> SEQ ID NO 70
<211> LENGTH: 58
<212> TYPE: DNA
<213> ORGANISM: Artificial Sequence
<220> FEATURE:
<223> OTHER INFORMATION: Synthetic
```

<400> SEQUENCE: 70
taatacgact cactatagct aggtgatgat gtcagattgt tttagagcta gaaatagc    58

<210> SEQ ID NO 71
<211> LENGTH: 58
<212> TYPE: DNA
<213> ORGANISM: Artificial Sequence
<220> FEATURE:
<223> OTHER INFORMATION: Synthetic

<400> SEQUENCE: 71
taatacgact cactatagga gcagagatgt gggaatgggt tttagagcta gaaatagc    58

<210> SEQ ID NO 72
<211> LENGTH: 58
<212> TYPE: DNA
<213> ORGANISM: Artificial Sequence
<220> FEATURE:
<223> OTHER INFORMATION: Synthetic

<400> SEQUENCE: 72
taatacgact cactataggg gactggggtc gggagggtgt tttagagcta gaaatagc    58

<210> SEQ ID NO 73
<211> LENGTH: 58
<212> TYPE: DNA
<213> ORGANISM: Artificial Sequence
<220> FEATURE:
<223> OTHER INFORMATION: Synthetic

<400> SEQUENCE: 73
taatacgact cactatagga gaaagctgga gaagggggt tttagagcta gaaatagc    58

<210> SEQ ID NO 74
<211> LENGTH: 58
<212> TYPE: DNA
<213> ORGANISM: Artificial Sequence
<220> FEATURE:
<223> OTHER INFORMATION: Synthetic

<400> SEQUENCE: 74
taatacgact cactataggc gcagggaagc gaccaactgt tttagagcta gaaatagc    58

<210> SEQ ID NO 75
<211> LENGTH: 58
<212> TYPE: DNA
<213> ORGANISM: Artificial Sequence
<220> FEATURE:
<223> OTHER INFORMATION: Synthetic

<400> SEQUENCE: 75
taatacgact cactatagga agaggggag agagttacgt tttagagcta gaaatagc    58

<210> SEQ ID NO 76
<211> LENGTH: 58
<212> TYPE: DNA
<213> ORGANISM: Artificial Sequence
<220> FEATURE:
<223> OTHER INFORMATION: Synthetic

<400> SEQUENCE: 76
taatacgact cactataggt ggaagagttt gtggaagggt tttagagcta gaaatagc    58

<210> SEQ ID NO 77

```
<211> LENGTH: 58
<212> TYPE: DNA
<213> ORGANISM: Artificial Sequence
<220> FEATURE:
<223> OTHER INFORMATION: Synthetic

<400> SEQUENCE: 77
taatacgact cactatagag ttcccagctg cacgcctcgt tttagagcta gaaatagc      58

<210> SEQ ID NO 78
<211> LENGTH: 58
<212> TYPE: DNA
<213> ORGANISM: Artificial Sequence
<220> FEATURE:
<223> OTHER INFORMATION: Synthetic

<400> SEQUENCE: 78
taatacgact cactatagga agagggaaac gtgtggctgt tttagagcta gaaatagc      58

<210> SEQ ID NO 79
<211> LENGTH: 58
<212> TYPE: DNA
<213> ORGANISM: Artificial Sequence
<220> FEATURE:
<223> OTHER INFORMATION: Synthetic

<400> SEQUENCE: 79
taatacgact cactataggg tgggtctcgg gactggcagt tttagagcta gaaatagc      58

<210> SEQ ID NO 80
<211> LENGTH: 58
<212> TYPE: DNA
<213> ORGANISM: Artificial Sequence
<220> FEATURE:
<223> OTHER INFORMATION: Synthetic

<400> SEQUENCE: 80
taatacgact cactatagga atgagggtcc tttgggaagt tttagagcta gaaatagc      58

<210> SEQ ID NO 81
<211> LENGTH: 58
<212> TYPE: DNA
<213> ORGANISM: Artificial Sequence
<220> FEATURE:
<223> OTHER INFORMATION: Synthetic

<400> SEQUENCE: 81
taatacgact cactataggg tgggggcgga aggggccgt tttagagcta gaaatagc       58

<210> SEQ ID NO 82
<211> LENGTH: 58
<212> TYPE: DNA
<213> ORGANISM: Artificial Sequence
<220> FEATURE:
<223> OTHER INFORMATION: Synthetic

<400> SEQUENCE: 82
taatacgact cactatagcg gccagagacc gagccctagt tttagagcta gaaatagc      58

<210> SEQ ID NO 83
<211> LENGTH: 58
<212> TYPE: DNA
<213> ORGANISM: Artificial Sequence
<220> FEATURE:
<223> OTHER INFORMATION: Synthetic

<400> SEQUENCE: 83
```
taatacgact cactataggt tgtggcagca gtcactgggt tttagagcta gaaatagc    58

<210> SEQ ID NO 84
<211> LENGTH: 58
<212> TYPE: DNA
<213> ORGANISM: Artificial Sequence
<220> FEATURE:
<223> OTHER INFORMATION: Synthetic

<400> SEQUENCE: 84
taatacgact cactataggg ccactgtagt cctccagggt tttagagcta gaaatagc    58

<210> SEQ ID NO 85
<211> LENGTH: 58
<212> TYPE: DNA
<213> ORGANISM: Artificial Sequence
<220> FEATURE:
<223> OTHER INFORMATION: Synthetic

<400> SEQUENCE: 85
taatacgact cactataggg agccagcccc tggccttcgt tttagagcta gaaatagc    58

<210> SEQ ID NO 86
<211> LENGTH: 58
<212> TYPE: DNA
<213> ORGANISM: Artificial Sequence
<220> FEATURE:
<223> OTHER INFORMATION: Synthetic

<400> SEQUENCE: 86
taatacgact cactatagtc ccaaaggcgg agggcgttgt tttagagcta gaaatagc    58

<210> SEQ ID NO 87
<211> LENGTH: 58
<212> TYPE: DNA
<213> ORGANISM: Artificial Sequence
<220> FEATURE:
<223> OTHER INFORMATION: Synthetic

<400> SEQUENCE: 87
taatacgact cactatagtg agtccgagca gaagaagagt tttagagcta gaaatagc    58

<210> SEQ ID NO 88
<211> LENGTH: 58
<212> TYPE: DNA
<213> ORGANISM: Artificial Sequence
<220> FEATURE:
<223> OTHER INFORMATION: Synthetic

<400> SEQUENCE: 88
taatacgact cactatagga gtccgagcag aagaagaagt tttagagcta gaaatagc    58

<210> SEQ ID NO 89
<211> LENGTH: 58
<212> TYPE: DNA
<213> ORGANISM: Artificial Sequence
<220> FEATURE:
<223> OTHER INFORMATION: Synthetic

<400> SEQUENCE: 89
taatacgact cactataggg cagccagcat gatgagacgt tttagagcta gaaatagc    58

<210> SEQ ID NO 90
<211> LENGTH: 58
<212> TYPE: DNA

<213> ORGANISM: Artificial Sequence
<220> FEATURE:
<223> OTHER INFORMATION: Synthetic

<400> SEQUENCE: 90
taatacgact cactatagct tctttgcttg ttcaaatggt tttagagcta gaaatagc     58

<210> SEQ ID NO 91
<211> LENGTH: 58
<212> TYPE: DNA
<213> ORGANISM: Artificial Sequence
<220> FEATURE:
<223> OTHER INFORMATION: Synthetic

<400> SEQUENCE: 91
taatacgact cactataggc agggtgagtg tctcagccgt tttagagcta gaaatagc     58

<210> SEQ ID NO 92
<211> LENGTH: 58
<212> TYPE: DNA
<213> ORGANISM: Artificial Sequence
<220> FEATURE:
<223> OTHER INFORMATION: Synthetic

<400> SEQUENCE: 92
taatacgact cactatagga actgtgtgtg ttgcaggggt tttagagcta gaaatagc     58

<210> SEQ ID NO 93
<211> LENGTH: 58
<212> TYPE: DNA
<213> ORGANISM: Artificial Sequence
<220> FEATURE:
<223> OTHER INFORMATION: Synthetic

<400> SEQUENCE: 93
taatacgact cactataggg gctgagagag ggacaagtgt tttagagcta gaaatagc     58

<210> SEQ ID NO 94
<211> LENGTH: 58
<212> TYPE: DNA
<213> ORGANISM: Artificial Sequence
<220> FEATURE:
<223> OTHER INFORMATION: Synthetic

<400> SEQUENCE: 94
taatacgact cactatagaa aacgtttcca agacatgagt tttagagcta gaaatagc     58

<210> SEQ ID NO 95
<211> LENGTH: 58
<212> TYPE: DNA
<213> ORGANISM: Artificial Sequence
<220> FEATURE:
<223> OTHER INFORMATION: Synthetic

<400> SEQUENCE: 95
taatacgact cactatagcc acgcccgcgg ggtgaagtgt tttagagcta gaaatagc     58

<210> SEQ ID NO 96
<211> LENGTH: 58
<212> TYPE: DNA
<213> ORGANISM: Artificial Sequence
<220> FEATURE:
<223> OTHER INFORMATION: Synthetic

<400> SEQUENCE: 96
taatacgact cactatagga gccctcaggc gaacctctgt tttagagcta gaaatagc     58

<210> SEQ ID NO 97
<211> LENGTH: 52
<212> TYPE: DNA
<213> ORGANISM: Artificial Sequence
<220> FEATURE:
<223> OTHER INFORMATION: Synthetic

<400> SEQUENCE: 97
cactctttcc ctacacgacg ctcttccgat ctcagatgcg atgacctttg tg    52

<210> SEQ ID NO 98
<211> LENGTH: 48
<212> TYPE: DNA
<213> ORGANISM: Artificial Sequence
<220> FEATURE:
<223> OTHER INFORMATION: Synthetic

<400> SEQUENCE: 98
ggagttcaga cgtgtgctct tccgatctag tcaccatgac gacagtgc    48

<210> SEQ ID NO 99
<211> LENGTH: 52
<212> TYPE: DNA
<213> ORGANISM: Artificial Sequence
<220> FEATURE:
<223> OTHER INFORMATION: Synthetic

<400> SEQUENCE: 99
cactctttcc ctacacgacg ctcttccgat ctcaggtccc ctaaaatggg tt    52

<210> SEQ ID NO 100
<211> LENGTH: 48
<212> TYPE: DNA
<213> ORGANISM: Artificial Sequence
<220> FEATURE:
<223> OTHER INFORMATION: Synthetic

<400> SEQUENCE: 100
ggagttcaga cgtgtgctct tccgatctgc tttatggtcc gctcagtc    48

<210> SEQ ID NO 101
<211> LENGTH: 52
<212> TYPE: DNA
<213> ORGANISM: Artificial Sequence
<220> FEATURE:
<223> OTHER INFORMATION: Synthetic

<400> SEQUENCE: 101
cactctttcc ctacacgacg ctcttccgat ctctcacctt tgggaagcat gt    52

<210> SEQ ID NO 102
<211> LENGTH: 48
<212> TYPE: DNA
<213> ORGANISM: Artificial Sequence
<220> FEATURE:
<223> OTHER INFORMATION: Synthetic

<400> SEQUENCE: 102
ggagttcaga cgtgtgctct tccgatctag ctctggcaca ccctctaa    48

<210> SEQ ID NO 103
<211> LENGTH: 52
<212> TYPE: DNA
<213> ORGANISM: Artificial Sequence
<220> FEATURE:

<223> OTHER INFORMATION: Synthetic

<400> SEQUENCE: 103
cactctttcc ctacacgacg ctcttccgat ctcaggtttg ggatttccag ag        52

<210> SEQ ID NO 104
<211> LENGTH: 46
<212> TYPE: DNA
<213> ORGANISM: Artificial Sequence
<220> FEATURE:
<223> OTHER INFORMATION: Synthetic

<400> SEQUENCE: 104
ggagttcaga cgtgtgctct tccgatctcc tgcaagtgcg caacag        46

<210> SEQ ID NO 105
<211> LENGTH: 52
<212> TYPE: DNA
<213> ORGANISM: Artificial Sequence
<220> FEATURE:
<223> OTHER INFORMATION: Synthetic

<400> SEQUENCE: 105
cactctttcc ctacacgacg ctcttccgat cttcctcaaa tttggatctg gc        52

<210> SEQ ID NO 106
<211> LENGTH: 48
<212> TYPE: DNA
<213> ORGANISM: Artificial Sequence
<220> FEATURE:
<223> OTHER INFORMATION: Synthetic

<400> SEQUENCE: 106
ggagttcaga cgtgtgctct tccgatctcc cccactatct ccttgaca        48

<210> SEQ ID NO 107
<211> LENGTH: 52
<212> TYPE: DNA
<213> ORGANISM: Artificial Sequence
<220> FEATURE:
<223> OTHER INFORMATION: Synthetic

<400> SEQUENCE: 107
cactctttcc ctacacgacg ctcttccgat ctttctgagc aagagaaggg ga        52

<210> SEQ ID NO 108
<211> LENGTH: 46
<212> TYPE: DNA
<213> ORGANISM: Artificial Sequence
<220> FEATURE:
<223> OTHER INFORMATION: Synthetic

<400> SEQUENCE: 108
ggagttcaga cgtgtgctct tccgatctct gcagcagcag caaact        46

<210> SEQ ID NO 109
<211> LENGTH: 52
<212> TYPE: DNA
<213> ORGANISM: Artificial Sequence
<220> FEATURE:
<223> OTHER INFORMATION: Synthetic

<400> SEQUENCE: 109
cactctttcc ctacacgacg ctcttccgat cttgcacccc tttcatctct ct        52

```
<210> SEQ ID NO 110
<211> LENGTH: 48
<212> TYPE: DNA
<213> ORGANISM: Artificial Sequence
<220> FEATURE:
<223> OTHER INFORMATION: Synthetic

<400> SEQUENCE: 110
ggagttcaga cgtgtgctct tccgatctca cctctcctct tcctccct                        48

<210> SEQ ID NO 111
<211> LENGTH: 52
<212> TYPE: DNA
<213> ORGANISM: Artificial Sequence
<220> FEATURE:
<223> OTHER INFORMATION: Synthetic

<400> SEQUENCE: 111
cactctttcc ctacacgacg ctcttccgat ctgagacttt cccccttgtt cc                   52

<210> SEQ ID NO 112
<211> LENGTH: 48
<212> TYPE: DNA
<213> ORGANISM: Artificial Sequence
<220> FEATURE:
<223> OTHER INFORMATION: Synthetic

<400> SEQUENCE: 112
ggagttcaga cgtgtgctct tccgatctac aggcagaagg aaaaccct                        48

<210> SEQ ID NO 113
<211> LENGTH: 52
<212> TYPE: DNA
<213> ORGANISM: Artificial Sequence
<220> FEATURE:
<223> OTHER INFORMATION: Synthetic

<400> SEQUENCE: 113
cactctttcc ctacacgacg ctcttccgat cttgccgttt aaaaacatcc aa                   52

<210> SEQ ID NO 114
<211> LENGTH: 50
<212> TYPE: DNA
<213> ORGANISM: Artificial Sequence
<220> FEATURE:
<223> OTHER INFORMATION: Synthetic

<400> SEQUENCE: 114
ggagttcaga cgtgtgctct tccgatctaa gtggtaggaa agcctcactg                      50

<210> SEQ ID NO 115
<211> LENGTH: 52
<212> TYPE: DNA
<213> ORGANISM: Artificial Sequence
<220> FEATURE:
<223> OTHER INFORMATION: Synthetic

<400> SEQUENCE: 115
cactctttcc ctacacgacg ctcttccgat ctaaggaacc tggagaccat ca                   52

<210> SEQ ID NO 116
<211> LENGTH: 48
<212> TYPE: DNA
<213> ORGANISM: Artificial Sequence
<220> FEATURE:
<223> OTHER INFORMATION: Synthetic
```

<400> SEQUENCE: 116
ggagttcaga cgtgtgctct tccgatctga aaggcactga gtgggaag  48

<210> SEQ ID NO 117
<211> LENGTH: 52
<212> TYPE: DNA
<213> ORGANISM: Artificial Sequence
<220> FEATURE:
<223> OTHER INFORMATION: Synthetic

<400> SEQUENCE: 117
cactctttcc ctacacgacg ctcttccgat ctggaaagaa acagcttgcc tg  52

<210> SEQ ID NO 118
<211> LENGTH: 48
<212> TYPE: DNA
<213> ORGANISM: Artificial Sequence
<220> FEATURE:
<223> OTHER INFORMATION: Synthetic

<400> SEQUENCE: 118
ggagttcaga cgtgtgctct tccgatctga agcctagcct gtcacctg  48

<210> SEQ ID NO 119
<211> LENGTH: 52
<212> TYPE: DNA
<213> ORGANISM: Artificial Sequence
<220> FEATURE:
<223> OTHER INFORMATION: Synthetic

<400> SEQUENCE: 119
cactctttcc ctacacgacg ctcttccgat ctcgtgttga agacctgact gg  52

<210> SEQ ID NO 120
<211> LENGTH: 48
<212> TYPE: DNA
<213> ORGANISM: Artificial Sequence
<220> FEATURE:
<223> OTHER INFORMATION: Synthetic

<400> SEQUENCE: 120
ggagttcaga cgtgtgctct tccgatctca atgaccacag caaagagc  48

<210> SEQ ID NO 121
<211> LENGTH: 52
<212> TYPE: DNA
<213> ORGANISM: Artificial Sequence
<220> FEATURE:
<223> OTHER INFORMATION: Synthetic

<400> SEQUENCE: 121
cactctttcc ctacacgacg ctcttccgat ctatctgtca gcaacctcac cc  52

<210> SEQ ID NO 122
<211> LENGTH: 47
<212> TYPE: DNA
<213> ORGANISM: Artificial Sequence
<220> FEATURE:
<223> OTHER INFORMATION: Synthetic

<400> SEQUENCE: 122
ggagttcaga cgtgtgctct tccgatctac tggcactcac ctccctc  47

<210> SEQ ID NO 123
<211> LENGTH: 52

<212> TYPE: DNA
<213> ORGANISM: Artificial Sequence
<220> FEATURE:
<223> OTHER INFORMATION: Synthetic

<400> SEQUENCE: 123
cactctttcc ctacacgacg ctcttccgat ctaacaagac caaggcactg ct    52

<210> SEQ ID NO 124
<211> LENGTH: 48
<212> TYPE: DNA
<213> ORGANISM: Artificial Sequence
<220> FEATURE:
<223> OTHER INFORMATION: Synthetic

<400> SEQUENCE: 124
ggagttcaga cgtgtgctct tccgatctct caaccctgga ggtctttg    48

<210> SEQ ID NO 125
<211> LENGTH: 52
<212> TYPE: DNA
<213> ORGANISM: Artificial Sequence
<220> FEATURE:
<223> OTHER INFORMATION: Synthetic

<400> SEQUENCE: 125
cactctttcc ctacacgacg ctcttccgat ctccatgttg agacacaggg tg    52

<210> SEQ ID NO 126
<211> LENGTH: 48
<212> TYPE: DNA
<213> ORGANISM: Artificial Sequence
<220> FEATURE:
<223> OTHER INFORMATION: Synthetic

<400> SEQUENCE: 126
ggagttcaga cgtgtgctct tccgatcttc aggaaattgc atcaggtg    48

<210> SEQ ID NO 127
<211> LENGTH: 46
<212> TYPE: DNA
<213> ORGANISM: Artificial Sequence
<220> FEATURE:
<223> OTHER INFORMATION: Synthetic

<400> SEQUENCE: 127
ggagttcaga cgtgtgctct tccgatctgt tccgacgctc cttgaa    46

<210> SEQ ID NO 128
<211> LENGTH: 52
<212> TYPE: DNA
<213> ORGANISM: Artificial Sequence
<220> FEATURE:
<223> OTHER INFORMATION: Synthetic

<400> SEQUENCE: 128
cactctttcc ctacacgacg ctcttccgat cttcagtgaa gtgctgtggg tc    52

<210> SEQ ID NO 129
<211> LENGTH: 48
<212> TYPE: DNA
<213> ORGANISM: Artificial Sequence
<220> FEATURE:
<223> OTHER INFORMATION: Synthetic

<400> SEQUENCE: 129
ggagttcaga cgtgtgctct tccgatcttg ccaatttaag agaacggg            48

<210> SEQ ID NO 130
<211> LENGTH: 52
<212> TYPE: DNA
<213> ORGANISM: Artificial Sequence
<220> FEATURE:
<223> OTHER INFORMATION: Synthetic

<400> SEQUENCE: 130
cactctttcc ctacacgacg ctcttccgat ctgggtcgtc agacaccaaa ac         52

<210> SEQ ID NO 131
<211> LENGTH: 50
<212> TYPE: DNA
<213> ORGANISM: Artificial Sequence
<220> FEATURE:
<223> OTHER INFORMATION: Synthetic

<400> SEQUENCE: 131
ggagttcaga cgtgtgctct tccgatctca acctcatctg ctctttcttg           50

<210> SEQ ID NO 132
<211> LENGTH: 47
<212> TYPE: DNA
<213> ORGANISM: Artificial Sequence
<220> FEATURE:
<223> OTHER INFORMATION: Synthetic

<400> SEQUENCE: 132
ggagttcaga cgtgtgctct tccgatctcc gggttctgga tcacttc              47

<210> SEQ ID NO 133
<211> LENGTH: 52
<212> TYPE: DNA
<213> ORGANISM: Artificial Sequence
<220> FEATURE:
<223> OTHER INFORMATION: Synthetic

<400> SEQUENCE: 133
cactctttcc ctacacgacg ctcttccgat ctagggagca tgtgtgtgtg ag        52

<210> SEQ ID NO 134
<211> LENGTH: 48
<212> TYPE: DNA
<213> ORGANISM: Artificial Sequence
<220> FEATURE:
<223> OTHER INFORMATION: Synthetic

<400> SEQUENCE: 134
ggagttcaga cgtgtgctct tccgatctgg aagtccttcc catgcttc             48

<210> SEQ ID NO 135
<211> LENGTH: 52
<212> TYPE: DNA
<213> ORGANISM: Artificial Sequence
<220> FEATURE:
<223> OTHER INFORMATION: Synthetic

<400> SEQUENCE: 135
cactctttcc ctacacgacg ctcttccgat cttcccttttt tcacacctttt cc      52

<210> SEQ ID NO 136
<211> LENGTH: 48
<212> TYPE: DNA
<213> ORGANISM: Artificial Sequence

```
<220> FEATURE:
<223> OTHER INFORMATION: Synthetic

<400> SEQUENCE: 136
ggagttcaga cgtgtgctct tccgatctct gtcgctgtac aaacatgg            48

<210> SEQ ID NO 137
<211> LENGTH: 52
<212> TYPE: DNA
<213> ORGANISM: Artificial Sequence
<220> FEATURE:
<223> OTHER INFORMATION: Synthetic

<400> SEQUENCE: 137
cactctttcc ctacacgacg ctcttccgat ctttccacaa agggagatca gc       52

<210> SEQ ID NO 138
<211> LENGTH: 48
<212> TYPE: DNA
<213> ORGANISM: Artificial Sequence
<220> FEATURE:
<223> OTHER INFORMATION: Synthetic

<400> SEQUENCE: 138
ggagttcaga cgtgtgctct tccgatcttt gcctttcatt gcacactc            48

<210> SEQ ID NO 139
<211> LENGTH: 53
<212> TYPE: DNA
<213> ORGANISM: Artificial Sequence
<220> FEATURE:
<223> OTHER INFORMATION: Synthetic

<400> SEQUENCE: 139
cactctttcc ctacacgacg ctcttccgat ctttccatag gccattctct ctc      53

<210> SEQ ID NO 140
<211> LENGTH: 48
<212> TYPE: DNA
<213> ORGANISM: Artificial Sequence
<220> FEATURE:
<223> OTHER INFORMATION: Synthetic

<400> SEQUENCE: 140
ggagttcaga cgtgtgctct tccgatctgc tgcctcacaa acttcaca            48

<210> SEQ ID NO 141
<211> LENGTH: 52
<212> TYPE: DNA
<213> ORGANISM: Artificial Sequence
<220> FEATURE:
<223> OTHER INFORMATION: Synthetic

<400> SEQUENCE: 141
cactctttcc ctacacgacg ctcttccgat ctaggcagcc actgacattc tt       52

<210> SEQ ID NO 142
<211> LENGTH: 48
<212> TYPE: DNA
<213> ORGANISM: Artificial Sequence
<220> FEATURE:
<223> OTHER INFORMATION: Synthetic

<400> SEQUENCE: 142
ggagttcaga cgtgtgctct tccgatctgg ggttgtcttc attggtga            48
```

<210> SEQ ID NO 143
<211> LENGTH: 50
<212> TYPE: DNA
<213> ORGANISM: Artificial Sequence
<220> FEATURE:
<223> OTHER INFORMATION: Synthetic

<400> SEQUENCE: 143
cactctttcc ctacacgacg ctcttccgat cttgcgcatg ctcagagttc          50

<210> SEQ ID NO 144
<211> LENGTH: 48
<212> TYPE: DNA
<213> ORGANISM: Artificial Sequence
<220> FEATURE:
<223> OTHER INFORMATION: Synthetic

<400> SEQUENCE: 144
ggagttcaga cgtgtgctct tccgatctcc aagtccatgg ctttcttt          48

<210> SEQ ID NO 145
<211> LENGTH: 52
<212> TYPE: DNA
<213> ORGANISM: Artificial Sequence
<220> FEATURE:
<223> OTHER INFORMATION: Synthetic

<400> SEQUENCE: 145
cactctttcc ctacacgacg ctcttccgat cttgagtttg gaggagcatt tg          52

<210> SEQ ID NO 146
<211> LENGTH: 48
<212> TYPE: DNA
<213> ORGANISM: Artificial Sequence
<220> FEATURE:
<223> OTHER INFORMATION: Synthetic

<400> SEQUENCE: 146
ggagttcaga cgtgtgctct tccgatctca atgagaaatg cctgtgga          48

<210> SEQ ID NO 147
<211> LENGTH: 52
<212> TYPE: DNA
<213> ORGANISM: Artificial Sequence
<220> FEATURE:
<223> OTHER INFORMATION: Synthetic

<400> SEQUENCE: 147
cactctttcc ctacacgacg ctcttccgat ctcagtgggg aagactgat gt          52

<210> SEQ ID NO 148
<211> LENGTH: 48
<212> TYPE: DNA
<213> ORGANISM: Artificial Sequence
<220> FEATURE:
<223> OTHER INFORMATION: Synthetic

<400> SEQUENCE: 148
ggagttcaga cgtgtgctct tccgatctcc gcaaacctga gatagcat          48

<210> SEQ ID NO 149
<211> LENGTH: 52
<212> TYPE: DNA
<213> ORGANISM: Artificial Sequence
<220> FEATURE:
<223> OTHER INFORMATION: Synthetic

<400> SEQUENCE: 149
cactctttcc ctacacgacg ctcttccgat ctagtcagga cttccccacc tt        52

<210> SEQ ID NO 150
<211> LENGTH: 48
<212> TYPE: DNA
<213> ORGANISM: Artificial Sequence
<220> FEATURE:
<223> OTHER INFORMATION: Synthetic

<400> SEQUENCE: 150
ggagttcaga cgtgtgctct tccgatcttg gttctacatc ccgaggag        48

<210> SEQ ID NO 151
<211> LENGTH: 52
<212> TYPE: DNA
<213> ORGANISM: Artificial Sequence
<220> FEATURE:
<223> OTHER INFORMATION: Synthetic

<400> SEQUENCE: 151
cactctttcc ctacacgacg ctcttccgat ctgactccct ctggttctgt gg        52

<210> SEQ ID NO 152
<211> LENGTH: 48
<212> TYPE: DNA
<213> ORGANISM: Artificial Sequence
<220> FEATURE:
<223> OTHER INFORMATION: Synthetic

<400> SEQUENCE: 152
ggagttcaga cgtgtgctct tccgatctga tgccaaaaag aggctgac        48

<210> SEQ ID NO 153
<211> LENGTH: 50
<212> TYPE: DNA
<213> ORGANISM: Artificial Sequence
<220> FEATURE:
<223> OTHER INFORMATION: Synthetic

<400> SEQUENCE: 153
cactctttcc ctacacgacg ctcttccgat ctagaagtcc agctccgcac        50

<210> SEQ ID NO 154
<211> LENGTH: 48
<212> TYPE: DNA
<213> ORGANISM: Artificial Sequence
<220> FEATURE:
<223> OTHER INFORMATION: Synthetic

<400> SEQUENCE: 154
ggagttcaga cgtgtgctct tccgatctaa aaagacggga aaggagga        48

<210> SEQ ID NO 155
<211> LENGTH: 52
<212> TYPE: DNA
<213> ORGANISM: Artificial Sequence
<220> FEATURE:
<223> OTHER INFORMATION: Synthetic

<400> SEQUENCE: 155
cactctttcc ctacacgacg ctcttccgat ctgacagcac cttctaccgc tc        52

<210> SEQ ID NO 156

```
<211> LENGTH: 48
<212> TYPE: DNA
<213> ORGANISM: Artificial Sequence
<220> FEATURE:
<223> OTHER INFORMATION: Synthetic

<400> SEQUENCE: 156
ggagttcaga cgtgtgctct tccgatctgg taagcagaca gccacaca        48

<210> SEQ ID NO 157
<211> LENGTH: 52
<212> TYPE: DNA
<213> ORGANISM: Artificial Sequence
<220> FEATURE:
<223> OTHER INFORMATION: Synthetic

<400> SEQUENCE: 157
cactctttcc ctacacgacg ctcttccgat ctgctgacag agcccaactc tt     52

<210> SEQ ID NO 158
<211> LENGTH: 48
<212> TYPE: DNA
<213> ORGANISM: Artificial Sequence
<220> FEATURE:
<223> OTHER INFORMATION: Synthetic

<400> SEQUENCE: 158
ggagttcaga cgtgtgctct tccgatctgc cttccaccgt tcattcta        48

<210> SEQ ID NO 159
<211> LENGTH: 51
<212> TYPE: DNA
<213> ORGANISM: Artificial Sequence
<220> FEATURE:
<223> OTHER INFORMATION: Synthetic

<400> SEQUENCE: 159
cactctttcc ctacacgacg ctcttccgat ctctggtgcc actctggaaa g     51

<210> SEQ ID NO 160
<211> LENGTH: 48
<212> TYPE: DNA
<213> ORGANISM: Artificial Sequence
<220> FEATURE:
<223> OTHER INFORMATION: Synthetic

<400> SEQUENCE: 160
ggagttcaga cgtgtgctct tccgatctgt tctctgccgt aggtgtcc        48

<210> SEQ ID NO 161
<211> LENGTH: 52
<212> TYPE: DNA
<213> ORGANISM: Artificial Sequence
<220> FEATURE:
<223> OTHER INFORMATION: Synthetic

<400> SEQUENCE: 161
cactctttcc ctacacgacg ctcttccgat ctcctcacag cagggtcttc tc     52

<210> SEQ ID NO 162
<211> LENGTH: 48
<212> TYPE: DNA
<213> ORGANISM: Artificial Sequence
<220> FEATURE:
<223> OTHER INFORMATION: Synthetic

<400> SEQUENCE: 162
```

```
ggagttcaga cgtgtgctct tccgatctcc tggtgtcagg aaaatgct                    48
```

<210> SEQ ID NO 163
<211> LENGTH: 52
<212> TYPE: DNA
<213> ORGANISM: Artificial Sequence
<220> FEATURE:
<223> OTHER INFORMATION: Synthetic

<400> SEQUENCE: 163

```
cactctttcc ctacacgacg ctcttccgat ctcctgcttc tcctcagctt ca              52
```

<210> SEQ ID NO 164
<211> LENGTH: 46
<212> TYPE: DNA
<213> ORGANISM: Artificial Sequence
<220> FEATURE:
<223> OTHER INFORMATION: Synthetic

<400> SEQUENCE: 164

```
ggagttcaga cgtgtgctct tccgatctga gctgctcacc acgacg                     46
```

<210> SEQ ID NO 165
<211> LENGTH: 52
<212> TYPE: DNA
<213> ORGANISM: Artificial Sequence
<220> FEATURE:
<223> OTHER INFORMATION: Synthetic

<400> SEQUENCE: 165

```
cactctttcc ctacacgacg ctcttccgat ctacactcac cacttccgtg tg              52
```

<210> SEQ ID NO 166
<211> LENGTH: 47
<212> TYPE: DNA
<213> ORGANISM: Artificial Sequence
<220> FEATURE:
<223> OTHER INFORMATION: Synthetic

<400> SEQUENCE: 166

```
ggagttcaga cgtgtgctct tccgatctgc ggagtatcct ggagctg                    47
```

<210> SEQ ID NO 167
<211> LENGTH: 51
<212> TYPE: DNA
<213> ORGANISM: Artificial Sequence
<220> FEATURE:
<223> OTHER INFORMATION: Synthetic

<400> SEQUENCE: 167

```
cactctttcc ctacacgacg ctcttccgat ctatcaccct ggacaacctc c               51
```

<210> SEQ ID NO 168
<211> LENGTH: 48
<212> TYPE: DNA
<213> ORGANISM: Artificial Sequence
<220> FEATURE:
<223> OTHER INFORMATION: Synthetic

<400> SEQUENCE: 168

```
ggagttcaga cgtgtgctct tccgatctaa gatgtgtgac ccagaggg                   48
```

<210> SEQ ID NO 169
<211> LENGTH: 52
<212> TYPE: DNA

<213> ORGANISM: Artificial Sequence
<220> FEATURE:
<223> OTHER INFORMATION: Synthetic

<400> SEQUENCE: 169
cactctttcc ctacacgacg ctcttccgat ctgcttagct aggccgaagt ca    52

<210> SEQ ID NO 170
<211> LENGTH: 48
<212> TYPE: DNA
<213> ORGANISM: Artificial Sequence
<220> FEATURE:
<223> OTHER INFORMATION: Synthetic

<400> SEQUENCE: 170
ggagttcaga cgtgtgctct ccgatctgc tcggggtag ggttatag    48

<210> SEQ ID NO 171
<211> LENGTH: 52
<212> TYPE: DNA
<213> ORGANISM: Artificial Sequence
<220> FEATURE:
<223> OTHER INFORMATION: Synthetic

<400> SEQUENCE: 171
cactctttcc ctacacgacg ctcttccgat ctgcacctga agagatgagg ct    52

<210> SEQ ID NO 172
<211> LENGTH: 48
<212> TYPE: DNA
<213> ORGANISM: Artificial Sequence
<220> FEATURE:
<223> OTHER INFORMATION: Synthetic

<400> SEQUENCE: 172
ggagttcaga cgtgtgctct ccgatctgg agattggggt gggtctat    48

<210> SEQ ID NO 173
<211> LENGTH: 52
<212> TYPE: DNA
<213> ORGANISM: Artificial Sequence
<220> FEATURE:
<223> OTHER INFORMATION: Synthetic

<400> SEQUENCE: 173
cactctttcc ctacacgacg ctcttccgat cttttcttca gaagctccac cc    52

<210> SEQ ID NO 174
<211> LENGTH: 48
<212> TYPE: DNA
<213> ORGANISM: Artificial Sequence
<220> FEATURE:
<223> OTHER INFORMATION: Synthetic

<400> SEQUENCE: 174
ggagttcaga cgtgtgctct ccgatcttc agcccttgct ctttgaat    48

<210> SEQ ID NO 175
<211> LENGTH: 50
<212> TYPE: DNA
<213> ORGANISM: Artificial Sequence
<220> FEATURE:
<223> OTHER INFORMATION: Synthetic

<400> SEQUENCE: 175
cactctttcc ctacacgacg ctcttccgat ctcccgagga ctctgtccct    50

<210> SEQ ID NO 176
<211> LENGTH: 48
<212> TYPE: DNA
<213> ORGANISM: Artificial Sequence
<220> FEATURE:
<223> OTHER INFORMATION: Synthetic

<400> SEQUENCE: 176
ggagttcaga cgtgtgctct tccgatctct tttctcctgc cgggtagt           48

<210> SEQ ID NO 177
<211> LENGTH: 52
<212> TYPE: DNA
<213> ORGANISM: Artificial Sequence
<220> FEATURE:
<223> OTHER INFORMATION: Synthetic

<400> SEQUENCE: 177
cactctttcc ctacacgacg ctcttccgat cttatctggg gatttgatgc ct       52

<210> SEQ ID NO 178
<211> LENGTH: 49
<212> TYPE: DNA
<213> ORGANISM: Artificial Sequence
<220> FEATURE:
<223> OTHER INFORMATION: Synthetic

<400> SEQUENCE: 178
ggagttcaga cgtgtgctct tccgatctga gtggttatct gccattgga           49

<210> SEQ ID NO 179
<211> LENGTH: 52
<212> TYPE: DNA
<213> ORGANISM: Artificial Sequence
<220> FEATURE:
<223> OTHER INFORMATION: Synthetic

<400> SEQUENCE: 179
cactctttcc ctacacgacg ctcttccgat ctgaaaggtc ctgccaagga at       52

<210> SEQ ID NO 180
<211> LENGTH: 48
<212> TYPE: DNA
<213> ORGANISM: Artificial Sequence
<220> FEATURE:
<223> OTHER INFORMATION: Synthetic

<400> SEQUENCE: 180
ggagttcaga cgtgtgctct tccgatctgt gtttcctggg ggaaagtt           48

<210> SEQ ID NO 181
<211> LENGTH: 52
<212> TYPE: DNA
<213> ORGANISM: Artificial Sequence
<220> FEATURE:
<223> OTHER INFORMATION: Synthetic

<400> SEQUENCE: 181
cactctttcc ctacacgacg ctcttccgat cttttttgttt tgggtgccat tt      52

<210> SEQ ID NO 182
<211> LENGTH: 48
<212> TYPE: DNA
<213> ORGANISM: Artificial Sequence
<220> FEATURE:

<223> OTHER INFORMATION: Synthetic

<400> SEQUENCE: 182
ggagttcaga cgtgtgctct tccgatcttt tccctgacct tgaaccag                48

<210> SEQ ID NO 183
<211> LENGTH: 52
<212> TYPE: DNA
<213> ORGANISM: Artificial Sequence
<220> FEATURE:
<223> OTHER INFORMATION: Synthetic

<400> SEQUENCE: 183
cactctttcc ctacacgacg ctcttccgat ctaatttcct ttcgccacac tg          52

<210> SEQ ID NO 184
<211> LENGTH: 48
<212> TYPE: DNA
<213> ORGANISM: Artificial Sequence
<220> FEATURE:
<223> OTHER INFORMATION: Synthetic

<400> SEQUENCE: 184
ggagttcaga cgtgtgctct tccgatctgg tcacaaatct gtcccctc                48

<210> SEQ ID NO 185
<211> LENGTH: 48
<212> TYPE: DNA
<213> ORGANISM: Artificial Sequence
<220> FEATURE:
<223> OTHER INFORMATION: Synthetic

<400> SEQUENCE: 185
ggagttcaga cgtgtgctct tccgatctac aggagattgg tacagcgg                48

<210> SEQ ID NO 186
<211> LENGTH: 52
<212> TYPE: DNA
<213> ORGANISM: Artificial Sequence
<220> FEATURE:
<223> OTHER INFORMATION: Synthetic

<400> SEQUENCE: 186
cactctttcc ctacacgacg ctcttccgat ctcttctgaa actaggcggc ag          52

<210> SEQ ID NO 187
<211> LENGTH: 47
<212> TYPE: DNA
<213> ORGANISM: Artificial Sequence
<220> FEATURE:
<223> OTHER INFORMATION: Synthetic

<400> SEQUENCE: 187
ggagttcaga cgtgtgctct tccgatctga ctgggactgc ggaagac                 47

<210> SEQ ID NO 188
<211> LENGTH: 52
<212> TYPE: DNA
<213> ORGANISM: Artificial Sequence
<220> FEATURE:
<223> OTHER INFORMATION: Synthetic

<400> SEQUENCE: 188
cactctttcc ctacacgacg ctcttccgat ctccctggcc taacaattca ga          52

```
<210> SEQ ID NO 189
<211> LENGTH: 48
<212> TYPE: DNA
<213> ORGANISM: Artificial Sequence
<220> FEATURE:
<223> OTHER INFORMATION: Synthetic

<400> SEQUENCE: 189
ggagttcaga cgtgtgctct tccgatctga ccccaactgg aatgtcac          48

<210> SEQ ID NO 190
<211> LENGTH: 52
<212> TYPE: DNA
<213> ORGANISM: Artificial Sequence
<220> FEATURE:
<223> OTHER INFORMATION: Synthetic

<400> SEQUENCE: 190
cactctttcc ctacacgacg ctcttccgat cttttcaggc ctagcaggaa ac       52

<210> SEQ ID NO 191
<211> LENGTH: 48
<212> TYPE: DNA
<213> ORGANISM: Artificial Sequence
<220> FEATURE:
<223> OTHER INFORMATION: Synthetic

<400> SEQUENCE: 191
ggagttcaga cgtgtgctct tccgatctcc cattctttgt cttgaccg             48

<210> SEQ ID NO 192
<211> LENGTH: 52
<212> TYPE: DNA
<213> ORGANISM: Artificial Sequence
<220> FEATURE:
<223> OTHER INFORMATION: Synthetic

<400> SEQUENCE: 192
cactctttcc ctacacgacg ctcttccgat ctgaggtctg gttgtcctgc tc        52

<210> SEQ ID NO 193
<211> LENGTH: 48
<212> TYPE: DNA
<213> ORGANISM: Artificial Sequence
<220> FEATURE:
<223> OTHER INFORMATION: Synthetic

<400> SEQUENCE: 193
ggagttcaga cgtgtgctct tccgatctca atgtcctcca gcaaatca             48

<210> SEQ ID NO 194
<211> LENGTH: 52
<212> TYPE: DNA
<213> ORGANISM: Artificial Sequence
<220> FEATURE:
<223> OTHER INFORMATION: Synthetic

<400> SEQUENCE: 194
cactctttcc ctacacgacg ctcttccgat cttgtgtact ctccactgcc ca        52

<210> SEQ ID NO 195
<211> LENGTH: 48
<212> TYPE: DNA
<213> ORGANISM: Artificial Sequence
<220> FEATURE:
<223> OTHER INFORMATION: Synthetic
```

<400> SEQUENCE: 195
ggagttcaga cgtgtgctct tccgatcttc agaacactcc cttttgcc    48

<210> SEQ ID NO 196
<211> LENGTH: 54
<212> TYPE: DNA
<213> ORGANISM: Artificial Sequence
<220> FEATURE:
<223> OTHER INFORMATION: Synthetic

<400> SEQUENCE: 196
cactctttcc ctacacgacg ctcttccgat ctgcaatgag aattttaatc accc    54

<210> SEQ ID NO 197
<211> LENGTH: 48
<212> TYPE: DNA
<213> ORGANISM: Artificial Sequence
<220> FEATURE:
<223> OTHER INFORMATION: Synthetic

<400> SEQUENCE: 197
ggagttcaga cgtgtgctct tccgatcttg cctaacaatg gacaccaa    48

<210> SEQ ID NO 198
<211> LENGTH: 52
<212> TYPE: DNA
<213> ORGANISM: Artificial Sequence
<220> FEATURE:
<223> OTHER INFORMATION: Synthetic

<400> SEQUENCE: 198
cactctttcc ctacacgacg ctcttccgat ctcagcaaac tcagcaagca aa    52

<210> SEQ ID NO 199
<211> LENGTH: 48
<212> TYPE: DNA
<213> ORGANISM: Artificial Sequence
<220> FEATURE:
<223> OTHER INFORMATION: Synthetic

<400> SEQUENCE: 199
ggagttcaga cgtgtgctct tccgatctgg aggggagaag agaggaaa    48

<210> SEQ ID NO 200
<211> LENGTH: 52
<212> TYPE: DNA
<213> ORGANISM: Artificial Sequence
<220> FEATURE:
<223> OTHER INFORMATION: Synthetic

<400> SEQUENCE: 200
cactctttcc ctacacgacg ctcttccgat ctcagtcctc acccttgtcc tc    52

<210> SEQ ID NO 201
<211> LENGTH: 48
<212> TYPE: DNA
<213> ORGANISM: Artificial Sequence
<220> FEATURE:
<223> OTHER INFORMATION: Synthetic

<400> SEQUENCE: 201
ggagttcaga cgtgtgctct tccgatctta agagcccacc acagatcc    48

<210> SEQ ID NO 202
<211> LENGTH: 52

```
<212> TYPE: DNA
<213> ORGANISM: Artificial Sequence
<220> FEATURE:
<223> OTHER INFORMATION: Synthetic

<400> SEQUENCE: 202
cactctttcc ctacacgacg ctcttccgat cttcctgcaa agaggaccct ta            52

<210> SEQ ID NO 203
<211> LENGTH: 48
<212> TYPE: DNA
<213> ORGANISM: Artificial Sequence
<220> FEATURE:
<223> OTHER INFORMATION: Synthetic

<400> SEQUENCE: 203
ggagttcaga cgtgtgctct tccgatctgc gtccttctga aaagcaaa                 48

<210> SEQ ID NO 204
<211> LENGTH: 48
<212> TYPE: DNA
<213> ORGANISM: Artificial Sequence
<220> FEATURE:
<223> OTHER INFORMATION: Synthetic

<400> SEQUENCE: 204
ggagttcaga cgtgtgctct tccgatctag ggttgagttt tgcattgg                 48

<210> SEQ ID NO 205
<211> LENGTH: 52
<212> TYPE: DNA
<213> ORGANISM: Artificial Sequence
<220> FEATURE:
<223> OTHER INFORMATION: Synthetic

<400> SEQUENCE: 205
cactctttcc ctacacgacg ctcttccgat cttagaagct ggttggggag tg            52

<210> SEQ ID NO 206
<211> LENGTH: 48
<212> TYPE: DNA
<213> ORGANISM: Artificial Sequence
<220> FEATURE:
<223> OTHER INFORMATION: Synthetic

<400> SEQUENCE: 206
ggagttcaga cgtgtgctct tccgatctct agctggcgaa caacacaa                 48

<210> SEQ ID NO 207
<211> LENGTH: 52
<212> TYPE: DNA
<213> ORGANISM: Artificial Sequence
<220> FEATURE:
<223> OTHER INFORMATION: Synthetic

<400> SEQUENCE: 207
cactctttcc ctacacgacg ctcttccgat ctggataggt aggcatggca ag            52

<210> SEQ ID NO 208
<211> LENGTH: 48
<212> TYPE: DNA
<213> ORGANISM: Artificial Sequence
<220> FEATURE:
<223> OTHER INFORMATION: Synthetic

<400> SEQUENCE: 208
```
ggagttcaga cgtgtgctct tccgatctta ccatggctgg ctctcaat                48

<210> SEQ ID NO 209
<211> LENGTH: 52
<212> TYPE: DNA
<213> ORGANISM: Artificial Sequence
<220> FEATURE:
<223> OTHER INFORMATION: Synthetic

<400> SEQUENCE: 209
cactctttcc ctacacgacg ctcttccgat ctctccttgg agtccagtgc at           52

<210> SEQ ID NO 210
<211> LENGTH: 48
<212> TYPE: DNA
<213> ORGANISM: Artificial Sequence
<220> FEATURE:
<223> OTHER INFORMATION: Synthetic

<400> SEQUENCE: 210
ggagttcaga cgtgtgctct tccgatctac tcacacctca tcttgccc                48

<210> SEQ ID NO 211
<211> LENGTH: 52
<212> TYPE: DNA
<213> ORGANISM: Artificial Sequence
<220> FEATURE:
<223> OTHER INFORMATION: Synthetic

<400> SEQUENCE: 211
cactctttcc ctacacgacg ctcttccgat ctccagatgg cacattgtca ga           52

<210> SEQ ID NO 212
<211> LENGTH: 47
<212> TYPE: DNA
<213> ORGANISM: Artificial Sequence
<220> FEATURE:
<223> OTHER INFORMATION: Synthetic

<400> SEQUENCE: 212
ggagttcaga cgtgtgctct tccgatctcc tagtgactgc cgtctgc                 47

<210> SEQ ID NO 213
<211> LENGTH: 52
<212> TYPE: DNA
<213> ORGANISM: Artificial Sequence
<220> FEATURE:
<223> OTHER INFORMATION: Synthetic

<400> SEQUENCE: 213
cactctttcc ctacacgacg ctcttccgat ctgaaaactt gacccctgtc ca           52

<210> SEQ ID NO 214
<211> LENGTH: 47
<212> TYPE: DNA
<213> ORGANISM: Artificial Sequence
<220> FEATURE:
<223> OTHER INFORMATION: Synthetic

<400> SEQUENCE: 214
ggagttcaga cgtgtgctct tccgatctct cgtggacggc tacttcc                 47

<210> SEQ ID NO 215
<211> LENGTH: 52
<212> TYPE: DNA
<213> ORGANISM: Artificial Sequence

```
<220> FEATURE:
<223> OTHER INFORMATION: Synthetic

<400> SEQUENCE: 215
cactctttcc ctacacgacg ctcttccgat ctaccgagga gctttccaga at          52

<210> SEQ ID NO 216
<211> LENGTH: 47
<212> TYPE: DNA
<213> ORGANISM: Artificial Sequence
<220> FEATURE:
<223> OTHER INFORMATION: Synthetic

<400> SEQUENCE: 216
ggagttcaga cgtgtgctct ccgatcttg gggagaacca tcctcac                 47

<210> SEQ ID NO 217
<211> LENGTH: 52
<212> TYPE: DNA
<213> ORGANISM: Artificial Sequence
<220> FEATURE:
<223> OTHER INFORMATION: Synthetic

<400> SEQUENCE: 217
cactctttcc ctacacgacg ctcttccgat ctgtacagac gcctcacctt cc          52

<210> SEQ ID NO 218
<211> LENGTH: 50
<212> TYPE: DNA
<213> ORGANISM: Artificial Sequence
<220> FEATURE:
<223> OTHER INFORMATION: Synthetic

<400> SEQUENCE: 218
ggagttcaga cgtgtgctct ccgatctgc tgcacattga ataagtggtt              50

<210> SEQ ID NO 219
<211> LENGTH: 54
<212> TYPE: DNA
<213> ORGANISM: Artificial Sequence
<220> FEATURE:
<223> OTHER INFORMATION: Synthetic

<400> SEQUENCE: 219
cactctttcc ctacacgacg ctcttccgat ctaacatctt ccttgatggg aaaa        54

<210> SEQ ID NO 220
<211> LENGTH: 49
<212> TYPE: DNA
<213> ORGANISM: Artificial Sequence
<220> FEATURE:
<223> OTHER INFORMATION: Synthetic

<400> SEQUENCE: 220
ggagttcaga cgtgtgctct ccgatctca atttcctcct ctgttaccc                49

<210> SEQ ID NO 221
<211> LENGTH: 52
<212> TYPE: DNA
<213> ORGANISM: Artificial Sequence
<220> FEATURE:
<223> OTHER INFORMATION: Synthetic

<400> SEQUENCE: 221
cactctttcc ctacacgacg ctcttccgat cttcatgtca ctttggcctg aa          52
```

<210> SEQ ID NO 222
<211> LENGTH: 48
<212> TYPE: DNA
<213> ORGANISM: Artificial Sequence
<220> FEATURE:
<223> OTHER INFORMATION: Synthetic

<400> SEQUENCE: 222
ggagttcaga cgtgtgctct ccgatctct agggagagcc tcacagga         48

<210> SEQ ID NO 223
<211> LENGTH: 52
<212> TYPE: DNA
<213> ORGANISM: Artificial Sequence
<220> FEATURE:
<223> OTHER INFORMATION: Synthetic

<400> SEQUENCE: 223
cactctttcc ctacacgacg ctcttccgat ctctctcccc ctcttcttcc at         52

<210> SEQ ID NO 224
<211> LENGTH: 48
<212> TYPE: DNA
<213> ORGANISM: Artificial Sequence
<220> FEATURE:
<223> OTHER INFORMATION: Synthetic

<400> SEQUENCE: 224
ggagttcaga cgtgtgctct ccgatctgt tgtttctgtg ggtgcctt         48

<210> SEQ ID NO 225
<211> LENGTH: 52
<212> TYPE: DNA
<213> ORGANISM: Artificial Sequence
<220> FEATURE:
<223> OTHER INFORMATION: Synthetic

<400> SEQUENCE: 225
cactctttcc ctacacgacg ctcttccgat ctaagcatga gtgcctcttt cc         52

<210> SEQ ID NO 226
<211> LENGTH: 48
<212> TYPE: DNA
<213> ORGANISM: Artificial Sequence
<220> FEATURE:
<223> OTHER INFORMATION: Synthetic

<400> SEQUENCE: 226
ggagttcaga cgtgtgctct ccgatcttc ggttaatccc ttcccttc         48

<210> SEQ ID NO 227
<211> LENGTH: 52
<212> TYPE: DNA
<213> ORGANISM: Artificial Sequence
<220> FEATURE:
<223> OTHER INFORMATION: Synthetic

<400> SEQUENCE: 227
cactctttcc ctacacgacg ctcttccgat ctcatgcgtg atgacgtaga gg         52

<210> SEQ ID NO 228
<211> LENGTH: 48
<212> TYPE: DNA
<213> ORGANISM: Artificial Sequence
<220> FEATURE:
<223> OTHER INFORMATION: Synthetic

<400> SEQUENCE: 228
ggagttcaga cgtgtgctct tccgatcttc gcacacttaa ggctaacg                48

<210> SEQ ID NO 229
<211> LENGTH: 52
<212> TYPE: DNA
<213> ORGANISM: Artificial Sequence
<220> FEATURE:
<223> OTHER INFORMATION: Synthetic

<400> SEQUENCE: 229
cactctttcc ctacacgacg ctcttccgat ctaagacgcc attacaagtg cc            52

<210> SEQ ID NO 230
<211> LENGTH: 48
<212> TYPE: DNA
<213> ORGANISM: Artificial Sequence
<220> FEATURE:
<223> OTHER INFORMATION: Synthetic

<400> SEQUENCE: 230
ggagttcaga cgtgtgctct tccgatctgc gtgtctaaag gtccctca                48

<210> SEQ ID NO 231
<211> LENGTH: 52
<212> TYPE: DNA
<213> ORGANISM: Artificial Sequence
<220> FEATURE:
<223> OTHER INFORMATION: Synthetic

<400> SEQUENCE: 231
cactctttcc ctacacgacg ctcttccgat ctctcaccaa gtagctcagg gc            52

<210> SEQ ID NO 232
<211> LENGTH: 48
<212> TYPE: DNA
<213> ORGANISM: Artificial Sequence
<220> FEATURE:
<223> OTHER INFORMATION: Synthetic

<400> SEQUENCE: 232
ggagttcaga cgtgtgctct tccgatctgg actgtcgtaa ggggatga                48

<210> SEQ ID NO 233
<211> LENGTH: 51
<212> TYPE: DNA
<213> ORGANISM: Artificial Sequence
<220> FEATURE:
<223> OTHER INFORMATION: Synthetic

<400> SEQUENCE: 233
cactctttcc ctacacgacg ctcttccgat ctgaattctg aaagccgctg g             51

<210> SEQ ID NO 234
<211> LENGTH: 48
<212> TYPE: DNA
<213> ORGANISM: Artificial Sequence
<220> FEATURE:
<223> OTHER INFORMATION: Synthetic

<400> SEQUENCE: 234
ggagttcaga cgtgtgctct tccgatctcg ctccacttct ctactcgc                48

<210> SEQ ID NO 235

```
<211> LENGTH: 52
<212> TYPE: DNA
<213> ORGANISM: Artificial Sequence
<220> FEATURE:
<223> OTHER INFORMATION: Synthetic

<400> SEQUENCE: 235
cactctttcc ctacacgacg ctcttccgat ctccaactttt ggggactgaa ga          52

<210> SEQ ID NO 236
<211> LENGTH: 48
<212> TYPE: DNA
<213> ORGANISM: Artificial Sequence
<220> FEATURE:
<223> OTHER INFORMATION: Synthetic

<400> SEQUENCE: 236
ggagttcaga cgtgtgctct tccgatctgc ttccaggatt tggaatga               48

<210> SEQ ID NO 237
<211> LENGTH: 52
<212> TYPE: DNA
<213> ORGANISM: Artificial Sequence
<220> FEATURE:
<223> OTHER INFORMATION: Synthetic

<400> SEQUENCE: 237
cactctttcc ctacacgacg ctcttccgat ctgcttctcc ctgtctgagg tg          52

<210> SEQ ID NO 238
<211> LENGTH: 48
<212> TYPE: DNA
<213> ORGANISM: Artificial Sequence
<220> FEATURE:
<223> OTHER INFORMATION: Synthetic

<400> SEQUENCE: 238
ggagttcaga cgtgtgctct tccgatctgc aggtaggtga gttccagg               48

<210> SEQ ID NO 239
<211> LENGTH: 52
<212> TYPE: DNA
<213> ORGANISM: Artificial Sequence
<220> FEATURE:
<223> OTHER INFORMATION: Synthetic

<400> SEQUENCE: 239
cactctttcc ctacacgacg ctcttccgat cttcctacgt caagcagttc cc          52

<210> SEQ ID NO 240
<211> LENGTH: 48
<212> TYPE: DNA
<213> ORGANISM: Artificial Sequence
<220> FEATURE:
<223> OTHER INFORMATION: Synthetic

<400> SEQUENCE: 240
ggagttcaga cgtgtgctct tccgatctgg cattctctga agagtggg               48

<210> SEQ ID NO 241
<211> LENGTH: 50
<212> TYPE: DNA
<213> ORGANISM: Artificial Sequence
<220> FEATURE:
<223> OTHER INFORMATION: Synthetic

<400> SEQUENCE: 241
```

```
cactctttcc ctacacgacg ctcttccgat ctctgctcgg tctggggtct          50
```

<210> SEQ ID NO 242
<211> LENGTH: 46
<212> TYPE: DNA
<213> ORGANISM: Artificial Sequence
<220> FEATURE:
<223> OTHER INFORMATION: Synthetic

<400> SEQUENCE: 242

```
ggagttcaga cgtgtgctct tccgatctga agccggcgga aatacc              46
```

<210> SEQ ID NO 243
<211> LENGTH: 52
<212> TYPE: DNA
<213> ORGANISM: Artificial Sequence
<220> FEATURE:
<223> OTHER INFORMATION: Synthetic

<400> SEQUENCE: 243

```
cactctttcc ctacacgacg ctcttccgat ctagtctgta aactcgcgca gg       52
```

<210> SEQ ID NO 244
<211> LENGTH: 48
<212> TYPE: DNA
<213> ORGANISM: Artificial Sequence
<220> FEATURE:
<223> OTHER INFORMATION: Synthetic

<400> SEQUENCE: 244

```
ggagttcaga cgtgtgctct tccgatctca gatgagttgc agttccca            48
```

<210> SEQ ID NO 245
<211> LENGTH: 52
<212> TYPE: DNA
<213> ORGANISM: Artificial Sequence
<220> FEATURE:
<223> OTHER INFORMATION: Synthetic

<400> SEQUENCE: 245

```
cactctttcc ctacacgacg ctcttccgat cttcacaggg aacctttgct ct       52
```

<210> SEQ ID NO 246
<211> LENGTH: 48
<212> TYPE: DNA
<213> ORGANISM: Artificial Sequence
<220> FEATURE:
<223> OTHER INFORMATION: Synthetic

<400> SEQUENCE: 246

```
ggagttcaga cgtgtgctct tccgatctct taccaggcag tcgctctc            48
```

<210> SEQ ID NO 247
<211> LENGTH: 52
<212> TYPE: DNA
<213> ORGANISM: Artificial Sequence
<220> FEATURE:
<223> OTHER INFORMATION: Synthetic

<400> SEQUENCE: 247

```
cactctttcc ctacacgacg ctcttccgat ctacatgaaa ttcaaggccg aa       52
```

<210> SEQ ID NO 248
<211> LENGTH: 48
<212> TYPE: DNA

<213> ORGANISM: Artificial Sequence
<220> FEATURE:
<223> OTHER INFORMATION: Synthetic

<400> SEQUENCE: 248
ggagttcaga cgtgtgctct tccgatctac ctgtctgtga ggtggagg            48

<210> SEQ ID NO 249
<211> LENGTH: 52
<212> TYPE: DNA
<213> ORGANISM: Artificial Sequence
<220> FEATURE:
<223> OTHER INFORMATION: Synthetic

<400> SEQUENCE: 249
cactctttcc ctacacgacg ctcttccgat ctagggatgg agctgactgc ta        52

<210> SEQ ID NO 250
<211> LENGTH: 48
<212> TYPE: DNA
<213> ORGANISM: Artificial Sequence
<220> FEATURE:
<223> OTHER INFORMATION: Synthetic

<400> SEQUENCE: 250
ggagttcaga cgtgtgctct tccgatctac cccagacacc cagtatga           48

<210> SEQ ID NO 251
<211> LENGTH: 52
<212> TYPE: DNA
<213> ORGANISM: Artificial Sequence
<220> FEATURE:
<223> OTHER INFORMATION: Synthetic

<400> SEQUENCE: 251
cactctttcc ctacacgacg ctcttccgat cttttcctct cttctcccct cc        52

<210> SEQ ID NO 252
<211> LENGTH: 48
<212> TYPE: DNA
<213> ORGANISM: Artificial Sequence
<220> FEATURE:
<223> OTHER INFORMATION: Synthetic

<400> SEQUENCE: 252
ggagttcaga cgtgtgctct tccgatctct gccacaaagg ggttaaaa           48

<210> SEQ ID NO 253
<211> LENGTH: 52
<212> TYPE: DNA
<213> ORGANISM: Artificial Sequence
<220> FEATURE:
<223> OTHER INFORMATION: Synthetic

<400> SEQUENCE: 253
cactctttcc ctacacgacg ctcttccgat ctgtttctca tctgtgcccc tc        52

<210> SEQ ID NO 254
<211> LENGTH: 48
<212> TYPE: DNA
<213> ORGANISM: Artificial Sequence
<220> FEATURE:
<223> OTHER INFORMATION: Synthetic

<400> SEQUENCE: 254
ggagttcaga cgtgtgctct tccgatctgt tgcccaccct agtcattg            48

<210> SEQ ID NO 255
<211> LENGTH: 52
<212> TYPE: DNA
<213> ORGANISM: Artificial Sequence
<220> FEATURE:
<223> OTHER INFORMATION: Synthetic

<400> SEQUENCE: 255
cactctttcc ctacacgacg ctcttccgat ctaagaaagg caagaagcct gg    52

<210> SEQ ID NO 256
<211> LENGTH: 48
<212> TYPE: DNA
<213> ORGANISM: Artificial Sequence
<220> FEATURE:
<223> OTHER INFORMATION: Synthetic

<400> SEQUENCE: 256
ggagttcaga cgtgtgctct tccgatctgc tggcctgaga cattccta    48

<210> SEQ ID NO 257
<211> LENGTH: 52
<212> TYPE: DNA
<213> ORGANISM: Artificial Sequence
<220> FEATURE:
<223> OTHER INFORMATION: Synthetic

<400> SEQUENCE: 257
cactctttcc ctacacgacg ctcttccgat ctttggaact tgtttccag gc    52

<210> SEQ ID NO 258
<211> LENGTH: 48
<212> TYPE: DNA
<213> ORGANISM: Artificial Sequence
<220> FEATURE:
<223> OTHER INFORMATION: Synthetic

<400> SEQUENCE: 258
ggagttcaga cgtgtgctct tccgatctgg caacaagcag ttcaaaca    48

<210> SEQ ID NO 259
<211> LENGTH: 53
<212> TYPE: DNA
<213> ORGANISM: Artificial Sequence
<220> FEATURE:
<223> OTHER INFORMATION: Synthetic

<400> SEQUENCE: 259
cactctttcc ctacacgacg ctcttccgat cttggctctc acctgacagt ctt    53

<210> SEQ ID NO 260
<211> LENGTH: 48
<212> TYPE: DNA
<213> ORGANISM: Artificial Sequence
<220> FEATURE:
<223> OTHER INFORMATION: Synthetic

<400> SEQUENCE: 260
ggagttcaga cgtgtgctct tccgatctac aacagggctt gaagttgg    48

<210> SEQ ID NO 261
<211> LENGTH: 52
<212> TYPE: DNA
<213> ORGANISM: Artificial Sequence
<220> FEATURE:

<223> OTHER INFORMATION: Synthetic

<400> SEQUENCE: 261
cactctttcc ctacacgacg ctcttccgat ctagaggagc gatgcttctg ag    52

<210> SEQ ID NO 262
<211> LENGTH: 48
<212> TYPE: DNA
<213> ORGANISM: Artificial Sequence
<220> FEATURE:
<223> OTHER INFORMATION: Synthetic

<400> SEQUENCE: 262
ggagttcaga cgtgtgctct tccgatctac ttggtccatc catttcca    48

<210> SEQ ID NO 263
<211> LENGTH: 51
<212> TYPE: DNA
<213> ORGANISM: Artificial Sequence
<220> FEATURE:
<223> OTHER INFORMATION: Synthetic

<400> SEQUENCE: 263
cactctttcc ctacacgacg ctcttccgat ctcaggagct ccagtgacag c    51

<210> SEQ ID NO 264
<211> LENGTH: 48
<212> TYPE: DNA
<213> ORGANISM: Artificial Sequence
<220> FEATURE:
<223> OTHER INFORMATION: Synthetic

<400> SEQUENCE: 264
ggagttcaga cgtgtgctct tccgatctgg cacccagagt gagtgagt    48

<210> SEQ ID NO 265
<211> LENGTH: 52
<212> TYPE: DNA
<213> ORGANISM: Artificial Sequence
<220> FEATURE:
<223> OTHER INFORMATION: Synthetic

<400> SEQUENCE: 265
cactctttcc ctacacgacg ctcttccgat ctagagaccg agccctaagg ag    52

<210> SEQ ID NO 266
<211> LENGTH: 48
<212> TYPE: DNA
<213> ORGANISM: Artificial Sequence
<220> FEATURE:
<223> OTHER INFORMATION: Synthetic

<400> SEQUENCE: 266
ggagttcaga cgtgtgctct tccgatctct cacacactca cctcggtc    48

<210> SEQ ID NO 267
<211> LENGTH: 52
<212> TYPE: DNA
<213> ORGANISM: Artificial Sequence
<220> FEATURE:
<223> OTHER INFORMATION: Synthetic

<400> SEQUENCE: 267
cactctttcc ctacacgacg ctcttccgat ctagaaaatt cccacggcta cc    52

```
<210> SEQ ID NO 268
<211> LENGTH: 48
<212> TYPE: DNA
<213> ORGANISM: Artificial Sequence
<220> FEATURE:
<223> OTHER INFORMATION: Synthetic

<400> SEQUENCE: 268
ggagttcaga cgtgtgctct tccgatctga ctgctcagga ggaggaag                48

<210> SEQ ID NO 269
<211> LENGTH: 58
<212> TYPE: DNA
<213> ORGANISM: Artificial Sequence
<220> FEATURE:
<223> OTHER INFORMATION: Synthetic

<400> SEQUENCE: 269
taatacgact cactatagcc ttgtccttgg gcacgcatgt tttagagcta gaaatagc     58

<210> SEQ ID NO 270
<211> LENGTH: 58
<212> TYPE: DNA
<213> ORGANISM: Artificial Sequence
<220> FEATURE:
<223> OTHER INFORMATION: Synthetic

<400> SEQUENCE: 270
taatacgact cactatagcc ttgtccttgg gcacgcatgt tttagagcta gaaatagc     58

<210> SEQ ID NO 271
<211> LENGTH: 58
<212> TYPE: DNA
<213> ORGANISM: Artificial Sequence
<220> FEATURE:
<223> OTHER INFORMATION: Synthetic

<400> SEQUENCE: 271
taatacgact cactataggt gaccaaggag gaatttcagt tttagagcta gaaatagc     58

<210> SEQ ID NO 272
<211> LENGTH: 58
<212> TYPE: DNA
<213> ORGANISM: Artificial Sequence
<220> FEATURE:
<223> OTHER INFORMATION: Synthetic

<400> SEQUENCE: 272
taatacgact cactatagct ctcccaactg agctatttgt tttagagcta gaaatagc     58

<210> SEQ ID NO 273
<211> LENGTH: 58
<212> TYPE: DNA
<213> ORGANISM: Artificial Sequence
<220> FEATURE:
<223> OTHER INFORMATION: Synthetic

<400> SEQUENCE: 273
taatacgact cactataggc gttagactga agatctaagt tttagagcta gaaatagc     58

<210> SEQ ID NO 274
<211> LENGTH: 58
<212> TYPE: DNA
<213> ORGANISM: Artificial Sequence
<220> FEATURE:
<223> OTHER INFORMATION: Synthetic
```

<400> SEQUENCE: 274
taatacgact cactatagga tccacatctg ctggaagggt tttagagcta gaaatagc    58

<210> SEQ ID NO 275
<211> LENGTH: 58
<212> TYPE: DNA
<213> ORGANISM: Artificial Sequence
<220> FEATURE:
<223> OTHER INFORMATION: Synthetic

<400> SEQUENCE: 275
taatacgact cactataggc catgaattca tagggaatgt tttagagcta gaaatagc    58

<210> SEQ ID NO 276
<211> LENGTH: 58
<212> TYPE: DNA
<213> ORGANISM: Artificial Sequence
<220> FEATURE:
<223> OTHER INFORMATION: Synthetic

<400> SEQUENCE: 276
taatacgact cactataged agctgtggct acaacatagt tttagagcta gaaatagc    58

<210> SEQ ID NO 277
<211> LENGTH: 58
<212> TYPE: DNA
<213> ORGANISM: Artificial Sequence
<220> FEATURE:
<223> OTHER INFORMATION: Synthetic

<400> SEQUENCE: 277
taatacgact cactataged cccaccaaag cccatgtagt tttagagcta gaaatagc    58

<210> SEQ ID NO 278
<211> LENGTH: 58
<212> TYPE: DNA
<213> ORGANISM: Artificial Sequence
<220> FEATURE:
<223> OTHER INFORMATION: Synthetic

<400> SEQUENCE: 278
taatacgact cactatagtc cagctgtggc tacaacatgt tttagagcta gaaatagc    58

<210> SEQ ID NO 279
<211> LENGTH: 58
<212> TYPE: DNA
<213> ORGANISM: Artificial Sequence
<220> FEATURE:
<223> OTHER INFORMATION: Synthetic

<400> SEQUENCE: 279
taatacgact cactatagag cagaagcagg gtacccttgt tttagagcta gaaatagc    58

<210> SEQ ID NO 280
<211> LENGTH: 58
<212> TYPE: DNA
<213> ORGANISM: Artificial Sequence
<220> FEATURE:
<223> OTHER INFORMATION: Synthetic

<400> SEQUENCE: 280
taatacgact cactataggt acatttaacc cagtttaggt tttagagcta gaaatagc    58

<210> SEQ ID NO 281
<211> LENGTH: 58

<212> TYPE: DNA
<213> ORGANISM: Artificial Sequence
<220> FEATURE:
<223> OTHER INFORMATION: Synthetic

<400> SEQUENCE: 281
taatacgact cactatagct gaggaagctc ttcattgggt tttagagcta gaaatagc    58

<210> SEQ ID NO 282
<211> LENGTH: 58
<212> TYPE: DNA
<213> ORGANISM: Artificial Sequence
<220> FEATURE:
<223> OTHER INFORMATION: Synthetic

<400> SEQUENCE: 282
taatacgact cactatagaa gatgcaagca ttttgaacgt tttagagcta gaaatagc    58

<210> SEQ ID NO 283
<211> LENGTH: 58
<212> TYPE: DNA
<213> ORGANISM: Artificial Sequence
<220> FEATURE:
<223> OTHER INFORMATION: Synthetic

<400> SEQUENCE: 283
taatacgact cactatagcc atctcctgct cgaagtccgt tttagagcta gaaatagc    58

<210> SEQ ID NO 284
<211> LENGTH: 58
<212> TYPE: DNA
<213> ORGANISM: Artificial Sequence
<220> FEATURE:
<223> OTHER INFORMATION: Synthetic

<400> SEQUENCE: 284
taatacgact cactataggg cagtgcagat gaaaaactgt tttagagcta gaaatagc    58

<210> SEQ ID NO 285
<211> LENGTH: 58
<212> TYPE: DNA
<213> ORGANISM: Artificial Sequence
<220> FEATURE:
<223> OTHER INFORMATION: Synthetic

<400> SEQUENCE: 285
taatacgact cactatagcc attcagtggc ctgagcaggt tttagagcta gaaatagc    58

<210> SEQ ID NO 286
<211> LENGTH: 58
<212> TYPE: DNA
<213> ORGANISM: Artificial Sequence
<220> FEATURE:
<223> OTHER INFORMATION: Synthetic

<400> SEQUENCE: 286
taatacgact cactatagge tcaggccact gaatgggtgt tttagagcta gaaatagc    58

<210> SEQ ID NO 287
<211> LENGTH: 58
<212> TYPE: DNA
<213> ORGANISM: Artificial Sequence
<220> FEATURE:
<223> OTHER INFORMATION: Synthetic

<400> SEQUENCE: 287
taatacgact cactatagcc agcttagaaa aataatcagt tttagagcta gaaatagc    58

<210> SEQ ID NO 288
<211> LENGTH: 58
<212> TYPE: DNA
<213> ORGANISM: Artificial Sequence
<220> FEATURE:
<223> OTHER INFORMATION: Synthetic

<400> SEQUENCE: 288
taatacgact cactatagag ccaaagagaa aggtacctgt tttagagcta gaaatagc    58

<210> SEQ ID NO 289
<211> LENGTH: 58
<212> TYPE: DNA
<213> ORGANISM: Artificial Sequence
<220> FEATURE:
<223> OTHER INFORMATION: Synthetic

<400> SEQUENCE: 289
taatacgact cactatagtg acgaacacaa agggaaaggt tttagagcta gaaatagc    58

<210> SEQ ID NO 290
<211> LENGTH: 58
<212> TYPE: DNA
<213> ORGANISM: Artificial Sequence
<220> FEATURE:
<223> OTHER INFORMATION: Synthetic

<400> SEQUENCE: 290
taatacgact cactatagcc ctatgttgta gccacagcgt tttagagcta gaaatagc    58

<210> SEQ ID NO 291
<211> LENGTH: 58
<212> TYPE: DNA
<213> ORGANISM: Artificial Sequence
<220> FEATURE:
<223> OTHER INFORMATION: Synthetic

<400> SEQUENCE: 291
taatacgact cactatagaa agggtaccct gcttctgcgt tttagagcta gaaatagc    58

<210> SEQ ID NO 292
<211> LENGTH: 52
<212> TYPE: DNA
<213> ORGANISM: Artificial Sequence
<220> FEATURE:
<223> OTHER INFORMATION: Synthetic

<400> SEQUENCE: 292
cactctttcc ctacacgacg ctcttccgat ctacataggc atcgaagacg ct    52

<210> SEQ ID NO 293
<211> LENGTH: 52
<212> TYPE: DNA
<213> ORGANISM: Artificial Sequence
<220> FEATURE:
<223> OTHER INFORMATION: Synthetic

<400> SEQUENCE: 293
cactctttcc ctacacgacg ctcttccgat ctaggcattg aagacgctca ct    52

<210> SEQ ID NO 294
<211> LENGTH: 52
<212> TYPE: DNA
<213> ORGANISM: Artificial Sequence

```
<220> FEATURE:
<223> OTHER INFORMATION: Synthetic

<400> SEQUENCE: 294
cactctttcc ctacacgacg ctcttccgat ctcttgggaa gcacataggc at          52

<210> SEQ ID NO 295
<211> LENGTH: 52
<212> TYPE: DNA
<213> ORGANISM: Artificial Sequence
<220> FEATURE:
<223> OTHER INFORMATION: Synthetic

<400> SEQUENCE: 295
cactctttcc ctacacgacg ctcttccgat ctacaaagca cacatgcaac ct          52

<210> SEQ ID NO 296
<211> LENGTH: 52
<212> TYPE: DNA
<213> ORGANISM: Artificial Sequence
<220> FEATURE:
<223> OTHER INFORMATION: Synthetic

<400> SEQUENCE: 296
cactctttcc ctacacgacg ctcttccgat cttctgcaca ccttcagacc ag          52

<210> SEQ ID NO 297
<211> LENGTH: 52
<212> TYPE: DNA
<213> ORGANISM: Artificial Sequence
<220> FEATURE:
<223> OTHER INFORMATION: Synthetic

<400> SEQUENCE: 297
cactctttcc ctacacgacg ctcttccgat ctaatcggct tcgtctatgc ac          52

<210> SEQ ID NO 298
<211> LENGTH: 53
<212> TYPE: DNA
<213> ORGANISM: Artificial Sequence
<220> FEATURE:
<223> OTHER INFORMATION: Synthetic

<400> SEQUENCE: 298
cactctttcc ctacacgacg ctcttccgat ctttggaaat gacagatttg gga         53

<210> SEQ ID NO 299
<211> LENGTH: 52
<212> TYPE: DNA
<213> ORGANISM: Artificial Sequence
<220> FEATURE:
<223> OTHER INFORMATION: Synthetic

<400> SEQUENCE: 299
cactctttcc ctacacgacg ctcttccgat ctggaccaat cctgaacgaa ag          52

<210> SEQ ID NO 300
<211> LENGTH: 52
<212> TYPE: DNA
<213> ORGANISM: Artificial Sequence
<220> FEATURE:
<223> OTHER INFORMATION: Synthetic

<400> SEQUENCE: 300
cactctttcc ctacacgacg ctcttccgat ctggtatcgt ggacggagag tc          52
```

<210> SEQ ID NO 301
<211> LENGTH: 57
<212> TYPE: DNA
<213> ORGANISM: Artificial Sequence
<220> FEATURE:
<223> OTHER INFORMATION: Synthetic

<400> SEQUENCE: 301
cactctttcc ctacacgacg ctcttccgat ctcaaaataa gggttctatt aggcaaa    57

<210> SEQ ID NO 302
<211> LENGTH: 52
<212> TYPE: DNA
<213> ORGANISM: Artificial Sequence
<220> FEATURE:
<223> OTHER INFORMATION: Synthetic

<400> SEQUENCE: 302
cactctttcc ctacacgacg ctcttccgat ctggattggt gtgcaagtgt tg    52

<210> SEQ ID NO 303
<211> LENGTH: 52
<212> TYPE: DNA
<213> ORGANISM: Artificial Sequence
<220> FEATURE:
<223> OTHER INFORMATION: Synthetic

<400> SEQUENCE: 303
cactctttcc ctacacgacg ctcttccgat ctatatttgt attgccgtgg gc    52

<210> SEQ ID NO 304
<211> LENGTH: 52
<212> TYPE: DNA
<213> ORGANISM: Artificial Sequence
<220> FEATURE:
<223> OTHER INFORMATION: Synthetic

<400> SEQUENCE: 304
cactctttcc ctacacgacg ctcttccgat ctctaacgcc taaaacggaa gc    52

<210> SEQ ID NO 305
<211> LENGTH: 52
<212> TYPE: DNA
<213> ORGANISM: Artificial Sequence
<220> FEATURE:
<223> OTHER INFORMATION: Synthetic

<400> SEQUENCE: 305
cactctttcc ctacacgacg ctcttccgat ctaggcatta ggaaatacgc cc    52

<210> SEQ ID NO 306
<211> LENGTH: 52
<212> TYPE: DNA
<213> ORGANISM: Artificial Sequence
<220> FEATURE:
<223> OTHER INFORMATION: Synthetic

<400> SEQUENCE: 306
cactctttcc ctacacgacg ctcttccgat ctgctggagg tggagtgtgt ct    52

<210> SEQ ID NO 307
<211> LENGTH: 54
<212> TYPE: DNA
<213> ORGANISM: Artificial Sequence
<220> FEATURE:
<223> OTHER INFORMATION: Synthetic

<400> SEQUENCE: 307
cactctttcc ctacacgacg ctcttccgat cttcagatac aagcttctgg gaca                54

<210> SEQ ID NO 308
<211> LENGTH: 52
<212> TYPE: DNA
<213> ORGANISM: Artificial Sequence
<220> FEATURE:
<223> OTHER INFORMATION: Synthetic

<400> SEQUENCE: 308
cactctttcc ctacacgacg ctcttccgat ctaagagaaa ggtgcctggg tt                  52

<210> SEQ ID NO 309
<211> LENGTH: 52
<212> TYPE: DNA
<213> ORGANISM: Artificial Sequence
<220> FEATURE:
<223> OTHER INFORMATION: Synthetic

<400> SEQUENCE: 309
cactctttcc ctacacgacg ctcttccgat ctaagaagcc aaagagcaag gg                  52

<210> SEQ ID NO 310
<211> LENGTH: 50
<212> TYPE: DNA
<213> ORGANISM: Artificial Sequence
<220> FEATURE:
<223> OTHER INFORMATION: Synthetic

<400> SEQUENCE: 310
cactctttcc ctacacgacg ctcttccgat ctggttcaac tgaagcgcca                     50

<210> SEQ ID NO 311
<211> LENGTH: 51
<212> TYPE: DNA
<213> ORGANISM: Artificial Sequence
<220> FEATURE:
<223> OTHER INFORMATION: Synthetic

<400> SEQUENCE: 311
cactctttcc ctacacgacg ctcttccgat ctagaaagct acccgggttc a                   51

<210> SEQ ID NO 312
<211> LENGTH: 52
<212> TYPE: DNA
<213> ORGANISM: Artificial Sequence
<220> FEATURE:
<223> OTHER INFORMATION: Synthetic

<400> SEQUENCE: 312
cactctttcc ctacacgacg ctcttccgat ctttaatagc ctgctccacc ca                  52

<210> SEQ ID NO 313
<211> LENGTH: 52
<212> TYPE: DNA
<213> ORGANISM: Artificial Sequence
<220> FEATURE:
<223> OTHER INFORMATION: Synthetic

<400> SEQUENCE: 313
cactctttcc ctacacgacg ctcttccgat ctacctgggt tcaactaaag cg                  52

<210> SEQ ID NO 314

<210> SEQ ID NO 315
<211> LENGTH: 52
<212> TYPE: DNA
<213> ORGANISM: Artificial Sequence
<220> FEATURE:
<223> OTHER INFORMATION: Synthetic

<400> SEQUENCE: 314
cactctttcc ctacacgacg ctcttccgat ctactaaagc accagcctgc tc    52

<210> SEQ ID NO 315
<211> LENGTH: 52
<212> TYPE: DNA
<213> ORGANISM: Artificial Sequence
<220> FEATURE:
<223> OTHER INFORMATION: Synthetic

<400> SEQUENCE: 315
cactctttcc ctacacgacg ctcttccgat ctgttcaact gaagcaccag cc    52

<210> SEQ ID NO 316
<211> LENGTH: 52
<212> TYPE: DNA
<213> ORGANISM: Artificial Sequence
<220> FEATURE:
<223> OTHER INFORMATION: Synthetic

<400> SEQUENCE: 316
cactctttcc ctacacgacg ctcttccgat ctcaactaaa gcgccagcct ac    52

<210> SEQ ID NO 317
<211> LENGTH: 52
<212> TYPE: DNA
<213> ORGANISM: Artificial Sequence
<220> FEATURE:
<223> OTHER INFORMATION: Synthetic

<400> SEQUENCE: 317
cactctttcc ctacacgacg ctcttccgat ctgcactagc ttgctccact ca    52

<210> SEQ ID NO 318
<211> LENGTH: 52
<212> TYPE: DNA
<213> ORGANISM: Artificial Sequence
<220> FEATURE:
<223> OTHER INFORMATION: Synthetic

<400> SEQUENCE: 318
cactctttcc ctacacgacg ctcttccgat ctgccaatga gaaaggttcc tg    52

<210> SEQ ID NO 319
<211> LENGTH: 52
<212> TYPE: DNA
<213> ORGANISM: Artificial Sequence
<220> FEATURE:
<223> OTHER INFORMATION: Synthetic

<400> SEQUENCE: 319
cactctttcc ctacacgacg ctcttccgat ctggtacttg gtgtcagcca gc    52

<210> SEQ ID NO 320
<211> LENGTH: 51
<212> TYPE: DNA
<213> ORGANISM: Artificial Sequence
<220> FEATURE:
<223> OTHER INFORMATION: Synthetic

<400> SEQUENCE: 320
cactctttcc ctacacgacg ctcttccgat ctaactgaag ctccagcctg c    51

<210> SEQ ID NO 321
<211> LENGTH: 53
<212> TYPE: DNA
<213> ORGANISM: Artificial Sequence
<220> FEATURE:
<223> OTHER INFORMATION: Synthetic

<400> SEQUENCE: 321
cactctttcc ctacacgacg ctcttccgat ctgacaaacg tacctgggtt caa    53

<210> SEQ ID NO 322
<211> LENGTH: 52
<212> TYPE: DNA
<213> ORGANISM: Artificial Sequence
<220> FEATURE:
<223> OTHER INFORMATION: Synthetic

<400> SEQUENCE: 322
cactctttcc ctacacgacg ctcttccgat ctcgacctct ggaaggagac tg    52

<210> SEQ ID NO 323
<211> LENGTH: 52
<212> TYPE: DNA
<213> ORGANISM: Artificial Sequence
<220> FEATURE:
<223> OTHER INFORMATION: Synthetic

<400> SEQUENCE: 323
cactctttcc ctacacgacg ctcttccgat ctcgacctct ggaaggagac ag    52

<210> SEQ ID NO 324
<211> LENGTH: 53
<212> TYPE: DNA
<213> ORGANISM: Artificial Sequence
<220> FEATURE:
<223> OTHER INFORMATION: Synthetic

<400> SEQUENCE: 324
cactctttcc ctacacgacg ctcttccgat ctcttgtggc tacaacatag ggg    53

<210> SEQ ID NO 325
<211> LENGTH: 52
<212> TYPE: DNA
<213> ORGANISM: Artificial Sequence
<220> FEATURE:
<223> OTHER INFORMATION: Synthetic

<400> SEQUENCE: 325
cactctttcc ctacacgacg ctcttccgat ctaggaatcg atctcgtgaa gc    52

<210> SEQ ID NO 326
<211> LENGTH: 52
<212> TYPE: DNA
<213> ORGANISM: Artificial Sequence
<220> FEATURE:
<223> OTHER INFORMATION: Synthetic

<400> SEQUENCE: 326
cactctttcc ctacacgacg ctcttccgat cttgtgagag gatggtggtc aa    52

<210> SEQ ID NO 327
<211> LENGTH: 53
<212> TYPE: DNA

```
<213> ORGANISM: Artificial Sequence
<220> FEATURE:
<223> OTHER INFORMATION: Synthetic

<400> SEQUENCE: 327
cactctttcc ctacacgacg ctcttccgat ctgagtgtgc aattcacagc aaa        53

<210> SEQ ID NO 328
<211> LENGTH: 52
<212> TYPE: DNA
<213> ORGANISM: Artificial Sequence
<220> FEATURE:
<223> OTHER INFORMATION: Synthetic

<400> SEQUENCE: 328
cactctttcc ctacacgacg ctcttccgat ctgaatcgat ctcatgaagc cc         52

<210> SEQ ID NO 329
<211> LENGTH: 52
<212> TYPE: DNA
<213> ORGANISM: Artificial Sequence
<220> FEATURE:
<223> OTHER INFORMATION: Synthetic

<400> SEQUENCE: 329
cactctttcc ctacacgacg ctcttccgat ctaatcgatc tcgtgaagcc tg         52

<210> SEQ ID NO 330
<211> LENGTH: 53
<212> TYPE: DNA
<213> ORGANISM: Artificial Sequence
<220> FEATURE:
<223> OTHER INFORMATION: Synthetic

<400> SEQUENCE: 330
cactctttcc ctacacgacg ctcttccgat ctcaggaatc gatctcatga agg        53

<210> SEQ ID NO 331
<211> LENGTH: 52
<212> TYPE: DNA
<213> ORGANISM: Artificial Sequence
<220> FEATURE:
<223> OTHER INFORMATION: Synthetic

<400> SEQUENCE: 331
cactctttcc ctacacgacg ctcttccgat ctatcaatct tgtgtagccc gc         52

<210> SEQ ID NO 332
<211> LENGTH: 52
<212> TYPE: DNA
<213> ORGANISM: Artificial Sequence
<220> FEATURE:
<223> OTHER INFORMATION: Synthetic

<400> SEQUENCE: 332
cactctttcc ctacacgacg ctcttccgat cttaacccct gacctctgga ag         52

<210> SEQ ID NO 333
<211> LENGTH: 52
<212> TYPE: DNA
<213> ORGANISM: Artificial Sequence
<220> FEATURE:
<223> OTHER INFORMATION: Synthetic

<400> SEQUENCE: 333
cactctttcc ctacacgacg ctcttccgat ctctgactcc caacctctgg aa         52
```

<210> SEQ ID NO 334
<211> LENGTH: 53
<212> TYPE: DNA
<213> ORGANISM: Artificial Sequence
<220> FEATURE:
<223> OTHER INFORMATION: Synthetic

<400> SEQUENCE: 334
cactctttcc ctacacgacg ctcttccgat ctgacctaca gctacctgac ccc          53

<210> SEQ ID NO 335
<211> LENGTH: 52
<212> TYPE: DNA
<213> ORGANISM: Artificial Sequence
<220> FEATURE:
<223> OTHER INFORMATION: Synthetic

<400> SEQUENCE: 335
cactctttcc ctacacgacg ctcttccgat ctccctagac agcagcaact cc           52

<210> SEQ ID NO 336
<211> LENGTH: 52
<212> TYPE: DNA
<213> ORGANISM: Artificial Sequence
<220> FEATURE:
<223> OTHER INFORMATION: Synthetic

<400> SEQUENCE: 336
cactctttcc ctacacgacg ctcttccgat ctaaccatcc aaaagaccac ca           52

<210> SEQ ID NO 337
<211> LENGTH: 50
<212> TYPE: DNA
<213> ORGANISM: Artificial Sequence
<220> FEATURE:
<223> OTHER INFORMATION: Synthetic

<400> SEQUENCE: 337
cactctttcc ctacacgacg ctcttccgat ctccgccagg atagtggatg              50

<210> SEQ ID NO 338
<211> LENGTH: 54
<212> TYPE: DNA
<213> ORGANISM: Artificial Sequence
<220> FEATURE:
<223> OTHER INFORMATION: Synthetic

<400> SEQUENCE: 338
cactctttcc ctacacgacg ctcttccgat ctaagccctg aacttctctt tcaa         54

<210> SEQ ID NO 339
<211> LENGTH: 52
<212> TYPE: DNA
<213> ORGANISM: Artificial Sequence
<220> FEATURE:
<223> OTHER INFORMATION: Synthetic

<400> SEQUENCE: 339
cactctttcc ctacacgacg ctcttccgat cttttgtctt ttcagatccg cc           52

<210> SEQ ID NO 340
<211> LENGTH: 52
<212> TYPE: DNA
<213> ORGANISM: Artificial Sequence
<220> FEATURE:

<223> OTHER INFORMATION: Synthetic

<400> SEQUENCE: 340
cactctttcc ctacacgacg ctcttccgat ctccttcaaa acccagttcc aa        52

<210> SEQ ID NO 341
<211> LENGTH: 52
<212> TYPE: DNA
<213> ORGANISM: Artificial Sequence
<220> FEATURE:
<223> OTHER INFORMATION: Synthetic

<400> SEQUENCE: 341
cactctttcc ctacacgacg ctcttccgat ctgcaatgtc tgggtccta aa        52

<210> SEQ ID NO 342
<211> LENGTH: 52
<212> TYPE: DNA
<213> ORGANISM: Artificial Sequence
<220> FEATURE:
<223> OTHER INFORMATION: Synthetic

<400> SEQUENCE: 342
cactctttcc ctacacgacg ctcttccgat ctatgatgag atccgccatc ac        52

<210> SEQ ID NO 343
<211> LENGTH: 57
<212> TYPE: DNA
<213> ORGANISM: Artificial Sequence
<220> FEATURE:
<223> OTHER INFORMATION: Synthetic

<400> SEQUENCE: 343
cactctttcc ctacacgacg ctcttccgat ctttgtaagt ggtgattttc agtttga        57

<210> SEQ ID NO 344
<211> LENGTH: 52
<212> TYPE: DNA
<213> ORGANISM: Artificial Sequence
<220> FEATURE:
<223> OTHER INFORMATION: Synthetic

<400> SEQUENCE: 344
cactctttcc ctacacgacg ctcttccgat ctggtggaag ctatcaggac ca        52

<210> SEQ ID NO 345
<211> LENGTH: 52
<212> TYPE: DNA
<213> ORGANISM: Artificial Sequence
<220> FEATURE:
<223> OTHER INFORMATION: Synthetic

<400> SEQUENCE: 345
cactctttcc ctacacgacg ctcttccgat ctgtgacaaa aggtgacctg gg        52

<210> SEQ ID NO 346
<211> LENGTH: 57
<212> TYPE: DNA
<213> ORGANISM: Artificial Sequence
<220> FEATURE:
<223> OTHER INFORMATION: Synthetic

<400> SEQUENCE: 346
cactctttcc ctacacgacg ctcttccgat ctttcttcat ccctttactt tcttttt        57

```
<210> SEQ ID NO 347
<211> LENGTH: 52
<212> TYPE: DNA
<213> ORGANISM: Artificial Sequence
<220> FEATURE:
<223> OTHER INFORMATION: Synthetic

<400> SEQUENCE: 347
cactctttcc ctacacgacg ctcttccgat cttggctaag ctggtggaag tt          52

<210> SEQ ID NO 348
<211> LENGTH: 52
<212> TYPE: DNA
<213> ORGANISM: Artificial Sequence
<220> FEATURE:
<223> OTHER INFORMATION: Synthetic

<400> SEQUENCE: 348
cactctttcc ctacacgacg ctcttccgat cttagtgaca aacccaaagc cc          52

<210> SEQ ID NO 349
<211> LENGTH: 52
<212> TYPE: DNA
<213> ORGANISM: Artificial Sequence
<220> FEATURE:
<223> OTHER INFORMATION: Synthetic

<400> SEQUENCE: 349
cactctttcc ctacacgacg ctcttccgat ctcattaaca ctcagcccgt ga          52

<210> SEQ ID NO 350
<211> LENGTH: 52
<212> TYPE: DNA
<213> ORGANISM: Artificial Sequence
<220> FEATURE:
<223> OTHER INFORMATION: Synthetic

<400> SEQUENCE: 350
cactctttcc ctacacgacg ctcttccgat ctagcagaat ggctatgatg gg          52

<210> SEQ ID NO 351
<211> LENGTH: 53
<212> TYPE: DNA
<213> ORGANISM: Artificial Sequence
<220> FEATURE:
<223> OTHER INFORMATION: Synthetic

<400> SEQUENCE: 351
cactctttcc ctacacgacg ctcttccgat ctgggacaag ctaagccaat ttt         53

<210> SEQ ID NO 352
<211> LENGTH: 53
<212> TYPE: DNA
<213> ORGANISM: Artificial Sequence
<220> FEATURE:
<223> OTHER INFORMATION: Synthetic

<400> SEQUENCE: 352
cactctttcc ctacacgacg ctcttccgat ctttccggaa gaaggctaaa act         53

<210> SEQ ID NO 353
<211> LENGTH: 52
<212> TYPE: DNA
<213> ORGANISM: Artificial Sequence
<220> FEATURE:
<223> OTHER INFORMATION: Synthetic
```

```
<400> SEQUENCE: 353
cactctttcc ctacacgacg ctcttccgat cttgcatgca ttcacacaca at          52

<210> SEQ ID NO 354
<211> LENGTH: 55
<212> TYPE: DNA
<213> ORGANISM: Artificial Sequence
<220> FEATURE:
<223> OTHER INFORMATION: Synthetic

<400> SEQUENCE: 354
cactctttcc ctacacgacg ctcttccgat cttttgcaat gctttgcttt aaata       55

<210> SEQ ID NO 355
<211> LENGTH: 52
<212> TYPE: DNA
<213> ORGANISM: Artificial Sequence
<220> FEATURE:
<223> OTHER INFORMATION: Synthetic

<400> SEQUENCE: 355
cactctttcc ctacacgacg ctcttccgat ctaggtagtt tcatggatgc cg          52

<210> SEQ ID NO 356
<211> LENGTH: 52
<212> TYPE: DNA
<213> ORGANISM: Artificial Sequence
<220> FEATURE:
<223> OTHER INFORMATION: Synthetic

<400> SEQUENCE: 356
cactctttcc ctacacgacg ctcttccgat ctgctcacaa cacctaccca gg          52

<210> SEQ ID NO 357
<211> LENGTH: 52
<212> TYPE: DNA
<213> ORGANISM: Artificial Sequence
<220> FEATURE:
<223> OTHER INFORMATION: Synthetic

<400> SEQUENCE: 357
cactctttcc ctacacgacg ctcttccgat ctcaagaagg aaggctggaa ca          52

<210> SEQ ID NO 358
<211> LENGTH: 51
<212> TYPE: DNA
<213> ORGANISM: Artificial Sequence
<220> FEATURE:
<223> OTHER INFORMATION: Synthetic

<400> SEQUENCE: 358
cactctttcc ctacacgacg ctcttccgat ctatcctgga attcggtgag g           51

<210> SEQ ID NO 359
<211> LENGTH: 52
<212> TYPE: DNA
<213> ORGANISM: Artificial Sequence
<220> FEATURE:
<223> OTHER INFORMATION: Synthetic

<400> SEQUENCE: 359
cactctttcc ctacacgacg ctcttccgat ctcaccataa cagcactggt gg          52

<210> SEQ ID NO 360
<211> LENGTH: 52
```

<212> TYPE: DNA
<213> ORGANISM: Artificial Sequence
<220> FEATURE:
<223> OTHER INFORMATION: Synthetic

<400> SEQUENCE: 360
cactctttcc ctacacgacg ctcttccgat ctctggtcca tctatgggga ga        52

<210> SEQ ID NO 361
<211> LENGTH: 52
<212> TYPE: DNA
<213> ORGANISM: Artificial Sequence
<220> FEATURE:
<223> OTHER INFORMATION: Synthetic

<400> SEQUENCE: 361
cactctttcc ctacacgacg ctcttccgat ctcagtggtg gtaagcccat ct        52

<210> SEQ ID NO 362
<211> LENGTH: 52
<212> TYPE: DNA
<213> ORGANISM: Artificial Sequence
<220> FEATURE:
<223> OTHER INFORMATION: Synthetic

<400> SEQUENCE: 362
cactctttcc ctacacgacg ctcttccgat cttggggaga aattcgatga ag        52

<210> SEQ ID NO 363
<211> LENGTH: 52
<212> TYPE: DNA
<213> ORGANISM: Artificial Sequence
<220> FEATURE:
<223> OTHER INFORMATION: Synthetic

<400> SEQUENCE: 363
cactctttcc ctacacgacg ctcttccgat ctggtgactt cacacgccat aa        52

<210> SEQ ID NO 364
<211> LENGTH: 52
<212> TYPE: DNA
<213> ORGANISM: Artificial Sequence
<220> FEATURE:
<223> OTHER INFORMATION: Synthetic

<400> SEQUENCE: 364
cactctttcc ctacacgacg ctcttccgat cttccggagt ttatatgcca gg        52

<210> SEQ ID NO 365
<211> LENGTH: 54
<212> TYPE: DNA
<213> ORGANISM: Artificial Sequence
<220> FEATURE:
<223> OTHER INFORMATION: Synthetic

<400> SEQUENCE: 365
cactctttcc ctacacgacg ctcttccgat cttgctctac aaggtcacat gctt        54

<210> SEQ ID NO 366
<211> LENGTH: 53
<212> TYPE: DNA
<213> ORGANISM: Artificial Sequence
<220> FEATURE:
<223> OTHER INFORMATION: Synthetic

<400> SEQUENCE: 366

```
cactctttcc ctacacgacg ctcttccgat cttgccatgg acttaggatg act        53
```

<210> SEQ ID NO 367
<211> LENGTH: 52
<212> TYPE: DNA
<213> ORGANISM: Artificial Sequence
<220> FEATURE:
<223> OTHER INFORMATION: Synthetic

<400> SEQUENCE: 367

```
cactctttcc ctacacgacg ctcttccgat ctggccaaag gctgttcact aa         52
```

<210> SEQ ID NO 368
<211> LENGTH: 52
<212> TYPE: DNA
<213> ORGANISM: Artificial Sequence
<220> FEATURE:
<223> OTHER INFORMATION: Synthetic

<400> SEQUENCE: 368

```
cactctttcc ctacacgacg ctcttccgat ctttctgcac atgtatcccg tg         52
```

<210> SEQ ID NO 369
<211> LENGTH: 54
<212> TYPE: DNA
<213> ORGANISM: Artificial Sequence
<220> FEATURE:
<223> OTHER INFORMATION: Synthetic

<400> SEQUENCE: 369

```
cactctttcc ctacacgacg ctcttccgat cttccacgta atgatgactt ccaa       54
```

<210> SEQ ID NO 370
<211> LENGTH: 56
<212> TYPE: DNA
<213> ORGANISM: Artificial Sequence
<220> FEATURE:
<223> OTHER INFORMATION: Synthetic

<400> SEQUENCE: 370

```
cactctttcc ctacacgacg ctcttccgat cttgtaaagg tgctcaacat ttcttt     56
```

<210> SEQ ID NO 371
<211> LENGTH: 54
<212> TYPE: DNA
<213> ORGANISM: Artificial Sequence
<220> FEATURE:
<223> OTHER INFORMATION: Synthetic

<400> SEQUENCE: 371

```
cactctttcc ctacacgacg ctcttccgat ctaaacaatg ctaaatgatg gcaa       54
```

<210> SEQ ID NO 372
<211> LENGTH: 52
<212> TYPE: DNA
<213> ORGANISM: Artificial Sequence
<220> FEATURE:
<223> OTHER INFORMATION: Synthetic

<400> SEQUENCE: 372

```
cactctttcc ctacacgacg ctcttccgat ctccatcaga cttgtgtcca cg         52
```

<210> SEQ ID NO 373
<211> LENGTH: 52
<212> TYPE: DNA
<213> ORGANISM: Artificial Sequence -continued
<220> FEATURE:
<223> OTHER INFORMATION: Synthetic

<400> SEQUENCE: 373
cactctttcc ctacacgacg ctcttccgat ctgggcttat gcccaagact tt          52

<210> SEQ ID NO 374
<211> LENGTH: 53
<212> TYPE: DNA
<213> ORGANISM: Artificial Sequence
<220> FEATURE:
<223> OTHER INFORMATION: Synthetic

<400> SEQUENCE: 374
cactctttcc ctacacgacg ctcttccgat cttggtttta tgttgcctgc ttt         53

<210> SEQ ID NO 375
<211> LENGTH: 52
<212> TYPE: DNA
<213> ORGANISM: Artificial Sequence
<220> FEATURE:
<223> OTHER INFORMATION: Synthetic

<400> SEQUENCE: 375
cactctttcc ctacacgacg ctcttccgat cttggccata cactccaatg aa          52

<210> SEQ ID NO 376
<211> LENGTH: 53
<212> TYPE: DNA
<213> ORGANISM: Artificial Sequence
<220> FEATURE:
<223> OTHER INFORMATION: Synthetic

<400> SEQUENCE: 376
cactctttcc ctacacgacg ctcttccgat ctggatgctc cctgagtttc ttc         53

<210> SEQ ID NO 377
<211> LENGTH: 53
<212> TYPE: DNA
<213> ORGANISM: Artificial Sequence
<220> FEATURE:
<223> OTHER INFORMATION: Synthetic

<400> SEQUENCE: 377
cactctttcc ctacacgacg ctcttccgat cttccacctg ttccaagaga ctg         53

<210> SEQ ID NO 378
<211> LENGTH: 52
<212> TYPE: DNA
<213> ORGANISM: Artificial Sequence
<220> FEATURE:
<223> OTHER INFORMATION: Synthetic

<400> SEQUENCE: 378
cactctttcc ctacacgacg ctcttccgat ctgcaatgac tccagaggga ag          52

<210> SEQ ID NO 379
<211> LENGTH: 52
<212> TYPE: DNA
<213> ORGANISM: Artificial Sequence
<220> FEATURE:
<223> OTHER INFORMATION: Synthetic

<400> SEQUENCE: 379
cactctttcc ctacacgacg ctcttccgat ctattcacag ggaaaaggtc cc          52

<210> SEQ ID NO 380
<211> LENGTH: 52
<212> TYPE: DNA
<213> ORGANISM: Artificial Sequence
<220> FEATURE:
<223> OTHER INFORMATION: Synthetic

<400> SEQUENCE: 380
cactctttcc ctacacgacg ctcttccgat cttctcctca gcctggaaac at    52

<210> SEQ ID NO 381
<211> LENGTH: 52
<212> TYPE: DNA
<213> ORGANISM: Artificial Sequence
<220> FEATURE:
<223> OTHER INFORMATION: Synthetic

<400> SEQUENCE: 381
cactctttcc ctacacgacg ctcttccgat ctggtaacac ttgtggggca tt    52

<210> SEQ ID NO 382
<211> LENGTH: 52
<212> TYPE: DNA
<213> ORGANISM: Artificial Sequence
<220> FEATURE:
<223> OTHER INFORMATION: Synthetic

<400> SEQUENCE: 382
cactctttcc ctacacgacg ctcttccgat ctcagccatt cccttgatgt ct    52

<210> SEQ ID NO 383
<211> LENGTH: 52
<212> TYPE: DNA
<213> ORGANISM: Artificial Sequence
<220> FEATURE:
<223> OTHER INFORMATION: Synthetic

<400> SEQUENCE: 383
cactctttcc ctacacgacg ctcttccgat ctcggccgat atcaactttc tt    52

<210> SEQ ID NO 384
<211> LENGTH: 52
<212> TYPE: DNA
<213> ORGANISM: Artificial Sequence
<220> FEATURE:
<223> OTHER INFORMATION: Synthetic

<400> SEQUENCE: 384
cactctttcc ctacacgacg ctcttccgat ctgcatatac gtggccaaag ga    52

<210> SEQ ID NO 385
<211> LENGTH: 52
<212> TYPE: DNA
<213> ORGANISM: Artificial Sequence
<220> FEATURE:
<223> OTHER INFORMATION: Synthetic

<400> SEQUENCE: 385
cactctttcc ctacacgacg ctcttccgat cttttgaaca gtacccgttc cc    52

<210> SEQ ID NO 386
<211> LENGTH: 50
<212> TYPE: DNA
<213> ORGANISM: Artificial Sequence
<220> FEATURE:
<223> OTHER INFORMATION: Synthetic

<400> SEQUENCE: 386
cactctttcc ctacacgacg ctcttccgat ctaagcctgg cctcaccttt            50

<210> SEQ ID NO 387
<211> LENGTH: 52
<212> TYPE: DNA
<213> ORGANISM: Artificial Sequence
<220> FEATURE:
<223> OTHER INFORMATION: Synthetic

<400> SEQUENCE: 387
cactctttcc ctacacgacg ctcttccgat ctctcttcca gttttgccaa gg          52

<210> SEQ ID NO 388
<211> LENGTH: 52
<212> TYPE: DNA
<213> ORGANISM: Artificial Sequence
<220> FEATURE:
<223> OTHER INFORMATION: Synthetic

<400> SEQUENCE: 388
cactctttcc ctacacgacg ctcttccgat ctaaagtgct cccgttctgc ta          52

<210> SEQ ID NO 389
<211> LENGTH: 52
<212> TYPE: DNA
<213> ORGANISM: Artificial Sequence
<220> FEATURE:
<223> OTHER INFORMATION: Synthetic

<400> SEQUENCE: 389
cactctttcc ctacacgacg ctcttccgat ctcactaacc atgcaggaca cg          52

<210> SEQ ID NO 390
<211> LENGTH: 52
<212> TYPE: DNA
<213> ORGANISM: Artificial Sequence
<220> FEATURE:
<223> OTHER INFORMATION: Synthetic

<400> SEQUENCE: 390
cactctttcc ctacacgacg ctcttccgat ctaccacgct tggccttaat tt          52

<210> SEQ ID NO 391
<211> LENGTH: 55
<212> TYPE: DNA
<213> ORGANISM: Artificial Sequence
<220> FEATURE:
<223> OTHER INFORMATION: Synthetic

<400> SEQUENCE: 391
cactctttcc ctacacgacg ctcttccgat ctcttctgca ttttcacatt agcaa       55

<210> SEQ ID NO 392
<211> LENGTH: 50
<212> TYPE: DNA
<213> ORGANISM: Artificial Sequence
<220> FEATURE:
<223> OTHER INFORMATION: Synthetic

<400> SEQUENCE: 392
cactctttcc ctacacgacg ctcttccgat ctccacacct ggctcagagg            50

<210> SEQ ID NO 393

```
<211> LENGTH: 53
<212> TYPE: DNA
<213> ORGANISM: Artificial Sequence
<220> FEATURE:
<223> OTHER INFORMATION: Synthetic

<400> SEQUENCE: 393
cactctttcc ctacacgacg ctcttccgat ctgatttcat ccttgaagcc tcc          53

<210> SEQ ID NO 394
<211> LENGTH: 52
<212> TYPE: DNA
<213> ORGANISM: Artificial Sequence
<220> FEATURE:
<223> OTHER INFORMATION: Synthetic

<400> SEQUENCE: 394
cactctttcc ctacacgacg ctcttccgat ctggaagaca gccaggactt ca           52

<210> SEQ ID NO 395
<211> LENGTH: 50
<212> TYPE: DNA
<213> ORGANISM: Artificial Sequence
<220> FEATURE:
<223> OTHER INFORMATION: Synthetic

<400> SEQUENCE: 395
cactctttcc ctacacgacg ctcttccgat ctgcctccca ggttcaaaca              50

<210> SEQ ID NO 396
<211> LENGTH: 52
<212> TYPE: DNA
<213> ORGANISM: Artificial Sequence
<220> FEATURE:
<223> OTHER INFORMATION: Synthetic

<400> SEQUENCE: 396
cactctttcc ctacacgacg ctcttccgat cttccatgca aaccattcaa aa           52

<210> SEQ ID NO 397
<211> LENGTH: 59
<212> TYPE: DNA
<213> ORGANISM: Artificial Sequence
<220> FEATURE:
<223> OTHER INFORMATION: Synthetic

<400> SEQUENCE: 397
cactctttcc ctacacgacg ctcttccgat ctgaaattac ctattaacag atgctgaca    59

<210> SEQ ID NO 398
<211> LENGTH: 55
<212> TYPE: DNA
<213> ORGANISM: Artificial Sequence
<220> FEATURE:
<223> OTHER INFORMATION: Synthetic

<400> SEQUENCE: 398
cactctttcc ctacacgacg ctcttccgat ctcaagccag ggttaagtta cacag        55

<210> SEQ ID NO 399
<211> LENGTH: 60
<212> TYPE: DNA
<213> ORGANISM: Artificial Sequence
<220> FEATURE:
<223> OTHER INFORMATION: Synthetic

<400> SEQUENCE: 399
```

```
cactctttcc ctacacgacg ctcttccgat ctcaggagac catatgttta tttattgatt    60
```

<210> SEQ ID NO 400
<211> LENGTH: 52
<212> TYPE: DNA
<213> ORGANISM: Artificial Sequence
<220> FEATURE:
<223> OTHER INFORMATION: Synthetic

<400> SEQUENCE: 400

```
cactctttcc ctacacgacg ctcttccgat ctatccaaaa gaccaccacc tg    52
```

<210> SEQ ID NO 401
<211> LENGTH: 48
<212> TYPE: DNA
<213> ORGANISM: Artificial Sequence
<220> FEATURE:
<223> OTHER INFORMATION: Synthetic

<400> SEQUENCE: 401

```
ggagttcaga cgtgtgctct ccgatcttg cacatgagct ctctctgg    48
```

<210> SEQ ID NO 402
<211> LENGTH: 48
<212> TYPE: DNA
<213> ORGANISM: Artificial Sequence
<220> FEATURE:
<223> OTHER INFORMATION: Synthetic

<400> SEQUENCE: 402

```
ggagttcaga cgtgtgctct ccgatctgc taacgaggaa cttggcag    48
```

<210> SEQ ID NO 403
<211> LENGTH: 48
<212> TYPE: DNA
<213> ORGANISM: Artificial Sequence
<220> FEATURE:
<223> OTHER INFORMATION: Synthetic

<400> SEQUENCE: 403

```
ggagttcaga cgtgtgctct ccgatctca gcattttggc tcctctct    48
```

<210> SEQ ID NO 404
<211> LENGTH: 48
<212> TYPE: DNA
<213> ORGANISM: Artificial Sequence
<220> FEATURE:
<223> OTHER INFORMATION: Synthetic

<400> SEQUENCE: 404

```
ggagttcaga cgtgtgctct ccgatctgg atggtggcca agaagtta    48
```

<210> SEQ ID NO 405
<211> LENGTH: 48
<212> TYPE: DNA
<213> ORGANISM: Artificial Sequence
<220> FEATURE:
<223> OTHER INFORMATION: Synthetic

<400> SEQUENCE: 405

```
ggagttcaga cgtgtgctct ccgatcttc ctgtaaacac ccgtgaca    48
```

<210> SEQ ID NO 406
<211> LENGTH: 47
<212> TYPE: DNA

```
<213> ORGANISM: Artificial Sequence
<220> FEATURE:
<223> OTHER INFORMATION: Synthetic

<400> SEQUENCE: 406
ggagttcaga cgtgtgctct tccgatctgc aaaacgacca ggaggat        47

<210> SEQ ID NO 407
<211> LENGTH: 52
<212> TYPE: DNA
<213> ORGANISM: Artificial Sequence
<220> FEATURE:
<223> OTHER INFORMATION: Synthetic

<400> SEQUENCE: 407
ggagttcaga cgtgtgctct tccgatctag cattcctaca caattactgc tg     52

<210> SEQ ID NO 408
<211> LENGTH: 47
<212> TYPE: DNA
<213> ORGANISM: Artificial Sequence
<220> FEATURE:
<223> OTHER INFORMATION: Synthetic

<400> SEQUENCE: 408
ggagttcaga cgtgtgctct tccgatctgc cctgggagac cttacaa        47

<210> SEQ ID NO 409
<211> LENGTH: 48
<212> TYPE: DNA
<213> ORGANISM: Artificial Sequence
<220> FEATURE:
<223> OTHER INFORMATION: Synthetic

<400> SEQUENCE: 409
ggagttcaga cgtgtgctct tccgatctgg aaaagacaag caagccag       48

<210> SEQ ID NO 410
<211> LENGTH: 48
<212> TYPE: DNA
<213> ORGANISM: Artificial Sequence
<220> FEATURE:
<223> OTHER INFORMATION: Synthetic

<400> SEQUENCE: 410
ggagttcaga cgtgtgctct tccgatctag gggtgagtga atgacagg       48

<210> SEQ ID NO 411
<211> LENGTH: 48
<212> TYPE: DNA
<213> ORGANISM: Artificial Sequence
<220> FEATURE:
<223> OTHER INFORMATION: Synthetic

<400> SEQUENCE: 411
ggagttcaga cgtgtgctct tccgatctga agacaaccga attaggcg       48

<210> SEQ ID NO 412
<211> LENGTH: 48
<212> TYPE: DNA
<213> ORGANISM: Artificial Sequence
<220> FEATURE:
<223> OTHER INFORMATION: Synthetic

<400> SEQUENCE: 412
ggagttcaga cgtgtgctct tccgatcttt tgtctttggt tccttcgg       48
```

<210> SEQ ID NO 413
<211> LENGTH: 48
<212> TYPE: DNA
<213> ORGANISM: Artificial Sequence
<220> FEATURE:
<223> OTHER INFORMATION: Synthetic

<400> SEQUENCE: 413
ggagttcaga cgtgtgctct tccgatctgc cttgccttat cacctttg        48

<210> SEQ ID NO 414
<211> LENGTH: 48
<212> TYPE: DNA
<213> ORGANISM: Artificial Sequence
<220> FEATURE:
<223> OTHER INFORMATION: Synthetic

<400> SEQUENCE: 414
ggagttcaga cgtgtgctct tccgatctgc aaaacgacca ggaggata        48

<210> SEQ ID NO 415
<211> LENGTH: 48
<212> TYPE: DNA
<213> ORGANISM: Artificial Sequence
<220> FEATURE:
<223> OTHER INFORMATION: Synthetic

<400> SEQUENCE: 415
ggagttcaga cgtgtgctct tccgatctat acacttctgg gattggcg        48

<210> SEQ ID NO 416
<211> LENGTH: 48
<212> TYPE: DNA
<213> ORGANISM: Artificial Sequence
<220> FEATURE:
<223> OTHER INFORMATION: Synthetic

<400> SEQUENCE: 416
ggagttcaga cgtgtgctct tccgatctga agatcaaggt gggtggtg        48

<210> SEQ ID NO 417
<211> LENGTH: 48
<212> TYPE: DNA
<213> ORGANISM: Artificial Sequence
<220> FEATURE:
<223> OTHER INFORMATION: Synthetic

<400> SEQUENCE: 417
ggagttcaga cgtgtgctct tccgatctac acccaacacc acgaagat        48

<210> SEQ ID NO 418
<211> LENGTH: 48
<212> TYPE: DNA
<213> ORGANISM: Artificial Sequence
<220> FEATURE:
<223> OTHER INFORMATION: Synthetic

<400> SEQUENCE: 418
ggagttcaga cgtgtgctct tccgatctac aaccctttg ttcccta        48

<210> SEQ ID NO 419
<211> LENGTH: 48
<212> TYPE: DNA
<213> ORGANISM: Artificial Sequence
<220> FEATURE:

<223> OTHER INFORMATION: Synthetic

<400> SEQUENCE: 419
ggagttcaga cgtgtgctct tccgatctcc cagccacaag tttgtttt     48

<210> SEQ ID NO 420
<211> LENGTH: 48
<212> TYPE: DNA
<213> ORGANISM: Artificial Sequence
<220> FEATURE:
<223> OTHER INFORMATION: Synthetic

<400> SEQUENCE: 420
ggagttcaga cgtgtgctct tccgatcttg aagaaacaag gcaaggct     48

<210> SEQ ID NO 421
<211> LENGTH: 48
<212> TYPE: DNA
<213> ORGANISM: Artificial Sequence
<220> FEATURE:
<223> OTHER INFORMATION: Synthetic

<400> SEQUENCE: 421
ggagttcaga cgtgtgctct tccgatcttg tgggagatga caccacac     48

<210> SEQ ID NO 422
<211> LENGTH: 48
<212> TYPE: DNA
<213> ORGANISM: Artificial Sequence
<220> FEATURE:
<223> OTHER INFORMATION: Synthetic

<400> SEQUENCE: 422
ggagttcaga cgtgtgctct tccgatctgg gagaggacac cacacttc     48

<210> SEQ ID NO 423
<211> LENGTH: 48
<212> TYPE: DNA
<213> ORGANISM: Artificial Sequence
<220> FEATURE:
<223> OTHER INFORMATION: Synthetic

<400> SEQUENCE: 423
ggagttcaga cgtgtgctct tccgatctac tgtgcctggc ctgaaata     48

<210> SEQ ID NO 424
<211> LENGTH: 48
<212> TYPE: DNA
<213> ORGANISM: Artificial Sequence
<220> FEATURE:
<223> OTHER INFORMATION: Synthetic

<400> SEQUENCE: 424
ggagttcaga cgtgtgctct tccgatctct cacgaacacg tatccacg     48

<210> SEQ ID NO 425
<211> LENGTH: 49
<212> TYPE: DNA
<213> ORGANISM: Artificial Sequence
<220> FEATURE:
<223> OTHER INFORMATION: Synthetic

<400> SEQUENCE: 425
ggagttcaga cgtgtgctct tccgatctgc atgaggccca ttgtagtaa     49

<210> SEQ ID NO 426
<211> LENGTH: 53
<212> TYPE: DNA
<213> ORGANISM: Artificial Sequence
<220> FEATURE:
<223> OTHER INFORMATION: Synthetic

<400> SEQUENCE: 426
ggagttcaga cgtgtgctct tccgatctac tcatcttctg tgattttgtt tca         53

<210> SEQ ID NO 427
<211> LENGTH: 48
<212> TYPE: DNA
<213> ORGANISM: Artificial Sequence
<220> FEATURE:
<223> OTHER INFORMATION: Synthetic

<400> SEQUENCE: 427
ggagttcaga cgtgtgctct tccgatctat tcccatgctg acttttgc                48

<210> SEQ ID NO 428
<211> LENGTH: 48
<212> TYPE: DNA
<213> ORGANISM: Artificial Sequence
<220> FEATURE:
<223> OTHER INFORMATION: Synthetic

<400> SEQUENCE: 428
ggagttcaga cgtgtgctct tccgatctgg aagggacacc acacttct                48

<210> SEQ ID NO 429
<211> LENGTH: 49
<212> TYPE: DNA
<213> ORGANISM: Artificial Sequence
<220> FEATURE:
<223> OTHER INFORMATION: Synthetic

<400> SEQUENCE: 429
ggagttcaga cgtgtgctct tccgatcttg ccctttatgt gtgtgtgtg               49

<210> SEQ ID NO 430
<211> LENGTH: 52
<212> TYPE: DNA
<213> ORGANISM: Artificial Sequence
<220> FEATURE:
<223> OTHER INFORMATION: Synthetic

<400> SEQUENCE: 430
ggagttcaga cgtgtgctct tccgatctgg acacttatgt tgattccagt gt           52

<210> SEQ ID NO 431
<211> LENGTH: 50
<212> TYPE: DNA
<213> ORGANISM: Artificial Sequence
<220> FEATURE:
<223> OTHER INFORMATION: Synthetic

<400> SEQUENCE: 431
ggagttcaga cgtgtgctct tccgatcttg ctgttggaga aaatgtgttt              50

<210> SEQ ID NO 432
<211> LENGTH: 52
<212> TYPE: DNA
<213> ORGANISM: Artificial Sequence
<220> FEATURE:
<223> OTHER INFORMATION: Synthetic

```
<400> SEQUENCE: 432
ggagttcaga cgtgtgctct tccgatctgc aagactctgt ctcgtaaaca tt         52

<210> SEQ ID NO 433
<211> LENGTH: 48
<212> TYPE: DNA
<213> ORGANISM: Artificial Sequence
<220> FEATURE:
<223> OTHER INFORMATION: Synthetic

<400> SEQUENCE: 433
ggagttcaga cgtgtgctct tccgatctaa aagttccatt ggctgtgg              48

<210> SEQ ID NO 434
<211> LENGTH: 52
<212> TYPE: DNA
<213> ORGANISM: Artificial Sequence
<220> FEATURE:
<223> OTHER INFORMATION: Synthetic

<400> SEQUENCE: 434
ggagttcaga cgtgtgctct tccgatctgg tgctaaaaca aacgttatca aa         52

<210> SEQ ID NO 435
<211> LENGTH: 49
<212> TYPE: DNA
<213> ORGANISM: Artificial Sequence
<220> FEATURE:
<223> OTHER INFORMATION: Synthetic

<400> SEQUENCE: 435
ggagttcaga cgtgtgctct tccgatcttc agaatttcac tgcatcgtg             49

<210> SEQ ID NO 436
<211> LENGTH: 48
<212> TYPE: DNA
<213> ORGANISM: Artificial Sequence
<220> FEATURE:
<223> OTHER INFORMATION: Synthetic

<400> SEQUENCE: 436
ggagttcaga cgtgtgctct tccgatctaa atccccacct tatctggc              48

<210> SEQ ID NO 437
<211> LENGTH: 48
<212> TYPE: DNA
<213> ORGANISM: Artificial Sequence
<220> FEATURE:
<223> OTHER INFORMATION: Synthetic

<400> SEQUENCE: 437
ggagttcaga cgtgtgctct tccgatctcc agcactggaa gctctttt              48

<210> SEQ ID NO 438
<211> LENGTH: 52
<212> TYPE: DNA
<213> ORGANISM: Artificial Sequence
<220> FEATURE:
<223> OTHER INFORMATION: Synthetic

<400> SEQUENCE: 438
ggagttcaga cgtgtgctct tccgatctag gatatgcttg aattattttc cg         52

<210> SEQ ID NO 439
<211> LENGTH: 48
```

<210> SEQ ID NO 439
<211> LENGTH: 48
<212> TYPE: DNA
<213> ORGANISM: Artificial Sequence
<220> FEATURE:
<223> OTHER INFORMATION: Synthetic

<400> SEQUENCE: 439
ggagttcaga cgtgtgctct tccgatctac cttgggccac tcttcttt     48

<210> SEQ ID NO 440
<211> LENGTH: 48
<212> TYPE: DNA
<213> ORGANISM: Artificial Sequence
<220> FEATURE:
<223> OTHER INFORMATION: Synthetic

<400> SEQUENCE: 440
ggagttcaga cgtgtgctct tccgatcttc accctaggtg gcacagat     48

<210> SEQ ID NO 441
<211> LENGTH: 51
<212> TYPE: DNA
<213> ORGANISM: Artificial Sequence
<220> FEATURE:
<223> OTHER INFORMATION: Synthetic

<400> SEQUENCE: 441
ggagttcaga cgtgtgctct tccgatctgc acttcgctaa gaactgtctt c     51

<210> SEQ ID NO 442
<211> LENGTH: 48
<212> TYPE: DNA
<213> ORGANISM: Artificial Sequence
<220> FEATURE:
<223> OTHER INFORMATION: Synthetic

<400> SEQUENCE: 442
ggagttcaga cgtgtgctct tccgatctga tagcactgct ccagggat     48

<210> SEQ ID NO 443
<211> LENGTH: 53
<212> TYPE: DNA
<213> ORGANISM: Artificial Sequence
<220> FEATURE:
<223> OTHER INFORMATION: Synthetic

<400> SEQUENCE: 443
ggagttcaga cgtgtgctct tccgatctaa acaaacaaac aaacaatgca tac     53

<210> SEQ ID NO 444
<211> LENGTH: 47
<212> TYPE: DNA
<213> ORGANISM: Artificial Sequence
<220> FEATURE:
<223> OTHER INFORMATION: Synthetic

<400> SEQUENCE: 444
ggagttcaga cgtgtgctct tccgatctgt ctgccctgga tggaaac     47

<210> SEQ ID NO 445
<211> LENGTH: 48
<212> TYPE: DNA
<213> ORGANISM: Artificial Sequence
<220> FEATURE:
<223> OTHER INFORMATION: Synthetic

<400> SEQUENCE: 445

```
ggagttcaga cgtgtgctct tccgatctat catccctaat gccaaagc          48
```

<210> SEQ ID NO 446
<211> LENGTH: 53
<212> TYPE: DNA
<213> ORGANISM: Artificial Sequence
<220> FEATURE:
<223> OTHER INFORMATION: Synthetic

<400> SEQUENCE: 446

```
ggagttcaga cgtgtgctct tccgatctca ttttatgatt ttaattgttg ggg     53
```

<210> SEQ ID NO 447
<211> LENGTH: 48
<212> TYPE: DNA
<213> ORGANISM: Artificial Sequence
<220> FEATURE:
<223> OTHER INFORMATION: Synthetic

<400> SEQUENCE: 447

```
ggagttcaga cgtgtgctct tccgatctgt tgggttaggg catttgtg           48
```

<210> SEQ ID NO 448
<211> LENGTH: 48
<212> TYPE: DNA
<213> ORGANISM: Artificial Sequence
<220> FEATURE:
<223> OTHER INFORMATION: Synthetic

<400> SEQUENCE: 448

```
ggagttcaga cgtgtgctct tccgatctat tgcacctggc ctatgtct           48
```

<210> SEQ ID NO 449
<211> LENGTH: 48
<212> TYPE: DNA
<213> ORGANISM: Artificial Sequence
<220> FEATURE:
<223> OTHER INFORMATION: Synthetic

<400> SEQUENCE: 449

```
ggagttcaga cgtgtgctct tccgatcttc caaaatctgt ggcttgtg           48
```

<210> SEQ ID NO 450
<211> LENGTH: 48
<212> TYPE: DNA
<213> ORGANISM: Artificial Sequence
<220> FEATURE:
<223> OTHER INFORMATION: Synthetic

<400> SEQUENCE: 450

```
ggagttcaga cgtgtgctct tccgatctca acagacactg gctgaagg           48
```

<210> SEQ ID NO 451
<211> LENGTH: 48
<212> TYPE: DNA
<213> ORGANISM: Artificial Sequence
<220> FEATURE:
<223> OTHER INFORMATION: Synthetic

<400> SEQUENCE: 451

```
ggagttcaga cgtgtgctct tccgatctgg tcctaagtct gtggctcg           48
```

<210> SEQ ID NO 452
<211> LENGTH: 48
<212> TYPE: DNA
<213> ORGANISM: Artificial Sequence
<220> FEATURE:
<223> OTHER INFORMATION: Synthetic

<400> SEQUENCE: 452
ggagttcaga cgtgtgctct tccgatcttc caaagaatac cagccacc          48

<210> SEQ ID NO 453
<211> LENGTH: 49
<212> TYPE: DNA
<213> ORGANISM: Artificial Sequence
<220> FEATURE:
<223> OTHER INFORMATION: Synthetic

<400> SEQUENCE: 453
ggagttcaga cgtgtgctct tccgatcttc cacccctgta aaagtacca          49

<210> SEQ ID NO 454
<211> LENGTH: 54
<212> TYPE: DNA
<213> ORGANISM: Artificial Sequence
<220> FEATURE:
<223> OTHER INFORMATION: Synthetic

<400> SEQUENCE: 454
ggagttcaga cgtgtgctct tccgatcttg tggttctctt tctagattcc tttt          54

<210> SEQ ID NO 455
<211> LENGTH: 48
<212> TYPE: DNA
<213> ORGANISM: Artificial Sequence
<220> FEATURE:
<223> OTHER INFORMATION: Synthetic

<400> SEQUENCE: 455
ggagttcaga cgtgtgctct tccgatctgg tggaagctat caggacca          48

<210> SEQ ID NO 456
<211> LENGTH: 48
<212> TYPE: DNA
<213> ORGANISM: Artificial Sequence
<220> FEATURE:
<223> OTHER INFORMATION: Synthetic

<400> SEQUENCE: 456
ggagttcaga cgtgtgctct tccgatctag atatgatgag atccgccg          48

<210> SEQ ID NO 457
<211> LENGTH: 50
<212> TYPE: DNA
<213> ORGANISM: Artificial Sequence
<220> FEATURE:
<223> OTHER INFORMATION: Synthetic

<400> SEQUENCE: 457
ggagttcaga cgtgtgctct tccgatctcc cagcatcttt acatgctttt          50

<210> SEQ ID NO 458
<211> LENGTH: 48
<212> TYPE: DNA
<213> ORGANISM: Artificial Sequence
<220> FEATURE:
<223> OTHER INFORMATION: Synthetic

<400> SEQUENCE: 458
ggagttcaga cgtgtgctct tccgatctag tacacagtgg ctgcccat          48

<210> SEQ ID NO 459
<211> LENGTH: 48
<212> TYPE: DNA
<213> ORGANISM: Artificial Sequence
<220> FEATURE:
<223> OTHER INFORMATION: Synthetic

<400> SEQUENCE: 459
ggagttcaga cgtgtgctct tccgatctgc cgaggaagca ttgtaaag          48

<210> SEQ ID NO 460
<211> LENGTH: 55
<212> TYPE: DNA
<213> ORGANISM: Artificial Sequence
<220> FEATURE:
<223> OTHER INFORMATION: Synthetic

<400> SEQUENCE: 460
ggagttcaga cgtgtgctct tccgatctaa taaaggatga cactttagaa ctgga    55

<210> SEQ ID NO 461
<211> LENGTH: 47
<212> TYPE: DNA
<213> ORGANISM: Artificial Sequence
<220> FEATURE:
<223> OTHER INFORMATION: Synthetic

<400> SEQUENCE: 461
ggagttcaga cgtgtgctct tccgatctac ccggccataa actcaag           47

<210> SEQ ID NO 462
<211> LENGTH: 50
<212> TYPE: DNA
<213> ORGANISM: Artificial Sequence
<220> FEATURE:
<223> OTHER INFORMATION: Synthetic

<400> SEQUENCE: 462
ggagttcaga cgtgtgctct tccgatctgt taaaacaaat gctttgggct         50

<210> SEQ ID NO 463
<211> LENGTH: 48
<212> TYPE: DNA
<213> ORGANISM: Artificial Sequence
<220> FEATURE:
<223> OTHER INFORMATION: Synthetic

<400> SEQUENCE: 463
ggagttcaga cgtgtgctct tccgatctcc ttgtctccaa ctcccaaa          48

<210> SEQ ID NO 464
<211> LENGTH: 48
<212> TYPE: DNA
<213> ORGANISM: Artificial Sequence
<220> FEATURE:
<223> OTHER INFORMATION: Synthetic

<400> SEQUENCE: 464
ggagttcaga cgtgtgctct tccgatcttt gcaccttcca cccataat          48

<210> SEQ ID NO 465
<211> LENGTH: 48
<212> TYPE: DNA
<213> ORGANISM: Artificial Sequence
<220> FEATURE:
<223> OTHER INFORMATION: Synthetic

<400> SEQUENCE: 465
ggagttcaga cgtgtgctct tccgatctag ctacatcttc accgccac         48

<210> SEQ ID NO 466
<211> LENGTH: 48
<212> TYPE: DNA
<213> ORGANISM: Artificial Sequence
<220> FEATURE:
<223> OTHER INFORMATION: Synthetic

<400> SEQUENCE: 466
ggagttcaga cgtgtgctct tccgatctga ggctacagct tcaccacc         48

<210> SEQ ID NO 467
<211> LENGTH: 48
<212> TYPE: DNA
<213> ORGANISM: Artificial Sequence
<220> FEATURE:
<223> OTHER INFORMATION: Synthetic

<400> SEQUENCE: 467
ggagttcaga cgtgtgctct tccgatctct caccaagctt caccatca         48

<210> SEQ ID NO 468
<211> LENGTH: 48
<212> TYPE: DNA
<213> ORGANISM: Artificial Sequence
<220> FEATURE:
<223> OTHER INFORMATION: Synthetic

<400> SEQUENCE: 468
ggagttcaga cgtgtgctct tccgatctgc ctccacaata ttcatgcc         48

<210> SEQ ID NO 469
<211> LENGTH: 48
<212> TYPE: DNA
<213> ORGANISM: Artificial Sequence
<220> FEATURE:
<223> OTHER INFORMATION: Synthetic

<400> SEQUENCE: 469
ggagttcaga cgtgtgctct tccgatcttg tggcctccac aatattca         48

<210> SEQ ID NO 470
<211> LENGTH: 48
<212> TYPE: DNA
<213> ORGANISM: Artificial Sequence
<220> FEATURE:
<223> OTHER INFORMATION: Synthetic

<400> SEQUENCE: 470
ggagttcaga cgtgtgctct tccgatcttg gtgatcttgc tggtcttg         48

<210> SEQ ID NO 471
<211> LENGTH: 48
<212> TYPE: DNA
<213> ORGANISM: Artificial Sequence
<220> FEATURE:
<223> OTHER INFORMATION: Synthetic

<400> SEQUENCE: 471
ggagttcaga cgtgtgctct tccgatctat tgattcatgc cctcttgc         48

<210> SEQ ID NO 472

```
<211> LENGTH: 48
<212> TYPE: DNA
<213> ORGANISM: Artificial Sequence
<220> FEATURE:
<223> OTHER INFORMATION: Synthetic

<400> SEQUENCE: 472
ggagttcaga cgtgtgctct tccgatctgg ccatagcaat ggtgatct            48

<210> SEQ ID NO 473
<211> LENGTH: 48
<212> TYPE: DNA
<213> ORGANISM: Artificial Sequence
<220> FEATURE:
<223> OTHER INFORMATION: Synthetic

<400> SEQUENCE: 473
ggagttcaga cgtgtgctct tccgatctta gtgtttgttc cgttcccc            48

<210> SEQ ID NO 474
<211> LENGTH: 47
<212> TYPE: DNA
<213> ORGANISM: Artificial Sequence
<220> FEATURE:
<223> OTHER INFORMATION: Synthetic

<400> SEQUENCE: 474
ggagttcaga cgtgtgctct tccgatcttt caccctgcca aagatca             47

<210> SEQ ID NO 475
<211> LENGTH: 48
<212> TYPE: DNA
<213> ORGANISM: Artificial Sequence
<220> FEATURE:
<223> OTHER INFORMATION: Synthetic

<400> SEQUENCE: 475
ggagttcaga cgtgtgctct tccgatctcc ctactgaaga ctggagcg            48

<210> SEQ ID NO 476
<211> LENGTH: 49
<212> TYPE: DNA
<213> ORGANISM: Artificial Sequence
<220> FEATURE:
<223> OTHER INFORMATION: Synthetic

<400> SEQUENCE: 476
ggagttcaga cgtgtgctct tccgatctcc tctgtgccta ttcagcagt           49

<210> SEQ ID NO 477
<211> LENGTH: 48
<212> TYPE: DNA
<213> ORGANISM: Artificial Sequence
<220> FEATURE:
<223> OTHER INFORMATION: Synthetic

<400> SEQUENCE: 477
ggagttcaga cgtgtgctct tccgatcttg aacaatggag cactcagc            48

<210> SEQ ID NO 478
<211> LENGTH: 48
<212> TYPE: DNA
<213> ORGANISM: Artificial Sequence
<220> FEATURE:
<223> OTHER INFORMATION: Synthetic

<400> SEQUENCE: 478
```
ggagttcaga cgtgtgctct tccgatctca gactggtctg aaagcgtg        48

<210> SEQ ID NO 479
<211> LENGTH: 48
<212> TYPE: DNA
<213> ORGANISM: Artificial Sequence
<220> FEATURE:
<223> OTHER INFORMATION: Synthetic

<400> SEQUENCE: 479
ggagttcaga cgtgtgctct tccgatcttg aagactggag cactcagc        48

<210> SEQ ID NO 480
<211> LENGTH: 48
<212> TYPE: DNA
<213> ORGANISM: Artificial Sequence
<220> FEATURE:
<223> OTHER INFORMATION: Synthetic

<400> SEQUENCE: 480
ggagttcaga cgtgtgctct tccgatcttc cagcacctga gttcactg        48

<210> SEQ ID NO 481
<211> LENGTH: 48
<212> TYPE: DNA
<213> ORGANISM: Artificial Sequence
<220> FEATURE:
<223> OTHER INFORMATION: Synthetic

<400> SEQUENCE: 481
ggagttcaga cgtgtgctct tccgatcttg cctattcagc agttccct        48

<210> SEQ ID NO 482
<211> LENGTH: 48
<212> TYPE: DNA
<213> ORGANISM: Artificial Sequence
<220> FEATURE:
<223> OTHER INFORMATION: Synthetic

<400> SEQUENCE: 482
ggagttcaga cgtgtgctct tccgatctaa gactggagca ctcagcgt        48

<210> SEQ ID NO 483
<211> LENGTH: 48
<212> TYPE: DNA
<213> ORGANISM: Artificial Sequence
<220> FEATURE:
<223> OTHER INFORMATION: Synthetic

<400> SEQUENCE: 483
ggagttcaga cgtgtgctct tccgatctta gaaggtggag atgctggc        48

<210> SEQ ID NO 484
<211> LENGTH: 48
<212> TYPE: DNA
<213> ORGANISM: Artificial Sequence
<220> FEATURE:
<223> OTHER INFORMATION: Synthetic

<400> SEQUENCE: 484
ggagttcaga cgtgtgctct tccgatctgg caacagacag gaccagat        48

<210> SEQ ID NO 485
<211> LENGTH: 49
<212> TYPE: DNA

```
<213> ORGANISM: Artificial Sequence
<220> FEATURE:
<223> OTHER INFORMATION: Synthetic

<400> SEQUENCE: 485
ggagttcaga cgtgtgctct tccgatcttt gtgcacgtta agcactctg           49

<210> SEQ ID NO 486
<211> LENGTH: 48
<212> TYPE: DNA
<213> ORGANISM: Artificial Sequence
<220> FEATURE:
<223> OTHER INFORMATION: Synthetic

<400> SEQUENCE: 486
ggagttcaga cgtgtgctct tccgatctaa gagagcttcc tgacacgc            48

<210> SEQ ID NO 487
<211> LENGTH: 50
<212> TYPE: DNA
<213> ORGANISM: Artificial Sequence
<220> FEATURE:
<223> OTHER INFORMATION: Synthetic

<400> SEQUENCE: 487
ggagttcaga cgtgtgctct tccgatcttc taagagccaa gacagcttcc          50

<210> SEQ ID NO 488
<211> LENGTH: 47
<212> TYPE: DNA
<213> ORGANISM: Artificial Sequence
<220> FEATURE:
<223> OTHER INFORMATION: Synthetic

<400> SEQUENCE: 488
ggagttcaga cgtgtgctct tccgatctag cttgttcctt tcagccg             47

<210> SEQ ID NO 489
<211> LENGTH: 48
<212> TYPE: DNA
<213> ORGANISM: Artificial Sequence
<220> FEATURE:
<223> OTHER INFORMATION: Synthetic

<400> SEQUENCE: 489
ggagttcaga cgtgtgctct tccgatctca atgcgtttcc ttttagcc            48

<210> SEQ ID NO 490
<211> LENGTH: 49
<212> TYPE: DNA
<213> ORGANISM: Artificial Sequence
<220> FEATURE:
<223> OTHER INFORMATION: Synthetic

<400> SEQUENCE: 490
ggagttcaga cgtgtgctct tccgatctag tattcttttg cctttcggc           49

<210> SEQ ID NO 491
<211> LENGTH: 48
<212> TYPE: DNA
<213> ORGANISM: Artificial Sequence
<220> FEATURE:
<223> OTHER INFORMATION: Synthetic

<400> SEQUENCE: 491
ggagttcaga cgtgtgctct tccgatctta tccatttctg cctctgcc            48
```

<210> SEQ ID NO 492
<211> LENGTH: 48
<212> TYPE: DNA
<213> ORGANISM: Artificial Sequence
<220> FEATURE:
<223> OTHER INFORMATION: Synthetic

<400> SEQUENCE: 492
ggagttcaga cgtgtgctct tccgatctcc cttttctttt cccagagg        48

<210> SEQ ID NO 493
<211> LENGTH: 48
<212> TYPE: DNA
<213> ORGANISM: Artificial Sequence
<220> FEATURE:
<223> OTHER INFORMATION: Synthetic

<400> SEQUENCE: 493
ggagttcaga cgtgtgctct tccgatctaa aagaaaatcg cctttcgg        48

<210> SEQ ID NO 494
<211> LENGTH: 47
<212> TYPE: DNA
<213> ORGANISM: Artificial Sequence
<220> FEATURE:
<223> OTHER INFORMATION: Synthetic

<400> SEQUENCE: 494
ggagttcaga cgtgtgctct tccgatcttc ttttcctttc agccgga         47

<210> SEQ ID NO 495
<211> LENGTH: 48
<212> TYPE: DNA
<213> ORGANISM: Artificial Sequence
<220> FEATURE:
<223> OTHER INFORMATION: Synthetic

<400> SEQUENCE: 495
ggagttcaga cgtgtgctct tccgatcttt gtctgcctca gctcaaga        48

<210> SEQ ID NO 496
<211> LENGTH: 48
<212> TYPE: DNA
<213> ORGANISM: Artificial Sequence
<220> FEATURE:
<223> OTHER INFORMATION: Synthetic

<400> SEQUENCE: 496
ggagttcaga cgtgtgctct tccgatctaa aactcccttc cttttggc        48

<210> SEQ ID NO 497
<211> LENGTH: 48
<212> TYPE: DNA
<213> ORGANISM: Artificial Sequence
<220> FEATURE:
<223> OTHER INFORMATION: Synthetic

<400> SEQUENCE: 497
ggagttcaga cgtgtgctct tccgatctcg acctctggaa ggagactg        48

<210> SEQ ID NO 498
<211> LENGTH: 48
<212> TYPE: DNA
<213> ORGANISM: Artificial Sequence
<220> FEATURE:

<223> OTHER INFORMATION: Synthetic

<400> SEQUENCE: 498
ggagttcaga cgtgtgctct tccgatctca ctgaccacct cgtcaaga        48

<210> SEQ ID NO 499
<211> LENGTH: 48
<212> TYPE: DNA
<213> ORGANISM: Artificial Sequence
<220> FEATURE:
<223> OTHER INFORMATION: Synthetic

<400> SEQUENCE: 499
ggagttcaga cgtgtgctct tccgatctga cctacagcta cccgaccc         48

<210> SEQ ID NO 500
<211> LENGTH: 48
<212> TYPE: DNA
<213> ORGANISM: Artificial Sequence
<220> FEATURE:
<223> OTHER INFORMATION: Synthetic

<400> SEQUENCE: 500
ggagttcaga cgtgtgctct tccgatctga acgtcaagca tcccaagt         48

<210> SEQ ID NO 501
<211> LENGTH: 48
<212> TYPE: DNA
<213> ORGANISM: Artificial Sequence
<220> FEATURE:
<223> OTHER INFORMATION: Synthetic

<400> SEQUENCE: 501
ggagttcaga cgtgtgctct tccgatctaa aagacgacca tccaccag         48

<210> SEQ ID NO 502
<211> LENGTH: 48
<212> TYPE: DNA
<213> ORGANISM: Artificial Sequence
<220> FEATURE:
<223> OTHER INFORMATION: Synthetic

<400> SEQUENCE: 502
ggagttcaga cgtgtgctct tccgatctat gatgctcacc cagagacc         48

<210> SEQ ID NO 503
<211> LENGTH: 48
<212> TYPE: DNA
<213> ORGANISM: Artificial Sequence
<220> FEATURE:
<223> OTHER INFORMATION: Synthetic

<400> SEQUENCE: 503
ggagttcaga cgtgtgctct tccgatctga gcagctcctc cttgagag         48

<210> SEQ ID NO 504
<211> LENGTH: 48
<212> TYPE: DNA
<213> ORGANISM: Artificial Sequence
<220> FEATURE:
<223> OTHER INFORMATION: Synthetic

<400> SEQUENCE: 504
ggagttcaga cgtgtgctct tccgatctag caaagtgggg tgtgagac         48

```
<210> SEQ ID NO 505
<211> LENGTH: 49
<212> TYPE: DNA
<213> ORGANISM: Artificial Sequence
<220> FEATURE:
<223> OTHER INFORMATION: Synthetic

<400> SEQUENCE: 505
ggagttcaga cgtgtgctct tccgatcttg ccagtgggat gataagaaa          49

<210> SEQ ID NO 506
<211> LENGTH: 48
<212> TYPE: DNA
<213> ORGANISM: Artificial Sequence
<220> FEATURE:
<223> OTHER INFORMATION: Synthetic

<400> SEQUENCE: 506
ggagttcaga cgtgtgctct tccgatctcg gatagtggat ggcaaagt            48

<210> SEQ ID NO 507
<211> LENGTH: 55
<212> TYPE: DNA
<213> ORGANISM: Artificial Sequence
<220> FEATURE:
<223> OTHER INFORMATION: Synthetic

<400> SEQUENCE: 507
ggagttcaga cgtgtgctct tccgatcttc attatattta gctttgttag cgaga    55

<210> SEQ ID NO 508
<211> LENGTH: 23
<212> TYPE: DNA
<213> ORGANISM: Artificial Sequence
<220> FEATURE:
<223> OTHER INFORMATION: Synthetic

<400> SEQUENCE: 508
agtaataata cgactcacta tag                                        23

<210> SEQ ID NO 509
<211> LENGTH: 50
<212> TYPE: DNA
<213> ORGANISM: Artificial Sequence
<220> FEATURE:
<223> OTHER INFORMATION: Synthetic

<400> SEQUENCE: 509
aaaaaaagca ccgactcggt gccactttt caagttgata acggactagc            50

<210> SEQ ID NO 510
<211> LENGTH: 50
<212> TYPE: DNA
<213> ORGANISM: Artificial Sequence
<220> FEATURE:
<223> OTHER INFORMATION: Synthetic

<400> SEQUENCE: 510
gttttagagc tagaaatagc aagttaaaat aaggctagtc cgttatcaac            50

<210> SEQ ID NO 511
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 511
aaaaaaagca ccgactcggt gcc                                            23

<210> SEQ ID NO 512
<211> LENGTH: 58
<212> TYPE: DNA
<213> ORGANISM: Artificial Sequence
<220> FEATURE:
<223> OTHER INFORMATION: Synthetic

<400> SEQUENCE: 512
aatgatacgg cgaccaccga gatctacact agatcgcaca ctctttccct acacgacg     58

<210> SEQ ID NO 513
<211> LENGTH: 58
<212> TYPE: DNA
<213> ORGANISM: Artificial Sequence
<220> FEATURE:
<223> OTHER INFORMATION: Synthetic

<400> SEQUENCE: 513
aatgatacgg cgaccaccga gatctacacc tctctataca ctctttccct acacgacg     58

<210> SEQ ID NO 514
<211> LENGTH: 58
<212> TYPE: DNA
<213> ORGANISM: Artificial Sequence
<220> FEATURE:
<223> OTHER INFORMATION: Synthetic

<400> SEQUENCE: 514
aatgatacgg cgaccaccga gatctacact atcctctaca ctctttccct acacgacg     58

<210> SEQ ID NO 515
<211> LENGTH: 58
<212> TYPE: DNA
<213> ORGANISM: Artificial Sequence
<220> FEATURE:
<223> OTHER INFORMATION: Synthetic

<400> SEQUENCE: 515
aatgatacgg cgaccaccga gatctacaca gagtagaaca ctctttccct acacgacg     58

<210> SEQ ID NO 516
<211> LENGTH: 58
<212> TYPE: DNA
<213> ORGANISM: Artificial Sequence
<220> FEATURE:
<223> OTHER INFORMATION: Synthetic

<400> SEQUENCE: 516
aatgatacgg cgaccaccga gatctacacg taaggagaca ctctttccct acacgacg     58

<210> SEQ ID NO 517
<211> LENGTH: 58
<212> TYPE: DNA
<213> ORGANISM: Artificial Sequence
<220> FEATURE:
<223> OTHER INFORMATION: Synthetic

<400> SEQUENCE: 517
aatgatacgg cgaccaccga gatctacaca ctgcataaca ctctttccct acacgacg     58

<210> SEQ ID NO 518
<211> LENGTH: 58
```

```
<212> TYPE: DNA
<213> ORGANISM: Artificial Sequence
<220> FEATURE:
<223> OTHER INFORMATION: Synthetic

<400> SEQUENCE: 518
aatgatacgg cgaccaccga gatctacaca aggagtaaca ctctttccct acacgacg      58

<210> SEQ ID NO 519
<211> LENGTH: 58
<212> TYPE: DNA
<213> ORGANISM: Artificial Sequence
<220> FEATURE:
<223> OTHER INFORMATION: Synthetic

<400> SEQUENCE: 519
aatgatacgg cgaccaccga gatctacacc taagcctaca ctctttccct acacgacg      58

<210> SEQ ID NO 520
<211> LENGTH: 58
<212> TYPE: DNA
<213> ORGANISM: Artificial Sequence
<220> FEATURE:
<223> OTHER INFORMATION: Synthetic

<400> SEQUENCE: 520
aatgatacgg cgaccaccga gatctacact gaaccttaca ctctttccct acacgacg      58

<210> SEQ ID NO 521
<211> LENGTH: 58
<212> TYPE: DNA
<213> ORGANISM: Artificial Sequence
<220> FEATURE:
<223> OTHER INFORMATION: Synthetic

<400> SEQUENCE: 521
aatgatacgg cgaccaccga gatctacact gctaagtaca ctctttccct acacgacg      58

<210> SEQ ID NO 522
<211> LENGTH: 58
<212> TYPE: DNA
<213> ORGANISM: Artificial Sequence
<220> FEATURE:
<223> OTHER INFORMATION: Synthetic

<400> SEQUENCE: 522
aatgatacgg cgaccaccga gatctacact aagttccaca ctctttccct acacgacg      58

<210> SEQ ID NO 523
<211> LENGTH: 58
<212> TYPE: DNA
<213> ORGANISM: Artificial Sequence
<220> FEATURE:
<223> OTHER INFORMATION: Synthetic

<400> SEQUENCE: 523
aatgatacgg cgaccaccga gatctacaca tagaggcaca ctctttccct acacgacg      58

<210> SEQ ID NO 524
<211> LENGTH: 58
<212> TYPE: DNA
<213> ORGANISM: Artificial Sequence
<220> FEATURE:
<223> OTHER INFORMATION: Synthetic

<400> SEQUENCE: 524
```

```
aatgatacgg cgaccaccga gatctacacg gctctgaaca ctctttccct acacgacg      58
```

<210> SEQ ID NO 525
<211> LENGTH: 58
<212> TYPE: DNA
<213> ORGANISM: Artificial Sequence
<220> FEATURE:
<223> OTHER INFORMATION: Synthetic

<400> SEQUENCE: 525

```
aatgatacgg cgaccaccga gatctacaca ggcgaagaca ctctttccct acacgacg      58
```

<210> SEQ ID NO 526
<211> LENGTH: 58
<212> TYPE: DNA
<213> ORGANISM: Artificial Sequence
<220> FEATURE:
<223> OTHER INFORMATION: Synthetic

<400> SEQUENCE: 526

```
aatgatacgg cgaccaccga gatctacact aatcttaaca ctctttccct acacgacg      58
```

<210> SEQ ID NO 527
<211> LENGTH: 58
<212> TYPE: DNA
<213> ORGANISM: Artificial Sequence
<220> FEATURE:
<223> OTHER INFORMATION: Synthetic

<400> SEQUENCE: 527

```
aatgatacgg cgaccaccga gatctacacc aggacgtaca ctctttccct acacgacg      58
```

<210> SEQ ID NO 528
<211> LENGTH: 57
<212> TYPE: DNA
<213> ORGANISM: Artificial Sequence
<220> FEATURE:
<223> OTHER INFORMATION: Synthetic

<400> SEQUENCE: 528

```
caagcagaag acggcatacg agatattggt cagtgactgg agttcagacg tgtgctc       57
```

<210> SEQ ID NO 529
<211> LENGTH: 57
<212> TYPE: DNA
<213> ORGANISM: Artificial Sequence
<220> FEATURE:
<223> OTHER INFORMATION: Synthetic

<400> SEQUENCE: 529

```
caagcagaag acggcatacg agattaaaaa tggtgactgg agttcagacg tgtgctc       57
```

<210> SEQ ID NO 530
<211> LENGTH: 57
<212> TYPE: DNA
<213> ORGANISM: Artificial Sequence
<220> FEATURE:
<223> OTHER INFORMATION: Synthetic

<400> SEQUENCE: 530

```
caagcagaag acggcatacg agatatcact gtgtgactgg agttcagacg tgtgctc       57
```

<210> SEQ ID NO 531
<211> LENGTH: 57
<212> TYPE: DNA
<213> ORGANISM: Artificial Sequence
<220> FEATURE:
<223> OTHER INFORMATION: Synthetic

<400> SEQUENCE: 531
caagcagaag acggcatacg agattatttc acgtgactgg agttcagacg tgtgctc    57

<210> SEQ ID NO 532
<211> LENGTH: 57
<212> TYPE: DNA
<213> ORGANISM: Artificial Sequence
<220> FEATURE:
<223> OTHER INFORMATION: Synthetic

<400> SEQUENCE: 532
caagcagaag acggcatacg agatatattg gcgtgactgg agttcagacg tgtgctc    57

<210> SEQ ID NO 533
<211> LENGTH: 57
<212> TYPE: DNA
<213> ORGANISM: Artificial Sequence
<220> FEATURE:
<223> OTHER INFORMATION: Synthetic

<400> SEQUENCE: 533
caagcagaag acggcatacg agattataca aggtgactgg agttcagacg tgtgctc    57

<210> SEQ ID NO 534
<211> LENGTH: 57
<212> TYPE: DNA
<213> ORGANISM: Artificial Sequence
<220> FEATURE:
<223> OTHER INFORMATION: Synthetic

<400> SEQUENCE: 534
caagcagaag acggcatacg agatatgatc tggtgactgg agttcagacg tgtgctc    57

<210> SEQ ID NO 535
<211> LENGTH: 57
<212> TYPE: DNA
<213> ORGANISM: Artificial Sequence
<220> FEATURE:
<223> OTHER INFORMATION: Synthetic

<400> SEQUENCE: 535
caagcagaag acggcatacg agattactct acgtgactgg agttcagacg tgtgctc    57

<210> SEQ ID NO 536
<211> LENGTH: 57
<212> TYPE: DNA
<213> ORGANISM: Artificial Sequence
<220> FEATURE:
<223> OTHER INFORMATION: Synthetic

<400> SEQUENCE: 536
caagcagaag acggcatacg agatataagc tagtgactgg agttcagacg tgtgctc    57

<210> SEQ ID NO 537
<211> LENGTH: 57
<212> TYPE: DNA
<213> ORGANISM: Artificial Sequence
<220> FEATURE:
<223> OTHER INFORMATION: Synthetic

<400> SEQUENCE: 537
caagcagaag acggcatacg agattagtat aggtgactgg agttcagacg tgtgctc    57

<210> SEQ ID NO 538
<211> LENGTH: 57
<212> TYPE: DNA
<213> ORGANISM: Artificial Sequence
<220> FEATURE:
<223> OTHER INFORMATION: Synthetic

<400> SEQUENCE: 538
caagcagaag acggcatacg agatattaca aggtgactgg agttcagacg tgtgctc    57

<210> SEQ ID NO 539
<211> LENGTH: 57
<212> TYPE: DNA
<213> ORGANISM: Artificial Sequence
<220> FEATURE:
<223> OTHER INFORMATION: Synthetic

<400> SEQUENCE: 539
caagcagaag acggcatacg agattaattg gcgtgactgg agttcagacg tgtgctc    57

<210> SEQ ID NO 540
<211> LENGTH: 57
<212> TYPE: DNA
<213> ORGANISM: Artificial Sequence
<220> FEATURE:
<223> OTHER INFORMATION: Synthetic

<400> SEQUENCE: 540
caagcagaag acggcatacg agatatctct acgtgactgg agttcagacg tgtgctc    57

<210> SEQ ID NO 541
<211> LENGTH: 57
<212> TYPE: DNA
<213> ORGANISM: Artificial Sequence
<220> FEATURE:
<223> OTHER INFORMATION: Synthetic

<400> SEQUENCE: 541
caagcagaag acggcatacg agattagatc tggtgactgg agttcagacg tgtgctc    57

<210> SEQ ID NO 542
<211> LENGTH: 57
<212> TYPE: DNA
<213> ORGANISM: Artificial Sequence
<220> FEATURE:
<223> OTHER INFORMATION: Synthetic

<400> SEQUENCE: 542
caagcagaag acggcatacg agatatgcgg acgtgactgg agttcagacg tgtgctc    57

<210> SEQ ID NO 543
<211> LENGTH: 57
<212> TYPE: DNA
<213> ORGANISM: Artificial Sequence
<220> FEATURE:
<223> OTHER INFORMATION: Synthetic

<400> SEQUENCE: 543
caagcagaag acggcatacg agattaatca gtgtgactgg agttcagacg tgtgctc    57

<210> SEQ ID NO 544
<211> LENGTH: 57
<212> TYPE: DNA
<213> ORGANISM: Artificial Sequence
<220> FEATURE:
<223> OTHER INFORMATION: Synthetic

<400> SEQUENCE: 544
caagcagaag acggcatacg agatattttc acgtgactgg agttcagacg tgtgctc       57

<210> SEQ ID NO 545
<211> LENGTH: 57
<212> TYPE: DNA
<213> ORGANISM: Artificial Sequence
<220> FEATURE:
<223> OTHER INFORMATION: Synthetic

<400> SEQUENCE: 545
caagcagaag acggcatacg agattacact gtgtgactgg agttcagacg tgtgctc       57

<210> SEQ ID NO 546
<211> LENGTH: 57
<212> TYPE: DNA
<213> ORGANISM: Artificial Sequence
<220> FEATURE:
<223> OTHER INFORMATION: Synthetic

<400> SEQUENCE: 546
caagcagaag acggcatacg agatatggcc acgtgactgg agttcagacg tgtgctc       57

<210> SEQ ID NO 547
<211> LENGTH: 57
<212> TYPE: DNA
<213> ORGANISM: Artificial Sequence
<220> FEATURE:
<223> OTHER INFORMATION: Synthetic

<400> SEQUENCE: 547
caagcagaag acggcatacg agattaccgg tggtgactgg agttcagacg tgtgctc       57

<210> SEQ ID NO 548
<211> LENGTH: 57
<212> TYPE: DNA
<213> ORGANISM: Artificial Sequence
<220> FEATURE:
<223> OTHER INFORMATION: Synthetic

<400> SEQUENCE: 548
caagcagaag acggcatacg agatatcgaa acgtgactgg agttcagacg tgtgctc       57

<210> SEQ ID NO 549
<211> LENGTH: 57
<212> TYPE: DNA
<213> ORGANISM: Artificial Sequence
<220> FEATURE:
<223> OTHER INFORMATION: Synthetic

<400> SEQUENCE: 549
caagcagaag acggcatacg agattatagt tggtgactgg agttcagacg tgtgctc       57

<210> SEQ ID NO 550
<211> LENGTH: 57
<212> TYPE: DNA
<213> ORGANISM: Artificial Sequence
<220> FEATURE:
<223> OTHER INFORMATION: Synthetic

<400> SEQUENCE: 550
caagcagaag acggcatacg agatatcgta cggtgactgg agttcagacg tgtgctc       57

<210> SEQ ID NO 551

```
<211> LENGTH: 57
<212> TYPE: DNA
<213> ORGANISM: Artificial Sequence
<220> FEATURE:
<223> OTHER INFORMATION: Synthetic

<400> SEQUENCE: 551
caagcagaag acggcatacg agattagaat gagtgactgg agttcagacg tgtgctc      57

<210> SEQ ID NO 552
<211> LENGTH: 57
<212> TYPE: DNA
<213> ORGANISM: Artificial Sequence
<220> FEATURE:
<223> OTHER INFORMATION: Synthetic

<400> SEQUENCE: 552
caagcagaag acggcatacg agatatgcta ccgtgactgg agttcagacg tgtgctc      57

<210> SEQ ID NO 553
<211> LENGTH: 57
<212> TYPE: DNA
<213> ORGANISM: Artificial Sequence
<220> FEATURE:
<223> OTHER INFORMATION: Synthetic

<400> SEQUENCE: 553
caagcagaag acggcatacg agattaatcg tggtgactgg agttcagacg tgtgctc      57

<210> SEQ ID NO 554
<211> LENGTH: 57
<212> TYPE: DNA
<213> ORGANISM: Artificial Sequence
<220> FEATURE:
<223> OTHER INFORMATION: Synthetic

<400> SEQUENCE: 554
caagcagaag acggcatacg agatatatca gtgtgactgg agttcagacg tgtgctc      57

<210> SEQ ID NO 555
<211> LENGTH: 57
<212> TYPE: DNA
<213> ORGANISM: Artificial Sequence
<220> FEATURE:
<223> OTHER INFORMATION: Synthetic

<400> SEQUENCE: 555
caagcagaag acggcatacg agattagcgg acgtgactgg agttcagacg tgtgctc      57

<210> SEQ ID NO 556
<211> LENGTH: 57
<212> TYPE: DNA
<213> ORGANISM: Artificial Sequence
<220> FEATURE:
<223> OTHER INFORMATION: Synthetic

<400> SEQUENCE: 556
caagcagaag acggcatacg agatatgctc atgtgactgg agttcagacg tgtgctc      57

<210> SEQ ID NO 557
<211> LENGTH: 57
<212> TYPE: DNA
<213> ORGANISM: Artificial Sequence
<220> FEATURE:
<223> OTHER INFORMATION: Synthetic

<400> SEQUENCE: 557
``` caagcagaaag acggcatacg agattacgat tagtgactgg agttcagacg tgtgctc        57

<210> SEQ ID NO 558
<211> LENGTH: 57
<212> TYPE: DNA
<213> ORGANISM: Artificial Sequence
<220> FEATURE:
<223> OTHER INFORMATION: Synthetic

<400> SEQUENCE: 558 caagcagaaag acggcatacg agatatagga atgtgactgg agttcagacg tgtgctc        57

<210> SEQ ID NO 559
<211> LENGTH: 57
<212> TYPE: DNA
<213> ORGANISM: Artificial Sequence
<220> FEATURE:
<223> OTHER INFORMATION: Synthetic

<400> SEQUENCE: 559 caagcagaaag acggcatacg agatattagt tggtgactgg agttcagacg tgtgctc        57

<210> SEQ ID NO 560
<211> LENGTH: 57
<212> TYPE: DNA
<213> ORGANISM: Artificial Sequence
<220> FEATURE:
<223> OTHER INFORMATION: Synthetic

<400> SEQUENCE: 560 caagcagaaag acggcatacg agattacgaa acgtgactgg agttcagacg tgtgctc        57

<210> SEQ ID NO 561
<211> LENGTH: 57
<212> TYPE: DNA
<213> ORGANISM: Artificial Sequence
<220> FEATURE:
<223> OTHER INFORMATION: Synthetic

<400> SEQUENCE: 561 caagcagaaag acggcatacg agatatccgg tggtgactgg agttcagacg tgtgctc        57

<210> SEQ ID NO 562
<211> LENGTH: 57
<212> TYPE: DNA
<213> ORGANISM: Artificial Sequence
<220> FEATURE:
<223> OTHER INFORMATION: Synthetic

<400> SEQUENCE: 562 caagcagaaag acggcatacg agattaggcc acgtgactgg agttcagacg tgtgctc        57

<210> SEQ ID NO 563
<211> LENGTH: 57
<212> TYPE: DNA
<213> ORGANISM: Artificial Sequence
<220> FEATURE:
<223> OTHER INFORMATION: Synthetic

<400> SEQUENCE: 563 caagcagaaag acggcatacg agatatatcg tggtgactgg agttcagacg tgtgctc        57

<210> SEQ ID NO 564
<211> LENGTH: 57
<212> TYPE: DNA

```
<213> ORGANISM: Artificial Sequence
<220> FEATURE:
<223> OTHER INFORMATION: Synthetic

<400> SEQUENCE: 564
caagcagaag acggcatacg agattagcta ccgtgactgg agttcagacg tgtgctc      57

<210> SEQ ID NO 565
<211> LENGTH: 57
<212> TYPE: DNA
<213> ORGANISM: Artificial Sequence
<220> FEATURE:
<223> OTHER INFORMATION: Synthetic

<400> SEQUENCE: 565
caagcagaag acggcatacg agatatcgcc tggtgactgg agttcagacg tgtgctc      57

<210> SEQ ID NO 566
<211> LENGTH: 57
<212> TYPE: DNA
<213> ORGANISM: Artificial Sequence
<220> FEATURE:
<223> OTHER INFORMATION: Synthetic

<400> SEQUENCE: 566
caagcagaag acggcatacg agatataaaa tggtgactgg agttcagacg tgtgctc      57

<210> SEQ ID NO 567
<211> LENGTH: 57
<212> TYPE: DNA
<213> ORGANISM: Artificial Sequence
<220> FEATURE:
<223> OTHER INFORMATION: Synthetic

<400> SEQUENCE: 567
caagcagaag acggcatacg agattatggt cagtgactgg agttcagacg tgtgctc      57

<210> SEQ ID NO 568
<211> LENGTH: 57
<212> TYPE: DNA
<213> ORGANISM: Artificial Sequence
<220> FEATURE:
<223> OTHER INFORMATION: Synthetic

<400> SEQUENCE: 568
caagcagaag acggcatacg agatatattc cggtgactgg agttcagacg tgtgctc      57

<210> SEQ ID NO 569
<211> LENGTH: 57
<212> TYPE: DNA
<213> ORGANISM: Artificial Sequence
<220> FEATURE:
<223> OTHER INFORMATION: Synthetic

<400> SEQUENCE: 569
caagcagaag acggcatacg agatatgtat aggtgactgg agttcagacg tgtgctc      57

<210> SEQ ID NO 570
<211> LENGTH: 57
<212> TYPE: DNA
<213> ORGANISM: Artificial Sequence
<220> FEATURE:
<223> OTHER INFORMATION: Synthetic

<400> SEQUENCE: 570
caagcagaag acggcatacg agattaaagc tagtgactgg agttcagacg tgtgctc      57
```

<210> SEQ ID NO 571
<211> LENGTH: 57
<212> TYPE: DNA
<213> ORGANISM: Artificial Sequence
<220> FEATURE:
<223> OTHER INFORMATION: Synthetic

<400> SEQUENCE: 571
caagcagaag acggcatacg agatatcgat tagtgactgg agttcagacg tgtgctc    57

<210> SEQ ID NO 572
<211> LENGTH: 57
<212> TYPE: DNA
<213> ORGANISM: Artificial Sequence
<220> FEATURE:
<223> OTHER INFORMATION: Synthetic

<400> SEQUENCE: 572
caagcagaag acggcatacg agattagctc atgtgactgg agttcagacg tgtgctc    57

<210> SEQ ID NO 573
<211> LENGTH: 57
<212> TYPE: DNA
<213> ORGANISM: Artificial Sequence
<220> FEATURE:
<223> OTHER INFORMATION: Synthetic

<400> SEQUENCE: 573
caagcagaag acggcatacg agatatgaat gagtgactgg agttcagacg tgtgctc    57

<210> SEQ ID NO 574
<211> LENGTH: 57
<212> TYPE: DNA
<213> ORGANISM: Artificial Sequence
<220> FEATURE:
<223> OTHER INFORMATION: Synthetic

<400> SEQUENCE: 574
caagcagaag acggcatacg agattacgta cggtgactgg agttcagacg tgtgctc    57

<210> SEQ ID NO 575
<211> LENGTH: 57
<212> TYPE: DNA
<213> ORGANISM: Artificial Sequence
<220> FEATURE:
<223> OTHER INFORMATION: Synthetic

<400> SEQUENCE: 575
caagcagaag acggcatacg agatatcgtg atgtgactgg agttcagacg tgtgctc    57

<210> SEQ ID NO 576
<211> LENGTH: 57
<212> TYPE: DNA
<213> ORGANISM: Artificial Sequence
<220> FEATURE:
<223> OTHER INFORMATION: Synthetic

<400> SEQUENCE: 576
caagcagaag acggcatacg agatatacat cggtgactgg agttcagacg tgtgctc    57

<210> SEQ ID NO 577
<211> LENGTH: 57
<212> TYPE: DNA
<213> ORGANISM: Artificial Sequence
<220> FEATURE:

```
<223> OTHER INFORMATION: Synthetic

<400> SEQUENCE: 577
caagcagaag acggcatacg agatatgcct aagtgactgg agttcagacg tgtgctc        57

<210> SEQ ID NO 578
<211> LENGTH: 57
<212> TYPE: DNA
<213> ORGANISM: Artificial Sequence
<220> FEATURE:
<223> OTHER INFORMATION: Synthetic

<400> SEQUENCE: 578
caagcagaag acggcatacg agatattcaa gtgtgactgg agttcagacg tgtgctc        57

<210> SEQ ID NO 579
<211> LENGTH: 57
<212> TYPE: DNA
<213> ORGANISM: Artificial Sequence
<220> FEATURE:
<223> OTHER INFORMATION: Synthetic

<400> SEQUENCE: 579
caagcagaag acggcatacg agatatctga tcgtgactgg agttcagacg tgtgctc        57

<210> SEQ ID NO 580
<211> LENGTH: 57
<212> TYPE: DNA
<213> ORGANISM: Artificial Sequence
<220> FEATURE:
<223> OTHER INFORMATION: Synthetic

<400> SEQUENCE: 580
caagcagaag acggcatacg agatatgtag ccgtgactgg agttcagacg tgtgctc        57

<210> SEQ ID NO 581
<211> LENGTH: 57
<212> TYPE: DNA
<213> ORGANISM: Artificial Sequence
<220> FEATURE:
<223> OTHER INFORMATION: Synthetic

<400> SEQUENCE: 581
caagcagaag acggcatacg agatatttga ctgtgactgg agttcagacg tgtgctc        57

<210> SEQ ID NO 582
<211> LENGTH: 57
<212> TYPE: DNA
<213> ORGANISM: Artificial Sequence
<220> FEATURE:
<223> OTHER INFORMATION: Synthetic

<400> SEQUENCE: 582
caagcagaag acggcatacg agatatggaa ctgtgactgg agttcagacg tgtgctc        57

<210> SEQ ID NO 583
<211> LENGTH: 57
<212> TYPE: DNA
<213> ORGANISM: Artificial Sequence
<220> FEATURE:
<223> OTHER INFORMATION: Synthetic

<400> SEQUENCE: 583
caagcagaag acggcatacg agatattgac atgtgactgg agttcagacg tgtgctc        57
```

```
<210> SEQ ID NO 584
<211> LENGTH: 57
<212> TYPE: DNA
<213> ORGANISM: Artificial Sequence
<220> FEATURE:
<223> OTHER INFORMATION: Synthetic

<400> SEQUENCE: 584
caagcagaag acggcatacg agatatggac gggtgactgg agttcagacg tgtgctc      57

<210> SEQ ID NO 585
<211> LENGTH: 57
<212> TYPE: DNA
<213> ORGANISM: Artificial Sequence
<220> FEATURE:
<223> OTHER INFORMATION: Synthetic

<400> SEQUENCE: 585
caagcagaag acggcatacg agatatccac tcgtgactgg agttcagacg tgtgctc      57

<210> SEQ ID NO 586
<211> LENGTH: 57
<212> TYPE: DNA
<213> ORGANISM: Artificial Sequence
<220> FEATURE:
<223> OTHER INFORMATION: Synthetic

<400> SEQUENCE: 586
caagcagaag acggcatacg agatatcttt tggtgactgg agttcagacg tgtgctc      57

<210> SEQ ID NO 587
<211> LENGTH: 57
<212> TYPE: DNA
<213> ORGANISM: Artificial Sequence
<220> FEATURE:
<223> OTHER INFORMATION: Synthetic

<400> SEQUENCE: 587
caagcagaag acggcatacg agatattgag tggtgactgg agttcagacg tgtgctc      57

<210> SEQ ID NO 588
<211> LENGTH: 57
<212> TYPE: DNA
<213> ORGANISM: Artificial Sequence
<220> FEATURE:
<223> OTHER INFORMATION: Synthetic

<400> SEQUENCE: 588
caagcagaag acggcatacg agatatgcca tggtgactgg agttcagacg tgtgctc      57

<210> SEQ ID NO 589
<211> LENGTH: 57
<212> TYPE: DNA
<213> ORGANISM: Artificial Sequence
<220> FEATURE:
<223> OTHER INFORMATION: Synthetic

<400> SEQUENCE: 589
caagcagaag acggcatacg agatattgtt gggtgactgg agttcagacg tgtgctc      57

<210> SEQ ID NO 590
<211> LENGTH: 57
<212> TYPE: DNA
<213> ORGANISM: Artificial Sequence
<220> FEATURE:
<223> OTHER INFORMATION: Synthetic
```

```
<400> SEQUENCE: 590
caagcagaag acggcatacg agatatagct aggtgactgg agttcagacg tgtgctc      57

<210> SEQ ID NO 591
<211> LENGTH: 57
<212> TYPE: DNA
<213> ORGANISM: Artificial Sequence
<220> FEATURE:
<223> OTHER INFORMATION: Synthetic

<400> SEQUENCE: 591
caagcagaag acggcatacg agatattctg aggtgactgg agttcagacg tgtgctc      57

<210> SEQ ID NO 592
<211> LENGTH: 57
<212> TYPE: DNA
<213> ORGANISM: Artificial Sequence
<220> FEATURE:
<223> OTHER INFORMATION: Synthetic

<400> SEQUENCE: 592
caagcagaag acggcatacg agatatgtcg tcgtgactgg agttcagacg tgtgctc      57

<210> SEQ ID NO 593
<211> LENGTH: 57
<212> TYPE: DNA
<213> ORGANISM: Artificial Sequence
<220> FEATURE:
<223> OTHER INFORMATION: Synthetic

<400> SEQUENCE: 593
caagcagaag acggcatacg agatatgctg tagtgactgg agttcagacg tgtgctc      57

<210> SEQ ID NO 594
<211> LENGTH: 57
<212> TYPE: DNA
<213> ORGANISM: Artificial Sequence
<220> FEATURE:
<223> OTHER INFORMATION: Synthetic

<400> SEQUENCE: 594
caagcagaag acggcatacg agatatatta tagtgactgg agttcagacg tgtgctc      57

<210> SEQ ID NO 595
<211> LENGTH: 57
<212> TYPE: DNA
<213> ORGANISM: Artificial Sequence
<220> FEATURE:
<223> OTHER INFORMATION: Synthetic

<400> SEQUENCE: 595
caagcagaag acggcatacg agatattcgg gagtgactgg agttcagacg tgtgctc      57

<210> SEQ ID NO 596
<211> LENGTH: 57
<212> TYPE: DNA
<213> ORGANISM: Artificial Sequence
<220> FEATURE:
<223> OTHER INFORMATION: Synthetic

<400> SEQUENCE: 596
caagcagaag acggcatacg agatatcttc gagtgactgg agttcagacg tgtgctc      57

<210> SEQ ID NO 597
<211> LENGTH: 57
```

```
<212> TYPE: DNA
<213> ORGANISM: Artificial Sequence
<220> FEATURE:
<223> OTHER INFORMATION: Synthetic

<400> SEQUENCE: 597
caagcagaag acggcatacg agatattgcc gagtgactgg agttcagacg tgtgctc      57

<210> SEQ ID NO 598
<211> LENGTH: 57
<212> TYPE: DNA
<213> ORGANISM: Artificial Sequence
<220> FEATURE:
<223> OTHER INFORMATION: Synthetic

<400> SEQUENCE: 598
caagcagaag acggcatacg agattacgtg atgtgactgg agttcagacg tgtgctc      57

<210> SEQ ID NO 599
<211> LENGTH: 57
<212> TYPE: DNA
<213> ORGANISM: Artificial Sequence
<220> FEATURE:
<223> OTHER INFORMATION: Synthetic

<400> SEQUENCE: 599
caagcagaag acggcatacg agattaacat cggtgactgg agttcagacg tgtgctc      57

<210> SEQ ID NO 600
<211> LENGTH: 57
<212> TYPE: DNA
<213> ORGANISM: Artificial Sequence
<220> FEATURE:
<223> OTHER INFORMATION: Synthetic

<400> SEQUENCE: 600
caagcagaag acggcatacg agattagcct aagtgactgg agttcagacg tgtgctc      57

<210> SEQ ID NO 601
<211> LENGTH: 57
<212> TYPE: DNA
<213> ORGANISM: Artificial Sequence
<220> FEATURE:
<223> OTHER INFORMATION: Synthetic

<400> SEQUENCE: 601
caagcagaag acggcatacg agattatcaa gtgtgactgg agttcagacg tgtgctc      57

<210> SEQ ID NO 602
<211> LENGTH: 57
<212> TYPE: DNA
<213> ORGANISM: Artificial Sequence
<220> FEATURE:
<223> OTHER INFORMATION: Synthetic

<400> SEQUENCE: 602
caagcagaag acggcatacg agattactga tcgtgactgg agttcagacg tgtgctc      57

<210> SEQ ID NO 603
<211> LENGTH: 57
<212> TYPE: DNA
<213> ORGANISM: Artificial Sequence
<220> FEATURE:
<223> OTHER INFORMATION: Synthetic

<400> SEQUENCE: 603
```
caagcagaag acggcatacg agattagtag ccgtgactgg agttcagacg tgtgctc        57

<210> SEQ ID NO 604
<211> LENGTH: 57
<212> TYPE: DNA
<213> ORGANISM: Artificial Sequence
<220> FEATURE:
<223> OTHER INFORMATION: Synthetic

<400> SEQUENCE: 604
caagcagaag acggcatacg agattattga ctgtgactgg agttcagacg tgtgctc        57

<210> SEQ ID NO 605
<211> LENGTH: 57
<212> TYPE: DNA
<213> ORGANISM: Artificial Sequence
<220> FEATURE:
<223> OTHER INFORMATION: Synthetic

<400> SEQUENCE: 605
caagcagaag acggcatacg agattaggaa ctgtgactgg agttcagacg tgtgctc        57

<210> SEQ ID NO 606
<211> LENGTH: 57
<212> TYPE: DNA
<213> ORGANISM: Artificial Sequence
<220> FEATURE:
<223> OTHER INFORMATION: Synthetic

<400> SEQUENCE: 606
caagcagaag acggcatacg agattatgac atgtgactgg agttcagacg tgtgctc        57

<210> SEQ ID NO 607
<211> LENGTH: 57
<212> TYPE: DNA
<213> ORGANISM: Artificial Sequence
<220> FEATURE:
<223> OTHER INFORMATION: Synthetic

<400> SEQUENCE: 607
caagcagaag acggcatacg agattaggac gggtgactgg agttcagacg tgtgctc        57

<210> SEQ ID NO 608
<211> LENGTH: 57
<212> TYPE: DNA
<213> ORGANISM: Artificial Sequence
<220> FEATURE:
<223> OTHER INFORMATION: Synthetic

<400> SEQUENCE: 608
caagcagaag acggcatacg agattaccac tcgtgactgg agttcagacg tgtgctc        57

<210> SEQ ID NO 609
<211> LENGTH: 57
<212> TYPE: DNA
<213> ORGANISM: Artificial Sequence
<220> FEATURE:
<223> OTHER INFORMATION: Synthetic

<400> SEQUENCE: 609
caagcagaag acggcatacg agattaagga atgtgactgg agttcagacg tgtgctc        57

<210> SEQ ID NO 610
<211> LENGTH: 57
<212> TYPE: DNA
<213> ORGANISM: Artificial Sequence

```
<220> FEATURE:
<223> OTHER INFORMATION: Synthetic

<400> SEQUENCE: 610
caagcagaag acggcatacg agattacttt tggtgactgg agttcagacg tgtgctc      57

<210> SEQ ID NO 611
<211> LENGTH: 57
<212> TYPE: DNA
<213> ORGANISM: Artificial Sequence
<220> FEATURE:
<223> OTHER INFORMATION: Synthetic

<400> SEQUENCE: 611
caagcagaag acggcatacg agattatgag tggtgactgg agttcagacg tgtgctc      57

<210> SEQ ID NO 612
<211> LENGTH: 57
<212> TYPE: DNA
<213> ORGANISM: Artificial Sequence
<220> FEATURE:
<223> OTHER INFORMATION: Synthetic

<400> SEQUENCE: 612
caagcagaag acggcatacg agattacgcc tggtgactgg agttcagacg tgtgctc      57

<210> SEQ ID NO 613
<211> LENGTH: 57
<212> TYPE: DNA
<213> ORGANISM: Artificial Sequence
<220> FEATURE:
<223> OTHER INFORMATION: Synthetic

<400> SEQUENCE: 613
caagcagaag acggcatacg agattagcca tggtgactgg agttcagacg tgtgctc      57

<210> SEQ ID NO 614
<211> LENGTH: 57
<212> TYPE: DNA
<213> ORGANISM: Artificial Sequence
<220> FEATURE:
<223> OTHER INFORMATION: Synthetic

<400> SEQUENCE: 614
caagcagaag acggcatacg agattatgtt gggtgactgg agttcagacg tgtgctc      57

<210> SEQ ID NO 615
<211> LENGTH: 57
<212> TYPE: DNA
<213> ORGANISM: Artificial Sequence
<220> FEATURE:
<223> OTHER INFORMATION: Synthetic

<400> SEQUENCE: 615
caagcagaag acggcatacg agattaattc cggtgactgg agttcagacg tgtgctc      57

<210> SEQ ID NO 616
<211> LENGTH: 57
<212> TYPE: DNA
<213> ORGANISM: Artificial Sequence
<220> FEATURE:
<223> OTHER INFORMATION: Synthetic

<400> SEQUENCE: 616
caagcagaag acggcatacg agattaagct aggtgactgg agttcagacg tgtgctc      57
```

<210> SEQ ID NO 617
<211> LENGTH: 57
<212> TYPE: DNA
<213> ORGANISM: Artificial Sequence
<220> FEATURE:
<223> OTHER INFORMATION: Synthetic

<400> SEQUENCE: 617
caagcagaag acggcatacg agattatctg aggtgactgg agttcagacg tgtgctc    57

<210> SEQ ID NO 618
<211> LENGTH: 57
<212> TYPE: DNA
<213> ORGANISM: Artificial Sequence
<220> FEATURE:
<223> OTHER INFORMATION: Synthetic

<400> SEQUENCE: 618
caagcagaag acggcatacg agattagtcg tcgtgactgg agttcagacg tgtgctc    57

<210> SEQ ID NO 619
<211> LENGTH: 57
<212> TYPE: DNA
<213> ORGANISM: Artificial Sequence
<220> FEATURE:
<223> OTHER INFORMATION: Synthetic

<400> SEQUENCE: 619
caagcagaag acggcatacg agattagctg tagtgactgg agttcagacg tgtgctc    57

<210> SEQ ID NO 620
<211> LENGTH: 57
<212> TYPE: DNA
<213> ORGANISM: Artificial Sequence
<220> FEATURE:
<223> OTHER INFORMATION: Synthetic

<400> SEQUENCE: 620
caagcagaag acggcatacg agattaatta tagtgactgg agttcagacg tgtgctc    57

<210> SEQ ID NO 621
<211> LENGTH: 57
<212> TYPE: DNA
<213> ORGANISM: Artificial Sequence
<220> FEATURE:
<223> OTHER INFORMATION: Synthetic

<400> SEQUENCE: 621
caagcagaag acggcatacg agattatcgg gagtgactgg agttcagacg tgtgctc    57

<210> SEQ ID NO 622
<211> LENGTH: 57
<212> TYPE: DNA
<213> ORGANISM: Artificial Sequence
<220> FEATURE:
<223> OTHER INFORMATION: Synthetic

<400> SEQUENCE: 622
caagcagaag acggcatacg agattacttc gagtgactgg agttcagacg tgtgctc    57

<210> SEQ ID NO 623
<211> LENGTH: 57
<212> TYPE: DNA
<213> ORGANISM: Artificial Sequence
<220> FEATURE:
<223> OTHER INFORMATION: Synthetic

<400> SEQUENCE: 623
caagcagaag acggcatacg agattatgcc gagtgactgg agttcagacg tgtgctc      57

<210> SEQ ID NO 624
<211> LENGTH: 23
<212> TYPE: DNA
<213> ORGANISM: Artificial Sequence
<220> FEATURE:
<223> OTHER INFORMATION: Synthetic

<400> SEQUENCE: 624
gaggagctcc aagaagactg agg                                           23

<210> SEQ ID NO 625
<211> LENGTH: 36
<212> TYPE: DNA
<213> ORGANISM: Artificial Sequence
<220> FEATURE:
<223> OTHER INFORMATION: Synthetic

<400> SEQUENCE: 625
agcagtaccg ttgttgtcaa gactcatgaa cccaga                             36

<210> SEQ ID NO 626
<211> LENGTH: 12
<212> TYPE: PRT
<213> ORGANISM: Artificial Sequence
<220> FEATURE:
<223> OTHER INFORMATION: Synthetic

<400> SEQUENCE: 626

Ala Thr Gly Asn Asn Asp Leu Ser Met Phe Gly Ser
1               5                   10

<210> SEQ ID NO 627
<211> LENGTH: 34
<212> TYPE: DNA
<213> ORGANISM: Artificial Sequence
<220> FEATURE:
<223> OTHER INFORMATION: Synthetic

<400> SEQUENCE: 627
acaccaccca cccttagttc tactgtgctc atag                               34

<210> SEQ ID NO 628
<211> LENGTH: 12
<212> TYPE: PRT
<213> ORGANISM: Artificial Sequence
<220> FEATURE:
<223> OTHER INFORMATION: Synthetic

<400> SEQUENCE: 628

Thr Pro Pro Thr Leu Ser Ser Thr Val Leu Ile Val
1               5                   10

<210> SEQ ID NO 629
<211> LENGTH: 33
<212> TYPE: DNA
<213> ORGANISM: Artificial Sequence
<220> FEATURE:
<223> OTHER INFORMATION: Synthetic

<400> SEQUENCE: 629
acaccaccca ccttagttct actgtgctca tag                                33

<210> SEQ ID NO 630
<211> LENGTH: 10
<212> TYPE: PRT
<213> ORGANISM: Artificial Sequence
<220> FEATURE:
<223> OTHER INFORMATION: Synthetic

<400> SEQUENCE: 630

Thr Pro Pro Thr Leu Val Leu Leu Cys Ser
1               5                   10

<210> SEQ ID NO 631
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: n is t, a, c, or g

<400> SEQUENCE: 631
acaccaccca ccnttagttc tactgtgctc atag                                34

<210> SEQ ID NO 632
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: X is F, I, V, or L

<400> SEQUENCE: 632

Thr Pro Pro Thr Xaa Ser Ser Thr Val Leu Ile Val
1               5                   10

<210> SEQ ID NO 633
<211> LENGTH: 34
<212> TYPE: DNA
<213> ORGANISM: Artificial Sequence
<220> FEATURE:
<223> OTHER INFORMATION: Synthetic

<400> SEQUENCE: 633
acaccaccca cccttactta gttctactgt gctc                                34

<210> SEQ ID NO 634
<211> LENGTH: 6
<212> TYPE: PRT
<213> ORGANISM: Artificial Sequence
<220> FEATURE:
<223> OTHER INFORMATION: Synthetic

<400> SEQUENCE: 634

Thr Pro Pro Thr Leu Thr
1               5

<210> SEQ ID NO 635
<211> LENGTH: 34
<212> TYPE: DNA
<213> ORGANISM: Artificial Sequence
<220> FEATURE:
<223> OTHER INFORMATION: Synthetic

<400> SEQUENCE: 635
acaccaccct tacttagttc tactgtgctc atag                                      34

<210> SEQ ID NO 636
<211> LENGTH: 12
<212> TYPE: PRT
<213> ORGANISM: Artificial Sequence
<220> FEATURE:
<223> OTHER INFORMATION: Synthetic

<400> SEQUENCE: 636

Thr Pro Pro Leu Leu Ser Ser Thr Val Leu Ile Val
1               5                   10

<210> SEQ ID NO 637
<211> LENGTH: 35
<212> TYPE: DNA
<213> ORGANISM: Artificial Sequence
<220> FEATURE:
<223> OTHER INFORMATION: Synthetic

<400> SEQUENCE: 637
ggttcacctc agtcttcttg gagctcctca tttta                                     35

<210> SEQ ID NO 638
<211> LENGTH: 11
<212> TYPE: PRT
<213> ORGANISM: Artificial Sequence
<220> FEATURE:
<223> OTHER INFORMATION: Synthetic

<400> SEQUENCE: 638

Asn Val Glu Thr Lys Lys Ser Ser Arg Met Lys
1               5                   10

<210> SEQ ID NO 639
<211> LENGTH: 35
<212> TYPE: DNA
<213> ORGANISM: Artificial Sequence
<220> FEATURE:
<223> OTHER INFORMATION: Synthetic

<400> SEQUENCE: 639
caaagcgcct gaggaccggc aacatggtgc ggtcg                                     35

<210> SEQ ID NO 640
<211> LENGTH: 4
<212> TYPE: PRT
<213> ORGANISM: Artificial Sequence
<220> FEATURE:
<223> OTHER INFORMATION: Synthetic

<400> SEQUENCE: 640

Met Val Arg Ser
1

<210> SEQ ID NO 641
<211> LENGTH: 33
<212> TYPE: DNA
<213> ORGANISM: Artificial Sequence
<220> FEATURE:
<223> OTHER INFORMATION: Synthetic

<400> SEQUENCE: 641
ctcggccact tcctccagca gcctcggcgg tgc                                       33

<210> SEQ ID NO 642
<211> LENGTH: 11
<212> TYPE: PRT
<213> ORGANISM: Artificial Sequence
<220> FEATURE:
<223> OTHER INFORMATION: Synthetic

<400> SEQUENCE: 642

Glu Ala Val Glu Glu Leu Leu Arg Pro Pro Ala
1               5                   10

<210> SEQ ID NO 643
<211> LENGTH: 32
<212> TYPE: DNA
<213> ORGANISM: Artificial Sequence
<220> FEATURE:
<223> OTHER INFORMATION: Synthetic

<400> SEQUENCE: 643
cactctttcc ctacacgacg ctcttccgat ct                                    32

<210> SEQ ID NO 644
<211> LENGTH: 28
<212> TYPE: DNA
<213> ORGANISM: Artificial Sequence
<220> FEATURE:
<223> OTHER INFORMATION: Synthetic

<400> SEQUENCE: 644
ggagttcaga cgtgtgctct tccgatct                                         28

<210> SEQ ID NO 645
<211> LENGTH: 33
<212> TYPE: DNA
<213> ORGANISM: Artificial Sequence
<220> FEATURE:
<223> OTHER INFORMATION: Synthetic

<400> SEQUENCE: 645
tcgtcggcag cgtcagatgt gtataagaga cag                                   33

<210> SEQ ID NO 646
<211> LENGTH: 34
<212> TYPE: DNA
<213> ORGANISM: Artificial Sequence
<220> FEATURE:
<223> OTHER INFORMATION: Synthetic

<400> SEQUENCE: 646
gtctcgtggg ctcggagatg tgtataagag acag                                  34

<210> SEQ ID NO 647
<211> LENGTH: 14
<212> TYPE: DNA
<213> ORGANISM: Artificial Sequence
<220> FEATURE:
<223> OTHER INFORMATION: Synthetic

<400> SEQUENCE: 647
tcgtcggcag cgtc                                                        14

<210> SEQ ID NO 648
<211> LENGTH: 15
<212> TYPE: DNA
<213> ORGANISM: Artificial Sequence
<220> FEATURE:

```
<223> OTHER INFORMATION: Synthetic

<400> SEQUENCE: 648
gtctcgtggg ctcgg                                               15

<210> SEQ ID NO 649
<211> LENGTH: 23
<212> TYPE: DNA
<213> ORGANISM: Artificial Sequence
<220> FEATURE:
<223> OTHER INFORMATION: Synthetic

<400> SEQUENCE: 649
ggcagtgcag atgaaaaact ggg                                      23
```